US011085052B2

(12) United States Patent
Whyard et al.

(10) Patent No.: US 11,085,052 B2
(45) Date of Patent: Aug. 10, 2021

(54) PLANTS AND METHODS FOR CONTROLLING FUNGAL PLANT PATHOGENS

(71) Applicant: University of Manitoba, Winnipeg (CA)

(72) Inventors: Steve Whyard, Winnipeg (CA); Mark Belmonte, Winnipeg (CA)

(73) Assignee: University of Manitoba, Winnipeg (CA)

( * ) Notice: Subject to any disclaimer, the term of this patent is extended or adjusted under 35 U.S.C. 154(b) by 38 days.

(21) Appl. No.: 16/098,387

(22) PCT Filed: May 3, 2017

(86) PCT No.: PCT/IB2017/052578
§ 371 (c)(1),
(2) Date: Nov. 1, 2018

(87) PCT Pub. No.: WO2017/191580
PCT Pub. Date: Nov. 9, 2017

(65) Prior Publication Data

US 2019/0153467 A1 May 23, 2019

Related U.S. Application Data

(60) Provisional application No. 62/331,026, filed on May 3, 2016.

(51) Int. Cl.

| | |
|---|---|
| ***C12N 15/82*** | (2006.01) |
| ***A01H 5/00*** | (2018.01) |
| ***A01N 37/46*** | (2006.01) |
| ***A01N 63/30*** | (2020.01) |
| ***A01N 57/16*** | (2006.01) |

(52) U.S. Cl.
CPC .......... *C12N 15/8282* (2013.01); *A01H 5/00* (2013.01); *A01N 37/46* (2013.01); *A01N 57/16* (2013.01); *A01N 63/30* (2020.01)

(58) Field of Classification Search
CPC .............................................. C12N 15/8282
USPC ...................................................... 800/279
See application file for complete search history.

(56) References Cited

U.S. PATENT DOCUMENTS

| | | | |
|---|---|---|---|
| 2006/0247197 | A1 | 11/2006 | Van De et al. |
| 2006/0272049 | A1 | 11/2006 | Waterhouse et al. |
| 2016/0032314 | A1 | 2/2016 | Jin |

FOREIGN PATENT DOCUMENTS

| | | | |
|---|---|---|---|
| WO | WO 2005/000007 A2 | | 1/2005 |
| WO | WO 2005/049841 A1 | | 6/2005 |
| WO | WO 2006/047495 A2 | | 5/2006 |
| WO | WO2006047495 | * | 5/2006 |
| WO | WO 2011/112570 A1 | | 9/2011 |
| WO | WO 2013/050410 A1 | | 4/2013 |
| WO | WO 2014/062989 A2 | | 4/2014 |

OTHER PUBLICATIONS

Genbank Accession No. JP576168 (2012).*

Austein et al., "Identification and application of exogenous dsRNA confers plant protection against *Sclerotinia sclerotiorum* and *Botrytis cinerea*," May 9, 2018, *Scientific Reports*, 8:7320.

Mao et al., "RNAseq and histological analysis of the canola—Sclerotinia pathosystem," Nov. 2014, *Phytopathology*, 104(11): Suppl. 3, p. 74.

Ali et al., "RNA interference in designing transgenic crops" Jul./Aug./Sep./Oct. 2010 *GM Crops*, 1(4):207-213.

Baharlouei et al., "Biological control of *Sclerotinia sclerotiorum* (oilseed rape isolate) by an effective antagonist *Streptomyces*" Jun. 2011 *African Journal of Biotechnology*, 10(30):5785-5794.

Garg et al., "The infection processes of *Sclerotinia sclerotiorum* in cotyledon tissue of a resistant and a susceptible genotype of *Brassica napus*" Oct. 2010 *Annals of Botany*, 106:897-908.

Hu et al., "Formulations of the endophytic bacterium *Bacillus subtilis* Tu-100 suppress *Sclerotinia sclerotiorum* on oilseed rape and improve plant vigor in field trials conducted at separate locations" Jul. 2011 *Canadian Journal of Microbiology*, 57:539-546.

Hu et al., "Down-regulation of *Fusarium oxysporum* endogenous genes by Host-Delivered RNA interference enhances disease resistance" Jan. 2015 *Frontiers in Chemistry*, 3:1.

International Patent Application No. PCT/IB2017/052578, filed May 3, 2017; International Search Report / Written Opinion dated Jul. 18, 2017; 9 pages.

International Patent Application No. PCT/IB2017/052578, filed May 3, 2017; International Preliminary Report on Patentability dated Nov. 6, 2018; 6 pages.

Jacque et al., "Modulation of HIV-1 replication by RNA interference." Jul. 2002 *Nature*, 418 (6896):435-438.

Litholdo et al., "Genetic diversity and mycelial compatibility groups of the plant-pathogenic fungus *Sclerotinia sclerotiorum* in Brazil" May 2011 *Genetics and Molecular Research*, 10(2):868-877.

McCormick et al., "Leaf disc transformation of cultivated tomato (*L. esculentum*) using *Agrobacterium tumefaciens*" Apr. 1986 *Plant Cell Reports*, 5 (2):81-84.

Sambrook et al., *Molecular cloning: a laboratory manual*, 2nd ed. Cold Spring Harbor Laboratory Press: Cold Spring Harbor, New York; 1989. Cover page, title page, and table of contents. 30 pgs.

Sui et al., "A DNA vector-based RNAi technology to suppress gene expression in mammalian cells" Apr. 2002 *Proceedings of the National Academy of Sciences of the United States of America*, 99 (8):5515-5520.

(Continued)

*Primary Examiner* — Li Zheng
(74) *Attorney, Agent, or Firm* — Mueting Raasch Group

(57) ABSTRACT

Provided herein are plants that reduce growth of a fungal pathogen, increase resistance of the plant to a fungal pathogen, or a combination thereof. The plant includes a polynucleotide that reduces expression of a coding region present in a fungal pathogen, such as *Sclerotinia sclerotiorum* or *Botrytis cinerea*. The polynucleotide can be present on the surface of the plant, expressed by a plant, or a combination thereof. Also provided are methods of making and methods of using the plants.

26 Claims, 29 Drawing Sheets

Specification includes a Sequence Listing.

(56) References Cited

OTHER PUBLICATIONS

Tinoco et al., "In vivo trans-specific gene silencing fungal cells by in planta expression of a double-stranded RNA" Mar. 2010 *BMC Biology*, 8:27.

Wang et al., "Bidirectional cross-kingdom RNAi and fungal uptake of external RNAs confer plant protection" Sep. 2016 *Nature Plants*, 2:16151.

Zhao et al., "Analysis of gene expression profiles in response to *Sclerotinia sclerotiorum* in *Brassica napus*" Dec. 2007 *Planta*, 227(1):13-24.

* cited by examiner

FIG. 1A

SEQ ID NO:1

AUGUCAAGCGUGCUAGACAAGCUUUUCGAAACUACGACUGGAGCUGUAUCUUCGACAACUGGCAAAGUUUU
AAAGACCACUGCAGGUGCGGUAGGUAAGGGAGCUGCCUGGACUUGGGAAACUCCUGUUGUAAAGGGAGUGA
GAACUACCGUCAAUGCUACAGCCAAUGUACUUGACAAGGCGACGCAACCAAUUCGACAGACAGAGGCAUAU
AAGAAUGUCAAGAACGUGAUUGAUGAUGGAAGUAGUUCGAGGUACGGAGGGUGGGUGGAGAAGGAAGAGAG
ACGGAAAGCAAGAGAAUUACGGGAAUUAGAAGAAGGAACCACUGGCAAAAGCAAGGAGGUUCCUGUAGAAG
ACCCGAACGCCGGCACAAACGUUACCGUACACAAAGACUCCGCAUACAAGGAGGCCUGGAGAGAUUUCCGU
GACUCAAAUAGACUCAUGCAAUCUUUAUUCUCCAUGAAAACCGUCUACAAUGAAUCUGAAAAUCCCUUAAU
CUCCACCGCCCGUAGCAUAUCCGACCGAGUCGCCGGAUUCUUCGCCGAAAACGAAACCGCCCAAGUAAUCA
AGAAAUUUCGUGAAAUGGAUCCCUCCUUCCAAAUGGAACCUUUCCUUCGCGAAAUGCGCGAAUACAUCCUC
CCUGAAGUCCUAGACGCCUACGUGAAAGGCGAUACUGAAACCCUCAAACUCUGGCUCUCAGCAGCUCAAUU
CUCCGUCUACGAUGCCCUUUCCAAGCAAUAUACAACCGCUGGUCUCAAAUCCGAUGGUCGCAUUCUCGAUA
UCAGACAUGUUGAAGUCCUAUCUGCAAGGAUGUUAGAUAAUGAUAUCCCAGUCUUCAUCAUUACAUGCAGA
ACACAGGAAGUCCACGUAUAUAGAAACGCGAAGACGAAUCAACUAGCCGCCGGCAUGGAAGAUAAGGUUCA
AUUGGUCACCUAUGCAAUUGGUGUUACGAGAGUAGCAGAAGAUGUUAAUAAUCCCGAGACGAGAGGUUGGA
GACUCAUUGAGUUGCAGAAGAGCGGAAGAGAUUAUAUAUGA

SEQ ID NO:2

AUGGCAACUCCAUCAACCGAGGGUUAUGCGCCCGAAUGGCUCGAGGUCGAGAAAACCCUGGGAGGUCGUCC
UCUCCUCGAAGGCAAGCCACUAGAAAUUAGAAAGCAAUACAGCGAACUAGUCCGCACCAUCGCAGCGCAAU
CCGCAGGCCCCGAUUCCUCCGUCCAAACUCGUGAUAUCUCCGCCGACGGAAUCCCAGUUCGUAUCUACACC
CCUCCAAAUACUUCUGCCGGAAACCCUCUUCCUCUAGGUGUAUAUUACCACGGCGGAGGCUGUUGCCUCGG
GGAUCUCGAUUCCGAGGAUCCGUGGUGUCGUUAUAUCGCUAAGACGGUUCCGUGUGUUCUCGUCUCAGUCG
AGUAUAGAUUAGGUCCUGAGUAUAAGAUGCCGGUCAUGUUGGAUGAUAGUCUUAAGGCUUUUGAAUGGGCA
CGAAACCACGCCUCAGAACUUAACGCCAACCCGGCGCAAGUCUUCACAAUCGGCGGUUCAGCAGGCGGCUG
UCUAUCUCUCACCGUAGCAAACGAUCUCAUCGUCGCUGGUAAAAAAGACCACAUCCAAGGCAUCGUCUCCC
UGGUCCCCGUAACCGCCCAUCCAUCUUCCAUCCCUGCCGCUUACAAGGAACACUAUAAAUCGUACGAGGAA
AACGCAGCUGGUGUUCCGAUUCUAGAUCGAGCCGCUAUGGAUGUAUUUCUUGGGGCUAUUGAGGCGGAUCC
UCAUGAUGAGAGAAUUUUUACAACGCUUUCCAAGCAUCUCGAUCAAUUUCCUCCUACGUAUAUUGCUACGU
GUGGGAAAGAUCCUUUAAGAGAUGAUGGUACGGUAUUGGAAAUAAUGUUGAAGGAGAAGGGGAUCAAGACG
AAGAGUGAUUUUUAUGAUGGUGUGCCGCAUUACUUUUGGAUGUUCCCCGGUAUGAAGGGUAGAGAUGAAUU
UUUGGACAAUGUUUGUGCGGGCGUGAAGUUCGUUUUGGGUAUUUAG

FIG. 1B

SEQ ID NO:3

AUGCAUAGUAAGGUUGUUAUUAUUGGCUCAGGCCCGGCGGCUCACACUGCUGCCGUAUAUCUUGCGCGUGC
GGAAUUAAAACCAAAUGGAAUUGCUGCCGGUGGACAAUUGACUACUACCACCGAUGUAGAGAAUUUCCCUG
GUUUCCCUAAAGGAAUCGGUGGACAAGAACUUAUGGAUAAUAUGCGCGCACAAUCCGAACGAUUCGGUACU
CAAAUCAUCACCGAAACAGUUGCAAAAGUUGAUCUCUCCAAACGUCCUUUCAAAUACUGGACCGAAUGGGA
UGACAAGACAGAACACACAGCAGAUUCCAUCAUCAUCGCUACGGGUGCAUCAGCUCGCAGACUCGGUCUUC
CAGGUGAGGAGAAAUACUGGCAAAAUGGUAUCUCUGCUUGCGCAGUCUGCGAUGGAGCCGUGCCAAUUUUC
AGAAAUAAGCCCUUGGUAGUUAUUGGUGGUGGAGAUAGUGCUGCGGAGGAAGCUAUGUUCCUUACGAAAUA
CGGAUCUCAUGUUACGGUUUUGGUCCGAAAAGAUCAUUUACGUGCAUCGAAAACGAUGGCUAAGAGAUUAC
UUGCCAACAAGAAAGUUACUGUUAAAUUCAACACGGUUGGAGGCGAAAUUACUGGUAAUGAUAAGGGAUUG
AUGACGCAUAUGGUUUUUAAGAACGUCGUUACUGGAGAGGAAGAGAAAGCAGAAGCCAAUGGAUUAUUCUA
UGCCGUAGGACAUGAUCCAGCUACUGCAUUGUUCAAAGAGCAAAUCGACACUGAUUCCGAGGGAUAUAUUG
UAACCAAGCCCGGAACGAGUUACACAAAUGUGGAGGGAGUUUUUGCCGCAGGUGAUGUUCAGGAUAAGAGA
UACAGACAGGCUAUUACUAGUGCCGGGUCUGGAUGUAUAGCAGCUUUGGAGGCAGAAAAAUUCCUCGCUGA
GCAAGAGGAUGGGGAAAAUGAUUUGGAGAAGACGGAUGCUGAAAAGGGUAGCAAUGUUGUUGUUCCUGAGU
AUAGAUCUAACCCUUUGCUUUAA

SEQ ID NO:4

AUGAAGACACAAUCUCUAAUCAGUAUGGGCUUAUUGCCUAUACUAUCAGUAAACGCAGCAUAUACCUGGCC
UUCAAAAUACGACGAAUUAGAGGAUAUUCUUUACCUACAAGCAGGAUACAGACGCUACGGAUUUAGAGACG
GUGUUACACCAUGUGGCUUCUCAGCUGAUGGUAGUAAUCGAGAGACAGCUGCAGAAUGGAUCAAAACGGCU
UACCAUGAUAUGGCAACGCAUGAUGUAGAAACUGGUCUUGGAGGACUUGAUGCUUCGAUAGCUUAUGAGCU
UGGUCGUGCAGAGAAUCCCGGUUCGGCUUUCAAUGGUACUUUUGGAUUCACAAACAACUAUGCCUCGAUCA
AAUCGUCUAACUCUGAUCUUCUCGCCAUGUCUGUCGUUGUUGCCUCCAUGGCAUGCGGAGGUCCAAUUAUU
CCAUUUCGAGCUGGACGAAUUGAUGCCGUGCAGGCUGGUGUACCAGGUGUCCCUCAACCUGAUCAAGAUUU
GGCCACGCACACUGCCAUUUUCGCAAAGCAGGGUUUCAACACUACCGAGAUGAUUACCAUGGUAGCAUGUG
GACAUGUUCUCGGAGGAGUUCAUGGCGUCGAUUUCCCUCAGAUUACUGGUGAUAAUAACGAAACUAGUUUC
CCACAUUUUAACAGCCAAUACGACAACUUUACCAACUCCAUCGUAACCGAAUACCUAGAGGAUAAAUCAAU
CGACGUGCUUGUGGUUGGCAAAAACGACACCUUUAACUCCGACAAGCGUAUCUUCGGUGCUGAUAACAACA
AAACCAUGACUUCUCUAGCAGAUCCUUCUAAUUUCCAAGCGCAGUGCCGCGACAUUUUUGCCCGCAUGAUC
GACACCGUUCCUGCAAGCGUCACACUUUCAGAAGUCAUCACCCCCAUCGAAGUGAAGCCAACCGAGCUUUC
CCUCGCCUUAGGCGCAAACAACACAUUAUCCUUCACAGGUUCUAUCCGCGUGCGUACCACCCACCGCAACG
CCGACAACGUUACCGUAUCCCUCCGCUACCGUGAUCGCAACAACAACCUCUCAAACACCACCAUCUCAACC
GAACGCGGACGCUGGCAACUAGGCCAAAGCUAUGGAUUCGCCAGGGAAGUCUUCACCUUCUAUGAAUUCGA
CACUGCUUUCGAUGUUACAUCCAGCAUCUCAUCUUUCGACGUCAUCAUCCAUACAGCUGGCGAAGCUGAUG
AGAUCAACACCAACAAUGGCCUCGGAUUUCCCGUCUCAGACGCAAUUCUUUUGCAAGCACCACAAUCCUGU
CAACCACAAAUAAUCGUGAAUGAAGCAGGCCAAUGGAAUCUCACCAUCACCGCCGCAGUCCGCGCCGAUCG
UGUCGGGGAACCUGUAGCUUUCGACUGGGUUUACAAACGCUUCAUCCAAGGCGUAAUGAUAAACCAAUUGG
AGGUACAACGUACGGUUAUGGAGAAAGCGAGUGAGGAGAUUGGUGGAUAUUAUCUUUACACGGCGACAAAG
CCAAUUGAUACGGUACAGUGGUCGACAACAUUUGACUUGGUAUUGGGCGAGGGAGACAAUGUCUCCAAGCU
UGAGUUCCUGUCGACUGGAAACUUGGCCUCUACCUCCUGGUUGGACGAAAAGGUACAGGAGAGGGAAGAUG
CACACAAAACUAGGAGGAGUGCUGUUGGUGCAAGGGAUAUCCUGUACUCGAUAUUAUUCGAUAUAGUUGCA
GCAACACAACAUGUCCUCAGAAUUUAA

SEQ ID NO:5

AUGGUUGCCUUUGCCAAAUCUCUCCAACUUUCCCUCUCACUCUUGGCAAGUACCGCCAUAGCCAUUCCCUU
CCCAUCAGAGCUCGAAUCCCGAGCUGAAAUCAACUCCGAUGCCGUUGUGGGAUUUCCCGAAACCGUUCCUA
GUGGCACAGUAGGCACACUCUAUGAAGCCUACAAACCAUACCUCGAUGUCGUAAAUGGCUGCGUACCAUUC
CCAGCCGUUGAUGCCGCUGGAAACACCAAUGCCGGGUUAAAACCAAGUGGCAGUAGCAAUGGUGAUUGCAG
UAGUAGUACCGGACAAGUAUAUGUUCGAGGUGCUCAAAAUGGUUCAUACUACGGACUGAUGUAUUCCUGGU
ACAUGCCCAAAGACGAGCCCUCACCAGGCAUCGGCCACCGCCACGACUGGGAAGGCGUAAUCCUCUGGCUC
AGCAGCUCCACCUCCACCACCGCCAGCAACAUCGUUGCCGUCUGUCCCUCCGCACACGGAGGCUGGGAUUG
CACCCGAGACCAAUACACACUCUCUGGCACAUUCCCUCUCAUCAAAUAUGAAGGCAUUUGGCCUCUCGAUC
AUUCCUGUGGUCUUACCAGUACUCAGGGUGGACGACAACCGAUGGUUGCGUGGGAAUCUCUUACACCAGCU

FIG. 1C

GCGCAAAGUGCGCUUGAGAAUACGGAUUUUGGAAAGGCGAAUGUUCCGUUCAAGAAUGCUAAUUUUGAGAA
UAACUUUGUGAAGGCUAGUAGUUUCUAG

SEQ ID NO:6

AUGGCCACAAAUACUACCAAGCCCAUACAUAGUCUUGUCAUUGAUGCAGGACCAAUAAUUAAGAAUGAUCC
CUCAGCCUCUACGCUUCUUGGACAAGCAGAAAACCUCUACACAAUUCCCCUCGUUAUUGACGAAAUCAAAG
AUGCCGUUACAAGAGCCAGAUUCGAAACCACCCUGCUACCUUUCCUCAAACUAAGAGCGCCUCGUUCAGCU
AGCAUUAAAGUUAUAACCGAUUUCGCACGGAAAACGGGUGAUUUGGAAGUACUUAGCAGACAGGAUAUCCA
UUUAAUGGCACUAGCAUAUGAGCUUGAAUGUGAACGGAAUCAUGGAGAUUGGAGAUUACGAAGUGUGCCAG
GACAGAAGAGAUUAAAUGGAGCUCCCCCUGCAUCAUUAACAGAAGAGAAACCGGCCGAUACCACAGAGGCG
CAAGAAGCAUCCAUGGAUGCUGCAGCGCAACCAAAAAUUGAAACUAGAGGCGCAUGGGGAACAUCAAUACC
UCAAGCAGCAGAAGAAUCCAGCAUCGAGACUCAAUCUAUUGAGGAAGCAUUAGAAGCCGCCCACAUAUCCA
CCAUCGAGGAGCCGGAAAGCAUAGACAAACCAGCAGAAGCAUCAGUCACAGGAGAACAGGCCGAAGAACCA
ACUUCCACAACAGAGCCCGAAACAACUCGCGAAACUGCGCAUGAAUCAACGAAUAUAGAAGAAGUUCCCGC
GUCCGAAUCCGACGCUGAAGACGACGGCGAAGGAUGGAUCACGCCUUCCAACCUCAAAAAGCACCAACAAA
AAGACAACAACGGCACCUUCGAGCCCCAGGAAGAACAAAAAACAAUCCAAGUAGCCACCAUCACCAGCGAU
UACGCCAUGCAAAACGUCAUGCUACGUAUGAACCUCAACUUACUCUCACCCUCUCUCCAACGCAUUCGUCA
ACUCAAAACCUGGGUCUUGCGAUGCCACGCCUGUUUUGGCAUCACCAGAGAUAUGACGAAGCAAUUCUGCG
GACGCUGCGGAAAACCCACUUUACUCCGAACAUCCUGCUCCACCGACAAAGAUGGAAAUGUCAAGGUGCAU
CUCAAGAAGAAUAUGCAAUGGAACAACAGAGGAAAUGUAUACAGUGUGCCCAAACCGGUUGCCGGGACAGC
GAAUGGAAAGAAUAUUAAGGGUGGUGGAAAGGGAGGGUGGGGUAAUGAUUUGAUAUUGGCUGAAGAUCAAA
AGGAGUAUGUGAGAGAAAUGGCUACUUCUAGGAGAAAGAAGGACAAGGAUCUCAUGGAUGAAGAUUAUCUA
CCCAGUAUUCUGACUGGAGACCGUGGGCGGGCAGGCGGUAGACCAAAAGUUGGAGCGGGCAAAAAUGUUAA
UUCCAAAAAGCGACAUUAG

SEQ ID NO:7

AUGAAGAACUUAUCUAUUCAACCUCAUCACCUACCCAACAAUAACAUCUGCAUUAAAGUUCUUGCUGAAGG
UGCUGCAAAUGUCAUAUAUCAGAUUACCAUUGAUCCAAAAUCACAGGGGGUUAUCGAGGUAGACAAGGAUC
AUCAAGAUUUGGAUUAUCUUUCUGGAAAAUUAUUACGUCUUCGAAAAGAUGUUCCUACUACCGCUCCAACU
UCAGAAUCAUACCAACAGUGGCUUACAUAUAUUGUACCCCUAUUCAAACCCGAACAAAUAGUCAUUCAAGA
AUUGAUUUACAUUGGUCACCUUAAUGUAAUCCCUGGUUUAAAUACUGAUCUCAGACGUUUUGAUAAUCCUG
GUACAUGUACCACGAAUCAUCUUGUCCCACCACCAAAAGGGAAAUUUUAUCGCUCCAGAGCUCAAAGUGGU
ACUUUCUUGGCAAAAGAUGAUUAUGGUCUUUUGAUUACAGAUAUGACACCUAGAAAAUCCGCACAAGAGAC
GGUUGUAGAAUUCAAACCAAAAUGGCUCUCACCAUCCCAUGAAUUACCAUCUAAAGCUAUCCGUUGCAGAA
CUUGUGCACUUCACGCACGUCGAGUAGCCUUUGGAGAAGAAAGAAAAAACACUGAUCUUCAAUCCUAUCUU
UGUCCACUCAAACUCGUCGAUGAUGACCCUAAAUUAAAAUUCGAAAGUUACCUAGCUUCCGCCUCUCAUGU
AUUACACAAACCUCAUGAAACACCCUCCGUACAAUCACUCGCAAGAUGGAUCCACGAAAAUCCAUUGCUAA
AACGACUUCGCGAUCUCCAAACCGAAUAUGAUCUCAAAGGAUCUCUAAAGACGGAAAAAGCAUCUCAUGAA
CUAUGUGUAGCGAUGACCUUGAGAGAUUGUUCCUUAUACAUACGAAUGGAUAAAAAUCAUCAAGUCAUAGA
AGCUCGUCUAGGAGAUUUAGAUUAUAAAUCACCUAAUAAGUAUUCAUCAUGGAGAAGAAAAGAACAGGAAU
UAAUCGACGAGGGAUGGUAUUGUGGUGAAGAAAGUAAGGAAUUAAAACAACCAAUCGAUGAAUGUUUAUUA
UCACGAAGGAUUUGA

SEQ ID NO:8

AUGGCUCCCAUCAUGGAUGCACUCCCAAUCGUCGAGGACAAGCCAACGGCUGCUGUCACUGACUUCUCGGU
CUCCAGUCCUCAAGAUGGAGCUGUUGUUGCGCCACCUACCACAGUCUACCAGACCGGUGCCACCAAGUUGA
AGAACAUGCUCAGAGACUCGAAUGAGUUGAUUGUUUGUCCCGGUGUCUAUGAUGGAAUCUCAACCCGAGUU
GCCCUUCAAGUUGGCUUCCCAGCUCUUUACAUGACCGGAGCAGGCACUACUGCUUCCCGCCUUGGAAUGGC
AGAUCUCGGCAUUGCUCAUCUUUCCGACAUGAAGGACCACGCUGAGAUGAUUGCAAACCUCGACCCUUUUG
GACCACCCUUGAUUGCUGAUAUGGACACCGGAUACGGUGGACCUCUCAUUGUUGACAAAGCCGUCAAGGCC
UACAUCAGAGCCGGUGUUGCUGGAUUCCAUAUCGAAGAUCAAAUUCAAAACAAGCGUUGUGGCCAUCUUGC
AGGCAAGAAGGUUGUCCCUGAAGAAGAGUACUACAUGAGAAUUCGUGCCGCCAAGGGUGCCAAAGAUGCCA
UGAAAUCCGAUAUUGUGUUGAUUGCACGCACAGAUGCGCUCCAACAACUUGGUUAUGAUGAGUGCGUCAAA
CGUUUGAAGGUUGCUCGUGAGCUUGGUGCAGAUGUUGGCUUGCUCGAGGGUUACACUUCAAAGGAGAUGGC

FIG. 1D

UGCAAAGACUGUUAAGGAGUUCGCCCCAUGGCCAAUACUUUUGAACAUGGUCGAGAACGGCGCUACUCCUA
UCAUCACCACCAAGGAGGCACAAGAGAUGGGAUUCCGUAUCAUGAUCUUCUCCUUCGCUGCUCUCGCCCCA
GCCAUGUUGGCUAUCCAAGAGACUUUCGUGCGUUUGAAGAACGAGGGUGUCGUAGGAACUCCAAAGAACGU
UACACCAAGGGCCUUGUUUGAGGUAUGCGGUCUGCAAGAGAGUAUUGUUAUUGAUACUGCGGCUGGUGGUG
GGGCUUUCGCCGAUGGUGUUUAA

SEQ ID NO:9

AUGGUUGCCUUCUCAAAAUCAUUACAGCUUUCCCUUUCGGUCUUGGCAUCUACAGUCAUUGCCAUCCCUAC
ACCAUCACAACUUGAGUCUCGGGCCGUUAUCGAUUCCGAUGCCGUUGUAGGAUUUGCCGAAACUGUUCCCA
GUGGGACCGUAGGAACAGUUUAUGAGGCAUAUAAACCAUUCCUUAAAGUCGUAAAUGGAUGCGUACCAUUC
CCUGCCGUCGAUGCAUCGGGUAACACAGGUGGUGGUUUGUCACCAACUGGCAGUAGCAAUGGUGGUUGCAG
CAGCAGUACCGGUCAAGUAUAUGUUCGAGGAGGACAAAGCGGAUCAAACUACGCCAUCAUGUACUCCUGGU
ACAUGCCAAAGGACGAGCCCUCAACCGGUAUUGGUCACCGUCACGAUUGGGAAGGUGUAAUUGUCUGGCUC
UCCAGCGCCACCGCCACAACUGCCGACAACAUCUUAGCCGUUUGUCCUUCCGCCCACGGAGGCUGGGAUUG
UUCCACGGAUGGCUAUUCCCUUUCUGGUACCAGCCCUCUUAUCAAGUACGAAAGUAUCUGGCCCGUCGAUC
ACUCAAUGGGUCUUACUAGUACUGUUGGUGGAAAACAACCUAUGAUUGCUUGGGAGUCUUUACCAACUGCU
GCUCAAACUGCUCUUGAGAACACCGAUUUCGGUGCUGCGAAUGUUCCAUUCAUUCCGGCUGUUUUCACAGA
CAAUCUUGCGAAGGCUACUUUCUAG

SEQ ID NO:10

AUGAACGGGCUACGAACAGCGGCGACAAGGACGCCCACAAGUAAACAGAUUUCUCUGUCUUCAAUCGCGAG
ACCUUCAUCCAAUGGCUCCACCCUUCGUCGCCAGACAGUUCAACAAAAUCGGAAUUUACAAUUUUCUACAG
CGGGACAUUCGAGGCCUGCGACUCUUUCAUAUCCUGCGCCUUUGCGAUCACGAUUCCUUCCAGAAGAAAUU
AGAUCUGUAGCAUGCCCAGCAUCCUCGCGGCAUUUUCAUGAAAGCUGGAGAUUGGGCAAAGAAAAGAAGGC
AAAACCAGUAGAUCCAGCGGACGCAGCUGCAAAGGAAGAAGCUACAGAAGAAGAGCCUAGCAAAAAGGAUU
CUGCUAAAGACUCAGAAUCUACUUCUGGAGAGGGUAAGACUAAGGAAGAAGGAGAGGGCAGUGAAGGCAAA
AAAGAAGAAUCCAAAGAGGCACCUCCACCCCCACCACCCCACGGAGACAAAACUCCAUGGCAAGUCUUCAC
CGAAACCCUGCAAACCGAAUUCAAGGCAUCAAAAGAAUGGAAUGAAUCCACAAAGCAAUUAGCAGAAGGUG
CCCAUCAAUUUACAGAGAACGAAAACGUCAAGCGUGCUAGACAAGCUUUCGAAACUACUACUGGAGCAGUA
UCUUCGACGACAGGCAAAGUUUUAAAGACUACUGCAGGCGCAGUUGGUAAGGGAGCUGCUUGGACUUGGGA
AACUCCAGUAGUGAAGGGAGUAAGAACUACUGUCAAUGCCACAGCAAAUGUGCUUGACAAGGCGACACAAC
CAAUCCGACAAACGGAGGCAUACAAGAAUGUUAAGAAUGUGAUUGAUGAUGGAAGUAGUUCGAGGUAUGGA
GGAUGGGUUGAGAAGGAGGAGAGACGUAAAGCAAGAGAAUUGCGAGAAUUGCAAGAGGGUACCACCGGCAA
AACCAAGGAGGUCCCAAUAGAAGAUCCAAACGCCGGAACAAAUGUUACCCUGCACAAAGACUCAGCAUACA
AAGAGGCUUGGAGAGAUUUCCGGGACUCGAAUCGUGUCAUGCAAUCUUUAUUCUCCAUGAAAACCGUCUAC
AACGAAUCCGAGAAUCCCUUGAUCUCAACUGCCCGCAGCAUAUCUGAUCGAGUUGCUGGGUUCUUCGCCGA
AAAUGAAACCGCCCAAGUAAUUAAGAAAUUCCGCGAAAUGGACCCCUCAUUCCAAAUGGAACCUUUCCUCC
GCGAAAUGCGCGAGUACAUUCUCCCAGAAGUCCUCGAUGCCUACGUAAAAGGCGAUACCGAAACCCUCAAG
CUCUGGCUUUCCGCAGCCCAAUUUUCCGUCUAUGAUGCUCUCUCAAAACAAUACACAACUGCUGGUCUCAA
AUCUGAUGGCCGCAUUCUCGAUAUCCGACAUGUUGAAGUCCUCUCAGCGAGAAUGUUAGAUAAUGAUAUCC
CAGUUUUCAUCAUUACAUGCAGAACCCAAGAAGUUCACGUAUAUAGAAACGCAAAGACGAACCAAUUAGCU
GCUGGUAUGGAAGAUAAGGUACAACUGGUCACCUAUGCCAUUGGAGUUACAAGAGUGGCGGAAGAUGUUAA
UAAUCCAGAGACGAGAGGUUGGAGACUCAUUGAGUUGCAGAAGAGUGGAAGGGAUUACAUAUGA

SEQ ID NO:11

AUGGCUACAAAUACUACCAAACCUAUACAUAGUCUUAUCAUUGACGCAGGACCAAUUAUUAAGAAUGACCC
UUCAGUCUCUACGCUUCUUGGCCAAGCAGAAAACCUUUAUACAAUCCCCCUCGUUAUCGACGAAAUCAAAG
AUGCCGUCACAAGAGCCAGAUUCGAAACCACAUUACUACCCUUUCUCAAAUUAAGAGCGCCUAGAUCAGCU
AGCAUUAAAGUUAUAACUGAAUUCGCGCGCAAAACGGGUGAUCUGGAAGUACUCAGCAGACAGGAUAUCCA
UUUGAUGGCUUUAGCAUAUGAGCUUGAAUGUGAACGAAAUCAUGGAGAUUGGAGAUUACGAAGUGUACCCG
GACAAAAGAGAUUAAAUGGAGCACCUCCCGCAUCAUUAAGUGGCGAAAGACCUGCCGAUGCUACAGAGGCA
UCACAAACAUCUACAGAUGCAGCGGCGCAACCAGCAAUCGAAACCAGAGGCGCAUGGGGAACAUCAAUACC
UCAAGCAACAGAAGAAUCUACAGUGGAGACACAGCCCAUUGAGGAAGCAUUAGAGGCUACCCAUAUAUCAA
CAGCCGAUGAGGCAAAGAGCGCAGAGAAACCAGCAGAGGAUGCAGUCACAGAAGAAUCGACCAAAGAUGGA

FIG. 1E

GUCACAGAGGAACAAACCCAAGAACCAACCGCCGCAACAGAACCCGAAACCAUUCCAGAAACAAUCGAAGA
AGUUCCCGCCUCCGAAUCCGACGCCGAAUCCGACGGCGAAGGCUGGAUCACCCCCUCCAACCUCAAAAAGC
ACCAACAAAAAGACACUAACUCUUCGUUCUCCCCCAAGAAGAAUCCAAAACUAUCCAAGUAGCUACCAUC
ACCACCGAUUACGCCAUGCAAAACGUCAUGUUACGCAUGAACCUCAACCUCCUCUCCCCCUCUCUUCAACG
CAUCCGCCAGCUCAAAACUUGGGUCCUAAGGUGCCACGCUUGUUUCUCUAUCACUCGAGAAAUGACCCGAC
AAUUCUGUUCCCGCUGCGGUAAACCUACACUCCUCCGCACCUCUUGCUCAACCGAUAAAGACGGAGUGGUA
AAAAUCCACCUUAAGAAAAAUAUGCAGUGGAAUAACAGAGGAAAUGUAUACAGUGUCCCCAAACCAGUUGC
CGGGACAGCGAACGGAAAGAAUAUCAAAGGGGGUGGUAAAGGUGGAUGGGGUAAUGAUUUGAUAUUGGCGG
AGGAUCAAAAAGAAUACGUGAGAGAAAUGGCCACGGAAAAGAGGAGAAAGGAAAAGGAUCUUAUGGACGAA
GAUUAUUUACCUAGUAUCUUGACGGGAGAUCGUGGAAGAGCUGGUGGAAGACCAAAAGUUGGAGCAGGCAA
GAAUGUCAAUUCAAGGAAACGACAUUAG

SEQ ID NO:12

AUGAAGGGGUCAUCUUUAAUCAGUUUGGGCUUGCUACCCGUGCUGUCAGUUAAUGCGGCUUAUACUUGGCC
CUCAGAGUAUGAUCAACUAGAAGACAUUCUAUAUCUUCAGCAAGGUUUCAUACGUUUUGGCCUCAGAGAUG
GUGUUACGCCGUGCUCUUUCUCAUCGGAUGGAGGUGGUCGUCAGGCGGCUGCGGAAUGGAUAAGAACUGCU
UAUCAUGAUAUGGCUACCCAUGAUGUCGAUACUGGUCUUGGAGGACUUGAUGGUUCUAUAGCCUUUGAGCU
UGGGCGAGCGGAGAACCCUGGUGAUGCUUUCAAUUCUACCUUUGCAUUUACAGAAAACCUCCGCUCAAUCA
GAGCUUCGUCUUCCGAUCUUCUUGCAAUGUCCGUUGUCGUUGCCACAAUGGCUUGCGGCGGUCCAAUAAUU
CCAUUUAGAGGUGGACGAAUCGAUGCCAUGAAAGCUGGUGUUUCUGGCGUGCCCGAGCCUGAUCAAGAUUU
GGCGACACACACUGCAAUCUUCGCAAAGCAAGGAUUCAACACUGCUGAGAUGAUAACCAUGGUAGCAUGCG
GCCACACUCUCGGAGGUGUUCAUGGUGUCGAUUUUCCCCAGAUUACCGGCAACGGUGACGCAGAAAACUUC
CCAAAAUUCGACAGCACCUACACCGCAUUCGAUAACACUGUUGUAACAGAGUAUUUGGGGAACAAUUCAAC
CGACCCGCUUGUGAUCAGUAAAAAUGAUACCUUCAAUUCCGAUAAACGCAUUUUUGGCGCCGACAACAACA
AAACGAUGACUUCUUUAGCAGACCCAACCAAUUUCCAGAAACAAUGCUCUGACAUCUUCGCUCGAAUGAUC
GAUACUGUCCCUGCAGACGUCACACUUUCUGAAGUCAUCACACCUAUCGAAGUAAAGCCAUCGCAAAUUGC
UCUUACCCUAGCUGGAAAUAACACUCUAUCCUUCGGAGGAUACAUCCGCCUUCGCACCACCAACCGCAACG
CCGAUGAUGUGACCGUAUCCCUUCAAUACCGUGAUCGUAAUAACAAUACUUCGAACACCACAAUUCCCGUC
AGCAGAGAGAAUUACUUGUUGGGUCAAAGCUAUGGCUUCGGUUCAGAGGUGUUCACUUGGUAUGGAUUCAA
UACUGUUCUUGAUGCUAAAACCGGCAUUUCGUCUUUCGAUGUCAUCUUACAUACUGUCGGUGCAGCUGAUG
AAAUCAUCACCAAUAACGGUGGGGGUUUCCCACUCACAGACGCAAUUCUCUACCAACCAGCACAAUCCUGU
CAGCCACAGAUAUCUGUCAAUGACGCAGGCCAGUGGAAUAUAACAGUCACUGCAGCUGUUCGUGCUGAUCG
UAUCAACGAGCCUGUUGCCUUUGACUGGGUGUCUCAGCGUACCAUACCAGGCGCGAUGGUUAAAGCACUAG
AAGUGCAACGUACAGCUAUGGAGAAAGUGAGUGAGGAGAUCGAUGGAUAUUAUCUUUUCAGCGGAACCAGG
UCGCUCGAUAACGUACAAUGGUCUACUACUUUUGAUGUGGUAUUGGGAGAGGGAGAUGACGUAUCGAAAGU
AGAGUUCCAGUCGACGUCGGCAAUGGCCACGAGCUGCGAGGCAUUUUCUUGA

SEQ ID NO:13

AUGCAUAGCAAGGUUGUUAUUAUUGGCUCUGGCCCGGCGGCUCACACUGCUGCUGUUUAUCUUUCGCGCGC
GGAAUUGAAACCUGUUCUUUAUGAAGGUUUCCUUGCCAAUGGAAUUGCUGCCGGUGGUCAAUUGACUACCA
CUACUGAUGUAGAGAACUUCCCUGGUUUCCCCAAGGGAAUUGGCGGACAAGAACUGAUGGAUAACAUGCGC
GCACAAUCCGAACGAUUUGGCACCCAAAUCAUCACCGAAACCGUCGCCAAAGUAGAUCUCUCUAAACGUCC
UUUCAAAUACUGGACCGAAUGGGAUGACAAAACAGAACACACAGCCGAUUCUAUCAUCAUCGCUACUGGUG
CCUCUGCUCGCAGACUCGGUCUUCCAGGAGAGGAGAAAUAUUGGCAAAAUGGUAUCUCCGCAUGCGCAGUC
UGCGAUGGAGCCGUUCCAAUUUUCAGAAACAAGCCUUUGGUAGUUAUUGGUGGUGGAGACAGUGCUGCCGA
AGAGGCUAUGUUCCUCACGAAAUACGGAUCCCACGUUACUGUUUUGGUCCGAAAAGAUCAUCUACGUGCAU
CGAAAACGAUGGCGAAGAGAUUGCUUGCCAAUAAGAAAGUUACGGUUAGAUUCAACACUGUAGGAGGCGAA
AUCACCGGUGAUGAUAAGGGAUUGAUGACCCACAUGGUUUUCAAGAACGCCACUACUGGCGAGGAGGAAAA
GGUAGAGGCCAAUGGCUUGUUUUACGCAGUAGGACAUGAUCCAGCUACCGCAUUGUUCAAGGAACAAAUUG
AGACAGAUUCUGAGGGAUAUAUUGUCACCAAGCCCGGAACCAGUUACACCAACAUUGAGGGUGUUUUUGCU
GCUGGUGAUGUUCAGGAUAAGAGAUACAGACAGGCUAUUACUAGUGCAGGAUCUGGAUGUAUAGCAGCUCU
UGAGGCCGAGAAAUUCCUUGCUGAGCAAGAAGAUGCGGAAAAUGAUUUGGAAAAGACAGAUGCCGAGAAGG
GCAGCAAUGUUGUUGUUCCUGAGUAUAGAUCAAACCCUUUGCUUUAG

FIG. 1F

SEQ ID NO:42

AUGGCCACAAAUACUACCAAGCCCAUACAUAGUCUUGUCAUUGAUGCAGGACCAAUAAUUAAGAAUGAUC
CCUCAGCCUCUACGCUUCUUGGACAAGCAGAAAACCUCUACACAAUUCCCCUCGUUAUUGACGAAAUCAA
AGAUGCCGUUACAAGAGCCAGAUUCGAAACCACCCUGCUACCUUUCCUCAAACUAAGAGCGCCUCGUUCA
GCUAGCAUUAAAGUUAUAACCGAUUUCGCACGGAAAACGGGUGAUUUGGAAGUACUUAGCAGACAGGAUA
UCCAUUUAAUGGCACUAGCAUAUGAGCUUGAAUGUGAACGGAAUCAUGGAGAUUGGAGAUUACGAAGUGU
GCCAGGACAGAAGAGAUUAAAUGGAGCUCCCCCUGCAUCAUUAACAGAAGAGAAACCGGCCGAUACCACA
GAGGCGCAAGAAGCAUCCAUGGAUGCUGCAGCGCAACCAAAAAUUGAAACUAGAGGCGCAUGGGGAACAU
CAAUACCUCAAGCAGCAGAAGAAUCCAGCAUCGAGACUCAAUCUAUUGAGGAAGCAUUAGAAGCCGCCCA
CAUAUCCACCAUCGAGGAGCCGGAAAGCAUAGACAAACCAGCAGAAGCAUCAGUCACAGGAGAACAGGCC
GAAGAACCAACUUCCACAACAGAGCCCGAAACAACUCGCGAAACUGCGCAUGAAUCAACGAAUAUAGAAG
AAGUUCCCGCGUCCGAAUCCGACGCUGAAGACGACGGCGAAGGAUGGAUCACGCCUUCCAACCUCAAAAA
GCACCAACAAAAAGACAACAACGGCACCUUCGAGCCCCAGGAAGAACAAAAAACAAUCCAAGUAGCCACC
AUCACCAGCGAUUACGCCAUGCAAAACGUCAUGCUACGUAUGAACCUCAACUUACUCUCACCCUCUCUCC
AACGCAUUCGUCAACUCAAAACCUGGGUCUUGCGAUGCCACGCCUGUUUUGGCAUCACCAGAGAUAUGAC
GAAGCAAUUCUGCGGACGCUGCGGAAAACCCACUUUACUCCGAACAUCCUGCUCCACCGACAAAGAUGGA
AAUGUCAAGGUGCAUCUCAAGAAGAAUAUGCAAUGGAACAACAGAGGAAAUGUAUACAGUGUGCCCAAAC
CGGUUGCCGGGACAGCGAAUGGAAAGAAUAUUAAGGGUGGUGGAAAGGGAGGGUGGGGUAAUGAUUUGAU
AUUGGCUGAAGAUCAAAAGGAGUAUGUGAGAGAAAUGGCUACUUCUAGGAGAAAGAAGGACAAGGAUCUC
AUGGAUGAAGAUUAUCUACCCAGUAUUCUGACUGGAGACCGUGGGCGGGCAGGCGGUAGACCAAAAGUUG
GAGCGGGCAAAAAUGUUAAUUCCAAAAAGCGACAUUAG

SEQ ID NO:43

AUGUCGUCUUUUGCGCUAGAGAAGGAAUCGCCUUUGGGCUUCCUUUACAAUAAUGCUGUCGCUGGGGCUU
UGUCAAAUUCAUACAAUACUUUCCAAGAGAAGAGGGAAGCGCUGGGUCUUUCAAACCCCGGAACAGUUGA
GAAUAUUGCUAGAGAGGUUCAACGCGAUGUUUUUCUCAACAAUUACACAUUCUCUGGUCUGAGGGCGGAU
CUGACCAAGCCUUUCAGCAUGGCUCCAUUAUUCCAAGUCUCUCAUGCAUUCUCUAUGGGAUCUCAAGGUU
UACCACCAUAUACAUUUGGUGCUUUAUUCGGCACAAACAAGAUCUUUAUGCAAGGAAACAUGGACAAUGA
AGGUCAACUCACCACUCGAUUCAAUUACAGAUGGACUCCAGCUUUCGUUACCAAGACCCAACUACAAGUC
GCCCCUGGUCAAGCUAUGAUGCAAUUAGACAACGAGUAUACUGGAAAAGAUUUUACAGCUUCGAUCAAAU
CUCUUAACCCUUCAAUACUUGAUGGAGGAUUCACAGGUAUCUUUAUUGGUCAAUACUUACAAGCUGUUAC
UCCAAAUCUCGCUUUGGGUUUGGAGGCUGUCUGGCAACGAGCGGCAAUGAACCAAGGUCCCGAAACUGCA
GUCUCAUACUGUGCCAAAUACAAGGGUAGUGAUUGGAUCGCCAGUGCUCAAUUACAAGCCCAAGGAGCCG
UAAACACAUCUUUCUGGAGAAGAUUGACAGAUAAGGUCGAAGCUGGUGUGGAUCUUAACUUACAAUUCGC
CGGGUUGUCUGGAGCUGGUAUGAUGGGAGGACCUAUUAGAAAAGAGGGUGUCACAACUGUUGGUGCCAAG
UAUGACUUCCGAAUGUCUACUUUCAGAGCUCAAGUUGAUUCAACUGGAAAGCUGAGCUGCUUGUUAGAGA
AGAGAGUUGCACCACCUGUUCAACUUACCUUUGCCGCCGAGAUGGAUCAUUUCAAGCAAGCAGCAAAGAU
CGGAGUAGCAGUUUCCAUCGAAUCUGGCGACGAAGCGGUCGAAGAACAAGCAAUGGCAGCUGGAGGCGCU
CCUCCUCAAAUCCCAUUUUAA

SEQ ID NO:44

AUGGAUACAAAGCAGAAGAAGCGUUCUCAUUCAGAGACCAAUGGCUCUCAGAAAGCUCCAAAACGUCAAA
AGAUUCAAAAGACAUCCAAGAAGCAAAAGAAAGCCGCGCCUAAGAAGCCAGUUGCCGUGGAUUCCUUACC
AUGGAACGAAGUAACCAUGCCAGAUAUGUUCGAAGAUGCUGAGGGUUUCUAUGGAUUGGAGGAAGUAGAC
GAUGUUGAGGUUGUAAGGGAUGGCGAUGUUGUUACAUUUGUAUCUUCCAAAAUCCAGACGAAAAACAACG
AGGAUGAAGAGUUCGAAGGCUUUGGGGAUGAAGUUGAAGAUGGUGGGAAUGCCGCGACGGAUAAUACUGG
CGAAGUGAAGCCAAUUUUGAAACCUACGGAAGAAAGCACGAAAAACGACGUACCGCAGGGAAACAAACAA
AAAAUAGAGAAGAAAGCAAAGCCCGAGAAGAAAGACAAGAAAGAAGGGUCAAAUACCGAAGAAGGAGAAG
AAAAGGUACCAAGCAAAAAGGAGAAGAAGCAAAAACAAGAGAAGCCGCAAAAACAGCCAGUUGAUAAAGA
UGCUACCCUCAAACAAGAUCCUCUUAAGAAUGUCUUCGAGGCACUUGACGAAGAUGCCGCAGGAGAAGUC
GAGGUUUCAGGUUGGGUGGAGCUAGAUCUUUCAUCAAAUACUUUAAUGGCAUUAUCAAAAAUGGGCUUCU

FIG. 1G

CAAAGCCAACUCCAAUUCAAUCAGAGGCUAUACCAGAAGUACUCGCGGGACAUGAUGUUGUUGGAAAGGC
AUCUACAGGUUCUGGAAAAACAUUGGCAUUUGGAAUACCGAUAGUUGAAAAGUGGCUUGAGGUAUAUGGA
GAACUUGAUGAAGAUGAACUCAAGAAGAGCACAAGACCUCCAACCGCUUUAAUUCUUUCGCCUACGAGAG
AAUUGGCGCAUCAAUUGACUGAACAUAUCACAACUUUAUGUAAGGGCAUGCCUACAAGUCCAUAUGUAGC
UGCUGUUACUGGAGGACUUUCUGUACAAAAACAACAACGUCAAUUAUCCAAGGCAGAUAUAAUAAUCGGU
ACACCCGGUCGACUCUGGGAAGUUAUCAGCUCCAGCAAUGAAUUAUCAGCUGGUUUGAAACAGGUUAGAU
UUUUGGUCAUCGAUGAAGCGGAUAGACUUUUGACCGACGGGCAUUUCAAAGAAGCAGAGGAGAUUCUAAA
UGCGUUGGAUCGCACGCACGGGAAUGAAGAUGAUGACGAGGAAGACACAUUACCUCCCAGGCAGACUUUG
GUUUUCUCGGCCACUUUCCACAAAGGAUUGCAACAGAAACUUGCAGGCAAGGGCAAACAAUCUUUCAAGG
AUGAUAGUCAAUCUAUGGAGUACCUCUUGAAGAAGCUCAAUUUCAGGGAAGAAAAACCUAAAUUUGUUGA
UGUCAACCCUAUCUCGCAAAUGGCAGCAAAUCUGAAAGAGGGCAUGGUAGAAUGUGGUGGAGAAGAAAAG
GAUCUCUACCUAUAUUCUCUCCUUCUACAUCAUCCAAAUCAACGUACACUCAUCUUCACAAACUCAAUCC
AUUCCGUCCGUCGUCUAACCCCUAUGCUUCAAACCCUCAACAUCCCAGCCCACUCCCUCCACUCCCAAAU
GAUCCAAAAAGCACGCAUGCGGUCCAUUGAAAAAUUCUCCCGAACAAACAACACCGGCUCAGUCCUCGUA
GCAACCGACGUCGCAGCCCGCGGUCUCGACAUCGGAGGCGUCCAAUUAGUAAUCCAUUACCACCUUCCCC
GCACCGCAGACAUGUAUGUGCACCGCUCCGGUCGAACCGCGCGUGCCGCCGCAUCCGGAUCCAGUAUCCU
CCUCUGUGGCCCCGAAGAAGUAGUCGGAACCCGCCGCUUGGUAGCUAAGGUCCACGCGCAAAAUGCUCUU
CACGGAGAAGGCAAAAAAUCCAAAUUCUACAUCCGCUCCCUCGAUAUCGACCGCAGGGUAGUCUCUCGUU
UAAAACCGCGCGUUACCCUCGCGAAAAAAAUAGCUGAUAGCGCUCUCGCAAAAGAGAAAAAAGGCCACGA
UGACGAUUGGGUUAAAAACGCAGCGGAAGAACUAGGCGUUGAAUACGACAGUGAGGAAUUCGAAGCAUUA
GGCGGAGGAAGAAAGGGGAGAGGAACGGGAAGAAGAAUGAAGGAGAAAGAAGCGAGGGGUAUGAGUAAAG
GGGAGGUUGGGGCCCUCAGAGCAGAAUUGAGAGCCCUGUUGGCUCAGAGGGUUAAUGUGGGUGUUAGUGA
GAGGUAUUUGACGAGUGGAACGGUUAAUGUUAAUGAUUUGUUGAAGGGGGCUAAGGGUGAGUGGUUGGGU
GAGGUGGAGGGUAUUGGGAUGGAGGAUGAUUGA

SEQ ID NO:45

AUGGCCGCCGAGCAAAGAAAGCUGUUAGAGCAGCUGAUGGGCGCGGGGGCAUCAUCUCGCGCAGCUCAAC
UGUCAAUCACAGAUCCAAAGAUCUGCCGUUCCUUCCUCGUCGGCACCUGUCCUCACGAUCUCUUUACGAA
UACAAAGCAAGACUUGGGGCCAUGUCCAAAAAUUCAUUCAGAACCUUUGAAGACGGAGUAUGAGGCUGCA
GCCCCUCCCCAAAAACAAAAAUGGGGAUUCGAAUACGAUUACAUGCGUGACUUACAGAAGUAUAUCGAUG
AAUGCAAUAGGAGGAUAGAUGUUGCGCAGCGACGCCUGGAGAAAACGCCCGAUGAAAUUCGACAGACGAA
CGCCCUGCUGAAACAAAUAUCUGACCUAUCGAAAUCUAUUGAGACAGGGUUGUUGGAGAUUCAGAUUCUA
GGAGAACAAUCGGAGGUAUCGCGCGCCUAUGAGGAAUUCUUCCGCAUCAGACAAGCUAUGCAGACGAAAG
UGGAGAAGGAAAAGGAGUUGAAGGCACUAUCAGACACCAGUGGACCUUCGGGACACCAGAAGUUACAAGU
CUGUGAUGUCUGUGGGGCUUAUUUGAGCCGGUUGGAUAAUGAUAGGAGAUUGGCGGACCAUUUUUACGGG
AAAAUGCAUUUGGGUUACGCGCAAAUGAGGAAGACAUACGACGCAUUUCCGAAAGAGAUGAAGAGGUCAA
GACCUAUGGUAGAUGAUAUGGAUCACACCUCGGCGGUAAGAGGCUACGAUGGAGGAUAUGGCGACGGCGG
AUACGGCGGCAGGGGGGGCGGGUAUGGAGGUCGUGGUGGAGGGAGAGGUGGCUUCAGAGGCAGGGGAAGG
GGAUUCAGAGGUGGAUGGUAG

SEQ ID NO:46

AUGUCUUUCAGAAAUCCUAAAGCUGUAGGACAGCUUACAAAAAGAACUUCACAAGCUACUAUCUCACGCC
UCACAAGCAAUGUCUCUCCCACCACAACCUCAUUAUUGCAAAGGAACAACGCAGACCAGUCCAGACCUUU
UGCGACUCCAGUGCCGCCGGUGACACAAGAUGCGACGGGAAGGAGGGGACCCACGGCAAUGGUGCUCAUG
AAUAUGGGUGGUCCACAAACCACAGAUGAAGUUGGGGAUUUCUUAAAUGCCGAUUUAAUUCCUCUUGGAC
GUUUUCAAAACUACCUUGGACCUCUCAUUUCGAAACGUCGUACGCCGAAGAUUCAAAAGCAAUAUGCUGC
AAUUGGUGGCGGCUCCCCAAUUCGAAAAUGGUCAGAACAUCAGGCCGAAGAGAUGUGCAAGUUAUUAGAC
AAAAUGUCACCCGAAACCGCACCACACAAACCAUACGUUGCAUUCAGAUAUGCGAAUCCUUUGACUGAAG
AGAUGUAUAAUAAGUUGUUGGCGGAUGGUUUUGGAGGCGGGAAAGGUGGAAGAGCAGUAGCAUUCACACA
AUAUCCUCAAUACAGUUGUUCCACAACAGGAAGCAGUUUGAAUGAAUUAUGGAAGUGGAGACAGAGACUC
GAAGGAAAAGCUGCUGGAAGUCCAAAUGGUAGUGAUGGAACAAUCAAUUGGAGUAUUAUUGAUAGGUGGC
CAGCACACCCAGGUCUUGUUGAAGCUAUCGCACAAAACAUCGAGGCUACUUUAGCGACAUAUCCUGAAAA
GGAUAGAAAGGAUGUUGUAUUACUUUUCUCCGCCCAUAGUUUACCAAUGUCUGUGGUCAAUAGAGGUGAU
CCCUAUCCCGCCGAAGUUGCCGCUACAGUCUAUGCUGUGAUGCAAAGAUUAGGUCACUCCCAUGCAUAUA
GACUCUGUUGGCAAUCGCAAGUUGGGCCUAGUGCAUGGCUAGGAGCUCAAACGAGCGAUACUGUCGAGGA

FIG. 1H

AUAUGUCAAGAAGGGCCAAACGAAGCUCAUACUUAUUCCCGUCGCAUUCACAUCAGAUCAUAUCGAAACA
CUUUAUGAAUUAGACGAUGAAGUCAUUGGAGAAUCAGGCCACAAAGAUACUAUCAAGAGAUCUGAAAGUU
UGAAUGGCUCACCAGUAUUCAUUCAAGCAUUGGCCGACAUUGCUAAAGCACAUUUAGACAGCGGAAUUGC
CUGUAGUGUUCAAAUGGGAUUAAGAUGUCCUGGAUGCACGAGUGAGAAAUGCGCAGAGACUAAGAAAUUC
UUCGCUGGAAGUGAGAGAACAUUUGCCGCGUAA

SEQ ID NO:47

AUGUCGACUUUCAAAAGUACCAUCAACAUCACCCACAUUGGCACUGCUACUGCUGUGCUCGAAAUCGAUG
GCGUCAACUUCCUUACCGACCCUUUCUUCUCUCCAGCGGGUUCUAGUUUCCCCAUCAGGGAGGACUUCGC
ACUGGAGGUCUCAGAGGACCCUGCCCUUGGUCUGAACGAACUACCGCCAAUUGAUGCUGUUUUGCUCAGU
CAUGAAGAUCAUGCUGAUAACUUGGAUGAUUAUGGUCGCCAGCUGCUAAAUGGCCGUCACGUUUUCACUA
CUGUAGAUGGUGCUAAAAACCUGGCUCCGCGUCCAGCAGUCCGGGGAAUGAAGCCUUGGGAAAGCACAAG
CGUAAACUUGGGUGGCGUCAAAUACACUAUCACCGCCACGCCAACCCAACAUUUUCCCGGCAAUGAGUGU
ACCGGGUUUAUCUUGACGACUGAUCGGUUCGGCCACCAUGCUGAUGGACGUCCAAACGCGGUUUGGUUUA
CUGGUGACACGGUUUACAUUGAGGAGUUUGCCCGGAUUCCAGAACAAUUCCACGUUGUGGUGGCGCUGAU
GAAUCUGGGUUCGGCCUUCGUUGAGACUCCUAUUAGCGAUGGAAAGCUUGUCCAGAUCACUAUGGAUGGC
AAGCAAGCGGGAUCCCUAUUCCGAAUGCUUAAAGCGGACCAUCUGGUGCCGAUGCACUAUGAGUCUUGGG
GACACUUUACACAAUUUGGCAAGGAGUUGAUGGCCGACUUCAAGGAAGAAGGGGUAGAAGAGAAGGUCCG
GUGGUUAGUACCUGGCAAAGCUGACCCUGUACAUAUCAGGACCCUGUACACUUUUACCUCAAUUGCCCAC
AUUUGUAACGAUACUGUACCGGAGGCAGCGGCUGCCUGA

SEQ ID NO:48

AUGUCGAGCGUCACUGCAAAUUCUUUCGGUCCCGGUGCUUUCGACUUUCGGGAUCUGAGCAUGAAGCAUU
CUAAAUCAGACUACUUCAUGGUAAAACCCGUUCGUGGUUCUUCACCUACAGCAAGUUUGGCGGCAGAUCU
AUCACAGAAUUUUCACAUUGAUAUGAGCCCUCAAUUACCCACUCCUCGUCGAUCUCUAUUCACGUCGAAU
CUUUUUGGAACAUUGGAUGGCAGGGAUUGUGUUACUACUCCUCCAUUACCUUCCUCUUCACCAGGCCCAU
UGAAUGAAAGAAUGGAUAUUUCCCCUCUUCCCCAUAAGCAACCAUAUUUCUCUGCGCAAAUUGAGAUACC
AUCACCUACACCAGCAGGUACAACUACGGAAGAUACAACUAUGGGGUCAUCUCCAAUUCGUCCUAGUUUA
UUGGACGCCUCGAAACCUUUUGGUGCCGAAAGACGGAAAAAUUUAUUAUUACGACCAACCUUUUCACGCA
CCAAAGGUCAUUCAUCCAGCUCUCUGCCUCGACAAAACUCUGAUAGUCAAUCGCCUGCCUUCCGCUUCGG
UGCCGGAAGCAGCAAAUUGUCUACCUCCACAUCAAUGUCUUUGGGCGAAUGUUUUAUGGAAUCACCACCA
CGAGAACGUCGUUCACAAUCUGCGAAUAGUCCUACCAUGGCACCACCACCUCGACUAAGCAAACCGUUCU
CAAGUGUGUCAAGCAGAGUCGUGAAUGGAUCACCGAUUGGUAGUCACUCACGCAGAACUUCUAAUCCGUU
AGUUCGGCCUAGGAAACAAUUUCGACGAUCACUUAGCAUGUUUGAAAGCCCACAAGAUAUCGUCAAGGAG
AAGGAAAGUAUGUCAAGCAACUUGCAUACCGUUAUGGAUAUUGAUGAGAUACACCAACCAAUUUUACCAC
AUUUCUUCCAGGAAGGUCAACCUGACAGCAUUCCCAGGAUUGCCAAGGAGACCUUAUUGGAAAUUCUUGA
UGGGAAAUACGAUGAUGAAUAUGAUCAACGAAUGAUUGUUGAUUGCAGAUUCGAGUAUGAGUUUGAGGGU
GGACAUAUUGAUGGUGCUGUCAACUAUAAUGACAAAGAAUUAUUGACCAGUCAAUUGUUUGAAACAAAUA
UCCCUGGCAAAACCCUUCUAAUCUUUCAUUGCGAAUAUUCCGCACAUCGAGCACCCAUUAUGGCUCGUCA
CGUACGACAACAGGAUCGUACAACUAACGUCGAACAAUACCCUAAGCUUUCCUACCCUGAAGUGUAUAUC
CUCGAUGGUGGUUAUAGUGCUUUCUUCACAGAACAUCAAGGCCGUUGCUUUCCUCAGAAUUACGUUGAGA
UGGAUGCUAAGGAACAUGCUUACACCUGUGAGAGGGAAAUGGGAAGACUUCGACAAAACAGAACUAAGCU
CAGCAGAGCACACACUUAUGCUAUUGGCCAACACGGACAAAUUGAUGACAGCCCCACUGCCCCUAGUCGA
UCAAAAUCAAGCGGCAUCCGUCUUCAUCUGCGAAAGGUUUAA

SEQ ID NO:49

AUGCAUAGUAAGGUUGUUAUUAUUGGCUCAGGCCCGGCGGCUCACACUGCUGCCGUAUAUCUUGCGCGUG
CGGAAUUAAAACCAAAUGGAAUUGCUGCCGGUGGACAAUUGACUACUACCACCGAUGUAGAGAAUUUCCC
UGGUUUCCCUAAAGGAAUCGGUGGACAAGAACUUAUGGAUAAUAUGCGCGCACAAUCCGAACGAUUCGGU
ACUCAAAUCAUCACCGAAACAGUUGCAAAAGUUGAUCUCUCCAAACGUCCUUUCAAAUACUGGACCGAAU
GGGAUGACAAGACAGAACACACAGCAGAUUCCAUCAUCAUCGCUACGGGUGCAUCAGCUCGCAGACUCGG
UCUUCCAGGUGAGGAGAAAUACUGGCAAAAUGGUAUCUCUGCUUGCGCAGUCUGCGAUGGAGCCGUGCCA
AUUUUCAGAAAUAAGCCCUUGGUAGUUAUUGGUGGUGGAGAUAGUGCUGCGGAGGAAGCUAUGUUCCUUA

FIG. 1I

CGAAAUACGGAUCUCAUGUUACGGUUUUGGUCCGAAAAGAUCAUUUACGUGCAUCGAAAACGAUGGCUAA
GAGAUUACUUGCCAACAAGAAAGUUACUGUUAAAUUCAACACGGUUGGAGGCGAAAUUACUGGUAAUGAU
AAGGGAUUGAUGACGCAUAUGGUUUUUAAGAACGUCGUUACUGGAGAGGAAGAGAAAGCAGAAGCCAAUG
GAUUAUUCUAUGCCGUAGGACAUGAUCCAGCUACUGCAUUGUUCAAAGAGCAAAUCGACACUGAUUCCGA
GGGAUAUAUUGUAACCAAGCCCGGAACGAGUUACACAAAUGUGGAGGGAGUUUUUGCCGCAGGUGAUGUU
CAGGAUAAGAGAUACAGACAGGCUAUUACUAGUGCCGGGUCUGGAUGUAUAGCAGCUUUGGAGGCAGAAA
AAUUCCUCGCUGAGCAAGAGGAUGGGGAAAAUGAUUUGGAGAAGACGGAUGCUGAAAAGGGUAGCAAUGU
UGUUGUUCCUGAGUAUAGAUCUAACCCUUUGCUUUAA

SEQ ID NO:50

AUGUCAAGCGUGCUAGACAAGCUUUUCGAAACUACGACUGGAGCUGUAUCUUCGACAACUGGCAAAGUUU
UAAAGACCACUGCAGGUGCGGUAGGUAAGGGAGCUGCCUGGACUUGGGAAACUCCUGUUGUAAAGGGAGU
GAGAACUACCGUCAAUGCUACAGCCAAUGUACUUGACAAGGCGACGCAACCAAUUCGACAGACAGAGGCA
UAUAAGAAUGUCAAGAACGUGAUUGAUGAUGGAAGUAGUUCGAGGUACGGAGGGUGGGUGGAGAAGGAAG
AGAGACGGAAAGCAAGAGAAUUACGGGAAUUAGAAGAAGGAACCACUGGCAAAAGCAAGGAGGUUCCUGU
AGAAGACCCGAACGCCGGCACAAACGUUACCGUACACAAAGACUCCGCAUACAAGGAGGCCUGGAGAGAU
UUCCGUGACUCAAAUAGACUCAUGCAAUCUUUAUUCUCCAUGAAAACCGUCUACAAUGAAUCUGAAAAUC
CCUUAAUCUCCACCGCCCGUAGCAUAUCCGACCGAGUCGCCGGAUUCUUCGCCGAAAACGAAACCGCCCA
AGUAAUCAAGAAAUUUCGUGAAAUGGAUCCCUCCUUCCAAAUGGAACCUUUCCUUCGCGAAAUGCGCGAA
UACAUCCUCCCUGAAGUCCUAGACGCCUACGUGAAAGGCGAUACUGAAACCCUCAAACUCUGGCUCUCAG
CAGCUCAAUUCUCCGUCUACGAUGCCCUUUCCAAGCAAUAUACAACCGCUGGUCUCAAAUCCGAUGGUCG
CAUUCUCGAUAUCAGACAUGUUGAAGUCCUAUCUGCAAGGAUGUUAGAUAAUGAUAUCCCAGUCUUCAUC
AUUACAUGCAGAACACAGGAAGUCCACGUAUAUAGAAACGCGAAGACGAAUCAACUAGCCGCCGGCAUGG
AAGAUAAGGUUCAAUUGGUCACCUAUGCAAUUGGUGUUACGAGAGUAGCAGAAGAUGUUAAUAAUCCCGA
GACGAGAGGUUGGAGACUCAUUGAGUUGCAGAAGAGCGGAAGAGAUUAUAUAUGA

SEQ ID NO:51

AUGGCAACUCCAUCAACCGAGGGUUAUGCGCCCGAAUGGCUCGAGGUCGAGAAAACCCUGGGAGGUCGUC
CUCUCCUCGAAGGCAAGCCACUAGAAAUUAGAAAGCAAUACAGCGAACUAGUCCGCACCAUCGCAGCGCA
AUCCGCAGGCCCCGAUUCCUCCGUCCAAACUCGUGAUAUCUCCGCCGACGGAAUCCCAGUUCGUAUCUAC
ACCCCUCCAAAUACUUCUGCCGGAAACCCUCUUCCUCUAGGUGUAUAUUACCACGGCGGAGGCUGUUGCC
UCGGGGAUCUCGAUUCCGAGGAUCCGUGGUGUCGUUAUAUCGCUAAGACGGUUCCGUGUGUUCUCGUCUC
AGUCGAGUAUAGAUUAGGUCCUGAGUAUAAGAUGCCGGUCAUGUUGGAUGAUAGUCUUAAGGCUUUUGAA
UGGGCACGAAACCACGCCUCAGAACUUAACGCCAACCCGGCGCAAGUCUUCACAAUCGGCGGUUCAGCAG
GCGGCUGUCUAUCUCUCACCGUAGCAAACGAUCUCAUCGUCGCUGGUAAAAAAGACCACAUCCAAGGCAU
CGUCUCCCUGGUCCCCGUAACCGCCCAUCCAUCUUCCAUCCCUGCCGCUUACAAGGAACACUAUAAAUCG
UACGAGGAAAACGCAGCUGGUGUUCCGAUUCUAGAUCGAGCCGCUAUGGAUGUAUUUCUUGGGGCUAUUG
AGGCGGAUCCUCAUGAUGAGAGAAUUUUUACAACGCUUUCCAAGCAUCUCGAUCAAUUUCCUCCUACGUA
UAUUGCUACGUGUGGGAAAGAUCCUUUAAGAGAUGAUGGUACGGUAUUGGAAAUAAUGUUGAAGGAGAAG
GGGAUCAAGACGAAGAGUGAUUUUUAUGAUGGUGUGCCGCAUUACUUUUGGAUGUUCCCCGGUAUGAAGG
GUAGAGAUGAAUUUUUGGACAAUGUUUGUGCGGGCGUGAAGUUCGUUUUGGGUAUUUAG

SEQ ID NO:52

AUGAAGACACAAUCUCUAAUCAGUAUGGGCUUAUUGCCUAUACUAUCAGUAAACGCAGCAUAUACCUGGC
CUUCAAAAUACGACGAAUUAGAGGAUAUUCUUUACCUACAAGCAGGAUACAGACGCUACGGAUUUAGAGA
CGGUGUUACACCAUGUGGCUUCUCAGCUGAUGGUAGUAAUCGAGAGACAGCUGCAGAAUGGAUCAAAACG
GCUUACCAUGAUAUGGCAACGCAUGAUGUAGAAACUGGUCUUGGAGGACUUGAUGCUUCGAUAGCUUAUG
AGCUUGGUCGUGCAGAGAAUCCCGGUUCGGCUUUCAAUGGUACUUUUGGAUUCACAAACAACUAUGCCUC
GAUCAAAUCGUCUAACUCUGAUCUUCUCGCCAUGUCUGUCGUUGUUGCCUCCAUGGCAUGCGGAGGUCCA
AUUAUUCCAUUUCGAGCUGGACGAAUUGAUGCCGUGCAGGCUGGUGUACCAGGUGUCCCUCAACCUGAUC
AAGAUUUGGCCACGCACACUGCCAUUUUCGCAAAGCAGGGUUUCAACACUACCGAGAUGAUUACCAUGGU
AGCAUGUGGACAUGUUCUCGGAGGAGUUCAUGGCGUCGAUUUCCCUCAGAUUACUGGUGAUAAUAACGAA
ACUAGUUUCCCACAUUUUAACAGCCAAUACGACAACUUUACCAACUCCAUCGUAACCGAAUACCUAGAGG
AUAAAUCAAUCGACGUGCUUGUGGUUGGCAAAAACGACACCUUUAACUCCGACAAGCGUAUCUUCGGUGC

FIG. 1J

UGAUAACAACAAAACCAUGACUUCUCUAGCAGAUCCUUCUAAUUUCCAAGCGCAGUGCCGCGACAUUUUU
GCCCGCAUGAUCGACACCGUUCCUGCAAGCGUCACACUUUCAGAAGUCAUCACCCCCAUCGAAGUGAAGC
CAACCGAGCUUUCCCUCGCCUUAGGCGCAAACAACACAUUAUCCUUCACAGGUUCUAUCCGCGUGCGUAC
CACCCACCGCAACGCCGACAACGUUACCGUAUCCCUCCGCUACCGUGAUCGCAACAACAACCUCUCAAAC
ACCACCAUCUCAACCGAACGCGGACGCUGGCAACUAGGCCAAAGCUAUGGAUUCGCCAGGGAAGUCUUCA
CCUUCUAUGAAUUCGACACUGCUUUCGAUGUUACAUCCAGCAUCUCAUCUUUCGACGUCAUCAUCCAUAC
AGCUGGCGAAGCUGAUGAGAUCAACACCAACAAUGGCCUCGGAUUUCCCGUCUCAGACGCAAUUCUUUUG
CAAGCACCACAAUCCUGUCAACCACAAAUAAUCGUGAAUGAAGCAGGCCAAUGGAAUCUCACCAUCACCG
CCGCAGUCCGCGCCGAUCGUGUCGGGGAACCUGUAGCUUUCGACUGGGUUUACAAACGCUUCAUCCAAGG
CGUAAUGAUAAACCAAUUGGAGGUACAACGUACGGUUAUGGAGAAAGCGAGUGAGGAGAUUGGUGGAUAU
UAUCUUUACACGGCGACAAAGCCAAUUGAUACGGUACAGUGGUCGACAACAUUUGACUUGGUAUUGGGCG
AGGGAGACAAUGUCUCCAAGCUUGAGUUCCUGUCGACUGGAAACUUGGCCUCUACCUCCUGGUUGGACGA
AAAGGUACAGGAGAGGGAAGAUGCACACAAAACUAGGAGGAGUGCUGUUGGUGCAAGGGAUAUCCUGUAC
UCGAUAUUAUUCGAUAUAGUUGCAGCAACACAACAUGUCCUCAGAAUUUAA

SEQ ID NO:53

AUGGUUGCCUUUGCCAAAUCUCUCCAACUUUCCCUCUCACUCUUGGCAAGUACCGCCAUAGCCAUUCCCU
UCCCAUCAGAGCUCGAAUCCCGAGCUGAAAUCAACUCCGAUGCCGUUGUGGGAUUUCCCGAAACCGUUCC
UAGUGGCACAGUAGGCACACUCUAUGAAGCCUACAAACCAUACCUCGAUGUCGUAAAUGGCUGCGUACCA
UUCCCAGCCGUUGAUGCCGCUGGAAACACCAAUGCCGGGUUAAAACCAAGUGGCAGUAGCAAUGGUGAUU
GCAGUAGUAGUACCGGACAAGUAUAUGUUCGAGGUGCUCAAAAUGGUUCAUACUACGGACUGAUGUAUUC
CUGGUACAUGCCCAAAGACGAGCCCUCACCAGGCAUCGGCCACCGCCACGACUGGGAAGGCGUAAUCCUC
UGGCUCAGCAGCUCCACCUCCACCACCGCCAGCAACAUCGUUGCCGUCUGUCCCUCCGCACACGGAGGCU
GGGAUUGCACCCGAGACCAAUACACACUCUCUGGCACAUUCCCUCUCAUCAAAUAUGAAGGCAUUUGGCC
UCUCGAUCAUUCCUGUGGUCUUACCAGUACUCAGGGUGGACGACAACCGAUGGUUGCGUGGGAAUCUCUU
ACACCAGCUGCGCAAAGUGCGCUUGAGAAUACGGAUUUUGGAAAGGCGAAUGUUCCGUUCAAGAAUGCUA
AUUUUGAGAAUAACUUUGUGAAGGCUAGUAGUUUCUAG

SEQ ID NO:54

AUGAAUAAAAUUACUUCAGAGUAUCUUGCGGCAGGUGGCAAUAGACAUCCUUCUGCUGCUGAUUGGGAUG
AAUCAGGACUUCUAGCCUAUGGAACUGAUAGAAAUAUCGCAUUAUGGUAUCCUGGAAAUGAAUCUUCCAG
AGGAGUUUUUGAACUUCUCAGUGCUCAUACCGAUACGGUUAAUGUCGUGAAAUUUAUCCCUAAAUCACAU
GGUCUCAUACUUAGUGGAUCGGUCGAUAAGACGGUGAGGAUUUGGAAACAGGAUGAUGUAUCAAAGAGUU
AUACUUGUAUUCAAACUAUUACCGAUCAUCAGAGCACGAUCAAUUGUAUAGCUGUCACAGAAGGCUCGAA
AAUCUUUGCUACAGGUUCGGCGGAUGCCGUUGUCAAGAUUUGGAAACUCGGUGAUGAUAAUGUUGCAAGU
UUGCAGCAAUCUAUCACGAUUACUCCGCGAUUAUUUCCAUUGGCAUUGGCUUUGAGCCCUUUGACUGGGG
CAUCGGAUUCUUUACUUCUUGCAGUAGCAGGCACAAAAGAUAUCAUUCAGCUUCACGUGCUCGAUGCUCA
AGCGGGAUCAGAAUUUAAAUAUAAGGCUACAUUAUCUGGACACGAAGGAUGGAUCAGAUCAUUAGAAUUC
ACACCAGAGAGCGAUAGUCCAACGAGUGAUUUACUCCCUCUCAUCAGCCAGUCAGGAUAAAUAUAUCCGAU
UGUGGAGAAUUCAUCAAGGCAAAGAAUUACCCGCCGCAGCAACCGCAGCCGAUCCAACAUUCGGAGCAUU
CAUGCCAGGAAAAUCUCUAUCCAACAAAGCGCAUCGAUUUCAAGCCCAAGAAUUAGAUUUCUCCGCCACA
UUCGAAGCGCUUCUCCUCGGACAUGAAGAUUGGAUCUACAGCACACGAUGGCUGAAGCCCACUCUAUCUU
CCAACCAAAAACCACAACUUCUCUCCUCCUCAGCCGAUAAUUCUCUCGCCAUCUGGGAGCCCGAUACUCA
CACAGGUGUCUGGGUAACCGUCGCACGCCUCGGAGAAAUCAGUGCGGAAAAAGGAUCUACCACCGCCACC
GGUAGCACGGGAGGUUUCUGGACCGGUCUCUGGUCACCCAAUGGCUCAACCGUCGUGUGUCUCGGACGAA
CUGGUAGUUGGCGUCUCUGGAACCAUGAUGCAUCUUCUGAUCGUUGGGCCCAGAGUCCGGCUAUUACCGG
UCAUGUGAAAGCGGUGAUGGGAAUCGCGUGGUCGAAGGAUGGAAGUUAUUUGCUAUCGACCAGUACGGAU
CAAACGACUAGGUUGCACGCGCAGUGGAAGAGAGAUGGAAAAGUUAGUUGGCAUGAGAUGGCUAGACCAC
AAAUUCAUGGUUAUGAUUUGAAUUGUAUUGAUUCGCUUGGAGAGACACAAUUCGUAUCCGGCGCCGACGA
GAAAUUACUUCGAGUAUUCAAUGAGCCCAGAGCAGUCGCCACACUACUCAACAAACUCUGUGGAAUCGGC
AGCGAGAAUAUCAACAACAUGCCCGACGCAGCAAAUAUGCCCGUACUAGGACUAUCCAACAAAGCCAUCG
AAGCCAUCAGCGACGAGCAAACCAUCGAAAAUCCCAACGACCACAAUCGCGAAGCCAUAGACCCCGCCUC
CAUCGUCCACAAAUCCACACUAGACCUCUCACACCCACCGCUCGAAGAUCAUCUCUCCCGCCACACACUG
UGGCCCGAAACCGAAAAACUCUACGGACACGGCUAUGAGAUUUCCGCACUAGCCACCUCCCACGAUGGCA
GCAUCAUCGCCACAGCCUGCAAAGCCAGCUCCAUCGAGCACGCCGUAAUCCGACUCUUCGAAACCCAAGA

FIG. 1K

AUGGCACGAGAUAAAACCACCUCUUACAGCUCACUCCCUCACAGCCGCUCGAUUACGUUUCUCACACGAU
GACAAGUAUUUACUUUCUGUGGGACGCGAUCGUCAAUGGGUUGUAUUUCAACGAGAUGAGCGAGAUCCGC
UUGUGUAUAAAUUGGUUGAGAGGAAUCUGAAGGGUCAUUCGAGGAUGAUUCUUGAUGCUGCUUGGGCUCC
UACUUUCUCUUCAUCUUCAUCUGUAUCGUCAUCUACAUCUACAUCAACAUCUACAAAUUCCCCCAUCUUC
GCAACAGCAGGAAGAGACAAACAAGUUAAAAUCUGGAGUCGCGACAGCAAAACCCAAGCCCAAACUGACA
CCAAUAUCGAAACAGAAACAGAGAAUAAUGCCGGAGGAUUCACAUGCAAAGCCACAAUACCAAGCGACGC
CCCCAUAACCGCGCUUGAUUUCCUCGACAAGAUCAUAGGAAACGCUAUAUAUUUAGCUAUAGGUACUGAA
CUGGGAAGAUUUAAUAUCUAUCGUGUUACUGUAGAUGGUGAUGCUAUUACUGUUACUGAGGUUUUAUUGG
AUAUGGGAUCUAGCAAAAACUAUUACCCCUCCAAAGCCAUCACGCAAUUAGCAUGGAAACCCCAGAGAUC
UAGCAAUAAUACUCCAGAGCACGACGAGAACAUAGAUAUGGAAUUGGCAAUUGCGAGUGAAGAUAGUUCU
UUGAGGAUUUAUUCUUUAUGUUGA

SEQ ID NO:55

AUGGGGGCGACAGGUUUCCUUCAUCAUAUUGGCACAUUUCUGCUCUUCGCAUCUGCUAUCCUUCUCCUCA
UUACAACUAUCUCCGCACCUGUUAUCAAUGAUAUCGGAAUCAUGAAAGUUAAAUUGACAAAUGGAACGGC
AUCACACCAUUCCGUUGUCUCAUUUGGUACAUUCGGAUAUUGUGUCUUGGAUGUCGAUUCAGACGGUAAU
GACUACUGCACCAAAAAACAUAUCGGCUACAACCCCGCUUCCACAAUGUCCCAAAUCGAAUCCACCCACU
UCAGCCACGCCUCCGAAGAUACAUCCAAAGCCCUAACCCGGGUCAUGAUCCUCCACCCCAUCGCCUGCGG
CAUAAUGUUCAUUGCAUUUCUCCUCGCUCUCGGCGCCGGAUUCAUCGGAUCAUUCCUCGCUGCGCUCGUC
UCUAGCAUCGCAUUUAUCAUCUCAGUCGUAGCCAUGGCAUGCGAUUUCGUGCUCUUUGGAAUCGUCAAAA
AUCAUGUAAAUGGUGAUAAGAGCGGUAGUCAUGCGUAUUUUAGCGUGGGCAUUUGGUGUAUUUUGGCGGC
GAUGAUUGCGGGGUUUUUGGGUGCGAUAGUAGUGUUUAUUACGUGUUUGAGUAAGAGGAUGCACAAGAAG
AGGAGUAGAGGGGUGGAGGAGAAGGGUUAUGUGGGGGGUGUGAAACCUGCUAGGAGACAUUUUUGGCAGA
GGAGGGGUUGA

SEQ ID NO:56

AUGCAGAGCGACGUCACUAUGCUUUUUUCCCGAAGAAGAGGAUCAAACAGCCAACCAUUGGAAGAGUCAU
GGUGUGAAUGCAAGGCCAAGAGCCUCAAAAAUUCAUCGGAUAUCACGGAUGACACCUCGGGAACAGGGCA
UAUGCAACUUGCAAGUGAAUUGAGUUCAACCCAAUUCCUCGGAAUGAGUGUUUCCGUGGAAGAAAGUCAU
CUUCGAUCUCAAUUCAUGCCAAAAGCCACCACUGGCAAGAGAAGUGAGUUGUGUGUCGGAAAGCAGAGAG
CGGGAGCAGAAGAAAAGUGCAUAUGGCAUGAGAUGAGGAAAGGAAAUACCAAUGACCAAGGACUAAUGAC
CAAUGAACGUCCUCCUUGUUUUACGAGCAGGCGGGGUAGUACUCGUAAAUAUACUUCUCUUCCAAGAUCA
UUGGUUCCAAAGGCUGUGGAAGGUCAAAUGGACUGA

FIG. 1L

SEQ ID NO:57

AUGACCACAAAACCCCUCGUUGGGUCACAAGCCCAACGACAGUCGCAAAGAUCAUUGAAUCCAAACGUUA
CCUCGAGACCCUCCCCACAAAGAAGCCUAUCGUCUACCUCCCCGACUCGAAGAUACAACGAAGCCUUCAU
AGACUUAACGCUUGAUGUGCCGGAUUCUACAUCUGUGCGUUAUGGACAAACCUCGAGAACAGGAGGGUCG
CGCUUGAAGCAAGAAAUUUCCAAUGAGUCGAGAAGUUCAAGUCAGACGGAGACAUCAAGCUCGGGUCCUU
CAAAUAUAAUAUCCAGUAGGCAGACUCUGCCUCCACGCGGUCGACCGCAGCUUCAUUUCGAUGUGCCUCA
UACGAGAGCCACCAGAUCCAGUUUGACGUCCGACCAAAACUACAGUCAAGUGUUUGCGAGACCAUUUCCU
CUUCCUGUUAGGCCCGGAAGACAUGCACCCCCAUUUGUGGAAAAGCCGAGCUCAUCAAUUGGGACAUCUG
GAAAGAAAGAUGCUCGCCCCAAACCUUUUGUUUUAGAGAUACCGCCCGCUGCGCCGUCUUAUUCACCAAA
CGGUCAUGCUGAUUUCUUCCCAUGGAACGGUAACCAUGCUGAAGACCAAUUCACUGAAAUUGUCAUCCGG
GGAGGCUUCUUCGACAAGUCGCAAAUGUCACAGAACGAAACUGGCUCGGCAAAAGCCUCUAUAUAUCCAU
CUUUAAAACACAAAAGCGGGCUCCAAACACUGUCAUCAUUGUUUUCCAGCGUUUUAGCUCAGCGGAGGGC
UCAUGGAAAUAUCACGGCGAACUCAACUUUCAAGCCGCCACCCCGUGUAACGGUUACGGACACGAAGAGA
GAAAUAUGGCUCAAGGAUCUAGCUAAUCCGACUAUAUCACUCCGCCGCCUCAGUCGAUCAAUUCCCCACG
GGAUUAGAGGUAAGGUGCUCCUAGAACAUUCCCUCAACAAAAACAUCCCUAUCGAGCGGGCCGUCUGGUU
AGCCAAGUGCGUAGGGGCAAAUGAACUGAGGUCUUUCAAGAGGAAGGGUGCGGGUGGUGCUUUUGCUAUG
GGAGGUGAGACGAAAUGGGUUAGAGACUUUACAGUUUGUGUUGAACAGGUGUUGGAGAGCAUAAUUGGAU
CAUGUGGAGAGAAGGACUUUCGUCGCAGGAUCUAUUACGCACCGCGAGCAUUAUCUAGAUUGGAUACUAU
CAUCCCUCGAGGCUACUUCUCAAGCCAAAUUACCAAUAUGGUUGUUGAUUGCCCAGGUGUAUUGGGAAGA
UAUUUUGAAGUAUCGGAGGUUCGGGCGCCGGUUCACAACUACUCUGCUGAAUCGUUUUUCAGAGCAUCCG
GAUUCUGA

SEQ ID NO:58

AUGGCGGACUACAAUACUUCCUCUGGUGGGAUGGUCGACCAUAAUGCCAAUCAAGGACAAUUACAUCGAA
GAAACGUUGUCGGUAUGGAAGAAGGACCUGAUGCUGAUGCACAACUCGCCGCUCAGUUUGGAUAUCAGCC
UGUUUUCAAAAGAGAAUUUGGAUACCUCUCGACUUUCUCCUUCGCCGUCUCUAUCAGUGGAUUGUUUGCU
ACUAUCAUGACCACUUUCUCCUACCCAAUAAUGUCUGGUGGAUCUGCUGCGGCCGUGUGGUGUUGGGCAA
UAUCUGGUGCUGGUUGCAUGUGUAUCGCUCUUUCUGUUGCUGAGCUGGUCUCUGCGUAUCCUACAUCCGG
CGGUUUAUACUUUACAAUUUCACGACUUGUACCGCAAGGUUGGGUGCCAUCUAUCAGUUGGGUUACUGGU
UGGUUGAAUCUUCUUGGACAGGUCGCUGGUGUUGCCUCAUCUCAAUAUGGUGCAUCUCAAAUGCUGCUAG
CAGCUGUUUCGAUCGGAAAAGAUUUCAACUACACAAUUGAUGCAAAUACAACAGUUGGUGUCAUGGCAGG
UCUUAUGGUUCUUACUGGCUUGGUCAAUUCUUUAUCUACCUACUGGAUGGAAAAGAUGACAAAGAGCUAC
GUUAUUUUCCAUGUUCUUGUUUUGGUAUCGUGCUGCAUUGCUCUUCUGGUCAAAACCCCGAACAAACAUA
AUGCCACCUAUGUAUUUACCGAUGUUGAUUCAACCUCCGGCUGGACCCCUGUAGGAUGGAGUUUCUUGUU
CGGUUUCCUUUCCGUUUCCUGGACCAUGACCGAUUAUGAUGCUACGGCGCACAUUACCGAAGAAAUUUCC
GAGCCAGAGAAAAAGGCACCCUGGGCUAUCUCCAUGGCUAUGCUUUUCACCUACAUCGCUGGAUUCCUCU
UCAACAUCGUACUUUGUUUCUGCAUGGGUGACCCAGCCGAGAUUCUUGGCACAAGUAUUGGUCAACCAGU
CGCUCAACUUUUCUAUAACAGUCUUGGAAAAGCAGGAGGUAUUUUCUACACCGUUUGCGGGUUCAUUAUU
CUUGAAUUCGUAUGCUUUACUGCUAUGCAAUCAUUGGCGCGAACAGUCUUCGCUUUCUCUCGUGAUAAGC
UUGUGCCAUUUUCCAAAGUCUGGACAAAAAUCUUACCCAUUACUGGAACGCCAAUCGCAGCUGUCUGGAU
CUCUGUUGCCCUGUGCAUUGCUAUCAACCUUAUCGGCCUUGGUUCCUACACUGCCAUUUCUGGAGUCUUC
AACGUUUGCGCCAUCGCUUUAGACUGGAGUUAUUGCAUUCCAAUUGCCUGUAAACUCAUGUUUGGCAAGU
UCGAGCCAGGCCCAUGGCAUAUGGGCAAAUUUAGUACUGCCGUAAAUGCAUGGGCUUGUAUCUGGACUGU
GUUUGUCAGUAUCAUCUUCAUUCUCCCGACGGAGCGACCAGUGACUGCCCUCAACAUGAACUACGCCAUC
GCCUUCCUAGGACUAAUCCUAGGAUUCUCUACCAUUUACUGGUAUGUUUCCGGCAAGAAGUUCUACACCG
GUCCUGUCAUCGAGGCCGCCGACGGAGACUCCCUCAGGAAUUCGUCAGACCGUGGCUCGAGGCAGGAGAA
GGUGGAGAACGGAAAUAAAUCAUAA

SEQ ID NO:59

AUGUUUGAACAACAGAGAUCAGAGAGCCCUGUUGGCAACCUGGAGAUGAAGAAGUCUGCCAAAGAAAAAG
UCACGCCGGUAUCGAGCGAGGAAGAUCUCAGCGAUCAGCCACCGGCACAACUAUUGUCCACGGCGAGAGA
AAUUGCUUUGGUGCUAACAUUGGCCGGAGCUGGUUUCCUUAAUAUUAUCUUUGUGCAAUCUGCUGUGAUU
AUGUUGCCAUCCAUUAGCGAAGCUCUCGGAAUACCCCCGAACCGACAACAAUGGAUCACGUCAUCAUACA
AUAUAGCAUUUGCCUGUGUUCUACUUCUCUGGGGUCGUCUUGCAGAUAUCUACGGCCGGCGAAUCUUUUU

FIG. 1M

CGUUUAUGGUUCGAUCUUUGUCACCAUCAUUACCGUCGUGAUUCCCUUCUCCCCCGGCGAAAUUGUCUUU
GACAUCUUACGAGCGCUGCAGGGGCUCGGUAGCGCCGCAACGGUUCCGUCCGCGGUCGGAAUCCUAAGCU
CCACCUUUCCACCUGGUAAAAGAGAACUUACGCGUUCGUUACUUAUACCGCCACUUCGGCCUUGGGAUC
GGUAAUGGGAAAUAUUAUGGGUGGGAUCAUCGGCGCUUACCUCAGCUGGAAAUGGGUCUUCUGGAUCAUU
GCUAUUCUUGCCGCUUUCACCACGGUGGCUGGUAUUAUUGUUAUUCCUCGACCUCAGGCGAAAACUAUUG
AUUCUGAUAGUAAAUUAUAUGUCGAUUGGAUUGGAGGAGCGUUGAUAUCGACAAGCUUGAUUACUCUUUU
GUUCGCUCUCACAGAGGGUGGUGGAAUUGGGUGGAGUACCCCUUGGAUUCCUGUGCUCAUUGUGGUAGCG
CUCCUCCUAAUGGUGGUCUUUUACUUUUGGCAGCGACAUUUGGAGCGUACCGAUCGCAGUCCACUAGUGA
AAGUUUCCAUGUUCAAAAAUAUGCAGUUUACAUCUGCUUUUGCUAUUAUCGGGUGUUUUUUCGCAUCUUA
CAAUAGCUAUUUGAUCUUUGCGACUUAUUUUUAUCAGGAUUAUCUCGGGCUAGGAGUUAUCGAAACAACA
GUACGCUUCCUUCCAGCUGGAGUUGCUGGCCUACUCGUAUCCUUCGUAACAGCCAAAGCCCUAACCAUCU
UCCCUGGUUUCUACGUCCUCGUCUUCUCAACCAUCUGCGGCACUCUAUCUCCUCUCCUCUUCGCCGUACC
CAUUUCUCCAAAUACAACAUAUUGGGCCUACGGUUUUCCCGCCAUGUGUCUCUGCAUCAGCGCAGACAUG
UUAUCACCGACAAUUAAUCUUUUCGUGGUACGUCGUCUCGACGAACGCGAUCAAUCGCUUGGAGGCGCGC
UUUUAAAUACCUCGAAUCAAGUUGGUAGAUCUCUAGGUUUGGCAAUUGCAACGGCUGUGCAGGGAGCGGU
GGGAAGUACAGGGAAAGAGGGAAUUUAUCGUGAUCCAUCGAUGCUUAAGGGACUGAGAGCGGCGGAGUGG
GUUAAUGUUGGGUUGGCUGCUGCGACGCUUCUUUUGGUUUUGGUAUUUUUUAGAGGAACGAGGCAUUCGG
GUGCUUCUUAG

SEQ ID NO:60

AUGGCAGACGACUCAGCACCUCUCGAGCCCAAGGGUAAACAAAUUGCCUCUGAAGAUACCCUCGGAGAUA
CUACCUCUAUCCAAGCACAAGUCGAAUCCGAAAAUGAAGAGGAUAAUGAUGAAACAACCACUGGCGCAAC
UGACACGCCAGCUACCGGAAAGAAGAAGAAAUCAAAGAGAAAGAAGAUAAAGGCCGCACUAGGAGUAGGA
GCAUCUUCAACUGGAUCAAGCGGAGAUACUACAAGAGACGACCUUUCAAAAGCUGUUGCGGGUCUCAGUA
AAUCUCAAAUUGGAGAACUACUCGCAUUAAAUCCGGCUCUGGCACAACAAAUUGGUGCUGUUGAUGGCGA
UCUGUCAGGGAAGCAAGCUGCAGAAGCUGUACGAAAGCUCAGUUUAGAGGAUAUCAUGACCGGUUUAGCC
UCAAGCGGGAAGAACGUUAAGGAAAUGGGCGCAUACAAGUUUUGGCAAACACAACCGGUUCCUAAGUUUG
GGGAAAGCUCAGAAGUUAUUGAAGAAGGUCCAUUCAAAAUUGUUGAUCCGGAACAAGUACCCAAAGAACC
UGGUCCACUGAUAUCUGGAUUUAAUUGGGUUACAAUGGAUAUGACAAGUGAUGAGGCUUUGCAAGAAGUC
UUCGAUUUAUUAUAUGGCCACUACGUUGAAGAUGAUGAAGCUAUGUUCCGAUUUAAUUACUCAAAGUCAU
UCCUCAGAUGGGCACUUAUGUCGCCAGGUUGGAGUAAGGAGUGGCACGUUGGUGUUCGAGCUACUGCAUC
AGGGAAGUUGGUCGCUUUCAUAUCAGCCAUACCAGUUGCACUUCGAGUACGAAACAAAACCCUCAAAGCC
UCCGAAGUCAACUUCCUUUGCAUCCACAAGAAGCUCCGAUCGAAACGAUUAGCCCCCGUUCUCAUUAAAG
AGAUUACACGUAGAUGUUACCUACAAGGGACAUGGCAGGCAAUCUAUACUGCUGGUGUUGUCUUACCUAA
GCCAGUCAGUACAUGUAGAUAUUAUCAUCGUUCUUUGGAUUGGAAAAAGCUACACGAGGUCAAAUUCAGU
CCCCUACCACCGGGAAGUACACCAGAGCGACAAGUUCGUAAAUUUGCUCUACCAUCGAAUACAUCCACUA
GAGGAUUGAGACCUAUGGAAUCCAAAGAUAUUGAUGCGGUCUUGGAUCUUCUAAAGAAGUACCUCGCAAA
AUUUGACAUGGCACCAGUUUUCACUAGAGAGGAAGUAGAGCAUUGGCUUUUCAAUAGAAUUGAGAAUCCU
GCUGAGCAAGUCAUCUGGUGUUAUGUUGUGGAGGACCCUACAACCAAGAAACUCACUGAUUUCUUUUCAU
UUUACUGUCUCGAAUCCUCCGUCAUUGGCCACCCCAAGCACACUAAUGUUCGCGCUGCCUAUCUUUUCUA
UUACGCCUCAACGAUUGCCCUUGAUCCAGCUAGCUCUAGAACCGAUCUUGGUAAACGCCUCAAUGAACUC
ACACAUGAUGCUCUUAUCAUUGCAAAGAAAUUUAAAUUCGAUGUCUUUAAUGCGUUGACGCUUAUGGAUA
AUACUUUGUUUUUGGAAGAGCAGAAGUUCGGUGCCGGUGAUGGCCAGUUACAUUAUUAUUUGUACAACUA
UAAGGCGAACAACAUCGCGGGUGGUGUGGAUAAAAUGAAUAGGAUCCAUUCUGCCGGAAGUGGGGUGGGU
GUCGUUAUGUUGUAA

SEQ ID NO:61

AUGAAGGCUAUAACUGUCCUCGUCGGCUUGAGCUGGCUUCGUUGGGCUUUAGCAGACGACAUUUAUUGCG
AUGCUAAUGUGCCAUGUGCCAUUGGAUGCUGCGGUGUUAAAAGCAAUGUUUGCGGUCUCGGUCCUAAUUA
UUGCAGUGCGGAGAACUGUAUCAAUAGUUGUGACGCCAAAGCUGAGUGUAACCCGGGUGGCUGGGCGUCC
GAGUACGUCAAUAGCACCACUUGCCCGCUCAAUGUCUGCUGUAGCGAGUAUGGAUUCUGUGGCACAGGCG
AGUCGUUCUGUGGGACCAAGACUCCCACCAUACCCUCCUGUGAUGUCGAUUCACAAUCAAUAACCCGUGU
CAUCGGUUACUAUGCCUCAGGUGGUGCUACUCGCGCAUGCGAUGCAAUGCUUCCAGAGUCCUUUCCCCAG
GGAAUUUAUUCGCACAUCUAUUUUGCUUUUGGCAGUAUCAACCCAGAUACUUUUGAAGUAAUCCCCGGAG
CAGAUGGUGAUGAAGCGCUUUAUACAAAGCUUUCGGCCCUCCAAACACGCGAUGCAACGCAGAAAUUCUG

FIG. 1N

GUUAUCCAUCGGAGGGUGGACUUUCACGGACAGUGACCAGGCUACAGCGACGACCUUUUCGGAUCUCGCC
GCCGCCGAUAUCACCCACCAGAAUGUGUUUUUCUCUUCCUUGACCCUUUUCAUGACGACGUGGGGAUUCU
CAGGCGUUGAUAUCGAUUGGGAGUAUCCCGCGGCCUCCGAUCGUAGUGGACGAACUGAAGAUUAUGCCAA
UUACCCGAAGUUCUUAGCCAAUUUGAAAUCAGCACUGGAUGAGUACAGCUAUGGUCUUUCCAUUACGCUG
CCUACCAGCUACUGGUAUCUACAGCAUUUUGAUCUGAUCUCCAUUGAACCCUCCGUGGAUUGGUUCAACU
ACAUGGCUUAUGAUUUACAUGGCACCUGGGACAUUGGGAAUGAGUGGACUGGUGCUAUUCUAGAUGCACA
CACAAACCUGACAGAAAUAGAAUCCUCAAUGAACUUGCUAUGGUGGAACAAUAUUACUUCGUCUAAGGUC
AACUUAGGUUUGGCCUUCUACGGCCGUAGUUUCACCAUUGCUAGCUCCAACUGCGACACCCCCGGCUGCG
CGUAUCUUUCGGCUGGAGACGAAGGCGUUUGCAGCGCUUCAGCUGGUAUCCUUCUGAGUAGUGAGAUCGA
ACAGAUCAUGAGUGAUAACGACCUUACCCCAGUUUUCUACAAGGACGCAGCUGUCAAAGCCAUAACUUGG
GAUAAUGACCAAUGGGUUUCAUUUGAUGAUCAGGAAACCUUCAAGAUCAAGAGCGAUUUUGCGAAGUCGC
AAUGUCUUGGGGGCGUUUUGGUUUGGUCUGUCGACUAUGAUGACAGCAAUAACACACUCUCACGAGGGCU
AGCAGCCGCGCUCGGCAAUGAAAUCAACAUAGAUACUUCCACAGGUCUAGCACUUACUGAAAGUGAGACA
UCGGAUACGACGACAACCAGUAAAGGCGGGCAGGAUGCGUACUGCCGAUUCACUAAUUGUGGAGAAACAU
GUCCCGCUGGUUUCACCACUGUUGUUCGAGGCGAUAAAAAAUCGCAACUUAUGCUCGACGGGUCGCAGUG
UUGGCCAGGUUCUGGACUUACGCAGACCUUGUGCUGUCCUACUUCAACCGACGUACCGACUUGUCAAUGG
CGAGGCUUUCACAACAAUGGUAAAUGCAAGGGCGGCUGCAACAGCGGCGAAGCUGAAGUGGGAACCAAUU
CCGCCGGAUGCAAGUCAGGCUAUCAAUCGGCUUGUUGUACCACUACAUCCUCGACAAAGCCCUAUUCCGA
GUGCGCGUGGACUUCUAGCUGUGAAAGCGAUGACACGUGCCCAUCAGGCUAUUCGAAUUUUAUCGUAGGG
UCCCGCGCGGGUUGGGGCGGACGAAAAAAAUCAUGCAGUGGAAAAAGAAAUACAACUAUUGCUGCGCAG
ACUCCGUUCCAGAUGCCUUCACCAACUGCGCUUGGGCUGGAUUUGAGGUUGCAUUCAAGAAUGAGAAAUA
CUGUAGCGAUACCUGCCCUUCAGGUACGAUUCGGAUUGCCGAACAGGAUGAUUUUGGACAAACGCCAAAC
GUUGAAAACUGCAUUUGGGGUAAGGAGGCAUAUUGUUGUGGUGGGACCGUUACGACAAGCACCGUAAGUC
CGCGAGCACCCACCUACCAGGACACCACAGCAAAGGAGUUUGAUGCUUAUCUCAAGAAAUACUUGGCGGC
ACCUAUAUGCCCUGGUGGGUUUGAAGCUGAGUACAGCGCCUCUUUCUCCUCCGAUCCUUUGGGGUGGAAG
CGAAGCAUAUCGCUAGAGAAGCGAGCCACCGACCAAGGCAUUACUCUCGAAGUUCUGAUUCCCAUUCUUU
CGACGUGGAUUACGUCCCAAUAUCCCCGAACUGACUUGAUGGAGAUCUGGAACGAUGAUACCAGUGAAGC
UGGAUUCGGUAGCAUGAAUUACACCGUUCUCAGGGAUACACUCUACCCGAACGCUUGGACGGGAGAUCCC
GAGUAUGCCACCGAUACCUUGCUAACCGAUAUGCUUUGUAACAUGGCUGAGGCAGCUAACGGACUUGAAA
ACCUGCAGACAGAUUCAUCAAUUUUGUGCGUGAGUCCUGAUGAUGAUGCUGGUACCUGGGAUGAUCUCGU
AACCACCAAACGAGAGAUCUCCGCCCGAAGACUCGAUGAAAUGGUUUCAACUGCCCGCACCGCCGACGGA
CUCCAGCCGUCUGUUUCUCAAGCCAUCAGAGGCGUAUUGAACGGUGAUUUGUCUCUGCAUUACCUUCGCU
GGCUCAAUCCAUCAGGUGCUCAAGUUAUAUUAGAGCUGGCCUUUUGGAUCGGUCCUACUGCAGGCGUGGC
CCCCACGGCAGCUCAGCGUGCCGCCUAUGCCGACACCACACAUACAGCUGCAGCCGAUCGCUGGAUCGUA
UUUCAUUUACAUAUCCCCCUGGAUCGAUACACAUUUAGACAAGAGAUCACGAAUGACGACACGUUUUGGC
AUCUGGGUGUCGGUACCAUAACUGUAUAUCAUGGCCAAACCGUCAAUAGAAGCCCCCCUCGAUCUGGUGA
CGACACACUCGAGCCCCGAGUAGAGUUUCGCUAUUCUUCCACUUAUGUUGGGGGCGUAAAUAACGGCAAC
AUGGCUAAUUACAAUGCACGCACUCAAGCUCUGUCUUGUCCUAUAGGCGACGAUAUUCAGACCAGAAUGU
AUCUAGGUCUAGACUUGAACGCUGCUGUUCAAGCAUCGAUACGACCUUCUGUGGGGGCUACCCUUGUAAA
UUCAUUUAAUCUUUGGAUGUAUGAGCAAGGAAUUACGAGUCUUACCAACUUGCAAUAUCUAUGGCCAUCA
UUGCCAGGGGAUCAAGGCGGUUUCGAACUUGUAGGUGGAUUCAAUGGAAAUUCCAAUCUCAAUCCUGAAU
AUGCAAAUGUUAGCGAGUGGAUUAUUCGUCACCAACCGGUAACAGUAUCGCCCUAUCGCGAAUUCCAGCA
GCCAGAUAAUAUUACAUCCGUCGCUCUGUUUGACCAUGACGGCACCACGGCCCUCUACGAAAAAGGUGAA
UACGCAAACGCCCUUUUAUGUCGAAUUGUCCAGCUCAAUGACGUGUCUGCAUUAAAUCAAUACUUGAUAA
GAGACCCCAUGCGCGGCUUGGUGGCAAAUCUAGCCAUUUACACGGACCCUUUCUACACCGCGACCUAUUA
UGCAUCUACCGAUUGUCUUCGCAUACUUCUGGAGCAUCACGCUAUCCAUGGAACUCCAGCUCAAUUCGAU
GCUCCCAACUCGACAGACUACCUGCUAUUAAAUGUGGCUAGUAGCAGAGCUCAUCUUGAUACGGCACGUU
UUCUGUUGGAUUGUCAACCUGCAUAUGUUGAUAUUCACGCCCGGAAAUGGGACAUGACGGCCUUGCUCUG
CGCAGCUGCUUCAUUUACCGCGCACCUUCCAGACAUAGCGCCAACACCGAGUGAACCAAAGGGAGACCUA
CGCCAUCACGUGGCUCGUAGUGAGGAGCUUAUGCAGCUUCUACUUGACCGAGGUGCUUGCGCUCGUGAUG
CUACAAAUUACGCGAACAUUCAUAAAACGGUUCUCAGUCUAGCUAUCUCUAGGGCUAGUCCUGAAUUUGU
GAAACGUCUCAUCGAUGAAGGUGCCGACGUGCAUGCAAAGACAGCAAGAGAGCUAGAGUCUUGGUCUGGA
UACGAUGAAAAGCUUCUCCAAGAUUUCACUCCUCUUCAUAUGGGUAGCUUGUACCUUAAUUCCGAAGGCA
UCCAAAUCCUGCUGGACUGUCGAGGCAGCGGUAUGGAAAUUUCAGAUAUGUUGUUAUGCCGGGAUAGUUC
UGGAUCUCUUCCUCUUCACUGGGCCGCUGGGAGCUUCAAUCAGCCUGAGAACGAAAUUUGGGCCAGAGAC
GAUAUUGUUGCCCAAGCUACCAAAACCAUUAAGUUACUCUUGAAAGAUAGCAAUCCCAGCUCUAUCAAAA
UUCCAGAUAAGCAAGGAAACACGCCCUUGCAUCUCGCAUCAUCUGGAGAAACAAAAAACGAUAGCGAACA

FIG. 1O

UUCCUUUGUCGCUCAGGCUAUUGUGAAGCUGUUGCUCGAACACGGCGCAGACGUGGGUCUACGUAAUCAA
AAAGGACAAACGCCGCUACAUUUGAUAACUAAGGAUACGGCACUGAUGGAACUCCUUCUGGCGAAUGGCG
CGGAUGUCAAUGACGCUGAUACAGAUGGCGAUACUGCCCUUCACUUUGCGGCGAGUAAUUUGCGUUAUAU
CGAAGCAGUGCGAUUUCUCAUCAGUAGAGGUGCUGAUCUCCAUGCUAAAAACUCCAAAGGAAUACACCA
CUACAUGAAGCAGCGGGCGGGUAUUAUAUAAAUGAUAAACGGCGUUUGACUAGUGGAUCCUAUCGCGAUG
GGAAUACGCGUUGGACAAACGCUGAUUUGAUGAGAUUGCAGGACGAAGUUAUAGGUGUCUUUUUGGAUGC
UGGAUGUGAUCUUGAUGGCCAGUGUAAUUUAGCUGCUAAAACAGCUCGAAUGAUACUGGAGGAAACGAGG
CAAAAAUGGGAAGAAAGGGAAGAAACUUGGAGGAAAAGGGACCAACUAAGGGCCGGAAGGGGAAGAGGAA
GAGGUAGGGGAAGGUAG

SEQ ID NO:62

AUGGCUCCACUUCGAUCAACGGCGCUCUCGCGCGAUACAAAUGAGACUAGUAUUCAACUGGCUAUCAAUC
UCGAUGGAGGGGAAUUCCCAGCAGAUACUGAUAAGAAGUUAUUCAGUGGUGAAGAGGGGCAUGCUUCCCA
AGUCUCAAAAUCGCAACAUAUUGCUAUACAUACCGGAAUUGGGUUUUUGGAUCAUAUGUUGCAUGCUUUG
GCAAAGCAUGCUGGUUGGAGUUUGGCGAUCAAUUGUAAAGGAGAUUUACACAUUGAUGAUCACCAUACCG
CUGAAGAUGUAUGCAUUGCACUUGGUACAUCAUUUGCCAAAGCUCUUGGCUCUCCUGUAGGAAUCGCACG
UUUCGGAUCCGCAUACUGUCCUCUCGAUGAAGCACUUUCGCGAGCUGUUGUCGAUAUUUCAAAUCGUCCG
UUUAGUGUGAUAGAUUUGGGACUCAAGAGAGAGAAGAUUGGAGACUUGAGCUGUGAAAUGAUACCACAUU
GUCUGCAAAGUUUCGCGCAGGGUGCAAGAAUCACUUUGCAUGUGGAUUGUUUGAGGGGUGAUAAUGAUCA
UCAUAGGGCGGAGAGUGCCUUUAAAGCGUUGGCUGUGGCGGUUAGACAGGCUACUUCGAUAGUGAAAGGU
AGAGAGGGUGAGGUUCCAAGUACGAAGGGUACUUUGAGUACUUGA

SEQ ID NO:63

AUGGCGGCUGAAUUAAUCGACUUUUAUCAGAACUUUCUACGAACGGGAUUAUACAAUGGCGGAUAUGAUG
AUGAACUUCUCGCUCUUGCAGGAGAUGAUUCUUCUGGAGAAGAACAGGUCGCAACAAAUGAUGGGGGAAG
ACACAGUUCUUCAUCGCCUGAUCGUAAUGGUGCGGUAAAGAGUGCAGCUAAGAAAGGUGGAAAGAAGGGG
GGUAGACGAAAUGAUGAUUCUGAGGAAGAAGGUGAAGCUUCUUCCGGUGAUGAAUCUGUUCGUUCGGAAC
GAUCAGCUCCAAUGGAUGAAUCUGAUUCCGAUUCCGAUGGCCCAAGUUUUCGCGAUGAUGCUGAUCGAUA
UCCUCUCGAAGGUCGUUUUAUGAAUGCAGCCGAUAAAGCAAGUAUUAUGUCUAUGCCUGAAAUUCAACGU
GAGCAGGUCUUGGCUGAUCGUGCCCAAGAGAUUGAAAGGACCGUCAAAAUAGAGCACUUCGUCAACUGU
UAAAUGCCCGUGAUGCAGAGAAUAAAAAAGCGGACAAAAAGCGCAAGGCAGGUACCGCGGAUUUGGAGGA
AAACCAGCGCAAAACGUCUCGUCAACGUACCAAGCUUGGUGGUGGGAAGGUUGGGGAAGCUAGCACUGGA
AUUGACAGUCUUAAGCGUGCAAGAGCUGAGAAAAACGAUCGACAACGUCGUCGCGAUCAAGAUAAGGAGC
GCCGUGGGGAUGAUGGUCGAAGAGAUACCCGGGACGAUUAUUCAGAUGACGAUGGUGAUGGGGAUAGUGA
GGUUGAAUGGACAGCAUCAAAGUCAAAGAAAAGGUCUGCAUCUCCAGAUUACCGAGAUGCAGAACCGGCG
GUUCUCUAUGAUCUUGAACGAGUUCGAGUUGGUAGAAGUAGAUUUGCCAUGGUCUGCUUUUAUCCUGGGU
UUGAUGAAGCUAUUACUGGAUGCUUUGUUCGAGUAAAUAUUGGUGUUGAUAAGGAGACAAAUCAAAACCU
UUAUCGCAUGGGACUUGUUAAAGGCUUCAAAGAAGAUAAACCAUACGCUAUGAUGUCUAGUAACGGAAAG
CAAUUUUCGACAACACAAUAUGUGAUUGCUGCACAUGGUAAAUCUGAGAGAUCAUGGCCAUUUAUCGCAU
GUUCAGAUUCUCGAUUUACAGAGGCUGAAUGGCAAAGAUAUAAGCAAAAUUGUAUCGCUGAUGGCAUACC
UGUUCCGACAAAACCAAAGUUGAUGCAAAAGUGUGCAGAGAUUAAUGCUCUUGUUAACAGACCUUGGACU
GAAGCCGAGCUACAAGAGAAGUUGAAGAAAUCCGGUGUAUUGACGGAAAAGUGGAAUGCAACCGAACGUG
UGCGUCUUAACAACGCUAUCAAGGAACAGAAAGCCCUUGGCAAUACCGAAAUGGAAGAAAAGUAUCGUUC
AGAACUUGAAGCGCUCGAGAAUUCCAAACUGGCUUAUGGAACCACCCUCAAAUCAACGCCGAAGAAGAUG
GUUCACUCUCAACAAGACCGACUUGCCGAAUUAAAUCGAUUAAAUCGUCGCAAAAAUAUCGAGGAAGUAC
GUCAAGCGCAAAUCAAUGAACGUCGUGCAGCUCGACAGGCUGAAGCAGCGAUUGCUCGUGGAGAAGUAGU
UGAUGAAGAUCACUCAAGGCGUGUCAAAACUCGUGCUACUUUCAAACAUGAUCAUACUGGAGGUAAGGAU
AGCGCAACUGCUACUCCAGUUAGUGGUACUUCGACCAAUAAUACCCCUAAACUUGUGGCUAAGAAAGAUG
CUUUACCGGUACCGAAUUUUAGUAAGCUACAAACGUCCAUGAAGGGUGGAGUUCCUGGAUUCAGAAAACC
UUUGAUGGACGAUGAUAUUAUUGCUAGUAUCGAUAUUGGUAUUAGUGAUGAUUUAGAGUUGUAA

FIG. 1P

SEQ ID NO:64

AUGACUCAACCUAUCGAAGUAUGGACGUCGAUUCCAGGUCCUAAUCCUUGGAAGAAACUAGCUAUCAUCG
ACCCCAAUACCGACUUGACACUUUGGGAAUCAGGCGCCAUCUUACAAUAUCUUGUCAAACAGUAUGAUAC
GGAGAAGAAGUUGACCUGCGAGAAGUUGCAAGACGAACAUCUCCUCAAUCAAUGGCUCAUGUUCCAAAUG
AGCGGUCAGGGCCCAUAUUUCGGACAAUGCGGCUGGUUCAAUAUCCUGCAUUCCGAGAAGAUCCCAUCCG
CCAUCGAGCGUUACAAUAACGAGGUCGCCCGCAUCCUCGGGGUAUUGGAACGUUCGCUCGAAGGAAAACA
AUGGCUUGUUGGUGACAAGUUUACCUUCGCUGAUCUUUCUUUUGCUCCUUGGAACGACAGAAUUGACACG
UUGUUUUCAUAUCCACCUUGUUCUUACGAAGAUAAUCUUCUUAGAAAGUUCCCCAACGUGGAUGCUUGGC
ACAAGAGAAUAACAGAGAGGCCAGCUUGGAAGAGGUCCAUGAUUGACAGGGAGAAGAGAAUGGCCACUUU
GGGCUUGAUGCCAAAUGGUAUGCCCAAGGGAGUCUCAAACAUGGAAGAAUACGUAGCCAAAAUGGAGGCC
GAAGGAGAUGCCUAG

SEQ ID NO:65

AUGGGUAUUCUCGAAACAAUUGCCGGGCCAUUGGCUCAAGAGAUUUCGCAAAGGUCAACCUUUGCUGUUG
UUGCUGCUGGCGUGGCAGCAUUCGUCGUUCUAUCUGUCAUUCUCAAUGUCCUGAAUCAAGUGUUAUUUGC
GAACCCCAAUGAACCACCAGUGGUCUUCCACUGGUUUCCAAUCAUUGGUAGCACCGUCACUUAUGGUAUG
GACCCUUAUAAAUUCUUCUUCGAGUGUCGCGCAAAGUACGGUGAUAUUUUCACAUUUGUCUUGCUCGGAA
AGAAGAAUACAGUAUAUCUUGGACGAAAUGGCAAUGACUUUAUUCUCAAUGGCAAGCUUAAGGAUCUCAA
UGCGGAGGAAAUAUAUACUGUUUUGACAACUCCCGUGUUUGGAAAGGAUGUAGUCUACGAUUGCCCCAAU
GCGAAAUUGAUGGAGCAAAAAAAGUUCAUGAAAAUUGGCUUGUCUACUGAAGCUUUCCGAUCCUACGUCC
CAAUUAUACAAAUGGAAGUGGAAAACUUCAUGAAACGUUCUUCGGUAUUCAAGGGACAAAAGGGAACUGC
CGAUAUUGGUCCCGCUAUGGCUGAAAUCACCAUCUAUACCGCUUCGCAUACUCUACAAGGAAAGGAAGUC
CGUGAUCGAUUUGAUACUACUUUCGCCUCUCUCUACCACGACCUUGAUAUGGGCUUUAGUCCCAUCAACU
UUAUGCUUCACUGGGCUCCUCUUCCUCACAACCGUGCCCGCGACCAUGCGCAGAGAACUGUCGCAGCAAC
AUAUAUGGAUAUUAUUAAAAAACGACGUGCUCAGGCUACGGAAGCCGACUUCAAAUCCGACAUUAUGUGG
CAAUUGAUGCGCUCGUCCUACAAAGAUGGAACCCCCGUUCCAGACCGAGAGAUUGCUCACAUGAUGAUCG
CUCUUCUCAUGGCCGGACAGCACUCUUCCUCAUCUUCUAUCUCUUGGAUUCUGCUUCGUCUUGCCUCACG
CCCAGAUAUCAUGGAAGAACUCUAUCAAGAACAAAUCCAAGUUCUGGGCGCCGAUCUCCCUGCUCUCAAG
UACGAGGACCUGGCCAAACUUCCUCUUCAUCAAAACAUCUUGAAGGAAACUCUCCGCAUCCACACUCCCA
UCCAUUCUAUUAUGCGCAAAGUCACAACACCAAUGCCAAUUAGCGGAACAAAAUAUGUCAUUCCAACCUC
GCAUACUCUUAUGGCAUCUCCUGGUUGUACAAGUCGAGACGCGGAUUACUUCCCAGAGCCACUUGAGUGG
GACCCUCAUAGAUGGGACAUUGGCUCGGGCCGUGUAAUUGGCAAUGAUCAGGACGAAGAAUUCCAAGAUU
AUGGCUAUGGAAUGAUCAGCAAAGGUGCUUCUAGUCCUUACCUUCCAUUCGGUGCUGGCAGACACAGGUG
UAUCGGUGAACAAUUCGCCAAUGUACAGCUCAUCACUAUCAUGGCCACUGUGGUUAGAAUGUUCAAAUUC
AAGAACGUUGAUGGCAGCAAGGAUGUCAUUGGUACUGAUUACACCAGUUUAUUCACCAGGCCAUUGGCGC
CAGCAGUUAUAGCAUGGGAGCGACGAUAA

SEQ ID NO:66

AUGUUCUCUGCACGUGCAACCCGAGCAGCCGCACAGCGCGUCGCUCGCUCUCAAUCUAUCCGAACUCCAU
UCCAACGACGCUUCGCCAGCAGCGAGAGCACCUUCGCUGGCGCCGAGGAUAACGCUUUCAACCGGGAGCG
UCAGGCCGUUAAGGAUCAUGCUGCUGCUACUAGUGAUCUCUGGAGAAAAUUGUCAAUCUAUGCUACGAUU
CCUUGCUUGAUCAUCGCAAGUGUCAAUGCUAAGAUCUUGUGA

SEQ ID NO:67

AUGUCACCAAAACCAAUACUGCCUCCACCAAAGGCAACUCUGCCAUCAUCCAACACCAUUCUACCUGCAG
AUGCAAAGACACGAUUAAAAAGAGCUGAGAAUGCUAGGAAACGUUUAGCAGGCGGCCGCACGGUUAUCGA
AGAAUCAGACGAAGAAGAAGAAUCGGAUGACGAGGCAGAAUGGGAAUGGAUAUACGAAAGCGGGAGUCAU
GAAGAAACUGCUUCAUCGCCGCAGACCAAUGCCAGAGGGGACGAGAGCACAGCUGCCAAAAGAACCCGUC
GACUUUCCAGAAGCACAGGAGCUAGGAGAAUUAUUGGUGCUAAGGCUGGAAAAAUUGUCUGCAAGAUUGC
AGAUUGUGUUUUGAUAAAUAACGAUACUUCGAAUACAAAUUGGGUUGGGGUUAUAUCAGGAUUCGAGGAA
GAUGAGGACUAUGAUGAGAAUGCUGAAUCAUAUCUUGAUAUAAUGAAAGCCAGUAUCUGGUGGUUCAGUA
GCCCAAAGGAUAUACACAGUAAGACAAGGAAGCGUUCAGAUUUCUUGGAAAACGAGUUGUACAUAUCCUC
UGAUCCCGAUACAAUCUCUCUGGCGACCAUUAAUGGCAUUGCUACGAUCUUAUCCGAAGAAGCUUUCAAA
GCCAAAUAUCCGACAGGAAAAAUACCUAGAAAUCGAAAAGAAAAUGGGAAAACAUUCAUAUGUCGUCGAG

FIG. 1Q

GAUUACACAGUAAAUCUGUUACAUAUACAGAUGAAUUUAUCUGGGAGGAAGUAUAUCAUAAUACGGAGGA
UAGUGUUGAAAAGUUGAUCGAGAAGAUAGAGAAUAGCAUACCAAAUAAGAAGAGAAAGAAGCCUAUAUUU
UCCAGGAAGAAGCACGAAGAUGAUGACGACGCAAGUGUCGCAUCUGAGCAAGAGGAUUCAGAAGUGGAUG
AAGAAAUCUUUACAACACCGCGGAAAAGGCAAAAGACUACGAAAGCUAUAACACCUCGAAAACCACGUAC
GCCUUCCAAACUACUAACUCCAAGCCAUAAGAGAAUUGUCGUCAAAAAGCCACUAGAAUUCACACCUUUA
GGAAUGCGUAUGCUCUCACCAUCCGUUAAUGCUUCCCCUUUUCAAACAGCUCGAUUACGUCUUCACGUAU
CGUCCGUUCCUGAUAAUCUCCCGUGUCGUGAGGAAGAGUUCUCAUCCGUCUACACCCAUCUCGCAGCUGC
UAUUACAGAUGGCACAGGCUCUUGUAUUUACAUCUCCGGAACUCCAGGAACUGGAAAAACUGCGACGGUU
CGGGAAGUUGUUGCACAGCUUAAUGCAUCCGUUCUGGCCGACGAAUUAGAUCCUUUCAUAUUCGUCGAAA
UUAACGGAAUGAAAGUAACUGAUCCGCAUCAAUCAUAUGCAUUAUUGUGGGAAGCUCUGAGAGGGGACAG
AGUAAGUCCAAGUCAUGCAUUAGAUCUACUAGAAAGGGAAUUCAGCAAGCCAUCACCUAGGAGAGAACCA
UGUGUGGUGUUGAUGGACGAAUUGGAUCAGCUAGUGACCAAAAACCAAAGUGUCAUGUAUAAUUUCUUCA
ACUGGCCUGGUCUGAGGCAUUCAAAACUAAUCGUGCUCGCCGUGGCCAAUACCAUGGAUUUACCUGAACG
UACUCUUUCCAAUAAGAUUUCUUCACGUCUUGGUCUAACUCGUAUAACCUUCCCCGGCUACACCCAUGAG
CAACUCCAAACCAUCAUAACUUCCCGUCUAGCUGACGUCCCCUCUCACCUAAUCCAUCCGGACGCGAUUC
AAUUUGCCUCCCGCAAAGUCGCCUCUGUUUCCGGGGACGCCCGCCGCGCUUUAGAUAUCUGUCGACGAGC
CGUCGAAAUCGCAGAAUCAGAAUCCGUUUCUAUUCCAAACACGCCUUCGAAAACUCCAGGUCGUGAAGAG
AAGAAGGGGAAAGGUGUGGUUAGCAUAGCCACGGUUAAAAAAGCAAUUAAUGAAGCUACGACUAGUCCGC
UUCAACAAUAUUUGAGAGCAUGUCCACUGGCUACAAAAAUGUUUCUUGCAGCUCUGGUGCUCAGAUUGAG
GAGGGCGGGAACGGGUGAGUGUUUGGUGGGUGAAGUGGUGGAUGAGUGUAGGAGAAUGGCAAAGUUGGAU
ACGGGGGGAAGUGUGGUUGGGUAUCUACUUGCAGGUGCGGAGAACAAGGGAGGUGGCGGGGGAAAAACGA
AAGGGGCACAAGUAGGAAAAGGAGCAAGAGUUCAAGGAAUGGGUGAAGCGGCAAUGGAGCUUAUGGAGGC
GGGCGUUAUAGGAAUAGAGGUUCGAAAAGCGGAGAGGAUGGGAAAGGUUAGGUUGAGUAUUGGGGAGGAG
GAUGUUAAGGUUGCUUUUAGGGAUGAUCCGGAGAUUAGGGGGUUGGGGUUUAUGGGGUAG

SEQ ID NO:68

AUGAAAACCAACUCACCCGUCCGUCCCCCCCGCAGCACCCUCACCCGUAUCGAAACAUUCACCCACCUCU
CCCUCACCAUCCUCUGCAUCUCCCUCCUCCUCAAAACCCUCUCCAGAGAAAAUGGCGAACCGCUCAUCGC
CUCGCUCGCUUUCAGCGGUAUCGCCUUCUCAUCCACCUAUAGCAUGAUUCGCUGGCUCGGACCUACAUUC
CUGCGCGCCGGACUCAAGGGUCGCGAUCUCUCGAAGCGGGAUCGUAGAGAGGUUCCUGAGACGAUGGGGG
CGAUUUGCGCGGUGGUUUAUUUGUUGGUGGUCAUUGUUUUUAUUCCGUUUCCGUUUUAUAAGGAUAUUGU
GGCGGCGACGAGUGGAGGGGGGAAUAGGGAUGUGGUCAGGGAGAUGGAGAUGGAGGUGCGUGAUGUGGUG
CAGAAUGGGAGGUUUUUGCAUCGGUUUCCGCAUAGUAAGCUAGCAUCCUAUCUCUCCGCGGUUCUGUCCC
UCCAAUCCGUAGUAAUUCUUGGAAUUGGCGACGACCUCUUCGAUAUCCGCUGGCGCCAUAAAUUUUUCAU
UCCCGCCAUUGCCAGUAUCCCUAUUCUGAUCGUCUAUUUUGUCGAUUUCGGCGUCACCCAAAUCGUCGUA
CCAAUUCCCUUACAACCCUAUCUGGGCGAGCUUUUCCAACUCGGUCCCCUCUACUACAUCUACAUGGCUG
GGAUCGCCAUCUUCUGCCCCAACAGUAUCAACAUCCUCGCCGGCAUAAACGGCAUCGAAGUAUCCCAAUC
CCUCGUCAUUGCACUCCUCCUCGUCCUAAACGAUACCCUCUACCUCCUAACACCGUACCCACACCCAGCA
ACCGACUCGCAUCUCUUCUCCCUCUAUAUGCUCCUCCCCUUCAUCGGAGUCUCCCUCGCCCUCCUCUCCC
ACAACUGGUACCCAUCCUCCGUCUUCGUAGGCGACACCUACUGCUAUUUCGCCGGCAUGGUCUUCGCCAU
CUGCGGCAUCCUAGGUCAUUUCUCCAAAACCCUCCUCCUCCUCCUCAUCCCCCAAACCUUCAACUUCCUC
UACAGCACUCCCCAACUCUUCCACCUAAUCCCCUGUCCCCGCCACCGUCUUCCCCGCUACAACUCGCAAA
CCAAUCUCCUCGAACCCUCCAUCACCCCCUGGCCUCAACCCCCUAAACCGCACCAAGCAGCGCUCCUCCA
CCUCCUCCAUAAACUGCAUCUCCUCUCCCUCACAUUGAACAACGAAGGCAAAAUAAUCGAAAGCAGUAAU
UUCACCCUCUUGAAUCUAUGGCUUGUAUGGUUUGGUCCCAGGAGAGAAGAUCGCUUAGCCUUAGAAAUCU
UGGCCAUGCAGACUAUUUGUGGAUUAUUCGGCUUGUUUCAUAGUCAUUGGAUCUCAAUAUCAAUCACCAA
CUGCACUCCCUCUUCAUAG

SEQ ID NO:69

AUGGCAAAAGUACCAGCAGUAAAGAGGCGCAAGCUUACACCUCCUCCAACAGAAGGGGAAGAUUCAUCGC
CAUCGACUUUAGAGAAUGCGCCAAGUUCGAAUGCGUUUUUCAAGACGGCUUCAAAAUGGAAUUUAGAGCA
AGAUUACGAAACGAGACCUCGGAAAGGCAAGAAGGAAAAGAAAGAAAGUACAAGGUUACCAAUCAAGACU
AAGGAAGGAUUGAUUCAGCAGGUUGAAGCGCCAGUGGAGGUCAAUGAAGAAGAAAGUGAUUUGGAAUGGA
UUGGCGCAGACGAUGUCGAGGAGGAUGAGGAACCCGAAGAGAAGGUUGAGGAAAAGCCUUCUGUGCCGAU
CCGACAGCAGAUUAUGGAGGCCAAAGAAGAAUUAGCACGUAUAGCAUUGAUGUUGAAUGAGGAUCCGGAA

FIG. 1R

GAAAAUGUGGGAGCAUUUAGAGCUAUAGCAGAAUUCGGGAAAUCGCAAAACCUUACGAUCAAGAAAUUAG
CAUUGGCCACACAAUUAGCUGUUUACAAAGAUGUUAUUCCAGGAUACAGGAUAAGACCUUUAUCGGAAGA
GAAUAUGGAAGAAAAAGUUUCGAAAGAAGUACGAAAAUUGAGAGCAUACGAACAGGCUCUUGUGGGUGGA
UAUCAAGGAUAUGUGAAGGAGUUGGCUAGGCUUGUAACUUCUGGGAGACCCCAGAAUAAGAGUGAUGGUG
GCGCGAGCCUGUCAACGGUUGCCAUAUCCUGUGCUUGCGCAUUAUUAGAAGCUGUACCCCAUUUCAAUUU
UCGAUCGGAUCUAUUGAAGAUAUUGGUAGGAAAGCUUAGUACAAGACAGGUGGACAAUGAAUUCGUGAAG
UGUCGAGAGACCAUCGAAACAUUGUUCAAGAAUGACGAUGAUGGGACCUCAUCCUUGGACGCGGUAAAUA
UUUUGACGAGAAUGAUGAAAGGGAGAGGAUACAGAGUGGACGAAAGCGUAUUGAAUACCUUCUUACAUUU
GAGGUUACUGUCGGAAUUUUCUGGAAAAGCCUCUACGAAUCAUGUCGAGCAUGAGGAAGACAGCUUUGGA
GGCAAGAAACUUAAGGAGAAGAGAGUAUUUCGUACCAAGAAGGAGAGAAAAUUGAUGAAGGAGCGCAAAG
CAGUUGAAAAAGAGAUGAUUCAAGCCGAUGCAACAGUCAGCCACGAAGAUCGAGAGAGAAUGCAAUCGGA
AACCCUGAAAUUGGUGUUUGUGACAUAUUUCCGCAUUCUGAAAGUUCGCUCCCCAUCUCUUAUGGGCGCU
GUACUUGAAGGUUUAGCAAGAUACGCUCAUCUCAUCAAUCAAGAUUUCUUCGGUGAUCUUCUGGAAGCGC
UUAAGGACCUUAUUGGUCAUGCUGAGACAGGAGAUGAUGUCGAGGAAACCGAAGCAGAAGAUGAGGAUUC
AGAAUCCUCCCGCAAUCUCACCCGUGAAUCUCUCCUUUGCAUCAUCACCGCCUUCGCUCUUCUCGAGGGU
CAAGAUGCCCACAAAGCUCAAGCAUCGCUAAGCUUAGAUUUAAGCUUCUUCAUCACUCAUCUCUACCGCA
CUUUACACGCCCUCUCCCUCAACCCUGAUAUCGAACUUUGCUCCAAAUCCCUUCAUCUACCAGACCCCAA
UGCACCCUCAACCUCCAACAACAAAGUUAACAUCCAAACCACCACCGUCCUCCUCCUCAAAUCCCUCUCA
UCUGUCCUCUUACCUCCUCUGGCCGCACGCGCAGUCCCACCUCUCAGAAUUGCAGCUUUCACUAAACAAC
UUAUGACAUGUUCUCUUCAAUUACCUGAGAAAUCCGCUACGGCCAUGAUGGCUUUAUUAGGGAAAGUUGC
GAAAAUUCAUGAGACCAAAGUCAAAAGCCUGUGGAAUACAGAGGAGAGGAAAGGUGAUGGAAUGUUUGAU
GGAUGUAGUGCGGAAGUUGAAGGAAGUAACCCGAUGGCGAGUACGAUUUGGGAGGGAGAACUGCUGAGGU
UGCAUUAUUGCCCUGCGGUUAGAGAAGGCGUGAAAGUGGUGGAGAAGAAUGUGAUUGGUUUGAGGUGA

SEQ ID NO:70

AUGGACAUUGAGGACCACAAGAUAGCCGUCAGCAUAUCUUCCAUAAGCAAUGUACUACAACGGAUACCGG
UAGCUUCAGAACGACGAUCGCUCCAAGUUGAAAACGAUGUCAAAAGCUUAGACGACCUCAGAUCAUUAAA
CCGGGCAAGCAAAUCCCACAUUGGAUCUUGGCUUCGUCAUGAAGUGGAAGCACAGAUGCUACCGUUAAGU
ACAGCAUCGAAUGAGUGGAAUAGCACAUCACCUGCGGCUCCUGAUACUUCUGUGCUUAUGGCGGCUACAU
UUGGCAUCGUGCGAGACUAUCUUGAAAUUAUAGAUGAUUUCUCUAUGCUCGCCGAUGUGAUAAAGAUUGC
CACGGCAUCAACGGAUACUCAAACUAUUGCAUCGUGCGCCGAUACACUUAAUAUGCACGCCGAGAUAUUU
GCGGCCAUCGGAGCAAUUAAGGGCUUGUUUGAUGUUCUUCUUAAUCGCUCGCGUUCAUUUGCAGACGAUC
GUGACAUCAUGCCACGAGUCAUUCUGGCAUCCUUGUUGGACCUCUCAUCGAGAAUUCCCGACAGUCAGAA
UCUUACCGCUCGGCUCGCUCGCCAACUUGCUUUGAGUGAUAGAAAGUGUGCCGCCGACGUUUGUUCUCCU
GUAUCGGAUCAUAUGGCGGGUAGAUCACAAAAUAACGAGGCUGAGGCCGAGAGUAGCGCAACGCAAAAAG
UGGGCACUAUUGUAGCCACGGAAUUGCUUGCUUUAAUUGCGGCACCAAUCACCAUACCGGAGAUUCUGAC
AUCGGACGAAGCAUAUCGCGUCCGACUUGUACAAAGUCGUAUGCAAAUUGACAACCCUGAACUUACAUUG
ACGGUUAUUCGGUCAGCAAUCGAGGUGUGCUCUACAGUUGUCCGCGAUAUAUCAUCCAACGCCCUCCACC
CCUUAAACGUCUUAGGUGGUCCAGCCAUGCAUGAAAUACUUCAGACGCUAGUCUUGAUUGGUGGUGAUAU
GGCCACAAAAAUCCUGGUGCAGCCUUUAUCACCUGGGUCUAUCGAUGAGGAUGCUUCCAAACUAAUGGUA
ACCGCGAUAAACAAGCUUUUGGCGCCUAUACAUCAGCGUGAAACCUCCAAUUUUUCAGUGUGUGAUGCGC
UAAAAUCUGCGAAUUAUCUGAAUCUACCAUUUUGCCAAUUGAAGGUGGCGUCUACCUUCCGCUCUGGGAA
AAGUUCCCAACCCACUUCCAGGAAUAUGGUCCCUCCUCAGCUCGAUGACCUUAAUCGUGCCGUUGAGUCU
GCUAUAAUGGCAGGGGGUACGACAUGGGCUUGCAUUAUACCAUCAUUAGAUUUUGCUACCAUACAAUACU
UACGACGCGGUGCUGAGACCCAAUUGCUUGCGCUUUUCCACGCUGCCAAGGCCUCAGGCUACAACGACAU
GUUGGGGGAAGAGCACCAAUUGACGAAAGCAGAAAAUUUGUUGGUCAUCCUCGACUUGACCAUAGACGAG
AUGUAUACGGAAAAAGCAAACGCGCCAUAUAAUUCGCAUAGCUGCUUUGCGGAUAUCAUAAACUUACUCA
GCGGCGCCUCGCAAUACGUCGCUAGCACACAACAAAACGGUUGUAAAAUUGCAUUCUUCACAAAAUGGCU
ACCGCUGCUGUUAUCAUUCACAGCCUCACAAACAGUAGUAGCAGUGCUUUGA

SEQ ID NO:71

AUGCGCAUUCCAAUUAUUCUUGGAGGCUUAGCCUCAAUCGCUCUUGCUUGCGACAACCCAGAUCACGAUG
CUUGCGCUAACGCUUUCACCGUUUCUGCCGCAGCUGCUGGUCCUUUCUGCGCCACAUACACUCAAUCGGC
AAACGCGGCAACGACCGAUCUUCCCGCUUUUGCUUCAGCAUGUGCAUACAAGCCAAAGAAAUUGUCUAGU
GCAUGCAGCUGUCUUAGCGUACCCACCACUUUGGCUACUGUUUCCAAGAGCUCAAGCGCCGCUGUCAGCG

FIG. 1S

CUUCGGCCACCACCUCGGUCACAGCUUUAACUCACGUAGCAGUAACCACCUCCGCUUCAAGCACUGCAGU
CGCAUCCAGCGCAUCUGCAGCUAGCGCAGUCAUCACACCGGCACCAUCAGCCCCAGCCGGAUGCACAGCA
ACAGCUUAUGCUGAUAUUGCCUCCGUUGUUGCCUCGUGCACAAACAUCGUCUUGGAUAACAUUUCAGCAC
CAGCAAGCUCCACCAUUGAUCUUCAAAAGCUCAAAGACGGAACUACCGUCACUUUCUCCGGAAAGACUAC
UUUUGGAACCACUUCCGAUGAUAGCUUCAACCCAAUUGUCGUCAAGGGUAAGAACAUUACCCUUACUGGA
GCUCCUGGACACGUCAUUGAUGGAAAUGGACCUGCAUACUGGGAUGGAGAGGGUUCUAACGGAGGAACCA
AGAAGCCUGAUCACUUCUUCGUUGUAAAGGAUAUCGUCAAUGGUGUUAUCAGCAACCUCAACAUCCAAAA
CUGGCCUACUCACUGCUUCGAUAUCACCGGUGCCAAGGGUCUUACCGUCUCAGGACUUACCCUUGAUAAC
UCUGCUGGAGAUGCCCCUAACUCAGCAUCUGGCAGCAAAGCAGCCGCACACAACAGUGAUGGAUUUGACA
UUUCCAACUCCGACUCUGUAACCCUCAAGAACAUUGUUGUCAAGAACCAAGAUGAUUGCGUCGCCGUCAC
AUCUGGUUCUAACAUCCUCGUAACCGGAAUGGCCUGUUCAGGUGGCCACGGUCUCUCUAUCGGAUCCGUC
GGUGGAAAAUCCAACAACACCGUCUCUGGCGUUACCUUCUCCGACUCCACCAUCACCAACAGUCAAAACG
GAUGCCGCAUCAAGUCUAACUCUGGCAAGACCGGUACCAUCGAGAACGUCACUUACAGCAACAUCCAGAU
GUCCAACAUCUCCAACUACGGUAUCGACGUUCAACAAGAUUACUUGAACGGUGGACCAACUGGCGAGCCA
ACAAACGGCGUUACCAUCUCCAACAUUGCCUUCUCCGGCGUCACCGGUACAACCACUAGCAACGCAUACA
ACUACUACAUCCUUUGCGGAAGUGGCUCCUGCUCCAACUUCAAAUUCACAGAUGUUAGCAUCUCUGGAGG
UGGAAAGACCUCAUCCUGCAACUUCCCAUCUUCUGGAUGCCCUGCAUAA

SEQ ID NO:72

AUGGCAAAACCAAGGGGGAUUAAAUUCAAUCAUCGAAAUGGCCGCGCCGGUAGUGAUGGUCGCAGAAGCA
GUUUCUCCGAUAUCAGUGAAGCUGCCUCGGAGCCAAGCUCUCCAAAGAUAGCAAAGGCAGAUGGUGCAAG
CGAUGAGAAGAAAGAGACUGAUAUAGUUGUGCCAUCGGAAUACGAGAAGAAGAAGCAGACCUUUAUUACA
CGAUCGAUAUGGACAUUUGUAAUGAUUGGGGGGUUUUUUGCGUCCAUGUUCAUGGGGCAUAUAUAUAUCA
UCGGGAUUGUCACCGCAGUGCAGAUAAUAUCCUUCAAGGAAGUCAUUGCGAUUGCAAAUGUACCCAGUCG
AGCUCGUCGAUUACGCUUCACAAAAGCUUUGAAUUGGUAUUGGUUGGCCACUACCAUGUACUUCUUAUAU
GGCGAGAGAUUCGUAUUCUUUGUUGCUUCUCUUCAAGCAGGUCACUACAAGUUUCAGUUCACGCAAUUCG
CCUGGACUCAUAUGGCCCUGUACCUUAUCGUGGUCCAAGCCCAUUUCAUCAUGAACAACGUCUUUGAGGG
AAUGAUUUGGUUCUUCUUACCGGUGUCUCUGGUCAUUUGCAAUGAUAUAUUUGCUUAUAUCUGUGGUAUC
ACGUUUGGCCGAACCCAGCUCAUUAAACUCUCACCAAAGAAGACCGUCGAAGGUUUUGUUGGUGCUUGGG
UUUUGACAAUCAUUUUUGGUGUAGGCAUGACUAACGUACUCAUGCGGUACAAAUACUUCAUUUGCCCUGU
AAAUGAUCUUGGUGCCAACCUAUGGACCGGUCUUGAGUGUACACCAAACCCUGUUUUCUUGCCUCAUACC
UAUCAACUCCCUAUUUGGUUUCCAGUCUGGAAAUCCUUCUCCAUGGCACCUAUGCAAGGUCACAUUCUUG
UUUUUGGAACUUUUGCAUCACUCAUUGCACCUUUCGGUGGAUUCUUUGCUUCUGGACUGAAACGCACUUU
CAAAAUCAAGGAUUUCGGCGACUCGAUUCCAGGACACGGCGGAAUCACGGAUCGAAUGGAUUGUCAAUUU
AUCAUGGGUUUCUUUGCCUACGUCUAUUUCCACAGCUUCAUUGCUAUCUACAAAGUAUCACUUGGUGGUG
UCAUUGAAACUGUGAUCAACGGUUUAACGCCAGAGGAGCAAAUGGAACUUGUUAAGGGAAUCAGCAAACA
UCUCUAUAACCAAGGGGUCAUCGGCGACAAGGUAUUGGACUGUCUAAACGUGGCAGCGAGUAAGAGAUAA

SEQ ID NO:73

AUGUCGUUCUGGGAUAAGUUGACAGGGCGAAAGCCAUCAUCAAAAGACACUUCUAGUGGCGGAUCAACCU
UGAAUACCCCAACUGACACAUUCACACCUACACCCUUCAACCCUCAAGAAGGUCAAGAUGUCAACUCUUU
UCUUACAGGGCCAGAGCUCAUAGAUCCAUCACAACUUCAUCCUUUGGCUGGUCUGAACCAACAGACUCUA
GACUAUCUAUCCCUCGAAGAAUCUACUCUCUCGGAUCUUCCAGGAUCGCAAUCUGCCUUACCCUCGAGAG
GUUGGUCGGACGAUUUAUGUUAUGGUACCGGUGUUACAUAUUUGACGGCACUAACUGUGGGUGGUGCUUG
GGGAUUACAGGAGGGUUUGAGGAGGUCUGCGACGCAACCACCAAAGUUACGAUUGAACUCGGUGCUGAAC
GCUGUUACGAGGCGAGGGCCAUUCUUGGGCAACUCGGCAGGAGUAAUUGCUAUGGUUUACAACGGAUUCA
ACUCAUUUAUCGGACAUAUGAGGGGCAGGCAUGAUUCGGCGAACAGUGUUCUUGCAGGUGCGCUGAGUGG
GAUGAUUUUUAAAAGUACAAGAGGAGUUCGACCUAUGAUGAUUUCCGGUGGGAUCGUGGCUUCUGUAGCC
GGCGCAUGGGCACAAGAAAAGCAAUAUUUUAAAUGA

SEQ ID NO:74

AUGUCAUCAAUACCACCACCUCCACCGCCUGGAUGGAGCUCUUCGGCGCCUCCAUCAAUGCCUCUGGGCG
CGCCACCCGGUGCUCCUCCUCCUCCAGGUUAUCGACCACCAGCGGAUCCACAUGUUGCGAAGUUUGCGCA
GAAGAAGAAGGACUGGUUACGAUCUCAGCGAAAUCGAUUCGGCGAAAAACGAAAAGGUGGCUUCGUAGAA

FIG. 1T

ACUCAGAAGGCUGACAUGCCCCCAGAGCAUCUGCGAAAGAUCGUUAAGGACAUUGGAGAUGUAUCACAAA
AGAAAUUCAGCAGCGACAAACGAAGUUAUCUCGGUGCACUCAAGUUUAUGCCACAUGCCGUCAUGAAAUU
GUUGGAGAACAUGCCAAUGCCUUGGGAGUCUGCGAGGGAGGUAAAGGUGCUGUACCAUGUCAAUGGUUGC
CUGACUUUGGUUAAUGAGAUUCCACGAGUUAUAGAACCAGUGUUCCACGCACAAUGGGCUACGAUGUGGA
UUUGUAUGAGAAGAGAGAAGAGUGACAGAAGACAUUUCAAGAGGAUGAGAUUCCCGCCAUUCGACGACGA
AGAGCCGCCCCUAUCAUGGUCGGAGAACAUUGAAGACGUCGAGCCAUUGGAGCCAAUUCAACUGGAACUU
GAUGAGGGGGAAGACGGCGCUGUUUUUGAAUGGUUUUACGAGAAUCGACCACUUCUUGAUACUCCACAUA
UCAACGGCCCGAGUUACAAGGAAUGGAACCUUACGUUACCUCAAAUGGCAACUUUAUAUCGAUUGAGUCG
GCCAUUAUUAAGUGAUUUGGUUGACAAGAACUACUUUCACAUGUUCGAGCUGAAAAGCUUCCAGACCGCC
AAAGCUUUGAAUGUUGCGAUUCCUGGUGGUCCUCGAUUCGAACCUUUAUAUAAAGAUGUGGAUCCUAAUG
AUGAAGAUUUUGGAGAGUUCAAUGCUAUUGAUCGCAUCAUCUUCCGAGCUCCAAUUAGGACAGAAUAUCG
UGUAGCAUAUCCCUACCUUUAUAAUUCACUGCCUCGCAGCGUUAAGCUUUCCUGGUUCUCGCAUCCGCAA
GUGGUAUACGUUCGUGCCGAGGAUCCAAGUUUACCAGCAUUUUAUUUCGAUCCCGUCAUCAACCCAAUCU
CUUCAAGAUCCGUCGCCCCUAAAAAUAUCACUAUCAGUCACGAAGACGAGAUAUUCGGACCCGGAAAUAA
UGAAGAGCCAGAAGAAGACGCUUUCAGAUUACCAGGUGGUGCCGAGCCAUUUCUAGCAGAUGAGGAGUUG
UACACAAGCGAGACCGCUUCAGCAAUCUCUUUGUGGUGGGCACCAUUUCCGUUUAAUCGAAGAUCUGGUC
GCAUGGUUCGGGCACAAGACGUACCUCUAGUAAAACAAUGGUACCUUGAGCAUUGCCCUCAGGGUCAACC
AGUAAAGGUCCGAGUUUCAUAUCAGAAGCUUCUGAAGACUUAUGUCUUGAACGAGCUGCAUAAGCGCAAG
CCGAAAGCACAGAGUAAACAGAGCUUGAUGAAGUCGUUGAAGCAAACGAAAUUCUUCCAGCAAACAACAA
UUGAUUGGGUUGAAGCUGGACUUCAAGUCUGCAGGCAGGGUUUCAAUAUGCUAAAUCUUCUGAUUCACCG
CAAGAACCUCACAUACCUACAUCUUGAUUAUAAUUUCAAUUUAAAGCCUGUUAAGACAUUGACAACAAAG
GAGAGAAAGAAGUCUCGAUUCGGCAAUGCAUUCCAUCUCAUGCGAGAGAUCUUGAAGAUGACCAAGCUCA
UCGUUGACGCACAAGUUCAGUAUCGCCUCGGCAAUAUCGAUGCUUUUCAACUCGCGGAUGGUAUUCUAUA
UGCUUUCAAUCAUGUUGGUCAGCUGACUGGAAUGUAUCGUUACAAGUACAAGCUGAUGCAUCAGAUUCGC
UCAUGUAAAGAUCUGAAGCAUUUAAUAUAUUAUCGAUUCAAUUCUGGACCCGUAGGUAAAGGACCUGGUU
GUGGUUUCUGGGCACCUGCUUGGAGAGUUUGGCUCUUUUUCAUGCGUGGUAUAAUUCCAUUACUUGAAAG
AUGGCUUGGAAACCUCCUCUCUAGGCAGUUUGAAGGACGUCAUAGCAAAGGUGUUGCAAAGACAGUCACG
AAACAACGUGUUGAGUCGCACUUUGAUCUUGAGUUGCGAGCAUCGGUCAUGGCCGAUCUUCUUGAUAUGA
UGCCGGAGGGUAUCAAGCAAAACAAGGUUCAAACGGUACUUCAACAUCUUUCAGAGGCAUGGAGAUGCUG
GAAGAGUAAUAUCCCUUGGAAGGUUCCAGGUUUACCGGCACCCAUCGAGAAUAUCAUUCUUCGUUAUGUG
AAGAGCAAGGCAGAUUGGUGGAUUUCUGUCGCUCACUACAAUCGUGAGCGUAUCCGUAGAGGAGCGACUG
UGGACAAAACCGUUGCAAAGAAGAAUCUUGGUCGUCUUACAAGACUUUGGCUCAAGGCUGAACAAGAGAG
GCAGCAUAACUAUAUGAAAGACGGUCCAUACGUGUCAUCCGAAGAAGCUGUCGCCAUCUAUACAACCACU
GUCCAUUGGCUGGAGUCACGAAAAUUCUCACCAAUUCCAUUCCCCAGUGUUUCCUACAAGCACGAUACCA
AAAUCCUCAUUCUUGCUUUGGAACGUCUUCGUGAAGCAUAUUCUGUGAAGGGACGAUUGAACCAAAGUCA
GCGUGAGGAACUGGCCUUGAUUGAGCAGGCUUAUGACAGUCCUGGAACCACUUUGGAGAGAAUCAAGCGC
UUCCUACUGACACAGAGAGCUUUUAAAGAAGUAGGAAUCGAUAUGAACGACAAUUAUAGCACAAUCAACC
CUGUAUAUGAUAUCGAGCCUGUGGAAAAGAUUAGUGAUGCCUAUCUUGACCAAUACCUCUGGUAUCAAGC
UGACCAGCGCCACCUUUUCCCUGCCUGGAUCAAGCCUUCCGAUUCCGAGGUCCCGCCCUUACUGACCUAU
AAAUGGGCUCAAGGUAUUAAUAACCUCGACAAAGUAUGGGAGACCGCAGAUGGAGAGUGUAAUGUUAUGA
UUGAAACACAAUUAUCCAAGGUAUACGAGAAGAUCGAUUUAACUCUUCUUAAUCGUUUGCUUCGACUUAU
CAUGGACCACAAUCUGGCUGAUUACAUAUCGUCCAAAAAUAACGUUCAAUUGACCUACAAAGAUAUGAAU
CACGUCAACAGUUACGGAAUGAUCAGAGGUCUUCAAUUCUCGGCCUUCGUUUUCCAGUACUAUGGACUUG
UUCUCGACCUCUUGCUUCUGGGCCUCCAACGCGCUAGUGAAAUUGCUGGACCACCAGCAGGUCCUAACGA
UUUCCUCCAAUUCCGCGAUCGGGAGACGGAAACAAGACAUCCAAUCCGUCUAUACACAAGAUAUAUUGAU
CGUAUCUGGGUAUUUUUCCGCUUUACGGCCGAUGAAUCGCGCGAUCUUAUCCAGCGCUUCCUUACAGAAC
AACCUGAUCCUAAUUUUGAAAAUGUCAUCGGCUACAAAAACAAGAAAUGCUGGCCAAGAGAUUCUAGAAU
GCGUCUCAUGAGACACGACGUCAAUCUUGGCCGUGCUGUUUUCUGGGACUUGAAGAACCGCUUACCAAGA
UCUGUUACCACGAUCGAAUGGGAUGAUACCUUUUCAAGCGUAUACAGCCGAGACAACCCGAAUUUACUUU
UCUCCAUGUGCGGUUUCGAAGUACGAAUUCUCCCUAAAAUUCGUAACCAGAAUGACGAAUUUCCUGUUAA
GGACAGCGUAUGGUCCUUGGUCGAUAACACCAGCAAGGAGAGAACGGCACAUGCAUUCUUGCAGGUCACA
GAGGAAGAUAUCGCGAAAUUCAAUAAUCGCAUUCGUCAAAUUUUGAUGUCAUCUGGGUCAACCACAUUCA
CAAAGAUUGCUAAUAAAUGGAAUACAACCUUGAUCGCCCUCUUCACAUAUUAUCGUGAAGCAGCUGUAUC
AACGGUCAACUUGCUGGAUACCAUUGUGAAAUGUGAGACGAAGAUUCAGACCAGAGUUAAGAUUGGUCUU
AAUUCUAAGAUGCCUUCUCGUUUCCCUCCUGCUGUUUUCUAUACACCAAAGGAACUUGGUGGUCUUGGUA
UGAUUUCCGGAUCACAUAUCCUCAUUCCUACGAGUGACAAAAGAUGGUCCAAGCAGACAGACGUUGGUGU
UACCCAUUAUCGUGCAGGAAUGAGCCAUGAUGAGGACACUCUUAUCCCUAACAUUUUCAGAUACAUCAUA

FIG. 1U

CCAUGGGAAGCUGAAUUUAUCGACUCCCAGCGUGUGUGGACUGAAUAUUCUCAGAAACGUCAGGAGGCGA
AUCAGCAAAAUCGAAGGUUGACACUUGAGGAUCUUGAAGAUAGUUGGGAUCGUGGAUUACCUCGUAUCAA
UACACUUUUCCAGAAAGAUAGAAGCACCUUGAGUUUUGAUAAAGGAUUCCGCGCACGUACUGAGUUCAAG
ACAUACCAACUUAUGAAGAGUAAUCCAUUUUGGUGGACUAGUCAACGUCACGAUGGUAAAUUGUGGAACC
UUAAUGCCUAUCGUACCGAUGUUAUCCAAGCACUUGGUGGUGUUGAAACCAUUCUUGAACAUACACUCUU
CAAGGCGACAGCAUUUCCAUCCUGGGAAGGUCUCUUUUGGGAAAAAGCAAGUGGAUUUGAAGAGCGAGUA
GACCCUUGCCCCCAAGUUUGA

SEQ ID NO:75

AUGUCUUCAGUUCCUCCAGUUUAUAUUGUCUCCGCUGUGAGAACACCCAUCGGUUCAUUCUUGGGUUCCC
UUUCUAGCAAGACUGCAACUGAACUCGGUGGCAUUGCCAUCAAGGCUGCCGUUGAACGUGUACCAGAAAU
CAAACCCGGAGAUGUUGAAGAAAUCUUCUUUGGUAAUGUUUUGUCCGCAAACUUGGGACAGAACCCUGCU
CGUCAAUGUGCUAUUGCUGGUGGCCUCACUGAAGGUGUAGUCUGCACCACCGUCAACAAAGUUUGUGCUU
CCGGCACUAAGGCAAUCAUCCUUGCCGCUCAGACAAUCAUCACUGGCAACGCCGAUAUAGUUGUAGCCGG
UGGUGCGGAGUCCAUGUCUAAUGUUCCUCAUUACCUUCCAACUCUCCGAAAUGGUGCCAAGUAUGGUGAC
CAAACUUUGGUAGACGGUGUUCUCAAGGACGGUCUCACCGAUGCCUACAACAAGAAAGAGCAUAUGGGAA
UGGCUGCUGAAGAGUGCCAUGUUGAUCACGACAUUAGCAGAGAGCAACAAGAUGAGUAUGCCAUCAAGUC
AUACCAAAAAGCACAAAAGGCGACUGAAGCCGGUAUCUUCAAGACCGAGAUUGUUCCAGUUGAAGUUAGC
GGUGGCCGCGGCAAGCCAAAUGUUAAGGUUGAGAAAGACGACGAGGUUAAGAACUUGAACAUUGAGAAGC
UCAAGGCCAUGAGACCUGCUUUCAUGCCUAACGGAGGAACUGUCACCGCACCAAAUGCUGCACCAAUUAA
CGACGGAGCUUCAGCUCUUGUCCUUGUCUCGGAGGCUAAGUUAAAGGAACUCGGUCUUAAACCUUUAGCA
AAGAUUCUUGGUUGGGGUGAUGCUGAAAAGGCACCAAGCAAGUUCACCACUGCACCAUCUUUGGCUAUUC
CUAAGGCUCUGAAGCAUGCCAAGAUUGAUGCUUCAGCCGUUGAUUACUAUGAGAUCAACGAGGCUUUCUC
GGUUGUCGCAUUGGCAAACAUGAAGAUUCUCGGAUUGGAUGAAUCCAAGGUCAACAUCCAUGGAGGUGCC
GUUGCUAUAGGACACCCUCUUGGUUGCUCCGGAGCUAGAAUCGUCACCACAUUGAUCAAUGUGUUGAGAG
AACAAAAGGCAAAGAUCGGUGUUGCUGGUAUCUGCAACGGUGGGGGUGGAGCCUCCGCUCUUGUCAUCGA
AUCUUUACAGUAA

SEQ ID NO:76

AUGGAUACUGCUUUCAAGACUUGGGAGCUUGACAACAACGUCCAGCUCGUGGAUCCCAACCGCGACGCCC
UCUACACCUACGACCCCAAAGAACAAAGAGCCAUCCAAGAUGCCAAACCAUGGAAGACCGACCCUCACCA
CUUCAAAAAUGUCCGGAUAUCCGCUGUCGCUCUUCUGAAAAUGGUUAUGCACGCCCGCUCUGGAGGUUCU
AUCGAAGUUAUGGGCUUAAUGCAGGGAAAGAUUGCGGGCGAUACUAUCAUCGUCACAGAUGCAUUCCGCC
UGCCUGUCGAAGGGACGGAAACUAGGGUGAAUGCUCAAGACGAAGCGAAUACAUAUAUGGUGGAGUACCU
ACAACACUGUAGAGAUCAGGGCAAGUUGGAGAAUGCUGUAGGCUGGUAUCAUAGUCACCCAGGCUAUGGU
UGUUGGUUGAGUGGCAUUGAUGUCGGGACGCAAGCGACGCAACAGAUGUUUUCGGACCCUUUCCUUGCUG
UGGUUAUUGAUCCUGAUCGCACUAUCUCUGCUGGGAAAGUCGAGAUCGGGGCAUUCAGAACCUAUCCUGA
UAAUUACAAGCCUGUGGAUGCAGGGUCUGGAGAUGGAUAUCAAACGAUUCCACUUGCAAAGAUUGAAGAU
UUUGGUGCACACAGCAGCCGAUAUUACUCUUUGGAGGUCUCACAUUUCAAGAGUUCAUUAGACACGCAUC
UUUUGGAGUUAUUAUGGAACAAAUAUUGGGUUCAGACAUUGAGUCAAAGUCCUUUAUUCACCAACCGCGA
AUACAGCAGCAAACAGAUGCUCGACUUGAGCUCCAAGAUUCGACAAGCUAGUUCUGGUAUUAUCCGUGGU
GGGAGAACACCUGCUGGAUCAUCGUUAAGCAAAGGGAUGGAUCAACAACUAAUGAAGGUAGUCAAGGAUA
GUAGCAAGAUUGCCGGUGAAGAGAUGACGGGUUUGAAGGCUGGCGAAGUCAAGGCACAGCUGUUCAAUGG
GUUAGGCGAGGCACCGAAGGCCACAGCUGCUCCACUUGCUCCGGCGGUGACGGCCGCAGAAUGA

SEQ ID NO:77

AUGUCUUCCGAACCACCUUUGGACCCCUACAAACCCUCUCUCUUCGAACUUUUGUCCUCCACCCAACUUU
CGUCACUCCUUCCUCCCUCUCUCCACUACCUCCUAACCAUCGCCACACACCGACAUCCGCGACACCUCCU
CCCAAUCCUCAACUCCUUUCACGAAAUCCACGCUCUCCUCUUCCUAGCAAUCGAACACCACUAUCUAACC
ACCUACUCUUCUUCAUUUGUCGAAAACUUUUAUUCUCUAAAACGGGAACGCGCCUUACCUGCGGCAGUAG
GCGAUCUGCGACUUACGGCCGAAGCAGCCAAUGCCAGUCUACGCGAAACGACAAAACUUACAAGAGGGGA
UGUAUGGAAGAAUCUUGCUGUGCUCGUUGGAAUUCCAUAUCUUAAACGUCGACUCGAUGAGUCUCAGGAG
AUCAAUGCACCGAGAGCACUUCUCGGCGCAAAUUAUACACGCAUGCCACCGAAUCCAACGCUCAAACAAC
GAUUUCUACAUUAUUAUCGUUGGUUUCUUACGAAUGUAUAUCCCAGCGUGAAUGCCGCAUAUUAUUUCAG

FIG. 1V

UAUCUUAGCAUUUAAUCUACGAUACCUAUUUUCGGGUUCGAAAUCUGGCUCUGGUGUAUAUUCCGAUCCA
UUUUUAUGGUUAAUAGGAACGCGGAUACGAAGAUUAAGUCAAGCAGAUUUCCAAGCUUUUGAAGCGAUUA
AGAAUGCUGCAUCUUCAAUACCAGGGUCGAAUCUAGGAAUAAGAAGUCUAUUGGAUCCAAGACUGGCAAU
GGGAAGAAUAGGUUCUGGAUUAAAACUAUUACUACCAACCAGUAUCUUUGCGCUGAAAUUCCUGGAAUGG
UGGCAUGCGAGUGAUUUUGCAAGACAAUUAUCUCGAAAAGCAAUAGAAGGAUUAGAAUUACCACCGCCUA
UUAUAUCAUACACCCCUUCUCCUGUAACAAAACCGGAGACCACGUCAAAAUCCUCAUCAGAAGAAAAACA
ACCGUCAGAAGUAGAAGAACCAACAAAUCCCCCGAUCUCAACCAUAACCCAACUCCCCAUCUAUGUCGUC
CCAGCUCCUUCCACCUCGACCUCCUUAGAAAAUUGCCCAAUCUGUCUCGAAGAAAUCACGACGCCAACCG
CGUGUCAAACAGGAUAUGUGUAUUGUUAUACUUGUAUUCAUAGGUGGAUUGAGGGGUUGCAUGAUUUGCA
GGAGAAGUUUAUGAAGGGUGAUGUGAAGGUGGAUGGGGAAGGGAAAGGAGAGAAGGGAAGAGAAGGGAAG
UGGGAAAGUGGAGCAGGCAGAUGUGCGGUUAGUGGACGGAGGGUAUUAGGGGGUGUCGGUGGGUUGAGGA
GGGUUUUGGUUUAA

SEQ ID NO:78

AUGGACGACAAGAAUGUAGAACUGGGCGUGAUCGCUAGGUCGUCGUCUUCUGAUGAGAUACCUCAUGCCG
GGUCGAAAGGCAAUACGAGCAGAGAUGAUCGAGAAAUGGCAUAUUUUGGAAAACGCCAGCAAUUGAAGCG
UAAUUUUGGCUUCUUGUCGAUUGCGGGUUUCGUCUGCAGUUUGCUUUCGACAUGGGAAGGAAUGUUCGCG
GUCUUCCUUUACGGAUUCCAAAACGGUGGACCGGCAGGAUUAGUUUACGGCUACAUCUUCUGUUUCUUUG
GUACAUUAUGUACGGUCGCCAGUUUGGCAGAGAUGUCCUCCAUGAUGCCCUUGAGCGGCGGCCAAUAUCA
CUGGGUGUCGAUUCUCGCCCCUAAGUCCCACGCAAAGUUCCUCUCAUACAUGACAGGCUGGCUUACGGUC
AUUGGCUGGCAAGCAGGCCAAGCAAGUGUUGCUUUCCUCUGCGCAACUUUAGUCCAGGCUUUGGUGAUAU
UAAAUCAUCCAACAUACGUCCCUGAGCGAUGGCAGGCAACUUUAAUAUUCUACGCGGUUCUAGCUGUUGU
UUUGUUUGUCAAUACGUAUUUGGCUCGCUGGUUGCCAAAGAUUGAAGGAUUGGUUCUUUGCAUCCAUAUA
CUUGGGUUCUUUGGUGUUCUUAUUCCUCUAGUCUACCUUGCAUCUCAUGGAAAGGCAAGUGAUGUCUUUG
CUACGUUUGUCAACGGUGGCGGUUGGUCCACAGAUGGAAUAUCAUUCUUUAUUGGCCUAAUUACAAGUGU
UUUCUCCUUUCUUGGAGCCGAUUCUGCUUGCCAUAUGAGUGAAGAAAUUCACAAUGCCUCUACCGUCGUG
CCUUGGGCAAUGAUCACCACGAUUCUUUUGAAUGGUGCUUUAGGUUUCGCACUGCUUAUAGCCCUUCUCU
UCUGUCUCGGAGAUAUCAAUGACGCUCUUACUUCUCCUACCGGCUUCCCGUUCAUUGAGAUAUUUAGGCA
AGCCACUAAUAGUAACUCUGCUGCAACUGGAAUGACAUGUAUCAUUGUGAUAAUCAUGUUUGCCGCGGCU
AUUGGUAUUAUGGCAACUGCCUCACGUUUAUUGUGGGCUUUCGCGAGAGACCAUGGAGUACCAGGUAGCG
CAUAUCUGUCUCGUGUGCACGAACCAACAGCACUACCAUUAUACUCUAUUCUAGUCAGUGCCAUUAUUUC
ACUCUUAUUGGCACUCAUAAAUAUUGGAAGCACUGCCGCAUUCAACUCGAUCGUCUCCGUUAAUGUUGCG
GCAUUCUUUACCUCCUACAUGAUACCUAUCGUCCUGAUCCUCAAAAAACGUCUUCGCAGAGAUCCAAUAA
AAGAUAAGAUACAUUGGGGACCGUGGAGAAUGGGUCCAAUUCUUGGUCCAAUUGUCAAUGUUGCCGGAUU
GAUUUAUUCGAUGAUCACCAUGUUUUUCAGCUUCUGGCCAAAUACACAAGUCGUUACUCCAGUUACCAUG
AAUUGGUCCUGUGUUAUUUUUGCUGCUGCUAUCAUUUACAGCGUGGUGUUCUACAUGAUUUGGGGUAAAC
ACUCUUACAAGUGGCCAAUAGUCGAUCCUAUAAGAAGGCAGCAGUAG

SEQ ID NO:79

AUGGCUACCACAGAUGUCUUUAUUAUAUCCUCUUCACCACCACGACGAUUGGUUUCUCAUAUUGCAUCUU
CACCGCCUUUACCUUCUUUAGACAAGAUGGUCAAUGGAAAGAAAGCCUCCAAUUUGCGACAAGGUAGUAG
UGUUGCACCUAUUCCUACAGGCGCGACAAUCUUUGCGAGCGCAUCCACUUUGUUGAGGGAAUCCUCUUCU
GGAUCUCUUCAAGGAUUUGACAACGCUCGGUCGUUUGUAACAUCUGCAGUGCAAGAUGAAAAUGAUUUGA
AGAAAUCUGCGAAACCGAAAGCCCCACGAAAAACGGCUCCAAAAAAGGAAGAUGGGACAGUUGAGAAGGU
GGCAAAAGCGUCUCGGAAGACUGUAAAAAAGAAGGAUAAAGAUGUUUCUGGGGAUUUCGUGGAUGAGUUA
GUGGGAGAGGCUGCAGAAAUUAUAGCCGAAAAGAAACCGCGAAAGCCUAGAGCUAAGAAGGGAGAUAAUG
CAGAAGGAAAGAGUGGGAGUGUUGCAGAGGCGACUGUGGAAAAGAAACCGCGCAAAUCUAGGGCUAAGAA
AGCGGUUGACGCUACAGGGGAGGAUCUUAAGGAGAAGGUACCGCGCAAAUCUAGGGCGAAGAAGACCGAU
GUUGAAGCUGGAAUUGAAACGGUGCCAAAGGAAAAGGCAGUGAGGAAGCCGCGAGCUAAGAACUCAGAUU
UGGACUCAAAUUUACAAUCUAAGAUGGUAAAAGGCAGAGUGACCAAGUCCGCCGUCAAUGCUUCAAAUAC
CCACAAAGUCGAAACCUCGAAAGCCGAUACAGGUAACAAACAUUUUGCGCCCAAUCCAAUCGUCGAAGAU
AUAGUUGCAGAUGAAGGAUUUGGUUUAGUGGAAGCAAUCAGGAGAAGAACGAAUUGGACUCCACCAAAAU
CGACAAAGGUUCCAAUUGACCUAGAGGAUAGUCCAGAAGCUCAAGAAUCAGACACCAGCAAAGGAUUCGC
AGAGUUAUUAGGGAGCUUUGGGUACAGCAGUUACCAGGCGGAUUCUAUAGAGAAGAGAAUAUCUUCUGGG
GUAUCCAAUGGAGCCGCUGCAACAAGGAAGAGGAAGUUAAUUGAGAUGGUCACUACAAAUAUUCCCAGAG

FIG. 1W

AACCCGGCUCAAAAACAACAAAAGAGAAAGCUGUCAAGAAGAAGGCUAGGACGCUCACCGACCUUGCCAC
AUCUGCUUAUGCAACAGCGGAAGAUGAUGAUAAUCUCCUUGAUGCGCCCACGCCUUUACUCCAAUACUUC
CCUCAUGCAGCUCCCGAAGGAUCCACAAAUAAUGGCUUCAAAAUACCGCCAAAGCCGAGGUCAAAGAGCC
CAAUGAAGAGAGUGCAAAAGUCAAAAACGGGCUCUGCAGAAGAGCCAAUUCUUCUAUCUCCAGAAUCUGC
GAUGAAGCAAGUUAGUAAUCAAGACUUUGUGUUCGGAACUUCAAGUCAAUUGGCAAGAGAAGACUCUCCU
UCAUUGCUACGCGAUUUACAUGAUGCUAUGCAAGCAUCUAAUGAAUUGGAUGAUUAUGAUGAUCCUUUCG
UUUCACCUCCUACCAAGAUAGCCGAGAGAGGAAAAGCUGUUGUUGCUGCGAAACGGAAUCUUUGGUCCAU
UGCUGCUCGUGAUAACCAUGGGGAUCUGAUGGAUGUUGAGACAAUAGACUUAGCACAUACACCAGUUGCG
AAGCCAGAUAGAAUCAUGCUAUCACAAAAGCCUUCAUCAUUAGUUACGCCCGGUAAGGAUGAUUGGUUUG
AUAUUGACGAAAUUGAAGAUAACCGACCCCCUUCUACUCAAGUUCCAUUAAGGGAGACGGGACCCAUUGA
GAGAUCUAUAAAUUUUCAACUUUUGGAUAGUCCUACUCAACCUAAGAAUACCUCGAAGGAUAGCUCCAAA
GUUUUCCCACAGAAGAAAGGCACCAAAUCUUUGGUUGAUAAAAGCACCACUCCUAAGAAGGUCGAUGCCU
CCAAGAUGCCUGACUACGAAUCAUUCACUACACCACAAUUGACGAGGGAAAUUCAAAAGUACAAGUUCAA
GCAAAUCAAAAGUCGAAAGAGGAUGAUUGAUUUAUUAAUUCAGUGUUAUGAAAGUCAGAAUCGUCCAGCC
UUGGGUGUUUUACAAGGAAACAUUCCAAUUAUCACGCAAAAUUCGUUGGAAAAGUCUAAAGAUGUAGCCG
ACUCAUCCACUCAGGUUAAGCCCACCAUUCCUUCUCCUCGACGAGGCCGAGCGAAGAAAGUUACUACCUC
CACUGCCUCAUUACCCAAAUCAAAGGCAAAGUCAAAGAUGACAGAUACAGUGGCAUUCUUAGAAAUGGAU
AGUGAUACACCACUCUCUAAGAUCCGCACACCCCAAAAAUCCCGUAAGGGAAAACAACCCCUCGAAGAUA
UUUUCGACUCUGAUCACCCUAUCACGCCAUCACCACCACGGCGAUCGGAUUCCCAAAUUCGAAAAAUAUC
CAAGGCUCUGGAAUUAUCUCCUGAUAAUAAUCAAGACGACGAAGCUCAGCAAGCACAGCUUUUCACUCAU
AUCUACACUGCAAUUACCAAAGCUCCACCUUCACAAGACCCAUUCAAUCCAAGCUGGCAUGAAAAAAUAC
UGCUCUAUGAUCCAAUUAUUCUAGAAGAUCUAGCAUCGUGGUUGAAUACUGGAGCACUGAGUAAAGUGGG
CUGGGAUGAAGAAGUAGCUCCAUUAGAAGUUAAGAAAUGGUGUGAAAGUAAGAGUAUUUGUUGUUUGUGG
AAGGAAAAUCAAGGUGGUGGGGCUAGGAGUAGAUAUUGA

SEQ ID NO:80

AUGGGAGAUUCAUCAGGUGCAGAUUAUAAACCGGAAUGGCUCGAGCUUGAAAAGUCCCUCGGUACACGUC
CUCUUCUCGUAGGUGAUCCAGCCAACAUCGAAGAGCAAUUCAACCGCCUACUCGCAGCGCUCGACGCUGA
GAGACCCCCUCCCGAUUCCUCAGUCCAGACUCGUGAUACUUCCGCAGACGGCGUUCCGUCCUACAAACAC
GCCUCGGAACUCCACGCCUCCCAAUCCCAACUCUUCACCAUUGGCAGCUCCGCCGGUGGCGGUCUAGCUC
UUACCGUAGCACACGACCUCAUCGGCGCAGGUAAAAAAUCACAAAUCAAAGGCAUCGUGGCCAUGGUCCC
CGUAACCGCACACCCAUCUUCUAUUCCCGCAGCCUACAAAAAUCACUACAAAUCCUACGAUGAGAAUGCG
CACGACGUGCCCAUUAUAGAUUUAGAUACGAUGAAUACGUUUUUCGGAGCCGUGGAUGCGGAUCCGCUGG
ACCCGAGAGUUUUUGUGACGCUCUCGAGUCAUUUGGAUGAGUUUCCUCCGACUUAUAUCGCUACGUGUGG
AAAGGAUCCGUUGCGGGAUGAUGGUCAGGUGUUGGAAAUGAUGUUGAAGGAUAAGGGUGUCACGACAAAG
AGUGAUUAUUAUGAAGGGGUACCGCAUUACUUUUGGCUUUUUCCCGGUAUUAAGGGUGGAGAUGAAUUUU
UGGAUAAUGUUAGUAAAGGGGUGAAGUUUGUUCUGGGUAUCUAG

SEQ ID NO:81

AUGUCAUCAAUACCACCACCUCCACCGCCUGGAUGGAGCUCUUCGGCGCCUCCAUCAAUGCCUCUGGGCG
CGCCACCCGGUGCUCCUCCUCCUCCAGGUUAUCGACCACCAGCGGAUCCACAUGUUGCGAAGUUUGCGCA
GAAGAAGAAGGACUGGUUACGAUCUCAGCGAAAUCGAUUCGGCGAAAAACGAAAAGGUGGCUUCGUAGAA
ACUCAGAAGGCUGACAUGCCCCCAGAGCAUCUGCGAAAGAUCGUUAAGGACAUUGGAGAUGUAUCACAAA
AGAAAUUCAGCAGCGACAAACGAAGUUAUCUCGGUGCACUCAAGUUUAUGCCACAUGCCGUCAUGAAAUU
GUUGGAGAACAUGCCAAUGCCUUGGGAGUCUGCGAGGGAGGUAAAGGUGCUGUACCAUGUCAAUGGUUGC
CUGACUUUGGUUAAUGAGAUUCCACGAGUUAUAGAACCAGUGUUCCACGCACAAUGGGCUACGAUGUGGA
UUUGUAUGAGAAGAGAGAAGAGUGACAGAAGACAUUUCAAGAGGAUGAGAUUCCCGCCAUUCGACGACGA
AGAGCCGCCCCUAUCAUGGUCGGAGAACAUUGAAGACGUCGAGCCAUUGGAGCCAAUUCAACUGGAACUU
GAUGAGGGGGAAGACGGCGCUGUUUUUGAAUGGUUUUACGAGAAUCGACCACUUCUUGAUACUCCACAUA
UCAACGGCCCGAGUUACAAGGAAUGGAACCUUACGUUACCUCAAAUGGCAACUUUAUAUCGAUUGAGUCG
GCCAUUAUUAAGUGAUUUGGUUGACAAGAACUACUUUCACAUGUUCGAGCUGAAAAGCUUCCAGACCGCC
AAAGCUUUGAAUGUUGCGAUUCCUGGUGGUCCUCGAUUCGAACCUUUAUAUAAAGAUGUGGAUCCUAAUG
AUGAAGAUUUUGGAGAGUUCAAUGCUAUUGAUCGCAUCAUCUUCCGAGCUCCAAUUAGGACAGAAUAUCG
UGUAGCAUAUCCCUACCUUUAUAAUUCACUGCCUCGCAGCGUUAAGCUUUCCUGGUUCUCGCAUCCGCAA
GUGGUAUACGUUCGUGCCGAGGAUCCAAGUUUACCAGCAUUUUAUUUCGAUCCCGUCAUCAACCCAAUCU

FIG. 1X

CUUCAAGAUCCGUCGCCCCUAAAAAUAUCACUAUCAGUCACGAAGACGAGAUAUUCGGACCCGGAAAUAA
UGAAGAGCCAGAAGAAGACGCUUUCAGAUUACCAGGUGGUGCCGAGCCAUUUCUAGCAGAUGAGGAGUUG
UACACAAGCGAGACCGCUUCAGCAAUCUCUUUGUGGUGGGCACCAUUUCCGUUUAAUCGAAGAUCUGGUC
GCAUGGUUCGGGCACAAGACGUACCUCUAGUAAAACAAUGGUACCUUGAGCAUUGCCCUCAGGGUCAACC
AGUAAAGGUCCGAGUUUCAUAUCAGAAGCUUCUGAAGACUUAUGUCUUGAACGAGCUGCAUAAGCGCAAG
CCGAAAGCACAGAGUAAACAGAGCUUGAUGAAGUCGUUGAAGCAAACGAAAUUCUUCCAGCAAACAACAA
UUGAUUGGGUUGAAGCUGGACUUCAAGUCUGCAGGCAGGGUUUCAAUAUGCUAAAUCUUCUGAUUCACCG
CAAGAACCUCACAUACCUACAUCUUGAUUAUAAUUUCAAUUUAAAGCCUGUUAAGACAUUGACAACAAAG
GAGAGAAAGAAGUCUCGAUUCGGCAAUGCAUUCCAUCUCAUGCGAGAGAUCUUGAAGAUGACCAAGCUCA
UCGUUGACGCACAAGUUCAGUAUCGCCUCGGCAAUAUCGAUGCUUUUCAACUCGCGGAUGGUAUUCUAUA
UGCUUUCAAUCAUGUUGGUCAGCUGACUGGAAUGUAUCGUUACAAGUACAAGCUGAUGCAUCAGAUUCGC
UCAUGUAAAGAUCUGAAGCAUUUAAUAUAUUAUCGAUUCAAUUCUGGACCCGUAGGUAAAGGACCUGGUU
GUGGUUUCUGGGCACCUGCUUGGAGAGUUUGGCUCUUUUUCAUGCGUGGUAUAAUUCCAUUACUUGAAAG
AUGGCUUGGAAACCUCCUCUCUAGGCAGUUUGAAGGACGUCAUAGCAAAGGUGUUGCAAAGACAGUCACG
AAACAACGUGUUGAGUCGCACUUUGAUCUUGAGUUGCGAGCAUCGGUCAUGGCCGAUCUUCUUGAUAUGA
UGCCGGAGGGUAUCAAGCAAAACAAGGUUCAAACGGUACUUCAACAUCUUUCAGAGGCAUGGAGAUGCUG
GAAGAGUAAUAUCCCUUGGAAGGUUCCAGGUUUACCGGCACCCAUCGAGAAUAUCAUUCUUCGUUAUGUG
AAGAGCAAGGCAGAUUGGUGGAUUUCUGUCGCUCACUACAAUCGUGAGCGUAUCCGUAGAGGAGCGACUG
UGGACAAAACCGUUGCAAAGAAGAAUCUUGGUCGUCUUACAAGACUUUGGCUCAAGGCUGAACAAGAGAG
GCAGCAUAACUAUAUGAAAGACGGUCCAUACGUGUCAUCCGAAGAAGCUGUCGCCAUCUAUACAACCACU
GUCCAUUGGCUGGAGUCACGAAAAUUCUCACCAAUUCCAUUCCCCAGUGUUUCCUACAAGCACGAUACCA
AAAUCCUCAUUCUUGCUUUGGAACGUCUUCGUGAAGCAUAUUCUGUGAAGGGACGAUUGAACCAAAGUCA
GCGUGAGGAACUGGCCUUGAUUGAGCAGGCUUAUGACAGUCCUGGAACCACUUUGGAGAGAAUCAAGCGC
UUCCUACUGACACAGAGAGCUUUUAAAGAAGUAGGAAUCGAUAUGAACGACAAUUAUAGCACAAUCAACC
CUGUAUAUGAUAUCGAGCCUGUGGAAAAGAUUAGUGAUGCCUAUCUUGACCAAUACCUCUGGUAUCAAGC
UGACCAGCGCCACCUUUUCCCUGCCUGGAUCAAGCCUUCCGAUUCCGAGGUCCCGCCCUUACUGACCUAU
AAAUGGGCUCAAGGUAUUAAUAACCUCGACAAAGUAUGGGAGACCGCAGAUGGAGAGUGUAAUGUUAUGA
UUGAAACACAAUUAUCCAAGGUAUACGAGAAGAUCGAUUUAACUCUUCUUAAUCGUUUGCUUCGACUUAU
CAUGGACCACAAUCUGGCUGAUUACAUAUCGUCCAAAAAUAACGUUCAAUUGACCUACAAAGAUAUGAAU
CACGUCAACAGUUACGGAAUGAUCAGAGGUCUUCAAUUCUCGGCCUUCGUUUUCCAGUACUAUGGACUUG
UUCUCGACCUCUUGCUUCUGGGCCUCCAACGCGCUAGUGAAAUUGCUGGACCACCAGCAGGUCCUAACGA
UUUCCUCCAAUUCCGCGAUCGGGAGACGGAAACAAGACAUCCAAUCCGUCUAUACACAAGAUAUAUUGAU
CGUAUCUGGGUAUUUUUCCGCUUUACGGCCGAUGAAUCGCGCGAUCUUAUCCAGCGCUUCCUUACAGAAC
AACCUGAUCCUAAUUUUGAAAAUGUCAUCGGCUACAAAAACAAGAAAUGCUGGCCAAGAGAUUCUAGAAU
GCGUCUCAUGAGACACGACGUCAAUCUUGGCCGUGCUGUUUUCUGGGACUUGAAGAACCGCUUACCAAGA
UCUGUUACCACGAUCGAAUGGGAUGAUACCUUUUCAAGCGUAUACAGCCGAGACAACCCGAAUUUACUUU
UCUCCAUGUGCGGUUUCGAAGUACGAAUUCUCCCUAAAAUUCGUAACCAGAAUGACGAAUUUCCUGUUAA
GGACAGCGUAUGGUCCUUGGUCGAUAACACCAGCAAGGAGAGAACGGCACAUGCAUUCUUGCAGGUCACA
GAGGAAGAUAUCGCGAAAUUCAAUAAUCGCAUUCGUCAAAUUUUGAUGUCAUCUGGGUCAACCACAUUCA
CAAAGAUUGCUAAUAAAUGGAAUACAACCUUGAUCGCCCUCUUCACAUAUUAUCGUGAAGCAGCUGUAUC
AACGGUCAACUUGCUGGAUACCAUUGUGAAAUGUGAGACGAAGAUUCAGACCAGAGUUAAGAUUGGUCUU
AAUUCUAAGAUGCCUUCUCGUUUCCCUCCUGCUGUUUUCUAUACACCAAAGGAACUUGGUGGUCUUGGUA
UGAUUUCCGGAUCACAUAUCCUCAUUCCUACGAGUGACAAAAGAUGGUCCAAGCAGACAGACGUUGGUGU
UACCCAUUAUCGUGCAGGAAUGAGCCAUGAUGAGGACACUCUUAUCCCUAACAUUUUCAGAUACAUCAUA
CCAUGGGAAGCUGAAUUUAUCGACUCCCAGCGUGUGUGGACUGAAUAUUCUCAGAAACGUCAGGAGGCGA
AUCAGCAAAAUCGAAGGUUGACACUUGAGGAUCUUGAAGAUAGUUGGGAUCGUGGAUUACCUCGUAUCAA
UACACUUUUCCAGAAAGAUAGAAGCACCUUGAGUUUUGAUAAAGGAUUCCGCGCACGUACUGAGUUCAAG
ACAUACCAACUUAUGAAGAGUAAUCCAUUUUGGUGGACUAGUCAACGUCACGAUGGUAAAUUGUGGAACC
UUAAUGCCUAUCGUACCGAUGUUAUCCAAGCACUUGGUGGUGUUGAAACCAUUCUUGAACAUACACUCUU
CAAGGCGACAGCAUUUCCAUCCUGGGAAGGUCUCUUUUGGGAAAAAGCAAGUGGAUUUGAAGAGCGAGUA
GACCCUUGCCCCCAAGUUUGA

SEQ ID NO:82

AUGGACAUUGAGGACCACAAGAUAGCCGUCAGCAUAUCUUCCAUAAGCAAUGUACUACAACGGAUACCGG
UAGCUUCAGAACGACGAUCGCUCCAAGUUGAAAACGAUGUCAAAAGCUUAGACGACCUCAGAUCAUUAAA
CCGGGCAAGCAAAUCCCACAUUGGAUCUUGGCUUCGUCAUGAAGUGGAAGCACAGAUGCUACCGUUAAGU

FIG. 1Y

ACAGCAUCGAAUGAGUGGAAUAGCACAUCACCUGCGGCUCCUGAUACUUCUGUGCUUAUGGCGGCUACAU
UUGGCAUCGUGCGAGACUAUCUUGAAAUUAUAGAUGAUUUCUCUAUGCUCGCCGAUGUGAUAAAGAUUGC
CACGGCAUCAACGGAUACUCAAACUAUUGCAUCGUGCGCCGAUACACUUAAUAUGCACGCCGAGAUAUUU
GCGGCCAUCGGAGCAAUUAAGGGCUUGUUUGAUGUUCUUCUUAAUCGCUCGCGUUCAUUUGCAGACGAUC
GUGACAUCAUGCCACGAGUCAUUCUGGCAUCCUUGUUGGACCUCUCAUCGAGAAUUCCCGACAGUCAGAA
UCUUACCGCUCGGCUCGCUCGCCAACUUGCUUUGAGUGAUAGAAAGUGUGCCGCCGACGUUUGUUCUCCU
GUAUCGGAUCAUAUGGCGGGUAGAUCACAAAAUAACGAGGCUGAGGCCGAGAGUAGCGCAACGCAAAAAG
UGGGCACUAUUGUAGCCACGGAAUUGCUUGCUUUAAUUGCGGCACCAAUCACCAUACCGGAGAUUCUGAC
AUCGGACGAAGCAUAUCGCGUCCGACUUGUACAAAGUCGUAUGCAAAUUGACAACCCUGAACUUACAUUG
ACGGUUAUUCGGUCAGCAAUCGAGGUGUGCUCUACAGUUGUCCGCGAUAUAUCAUCCAACGCCCUCCACC
CCUUAAACGUCUUAGGUGGUCCAGCCAUGCAUGAAAUACUUCAGACGCUAGUCUUGAUUGGUGGUGAUAU
GGCCACAAAAAUCCUGGUGCAGCCUUUAUCACCUGGGUCUAUCGAUGAGGAUGCUUCCAAACUAAUGGUA
ACCGCGAUAAACAAGCUUUUGGCGCCUAUACAUCAGCGUGAAACCUCCAAUUUUUCAGUGUGUGAUGCGC
UAAAAUCUGCGAAUUAUCUGAAUCUACCAUUUUGCCAAUUGAAGGUGGCGUCUACCUUCCGCUCUGGGAA
AAGUUCCCAACCCACUUCCAGGAAUAUGGUCCCUCCUCAGCUCGAUGACCUUAAUCGUGCCGUUGAGUCU
GCUAUAAUGGCAGGGGGUACGACAUGGGCUUGCAUUAUACCAUCAUUAGAUUUUGCUACCAUACAAUACU
UACGACGCGGUGCUGAGACCCAAUUGCUUGCGCUUUUCCACGCUGCCAAGGCCUCAGGCUACAACGACAU
GUUGGGGGAAGAGCACCAAUUGACGAAAGCAGAAAAUUUGUUGGUCAUCCUCGACUUGACCAUAGACGAG
AUGUAUACGGAAAAAGCAAACGCGCCAUAUAAUUCGCAUAGCUGCUUUGCGGAUAUCAUAAACUUACUCA
GCGGCGCCUCGCAAUACGUCGCUAGCACACAACAAAACGGUUGUAAAAUUGCAUUCUUCACAAAAUGGCU
ACCGCUGCUGUUAUCAUUCACAGCCUCACAAACAGUAGUAGCAGUGCUUUGA

SEQ ID NO:83

AUGGCGGCUGAAUUAAUCGACUUUUAUCAGAACUUUCUACGAACGGGAUUAUACAAUGGCGGAUAUGAUG
AUGAACUUCUCGCUCUUGCAGGAGAUGAUUCUUCUGGAGAAGAACAGGUCGCAACAAAUGAUGGGGGAAG
ACACAGUUCUUCAUCGCCUGAUCGUAAUGGUGCGGUAAAGAGUGCAGCUAAGAAAGGUGGAAAGAAGGGG
GGUAGACGAAAUGAUGAUUCUGAGGAAGAAGGUGAAGCUUCUUCCGGUGAUGAAUCUGUUCGUUCGGAAC
GAUCAGCUCCAAUGGAUGAAUCUGAUUCCGAUUCCGAUGGCCCAAGUUUUCGCGAUGAUGCUGAUCGAUA
UCCUCUCGAAGGUCGUUUUAUGAAUGCAGCCGAUAAAGCAAGUAUUAUGUCUAUGCCUGAAAUUCAACGU
GAGCAGGUCUUGGCUGAUCGUGCCCAAGAGAUUGAAAGGGACCGUCAAAAUAGAGCACUUCGUCAACUGU
UAAAUGCCCGUGAUGCAGAGAAUAAAAAAGCGGACAAAAAGCGCAAGGCAGGUACCGCGGAUUUGGAGGA
AAACCAGCGCAAAACGUCUCGUCAACGUACCAAGCUUGGUGGUGGGAAGGUUGGGGAAGCUAGCACUGGA
AUUGACAGUCUUAAGCGUGCAAGAGCUGAGAAAAACGAUCGACAACGUCGUCGCGAUCAAGAUAAGGAGC
GCCGUGGGGAUGAUGGUCGAAGAGAUACCCGGGACGAUUAUUCAGAUGACGAUGGUGAUGGGGAUAGUGA
GGUUGAAUGGACAGCAUCAAAGUCAAAGAAAAGGUCUGCAUCUCCAGAUUACCGAGAUGCAGAACCGGCG
GUUCUCUAUGAUCUUGAACGAGUUCGAGUUGGUAGAAGUAGAUUUGCCAUGGUCUGCUUUUAUCCUGGGU
UUGAUGAAGCUAUUACUGGAUGCUUUGUUCGAGUAAAUAUUGGUGUUGAUAAGGAGACAAAUCAAAACCU
UUAUCGCAUGGGACUUGUUAAAGGCUUCAAAGAAGAUAAACCAUACGCUAUGAUGUCUAGUAACGGAAAG
CAAUUUUCGACAACACAAUAUGUGAUUGCUGCACAUGGUAAAUCUGAGAGAUCAUGGCCAUUUAUCGCAU
GUUCAGAUUCUCGAUUUACAGAGGCUGAAUGGCAAAGAUAUAAGCAAAAUUGUAUCGCUGAUGGCAUACC
UGUUCCGACAAAACCAAAGUUGAUGCAAAAGUGUGCAGAGAUUAAUGCUCUUGUUAACAGACCUUGGACU
GAAGCCGAGCUACAAGAGAAGUUGAAGAAAUCCGGUGUAUUGACGGAAAAGUGGAAUGCAACCGAACGUG
UGCGUCUUAACAACGCUAUCAAGGAACAGAAAGCCCUUGGCAAUACCGAAAUGGAAGAAAAGUAUCGUUC
AGAACUUGAAGCGCUCGAGAAUUCCAAACUGGCUUAUGGAACCACCCUCAAAUCAACGCCGAAGAAGAUG
GUUCACUCUCAACAAGACCGACUUGCCGAAUUAAAUCGAUUAAAUCGUCGCAAAAAUAUCGAGGAAGUAC
GUCAAGCGCAAAUCAAUGAACGUCGUGCAGCUCGACAGGCUGAAGCAGCGAUUGCUCGUGGAGAAGUAGU
UGAUGAAGAUCACUCAAGGCGUGUCAAAACUCGUGCUACUUUCAAACAUGAUCAUACUGGAGGUAAGGAU
AGCGCAACUGCUACUCCAGUUAGUGGUACUUCGACCAAUAAUACCCCUAAACUUGUGGCUAAGAAAGAUG
CUUUACCGGUACCGAAUUUUAGUAAGCUACAAACGUCCAUGAAGGGUGGAGUUCCUGGAUUCAGAAAACC
UUUGAUGGACGAUGAUAUUAUUGCUAGUAUCGAUAUUGGUAUUAGUGAUGAUUUAGAGUUGUAA

SEQ ID NO:84

AUGGACGACAAGAAUGUAGAACUGGGCGUGAUCGCUAGGUCGUCGUCUUCUGAUGAGAUACCUCAUGCCG
GGUCGAAAGGCAAUACGAGCAGAGAUGAUCGAGAAAUGGCAUAUUUUGGAAAACGCCAGCAAUUGAAGCG
UAAUUUUGGCUUCUUGUCGAUUGCGGGUUUCGUCUGCAGUUUGCUUUCGACAUGGGAAGGAAUGUUCGCG

FIG. 1Z

GUCUUCCUUUACGGAUUCCAAAACGGUGGACCGGCAGGAUUAGUUUACGGCUACAUCUUCUGUUUCUUUG
GUACAUUAUGUACGGUCGCCAGUUUGGCAGAGAUGUCCUCCAUGAUGCCCUUGAGCGGCGGCCAAUAUCA
CUGGGUGUCGAUUCUCGCCCCUAAGUCCCACGCAAAGUUCCUCUCAUACAUGACAGGCUGGCUUACGGUC
AUUGGCUGGCAAGCAGGCCAAGCAAGUGUUGCUUUCCUCUGCGCAACUUUAGUCCAGGCUUUGGUGAUAU
UAAAUCAUCCAACAUACGUCCCUGAGCGAUGGCAGGCAACUUUAAUAUUCUACGCGGUUCUAGCUGUUGU
UUUGUUUGUCAAUACGUAUUUGGCUCGCUGGUUGCCAAAGAUUGAAGGAUUGGUUCUUUGCAUCCAUAUA
CUUGGGUUCUUUGGUGUUCUUAUUCCUCUAGUCUACCUUGCAUCUCAUGGAAAGGCAAGUGAUGUCUUUG
CUACGUUUGUCAACGGUGGCGGUUGGUCCACAGAUGGAAUAUCAUUCUUUAUUGGCCUAAUUACAAGUGU
UUUCUCCUUUCUUGGAGCCGAUUCUGCUUGCCAUAUGAGUGAAGAAAUUCACAAUGCCUCUACCGUCGUG
CCUUGGGCAAUGAUCACCACGAUUCUUUUGAAUGGUGCUUUAGGUUUCGCACUGCUUAUAGCCCUUCUCU
UCUGUCUCGGAGAUAUCAAUGACGCUCUUACUUCUCCUACCGGCUUCCCGUUCAUUGAGAUAUUUAGGCA
AGCCACUAAUAGUAACUCUGCUGCAACUGGAAUGACAUGUAUCAUUGUGAUAAUCAUGUUUGCCGCGGCU
AUUGGUAUUAUGGCAACUGCCUCACGUUUAUUGUGGGCUUUCGCGAGAGACCAUGGAGUACCAGGUAGCG
CAUAUCUGUCUCGUGUGCACGAACCAACAGCACUACCAUUAUACUCUAUUCUAGUCAGUGCCAUUAUUUC
ACUCUUAUUGGCACUCAUAAAUAUUGGAAGCACUGCCGCAUUCAACUCGAUCGUCUCCGUUAAUGUUGCG
GCAUUCUUUACCUCCUACAUGAUACCUAUCGUCCUGAUCCUCAAAAAACGUCUUCGCAGAGAUCCAAUAA
AAGAUAAGAUACAUUGGGGACCGUGGAGAAUGGGUCCAAUUCUUGGUCCAAUUGUCAAUGUUGCCGGAUU
GAUUUAUUCGAUGAUCACCAUGUUUUUCAGCUUCUGGCCAAAUACACAAGUCGUUACUCCAGUUACCAUG
AAUUGGUCCUGUGUUAUUUUUGCUGCUGCUAUCAUUUACAGCGUGGUGUUCUACAUGAUUUGGGGUAAAC
ACUCUUACAAGUGGCCAAUAGUCGAUCCUAUAAGAAGGCAGCAGUAG

SEQ ID NO:85

AUGGCAAAAGUACCAGCAGUAAAGAGGCGCAAGCUUACACCUCCUCCAACAGAAGGGGAAGAUUCAUCGC
CAUCGACUUUAGAGAAUGCGCCAAGUUCGAAUGCGUUUUUCAAGACGGCUUCAAAAUGGAAUUUAGAGCA
AGAUUACGAAACGAGACCUCGGAAAGGCAAGAAGGAAAAGAAAGAAAGUACAAGGUUACCAAUCAAGACU
AAGGAAGGAUUGAUUCAGCAGGUUGAAGCGCCAGUGGAGGUCAAUGAAGAAGAAAGUGAUUUGGAAUGGA
UUGGCGCAGACGAUGUCGAGGAGGAUGAGGAACCCGAAGAGAAGGUUGAGGAAAAGCCUUCUGUGCCGAU
CCGACAGCAGAUUAUGGAGGCCAAAGAAGAAUUAGCACGUAUAGCAUUGAUGUUGAAUGAGGAUCCGGAA
GAAAAUGUGGGAGCAUUUAGAGCUAUAGCAGAAUUCGGGAAAUCGCAAAACCUUACGAUCAAGAAAUUAG
CAUUGGCCACACAAUUAGCUGUUUACAAAGAUGUUAUUCCAGGAUACAGGAUAAGACCUUUAUCGGAAGA
GAAUAUGGAAGAAAAAGUUUCGAAAGAAGUACGAAAAUUGAGAGCAUACGAACAGGCUCUUGUGGGUGGA
UAUCAAGGAUAUGUGAAGGAGUUGGCUAGGCUUGUAACUUCUGGGAGACCCCAGAAUAAGAGUGAUGGUG
GCGCGAGCCUGUCAACGGUUGCCAUAUCCUGUGCUUGCGCAUUAUUAGAAGCUGUACCCCAUUUCAAUUU
UCGAUCGGAUCUAUUGAAGAUAUUGGUAGGAAAGCUUAGUACAAGACAGGUGGACAAUGAAUUCGUGAAG
UGUCGAGAGACCAUCGAAACAUUGUUCAAGAAUGACGAUGAUGGGACCUCAUCCUUGGACGCGGUAAAUA
UUUUGACGAGAAUGAUGAAAGGGAGAGGAUACAGAGUGGACGAAAGCGUAUUGAAUACCUUCUUACAUUU
GAGGUUACUGUCGGAAUUUUCUGGAAAAGCCUCUACGAAUCAUGUCGAGCAUGAGGAAGACAGCUUUGGA
GGCAAGAAACUUAAGGAGAAGAGAGUAUUUCGUACCAAGAAGGAGAGAAAAUUGAUGAAGGAGCGCAAAG
CAGUUGAAAAAGAGAUGAUUCAAGCCGAUGCAACAGUCAGCCACGAAGAUCGAGAGAGAAUGCAAUCGGA
AACCCUGAAAUUGGUGUUUGUGACAUAUUUCCGCAUUCUGAAAGUUCGCUCCCCAUCUCUUAUGGGCGCU
GUACUUGAAGGUUUAGCAAGAUACGCUCAUCUCAUCAAUCAAGAUUUCUUCGGUGAUCUUCUGGAAGCGC
UUAAGGACCUUAUUGGUCAUGCUGAGACAGGAGAUGAUGUCGAGGAAACCGAAGCAGAAGAUGAGGAUUC
AGAAUCCUCCCGCAAUCUCACCCGUGAAUCUCUCCUUUGCAUCAUCACCGCCUUCGCUCUUCUCGAGGGU
CAAGAUGCCCACAAAGCUCAAGCAUCGCUAAGCUUAGAUUUAAGCUUCUUCAUCACUCAUCUCUACCGCA
CUUUACACGCCCUCUCCCUCAACCCUGAUAUCGAACUUUGCUCCAAAUCCCUUCAUCUACCAGACCCCAA
UGCACCCUCAACCUCCAACAACAAAGUUAACAUCCAAACCACCACCGUCCUCCUCCUCAAAUCCCUCUCA
UCUGUCCUCUUACCUCCUCUGGCCGCACGCGCAGUCCCACCUCUCAGAAUUGCAGCUUUCACUAAACAAC
UUAUGACAUGUUCUCUUCAAUUACCUGAGAAAUCCGCUACGGCCAUGAUGGCUUUAUUAGGGAAAGUUGC
GAAAAUUCAUGAGACCAAAGUCAAAAGCCUGUGGAAUACAGAGGAGAGGAAAGGUGAUGGAAUGUUUGAU
GGAUGUAGUGCGGAAGUUGAAGGAAGUAACCCGAUGGCGAGUACGAUUUGGGAGGGAGAACUGCUGAGGU
UGCAUUAUUGCCCUGCGGUUAGAGAAGGCGUGAAAGUGGUGGAGAAGAAUGUGAUUGGUUUGAGGUGA

SEQ ID NO:86

AUGUCGGGACACCCACCACAACAAGGUGGUCAAUACGACGAAGGCUACGGCCAUCAAGCGGGCAAUACCG
AUUCUUAUUACCAAGAUGAGCACGGAGGGCAACAAUAUUAUGACAAUAAUGGUGGCUACGAACAGGGCCA

FIG. 1AA

CGGGGGUCAUCAGCAAGAAGGUGCUGAAGGAUAUUAUGAUGAAUCAGGCUAUUACAAUGCUGAUGCCAAC
AAUCCAUAUCAACAAGAAGGAGGGUACUACGAAGGUGGUGAUCAGCAUCAAGGCCAAUAUCAAGAUGAAU
ACUACAACGACCAGUACUAUGAUCAGGGGGGUGCAGCCGGCGGUGAGGCACCCCAAGCUAAACGUCGAGG
CGAUUCGGAAGAGGAUUCCGAAACCUUCAGCGACUUUACCAUGAGAUCAGACAUGGCUCGAGCCACCGAU
AUGGAUUACUAUGGACGCGGUGACGAGAGAUAUAACAGCUACAAUGAGAGUCAAAUGGGUGGUCGUGGUU
ACAGACCACCAUCUUCGCAGGUUUCAUAUGGUGGUAAUAGAUCCUCCGGAGCAUCGACGCCAAAUUACGG
CAUGGACUACAACAACGUCCUUCCACCUGGACAGCGAUCUAAGGAGCCGUAUCCUGCCUGGACCUCUGAC
GCUCAAAUUCCUCUGUCCAAAGAAGAAGUUGAGGACAUUUUCCUGGAUUUGACAGCCAAGUUUGGUUUCC
AGCGUGACAGCAUGAGAAACGUUUACGAUCAUUUGAUGACUCUGCUCGAUUCGAGAGCUUCGCGCAUGAC
CCCGAAUCAAGCGCUCCUGUCACUACACGCAGACUAUAUCGGUGGUGACAAUGCCAACUACCGAAAGUGG
UAUUUUGCUGCUCAUCUCGAUUUAGAUGAUGCGGUGGGAUUCGCCAGCAUGAAACUUGGCAAAGGAGAUC
GUCGUACUCGCAAAGCCCGCAAAGCAGCCAAGGCAGCGCCACCGGACCCUCAAAACGAGGCGCAAACCCU
UGAGCAAAUGGAGGGUGAUAACAGUCUCGAAGCUGCGGAGUACAGAUGGAAGACUCGUAUGAACCGAAUG
UCCCAACACGACCGAGUUCGUCAAUUGGCUCUCUACCUUCUCUGUUGGGGUGAGGCCAACCAGGUUCGAU
UCAUGCCCGAAGUUCUAUGCUUCAUUUUCAAAUGUGCAGAUGACUACCUCAACUCUCCUGCCUGCCAAAA
CUUGGUUGAACCAGUGGAAGAAUUAACAUUCCUCAACAACGUUAUAACGCCUCUUUACCAAUACUGUCGA
GAUCAAGGAUAUGAAAUUCAAGACGGCAAGUAUGUUCGACGAGAACGGGAUCAUAAUGAAAUUAUCGGGU
ACGAUGAUUGCAACCAGUUGUUUUGGUAUCCCGAGGGUAUUGAGAAAAUCGUCCUAGAAGAUAAGUCUCG
CUUGGUGGAUCUCCCUGUUGCGGAACGUUAUCUCAAACUCAAGGAUGUCAACUGGAACAAGUCCUUUUUC
AAAACGUACCUCGAAAAACGUUCUUGGUUCCACAUGUUGGUCAACUUCAAUCGCAUUUGGGUUAUCCACA
UCAGUGCCUUCUGGUUUUUUACUGCUAAGAAUUCGCCAACACUCCUGGAAAAGAAUUACCGACAACAGGA
GAACAAUCAGCCUCCUGCCUCUGCGCAGUGGUCCGCGGUUGCUUUGGGUGGUGCAAUUGCAAGUCUUAUU
AUGGUCGUCGCUACAAUCUGUGAAUGGUCCUAUGUUCCUCGUCGAUGGGCAGGUGCUCAGCAUUUGACCA
AGAAACUGUUGUUCCUCAUCGCUGUUCUCAUUCUCAAUGUCGCCCCAAGUGUGUACAUUUUCAUCAUUCC
CAACACACAGAAGACGAAGCUUGCUUUGAUUUUGGGCAUUGUCCAGUUCUUCAUCGCCCUGGUCACAUAC
UUCUUCUUCUCGAUCAUGCCUAUGGGAGGAUUGUUCGGUAGUUACUUGACCAGGAACUCCAGACAGUACG
UUGCUAGUCAGACCUUUACUGCCAGCUAUCCUCGUCUGACUGGUAAUGAUAUGUGGAUGUCUUACGGUCU
CUGGAUCACUGUCUUCGGAGCUAAACUUGCCGAGUCCUACGUCUUCUUGACCUUGUCCUUCCGUGAUCCU
AUCAGAUACUUGGACAGCAUGGAAAUCUCUUACUGUGCUGGUGAUGCUCUGUUUGGCGAUGUUCUCUGUA
AAUUACAGCCCAAGAUUCUCCUCGGUCUCAUGUUCGUCACCGAUCUUACGUUGUUCUUCUUGGAUACUUU
CAUGUGGUAUAUUAUCAUGAACGCCAUUUACUCGGUCGCUCGAUCCUUCUACCUUGGUGUUUCCAUCUGG
ACACCAUGGAGAAAUAUCUUCUCGCGUUUGCCAAAGCGUAUCUAUUCCAAGGUUCUCGCCACGACUGAUA
UGGAAAUCAAGUACAAGCCAAAGGUCCUCAUCUCUCAGAUCUGGAACGCUAUUGUCAUUUCCAUGUACAG
GGAGCAUCUCCUUGCUAUCGACCACGUCCAAAAGCUUCUCUACCAUCAAGUUCCUUCCGAACAAGAAGGC
AAAAGAACUCUCCGAGCGCCAACUUUCUUCGUCUCGCAGGAAGAUCACUCUUUCAAGACCGAAUUUUUCC
CAAACCAGAGUGAGGCCGAGCGUCGUAUCUCUUUCUUCGCUCAAUCUUUGUCAACUCCUAUUCCGGAACC
ACUUCCAGUCGAUAACAUGCCAACUUUCACUGUCAUGAUUCCGCAUUACGGAGAGAAGAUUUUGUUCUCC
CUGCGUGAAAUCAUUCGUGAAGAUGAGCCAUACUCCCGCGUUACUAUGCUUGAGUACUUGAAGCAAUUGC
ACCCUCACGAGUGGGAUUGCUUCGUAAAGGAUACUAAAAUUCUUGCAGAUGAGACCUCACAAUUUAAUGG
CGAUUACGAAAAGGAUGAGAAGAAUACUGCCAAGAGCAAGAUUGAUGAUCUUCCUUUCUAUUGCAUAGGU
UUCAAGUCGGCCGCUCCCGAGUACACUCUCCGCACACGUAUUUGGGCUUCUUUGAGAGCACAAACCCUUU
ACCGCACAAUCUCUGGUUUCAUGAAUUAUAGUCGUGCUAUCAAACUCCUCUAUCGUGUUGAAAAUCCCGA
AGUCGUUCAAAUGUUUGGUGGCAACUCGGACAAGCUUGAACGCGAGCUUGAGCGUAUGGCCCGUCGCAAG
UUUAAGCUAUGUGUUUCUAUGCAACGUUAUGCCAAAUUCAAGAAAGAGGAGAUGGAAAACACCGAAUUUC
UUCUCCGUGCCUACCCUGAUCUCCAAAUUGCUUACCUGGAUGAAGAAGCUCCUCUCGCCGAAGGGGAAGA
GCCACGUCUUUACUCCGCUCUCAUUGAUGGUCACUCCGAACUUAUGGAAAAUGGAAUGCGCAGACCCAAG
UUCCGCAUUCAACUUUCCGGUAACCCAAUUCUUGGUGAUGGAAAAUCUGACAACCAAAACCAUGCCAUCA
UCUUUUACCGCGGCGAGUACAUUCAACUUAUUGAUGCCAAUCAAGACAACUAUUUAGAAGAAUGCUUGAA
GAUUCGAAGUGUUUUGGCCGAGUUCGAGGAAAUGACAACUGAAAACGUCUCUCCUUACACUCCUGGUGUC
UCCAACCCCAAGGUCGCCCCGGUUGCCAUUCUCGGUGCUCGUGAAUAUAUUUUCUCUGAGAAUAUUGGUA
UUUUGGGAGAUGUCGCUGCCGGAAAGGAACAAACAUUCGGUACGCUCUUCGCACGUACGCUUGCUGCCAU
UGGUGGUAAGCUUCAUUAUGGACAUCCUGAUUUCCUGAACGGUAUCUUCAUGACUACGAGAGGUGGUGUU
UCCAAGGCUCAGAAGGGUCUUCAUCUUAACGAGGAUAUUUAUGCUGGUAUGACUGCACUUCUUCGUGGAG
GUCGCAUCAAGCAUUGCGAGUACUACCAGUGUGGUAAAGGUCGUGAUCUGGGUUUUGGCUCGAUUCUUAA
CUUCACCACAAAGAUUGGAACUGGUAUGGGUGAGCAAAUGCUUUCGCGUGAGUAUUAUUAUCUCGGUACU
CAACUUCCUAUUGAUCGCUUCUUGUCCUUCUACUAUGCCCAUCCUGGUUUCCAUUUGAACAAUAUGUUCA
UCAUGUUGUCCGUCAACUUGUUCAUGCUCUGCUUGAUCAACUUAGGAGCCCUCAGAAACCAGGUCAUCGA

FIG. 1BB

GUGUAAAUAUAACGUCAACGUCCCUAUUACCGAUCCACUCUAUCCAACUGGUUGUGCAAACAUCAUUCCC
AUUAUGAAUUGGGUUUAUCGUUGCAUUAUCUCCAUCUUCAUCGUGUUCUUCAUCUCUUUCGUACCCUUGA
CAUUACAGGAAUUGACAGAGCGUGGUUUCUGGCGUGCGGCUACCCGUCUCGGAAAGCAAUUCAGUUCUUU
GUCGCCUUUCUUCGAAGUUUUCGUCUGUCAAAUUUAUGCGAACGCUGUUCAGCAAGAUCUUUCGUUCGGU
GGUGCCCGAUACAUCGGAACGGGUCGUGGUUUCGCUACUGCCCGCAUUCCCUUCGGUAUUCUCUUCUCUC
GAUUCGCCGGUCCCUCGAUCUAUCUCGGAGCUAGAUUACUUAUGAUGUUGUUAUUCGCAACCAUCACUGU
CUGGCAAGCUGCGUUGGUAUACUUCUGGGUUACUCUCCUUGCUUUGUGCAUUUCUCCAUUCUUGUAUAAU
CCUCAUCAAUUUGCCUGGAACGAUUUCUUCAUUGACUACAGAGACUACCUCAGGUGGUUGUCUCGCGGAA
AUUCGCGUUCUCACGCAUCGAGUUGGAUUGCUUACUGCCGUCUCUCUCGUACUAGAAUUACAGGUUAUAA
ACGCAAGAUUCUUGGAGACCCAUCUGCCAAGAUGUCUGGCGACACUGCCCGUGCCUCAUUCUCCAAUCUC
UUCUUUGGAGAAAUCGUGGGACCGCUCAUGGUCGUUGCUCUCACCUUGAUUCCAUAUCUCUACAUAAAUG
CCCAGACUGGUGUCAUUCCAAGCAUCAACGAUAACGUCGAAACUAAAGCGACGAACGCCUUGAUUCGUGU
UGGUAUUGUAGCCUUGGCUCCUAUUGCAGUCAACGCAGGUGUCCUGGCUGUCAUGUUUAGUAUGGCUUGU
UGUAUGGGACCUCUCCUUGGCAUGUGUUGCAAGAAAUUCGGAUCCGUUCUCGCCGCAAUUGCACAUGCCC
UGGCCGUCGUCUUCUGCCUGGUUUUCUUCGAAGUCAUGUUCUUCUUGGAAGGAUUUGACUUCGCCAAGAC
UCUGUUGGGAAUGAUUGCGUCCGCCGCCAUUCAGAGAUUUGUCUACAAGCUCAUCAUCAGUCUAGCACUG
ACCAGAGAAUUGAAGACCGACACAUCCAAUAUAGCUUUCUGGACUGGUAAAUGGUAUUCCAUGGGUUGGC
ACACGAUUUCCCAACCUGGUCGUGAAUUUCUUUGUAAGAUCACCGAGCUUGGAAUGUUUGCUGGGGACUU
UGUUCUUGGUCAUCUCCUUCUCUUCAUCAUGCUUCCCGUCAUCGCCAUACCUCAAAUUGACAAGCUUCAU
UCUGUGAUGCUCUUCUGGCUUCGUCCCAGUCGACAAAUUCGUCCUCCAAUCUACUCCUUAAAGCAAUCCA
AGUUACGAAAGAAACGUGUCUGGCGGUACGCCUGUGUAUAUUUCGCUCUGUUUGUCGUCUUCCUCGCACU
GCUUGUGGGCCCACUUGUUGUUGGCAAGAAGAUCUUGACCCCUAGCUUGAUAAGUAAGAUUCCACAGAAG
CUCUUCCAGCCUAUCAACCAGAACAACAACGACACAAGAGGUUACAACCAGACCGGUACUGGUUGCGUGA
CAUGCUCCACAGCCUCUGCCACUUCAACCAAAACUGCUGCUGCUAAGAUUCGAUUGUUCUAA

SEQ ID NO:87

AUGCCGGGCCACAUAGAUUGUUAUCUCGAUUGCUCUUCAUUCUACAGCUACGCUGCAAUAGCACAUCUCC
GAAAGAACCGAGAAGUUCUUCUUACUCAUGAUGUUACCGUGAAUAUCAUUCCAGUCUUCCUCGGCGGCAU
AAACAACGGCUCGGGAAACAAACCGCCAUGGAGUCUUCCUGCCAAAGCAAAGUAUAGCAAAUUCGAUAGU
GCUCGCACGAUAUCAUAUCAUGGGCUUCCGGAUCUUCAAGCUCCUGAUUUCUUCCCGCCUGUGACACUUC
UUCCUCAAAGAGCACUCUGCUUCAUCAAAUCCCGUUAUCCUGUCGAAACAUUCGAGAAAACAUUCUUGAG
CAUUUUCAAUGCCCUUUGGGUUGCCCCUCACAAAAACAUCACGAUUCCUGACGAACUCCGGGAGUUCCUA
AGUAAGCUAGGCUCGUUCGAUGAGAAGCAGGUAGAGGAGAUUAUGGCAAUGGCGGCGGAGAAAGAGUGGA
AGGAUAAGUUACUGGAGAAUACAAAAGAUGCGCUUGGGAAGGGUGCAUUUGGGGCACCGUGGUUGUGGGU
UAGGAAUGGGGAGGGAUUGGAGGAACCGUUUUUUGGGAGUGAUAGGUUUCAUUUUAUUUGGAAGUUUUUA
GGGGUUGACUUUAGGGAUGUGGAGAUUGUGGAAGGUGAUAAGGGGGAAGGGAGGAAGAAGGCCAAGUUGU
GA

SEQ ID NO:88

AUGGCUGAUCGAAAUGCGUCAAAUACUUCAAAUGGUGAAUAUGAUCAUGCGUGGGCAAAAGAUUUAAGAC
AACAAUUCGAAGGUUUAUUAAGGACGAAAAGAUUAAAUGAAUUGGAUAGAUCAAGAUCACGAAAUCCUUC
ACCAUCACCUAGAGAACGAUCAUCUUCAUCAAAUCUCCGAGCUUCAUCUUCACAAAAUCAACCACAAUCU
UCCAACUUUCGACCCACUUCUUCAUCAAAUAAUCAAUCAAAACCUCCAACUCCUCCAGCAUAUUCUUCUA
CAAGAAGUUUACCAAAGAUUCCUUCUCCACCAGCAGAUGCUCAAUCACAAAAGUUUCGAAAUUUAUUAAU
CUCCAUCUCACAAACACCAACGAAAUAUGAAAAUCCCGGUUUAUUGGAUGAAGCUUUACAACAUUUACCA
CUAGAUAGAAUUUAUGGAGAAGCAGAAGAAGAAAGUCAAAUCUUACAAGCUGAGGCCGAAAGCAUGGGAG
AUGGAAGGAAACCAGAAUGGGGUUAUCAAGAUUGUGUCAUUCGAGCUUUACUGAGUAUGUUGUGUCGCGC
CGUUGGAGGUCGUGUAAGAUGGGUUUGGAAUGUUGAAGAUCAUGUUUGGACGGAAGUUUAUUCGGAUACG
AAAAAGAGAUGGAUUCAUGUUGAUGCAUGUGAAGAAGCUUGGGAUAAUCCAAGGUUAUAUGCCGAAGGUU
GGGGUAAGAAGAUGUCUUAUUGUAUUGCUUUUUCAAUGGAAGGUGCGACCGAUGUUACUCGAAGAUAUGU
ACGCAAACCCGAUCAUGCUCUCCCACGAAAUCGAUGUCCGGAAGAAGUUAUGUUAUAUAUUCAAAACGAA
AUUCGGGGACUUCGGAGAUCAAAUAUGAAUAAGGAUGAAAGAUUUCGAUUGGAAAAGGAAGAUGCGAGGG
AAGAUAAGGAAUUGAGGGGUUAUGUGGUAGCAUCAAUUGCGCAAUCCGUCGUAUCGAAUUUGAGACCAGA
AGGAUCGUCACAUCAACAAAUAACACCUCCACCUCCACGACAAGAAGAUCAGAAAUUACCAGCUGAACAA
CCUGGUAGACAAACUGGUGCACAAGAAUGGGCAAAUGCUAGAGGUGAAGCUGGAAGACGAAAUCAACAUC

FIG. 1CC

CAAGGGAUCCUUCACAACAUGGACCUUGA

SEQ ID NO:89

AUGUCGUUCUGGGAUAAGUUGACAGGGCGAAAGCCAUCAUCAAAAGACACUUCUAGUGGCGGAUCAACCU
UGAAUACCCCAACUGACACAUUCACACCUACACCCUUCAACCCUCAAGAAGGUCAAGAUGUCAACUCUUU
UCUUACAGGGCCAGAGCUCAUAGAUCCAUCACAACUUCAUCCUUUGGCUGGUCUGAACCAACAGACUCUA
GACUAUCUAUCCCUCGAAGAAUCUACUCUCUCGGAUCUUCCAGGAUCGCAAUCUGCCUUACCCUCGAGAG
GUUGGUCGGACGAUUUAUGUUAUGGUACCGGUGUUACAUAUUUGACGGCACUAACUGUGGGUGGUGCUUG
GGGAUUACAGGAGGGUUUGAGGAGGUCUGCGACGCAACCACCAAAGUUACGAUUGAACUCGGUGCUGAAC
GCUGUUACGAGGCGAGGGCCAUUCUUGGGCAACUCGGCAGGAGUAAUUGCUAUGGUUUACAACGGAUUCA
ACUCAUUUAUCGGACAUAUGAGGGGCAGGCAUGAUUCGGCGAACAGUGUUCUUGCAGGUGCGCUGAGUGG
GAUGAUUUUUAAAAGUACAAGAGGAGUUCGACCUAUGAUGAUUUCCGGUGGGAUCGUGGCUUCUGUAGCC
GGCGCAUGGGCACAAGAAAAGCAAUAUUUUAAAUGA

SEQ ID NO:90

AUGUCUUCCGAACCACCUUUGGACCCCUACAAACCCUCUCUCUUCGAACUUUUGUCCUCCACCCAACUUU
CGUCACUCCUUCCUCCCUCUCUCCACUACCUCCUAACCAUCGCCACACACCGACAUCCGCGACACCUCCU
CCCAAUCCUCAACUCCUUUCACGAAAUCCACGCUCUCCUCUUCCUAGCAAUCGAACACCACUAUCUAACC
ACCUACUCUUCUUCAUUUGUCGAAAACUUUUAUUCUCUAAAACGGGAACGCGCCUUACCUGCGGCAGUAG
GCGAUCUGCGACUUACGGCCGAAGCAGCCAAUGCCAGUCUACGCGAAACGACAAAACUUACAAGAGGGGA
UGUAUGGAAGAAUCUUGCUGUGCUCGUUGGAAUUCCAUAUCUUAAACGUCGACUCGAUGAGUCUCAGGAG
AUCAAUGCACCGAGAGCACUUCUCGGCGCAAAUUAUACACGCAUGCCACCGAAUCCAACGCUCAAACAAC
GAUUUCUACAUUAUUAUCGUUGGUUUCUUACGAAUGUAUAUCCCAGCGUGAAUGCCGCAUAUUAUUUCAG
UAUCUUAGCAUUUAAUCUACGAUACCUAUUUUCGGGUUCGAAAUCUGGCUCUGGUGUAUAUUCCGAUCCA
UUUUUAUGGUUAAUAGGAACGCGGAUACGAAGAUUAAGUCAAGCAGAUUUCCAAGCUUUUGAAGCGAUUA
AGAAUGCUGCAUCUUCAAUACCAGGGUCGAAUCUAGGAAUAAGAAGUCUAUUGGAUCCAAGACUGGCAAU
GGGAAGAAUAGGUUCUGGAUUAAAACUAUUACUACCAACCAGUAUCUUUGCGCUGAAAUUCCUGGAAUGG
UGGCAUGCGAGUGAUUUUGCAAGACAAUUAUCUCGAAAAGCAAUAGAAGGAUUAGAAUUACCACCGCCUA
UUAUAUCAUACACCCCUUCUCCUGUAACAAAACCGGAGACCACGUCAAAAUCCUCAUCAGAAGAAAAACA
ACCGUCAGAAGUAGAAGAACCAACAAAUCCCCCGAUCUCAACCAUAACCCAACUCCCCAUCUAUGUCGUC
CCAGCUCCUUCCACCUCGACCUCCUUAGAAAAUUGCCCAAUCUGUCUCGAAGAAAUCACGACGCCAACCG
CGUGUCAAACAGGAUAUGUGUAUUGUUAUACUUGUAUUCAUAGGUGGAUUGAGGGGUUGCAUGAUUUGCA
GGAGAAGUUUAUGAAGGGUGAUGUGAAGGUGGAUGGGGAAGGGAAAGGAGAGAAGGGAAGAGAAGGGAAG
UGGGAAAGUGGAGCAGGCAGAUGUGCGGUUAGUGGACGGAGGGUAUUAGGGGGUGUCGGUGGGUUGAGGA
GGGUUUUGGUUUAA

PLANTS AND METHODS FOR CONTROLLING FUNGAL PLANT PATHOGENS

CROSS-REFERENCE TO RELATED APPLICATIONS

This application is the § 371 U.S. National Stage of International Application No. PCT/IB32017/052578, filed May 3, 2017, which claims the benefit of U.S. Provisional Application No. 62/331,026, filed May 3, 2016, the disclosures of which are incorporated by reference herein in their entireties.

BACKGROUND

Canola is an important oilseed crop, contributing billions of dollars the economies of many countries (www.canola-council.org). Canola crops are threatened by a variety of fungal pathogens, but the most damaging is *Sclerotinia sclerotiorum*. This fungus occurs throughout the world including all canola growing regions of Canada (Baharlouei et al., 2011, African J Biotech 10: 5785-5794; Litholdo et al., 2010, Genetics Molec Res 10: 868-877; Hu et al., 2011, Can J Microbiology 57: 539-546), and causes stem rot of canola plants. Annual losses due to this fungus are highly variable, ranging from 5 to 100%; in 2010, 90% of Canadian canola crops showed some level of *Sclerotinia* infection and the loss to growers was estimated at $600 million (gov.mb.ca). Damage from *Sclerotinia* is mitigated primarily by crop rotations and foliar fungicides, but under damp climatic conditions, such methods are often insufficient to control the disease.

SUMMARY OF THE APPLICATION

Increasing public concern over the risk that chemicals pose to the environment and human health are compelling reasons to find safer (fungal or species-specific) alternatives to control necrotrophic fungal pathogens.

Provided herein are plants. In one embodiment, a plant includes a polynucleotide that reduces expression of a coding region. The coding region includes a sequence that has at least 80% identity to SS1G_06487, SS1G_01703, SS1G_05899, SS1G_02495, SS1G_11912, SS1G_07873, or SS1G_09665, or a homolog of SS1G_06487, SS1G_01703, SS1G_05899, SS1G_02495, SS1G_11912, SS1G_07873, or SS1G_09665, where the coding region is present in a fungal pathogen, and wherein the polynucleotide is on a surface of the plant. In one embodiment, growth of the fungal pathogen on or in the plant is reduced compared to a control plant. In one embodiment, resistance of the plant to the fungal pathogen is increased compared to a control plant. In one embodiment, lesion size after administration of the fungal pathogen to leaves of the plant is reduced by at least 3% compared to a control plant that does not include the polynucleotide. In one embodiment, the plant pathogen is *Sclerotinia sclerotiorum* or *Botrytis cinerea*. In one embodiment, the polynucleotide includes a double stranded RNA (dsRNA), where the dsRNA includes a nucleotide sequence that is substantially identical to a series of nucleotides of the coding region. In another embodiment, the polynucleotide includes a single stranded RNA (ssRNA), wherein the ssRNA includes a nucleotide sequence that is substantially complementary to a series of nucleotides of the coding region. In one embodiment, the polynucleotide includes at least 15 nucleotides.

In one embodiment, the polynucleotide reduces expression of the coding region in the fungal pathogen by at least 5% when the polynucleotide is introduced into the fungal pathogen and compared to a control fungal pathogen that does not include the polynucleotide. In one embodiment, the polynucleotide reduces expression of the coding region in the fungal pathogen present on the plant by at least 5% compared to a control fungal pathogen present on a control plant that does not include the polynucleotide. In one embodiment, the surface is a leaf, a flower, a fruit, a seed, a vegetable, or a combination thereof. In one embodiment, the plant further including a second polynucleotide that reduces expression of a coding region selected from SS1G_06487, SS1G_01703, SS1G_05899, SS1G_02495, SS1G_11912, SS1G_07873, or SS1G_09665, or a homolog thereof, and the second polynucleotide is on a surface of the plant. In one embodiment, the polynucleotide is a first polynucleotide, the plant further including a second polynucleotide that reduces expression of a coding region selected from SS1G_01703, SS1G_09665, or SS1G_08218, or a homolog thereof, and the second polynucleotide is expressed by the plant. In one embodiment, the plant is canola, mustard, flax, sunflower, corn, oat, cotton, camelina, crambe, safflower, rice, sunflower, soybean, peanut, rapeseed, coconut, oil palm, borage, potato, pea, bean, lentil, chickpea, or a forage legume.

Also provided is a method for making a plant. In one embodiment, the method includes applying a composition to a surface of the plant, wherein the composition includes the polynucleotide. In one embodiment, the applying includes spraying the plant, for instance, to a leaf, a flower, a fruit, a seed, a vegetable, or a combination thereof, of the plant. In one embodiment, the composition is applied at a dose of 0.1 nanogram polynucleotide per square millimeter (ng/$mm^2$).

Further provided herein is a transgenic plant and a cell of a transgenic plant. The transgenic plant includes a polynucleotide that reduces expression of a coding region having a sequence that has at least 80% identity to SS1G_01703, SS1G_09665, or SS1G_08218, or a homolog of SS1G_01703, SS1G_09665, or SS1G_08218, wherein the coding region is present in a fungal pathogen. In one embodiment, growth of the fungal pathogen on or in the plant is reduced compared to a control plant. In one embodiment, resistance of the plant to the fungal pathogen is increased compared to a control plant. In one embodiment, lesion size after administration of the fungal pathogen to leaves of the plant is reduced by at least 3% compared to a control plant that does not include the polynucleotide. In one embodiment, the plant pathogen is *Sclerotinia sclerotiorum* or *Botrytis cinerea*. In one embodiment, the polynucleotide includes a double stranded RNA (dsRNA), wherein the dsRNA includes a nucleotide sequence that is substantially identical to a series of nucleotides of the coding region. In one embodiment, the polynucleotide includes a single stranded RNA (ssRNA), wherein the ssRNA includes a nucleotide sequence that is substantially complementary to a series of nucleotides of the coding region. In one embodiment, the polynucleotide is at least 15 nucleotides.

In one embodiment, the polynucleotide reduces expression of the coding region in the fungal pathogen by at least 5% when the polynucleotide is introduced into the fungal pathogen and compared to a control fungal pathogen that does not include the polynucleotide. In one embodiment, the polynucleotide reduces expression of the coding region in the fungal pathogen present on the plant by at least 5% compared to a control fungal pathogen present on a control plant that does not include the polynucleotide. In one embodiment, the plant includes a vector that encodes the polynucleotide. In one embodiment, the vector is integrated into to plant genomic DNA. In one embodiment, the polynucleotide is a first polynucleotide, and the plant further includes a second polynucleotide that reduces expression of a coding region having a sequence that has at least 80% identity to SS1G_06487, SS1G_01703, SS1G_05899, SS1G_02495, SS1G_11912, SS1G_07873, or SS1G_09665, or a homolog of SS1G_06487, SS1G_01703, SS1G_05899, SS1G_02495, SS1G_11912, SS1G_07873, or SS1G_09665, wherein the second polynucleotide is on a surface of the plant. In one embodiment, the polynucleotide is a first polynucleotide, and the plant further includes a second polynucleotide that reduces expression of a coding region having a sequence that has at least 80% identity to SS1G_01703, SS1G_09665, or SS1G_08218, or a homolog of SS1G_01703, SS1G_09665, or SS1G_08218, wherein the second polynucleotide is on a surface of the plant, wherein the second polynucleotide is expressed by the plant.

Also provided herein is a method for making a transgenic plant. In one embodiment, the includes transforming a cell of a plant with a polynucleotide to obtain a recombinant plant cell, and generating a transgenic plant from the recombinant plant cell, where the plant includes a polynucleotide that reduces expression of a coding region having a sequence that has at least 80% identity to SS1G_01703, SS1G_09665, or SS1G_08218, or a homolog of SS1G_01703, SS1G_09665, or SS1G_08218, wherein the coding region is present in a fungal pathogen.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

It is understood that wherever embodiments are described herein with the language "include," "includes," or "including," and the like, otherwise analogous embodiments described in terms of "consisting of" and/or "consisting essentially of" are also provided.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 1A to FIG. 1CC shows examples of nucleotide sequences described herein.

DETAILED DESCRIPTION OF ILLUSTRATIVE EMBODIMENTS

Described herein is the use of polynucleotides, such as double-stranded RNAs (dsRNAs), to inhibit the growth of plant parasitic fungi. Certain polynucleotides, when absorbed by fungal cells, will interfere with mRNA molecules and selectively reduce the expression of one or more essential fungal genes, thereby reducing fungal growth, infection, or pathogenicity. The polynucleotides described herein are designed to target fungus genes and not affect the host plant genes. The polynucleotides can be applied to plants in at least two ways: 1) by a transgenic method, whereby the plant expresses a polynucleotide to inhibit the growth or infection of the fungus in the plant; or 2) the polynucleotide can be applied topically to plant leaves, such that the when fungal spores adhere to the plant and attempt to infect the plant cells, they encounter the polynucleotide and their growth is inhibited or the fungal infection is reduced.

Pathogenic fungi infect many commercial crops and can cause devastating impacts on crop yields. Chemical fungicides are routinely applied to plant seeds and as foliar sprays on young plants' leaves to minimize fungal infections. These chemical fungicides are broad-spectrum in their activity, and can adversely affect many fungi, including beneficial fungi in the soil that are important in maintaining nutrient cycling. The efficacy of the fungicides are also dependent on climate, as rains following the aerial spraying can wash off the fungicide, leaving the plants vulnerable to fungal spores.

The technology described herein provides a new class of anti-fungal agents that are designed to be specific for pathogenic fungi and will not adversely affect other fungi, plants, or animals. The technology is inherently sequence-specific, capable of reducing gene expression of individual genes, and consequently, it can be designed to be species-limited, targeting gene sequences within the pathogenic fungus, and not affecting others.

Provided herein is a method for reducing growth of a fungal plant pathogen. As used herein, "reduced growth" refers to reducing the ability of the fungus to replicate, to undergo metabolism, to infect a plant (e.g., colonize a plant, a step that may occur prior to disease), to be pathogenic (e.g., cause disease), or a combination thereof. "Reduced growth" includes a reduction in the ability of a fungal plant pathogen to replicate, undergo metabolism, or a combination thereof, for instance, and is similar to the result of using a fungistatic agent. In one embodiment, "reduced growth" refers to death of the fungal plant pathogen, and is similar to the result of using a fungicidal agent.

Also provided herein is a method for increasing the resistance of a plant to a fungal pathogen. As used herein, "resistance" refers to reduced signs of disease caused by a plant pathogen. Resistance can be the result of reduced growth of the plant pathogen, or the result of a reduced ability of the plant pathogen to cause signs of disease despite being present on or in the plant in substantial levels.

As used herein, unless otherwise noted "fungal plant pathogen," "fungal pathogen," "fungal cell," and "fungus" are used interchangeably and refer to a fungus that causes a disease in a plant. Examples of fungal pathogens include members of the family Sclerotiniaceae, such as members of the genus *Sclerotinia*. Examples of members of the genus *Sclerotinia* include *S. borealis, S. bulborum, S. homoeocarpa, S. minor, S. ricini, S. sclerotiorum, S. spermophila, S. sulcata, S. trifoliorum*, and *S. veratri*. In one embodiment, the fungal pathogen is *S. sclerotiorum*. Other examples of fungal pathogens include members of the family Trichomaceae, such as members of the genus *Aspergillus* (for example, *A. fumigatus, A. fischerianus* (also known as *Neosartorya fischeri*), *A. flavus, A. oryzae, A. clavatus, A. nidulans, A. terreus*); members of the *Botrytis* genus (for example, *B. cinerea*); members of the family Plectosphaerellaceae, such as members of the genus *Verticillium* (for example, *V. alfalfa, V. tenerum, V. dahlia*); members of the family Nectriaceae, such as members of the genus *Fusarium* (for example, *F. gaminearum, F. eumartii, F. martii, F. solani, F. striatum, Nectria cancri, Nectria haematococca*); members of the family Glomerellaceac, such as members of the genus *Colletotrichum* (for example, *C. gloeosporioides*); and members of the genus *Leptosphaeria* (for example, *L. maculans, L. biglobosa*). Other fungal pathogens include *Eutypa lata, Glarea lozoyensis, Neurospora crassa, Glomerella cingulate, Marssonina brunnea, Pyrenophora tritici-repentis, Coniosporium apollinis, Endocarpon pusillum.*

The methods include introducing into a fungus a polynucleotide. The polynucleotide may be introduced directly into the fungus by exposing the fungus to the polynucleotide, or by having a plant that is susceptible to the fungal pathogen express the polynucleotide.

As used herein, the tem "polynucleotide" refers to a polymeric form of nucleotides of any length, either ribonucleotides and/or deoxynucleotides, and includes both double- and single-stranded DNA and RNA. A polynucleotide may include nucleotide sequences having different functions, including for instance coding sequences, and non-coding sequences such as regulatory sequences. Coding sequence, non-coding sequence, and regulatory sequence are defined below. A polynucleotide can be obtained directly from a natural source, or can be prepared with the aid of recombinant, enzymatic, or chemical techniques. A polynucleotide can be linear or circular in topology. A polynucleotide can be, for example, a portion of a vector, such as an expression or cloning vector, or a fragment. A polynucleotide disclosed herein may be isolated. An "isolated" polynucleotide is one that has been removed from its natural environment. Polynucleotides that are produced by recombinant, enzymatic, or chemical techniques are considered to be isolated and purified by definition, since they were never present in a natural environment.

In one embodiment, the polynucleotide may be a double stranded RNA (dsRNA) that inhibits expression of a coding region. In another embodiment, the polynucleotide may be a DNA sequence that encodes a dsRNA. In other embodiments, the polynucleotide may be an antisense RNA, or a ribozyme. It should be understood that the sequences disclosed herein as DNA sequences can be converted from a DNA sequence to an RNA sequence by replacing each thymidine nucleotide with a uridine nucleotide.

Without intending to be limited by theory, it is believed that dsRNAs described herein mediate RNA interference (RNAi) of a mRNA. RNAi is the process of sequence-specific, post-transcriptional gene silencing, initiated by dsRNA that includes an antisense strand that is complementary or substantially complementary in sequence to a portion of the silenced mRNA. Silencing can result from degradation of specific mRNA, which often occurs when there is high complementarity between one strand of a dsRNA and a target mRNA. Antisense RNA is a single strand RNA (ssRNA) molecule that is complementary to, or antisense to, sequences found in a specific mRNA in a cell. Introduction of an antisense RNA into a cell results in association of the antisense RNA with the mRNA, and inhibition of translation of the mRNA. A ribozyme (also referred to as RNA enzyme or catalytic RNA) is an RNA molecule that catalyzes a chemical reaction, such as the cleavage of the phosphodiester backbone of an mRNA molecule. Ribozymes can be designed to include a polynucleotide sequence that is antisense to a target mRNA and thereby target and cleave the target mRNA.

As used herein, the terms "coding region" and "gene" are used interchangeably. A "coding region" is a nucleotide sequence that encodes an unprocessed preRNA (i.e., an RNA molecule that includes both exons and introns), and is processed to result in an mRNA that is translated into a polypeptide. The boundaries of a coding region are generally determined by a transcription initiation site at its 5' end and a transcription terminator at its 3' end.

Coding regions have been identified that, when expression is decreased, result in reduced growth of a fungal pathogen. In one embodiment, examples of coding regions that may be decreased to result in reduced growth encode mRNA sequences available at the Genbank accession numbers XM_001592197.1, XM_001592927.1, XM_001596225.1, or XM_001591197.1 (see Tables 5-7 of the Examples). Additional examples of mRNA sequences of coding regions that, when decreased, are expected to result in reduced growth include, but are not limited to, the mRNA sequences available at the Genbank accession XM_001597459.1, XM_001588982.1, XM_001590428.1, XM_001550999.1, XM_001556707.1, XM_001553668.1, XM_001556287.1, XM_001559983.1 (see Tables 3 and 10 of the Example). Additional examples of mRNA sequences of coding regions that, when decreased, are expected to result in reduced growth include, but are not limited to, the mRNA sequences available at the Genbank accession numbers listed in Example 2.

In one embodiment, the mRNA targeted may be used in methods where a polynucleotide, such as a dsRNA, is introduced into a fungal pathogen that is a member of the family Sclerotiniaceae, such as *S. sclerotiorum*. In other embodiments, a polynucleotide, such as a dsRNA, may be used with other fungal pathogens, where the dsRNA is directed to an mRNA that is encoded by a coding region that is a homologue.

Coding regions that are homologues are coding regions that share ancestry, e.g., they are both derived from a coding region present in a common ancestor. The skilled person can easily determine if a coding region in a fungal pathogen that is not a member of the family Sclerotiniaceae, or not a member of the genus *Sclerotinia*, is a homolog of a coding region encoding an mRNA disclosed herein through the use of routine methods. In one embodiment, the skilled person can use the nucleotide sequence of a coding region disclosed herein and design degenerate PCR primers for use in a low stringency PCR. Low stringency PCR is a routine method for identifying homologs of a known coding region. In another embodiment, the skilled person can use readily available databases to identify in another fungal plant pathogen a homolog of a coding region encoding an mRNA disclosed herein. Examples of suitable databases include, but are not limited to, GenBank (available through the world wide web at ncbi.nlm.nih.gov/genbank). (See Table 10 for the Example for examples of *B. cinerea* homologues of *S. sclerotiorum* coding regions)

In another embodiment, the skilled person can identify a homolog of a coding region disclosed herein by the level of sequence identity between the coding region encoding an mRNA disclosed herein and another coding region. In one embodiment, when two nucleotide sequences are being compared, percent identities greater than 50% are taken as evidence of possible homology. The E value (Expect value) indicates the number of hits (sequences) in the database searched that are expected to align to the query simply by chance, so an E value less than 0.01 (i.e., less than 1% chance of the sequence occurring randomly), coupled with a percent identity of greater than 50% is considered a suitable score to identify a probable homolog. Methods for determining nucleotide sequence identity between two sequences are readily available and routine in the art. In one embodiment, coding regions in a fungal pathogen that are homologues of a coding region encoding an mRNA or protein disclosed herein may be identified using the BLAST-N or the BLAST-X algorithm respectively against the non-redundant database at NCBI with default parameters. A candidate coding region is considered to be a homologue of a coding region encoding an mRNA disclosed herein if the candidate coding region has at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% nucleotide sequence identity to a respective coding region disclosed herein.

Decreased expression of one or more of the mRNA disclosed herein may result in reduced growth of the fungus, e.g., reduced ability of the fungus to replicate, undergo metabolism, infect a plant, be pathogenic, or a combination thereof.

In one embodiment, a polynucleotide used in a method described herein includes a sense strand and an anti-sense strand. The sense strand is at least 15 nucleotides in length; however, longer lengths are generally more desirable. Thus, the sense strand may be, but not limited to, at least 15, at least 25, at least 50, at least 100, at least 200, at least 300, or at least 400 nucleotides, for instance. In mammalian cells, dsRNAs greater than 30 nucleotides in length may induce an interferon-mediated cell immune response, leading to cell death. Fungus cells lack this interferon-based response, and longer dsRNAs can be delivered. The sense strand is substantially identical, or identical, to a series of nucleotides (e.g., at least 15 nucleotides, at least 25 nucleotides, etc.) of an mRNA that is targeted by the dsRNA, i.e., a target mRNA. The skilled person will recognize that nucleotides of the sense strand that are substantially identical, or identical, to a target mRNA will not be longer than the length of the target mRNA. As used herein, the term "identical" means the nucleotide sequence of the sense strand has the same nucleotide sequence as a portion of the target mRNA. As used herein, the term "substantially identical" means the sequence of the sense strand differs from the sequence of a target mRNA at some number of nucleotides, but the ability of the complementary antisense strand to bind to and silence expression of the target mRNA is maintained. For instance, the sequence of the sense strand differs from the sequence of a target mRNA at 1, 2, 3, 4, 5, 6, 7, 8, 9, 10, or more nucleotides, while the remaining nucleotides are identical to the sequence of the target mRNA. In another embodiment, the difference in nucleotides between the sequence of the sense strand and the target mRNA can be no greater than 1%, no greater than 5%, no greater than 10%, no greater than 15%, or no greater than 20% of the nucleotides, while the remaining nucleotides are identical to the sequence of the target mRNA.

The other strand of a dsRNA polynucleotide, referred to herein as the anti-sense strand, is substantially complementary, or complementary to the sense strand, and is therefore substantially complementary, or complementary, to a series of nucleotides (e.g., at least 15 nucleotides, at least 25 nucleotides, etc.) of a target mRNA. The term "complementary" refers to the ability of two single stranded polynucleotides to base pair with each other, where an adenine on one polynucleotide will base pair to a thymine or uridine on a second polynucleotide and a cytosine on one polynucleotide will base pair to a guanine on a second polynucleotide. An antisense strand that is "complementary" to another polynucleotide, such as a target mRNA, means the nucleotides of the antisense strand are complementary to a nucleotide sequence of a polynucleotide, such as a target mRNA. As used herein, the term "substantially complementary" means the antisense strand includes 1, 2, 3, 4, 5, 6, 7, 8, 9, 10, or more nucleotides that are not complementary to a nucleotide sequence of the target mRNA, while the remaining nucleotides are complementary to the sequence of the target mRNA. In another embodiment, the term "substantially complementary" means the antisense strand includes no greater than 1%, no greater than 5%, no greater than 10%, no greater than 15%, or no greater than 20% nucleotides that are not complementary to a nucleotide sequence of the target mRNA, while the remaining nucleotides are identical to the sequence of the target mRNA.

In one embodiment, the antisense strand is a single stranded RNA (ssRNA), and is not associated with a sense strand. Such an ssRNA is useful as an antisense polynucleotide for use in reducing translation of a mRNA that is a target of the antisense polynucleotide.

Also provided herein are the single stranded DNA polynucleotides corresponding to the sense strands and antisense strands disclosed herein. Also provided herein are the double stranded polynucleotides disclosed herein, including the complements of the single stranded polynucleotides.

A dsRNA described herein may include overhangs on one or both strands. An overhang is one or more nucleotides present in one strand of a double stranded RNA that are unpaired, i.e., they do not have a corresponding complementary nucleotide in the other strand of the double stranded polynucleotide. An overhang may be at the 3' end of a sense strand, an antisense strand, or both sense and antisense strands. An overhang is typically 1, 2, or 3 nucleotides in length. In one embodiment, the overhang is at the 3' terminus and has the sequence uracil-uracil (or thymine-thymine if it is a DNA). Without intending to be limiting, such an overhang may be used to increase the stability of a dsRNA. In one embodiment, if an overhang is present it is not considered when determining whether a sense strand is identical or substantially identical to a target mRNA, and it is not considered when determining whether an antisense strand is complementary or substantially complementary to a target mRNA.

The sense and antisense strands of a dsRNA described herein may also be covalently attached, for instance, by a spacer made up of nucleotides. Such a polynucleotide is often referred to in the art as a hairpin RNA or a short hairpin RNA (shRNA). Upon base pairing of the sense and antisense strands, the spacer region typically forms a loop. The number of nucleotides making up the loop can vary, and loops between 3 and 23 nucleotides have been reported (Sui et al., 2002, Proc. Nat'l. Acad. Sci. USA, 99:5515-5520;

Jacque et al., 2002, Nature, 418:435-438). In one embodiment, an shRNA includes a sense strand followed by a nucleotide loop and the analogous antisense strand. In one embodiment, the antisense strand can precede the nucleotide loop structure and the sense strand can follow.

A dsRNA described herein may be modified. Such modifications can be useful to increase stability of the polynucleotide in certain environments. Modifications can include a nucleic acid sugar, base, or backbone, or any combination thereof. The modifications can be synthetic, naturally occurring, or non-naturally occurring. A dsRNA can include modifications at one or more of the nucleic acids present in the polynucleotide. Examples of backbone modifications include, but are not limited to, phosphonoacetates, thiophosphonoacetates, phosphorothioates, phosphorodithioates, phosphoramidates, methyl phosphonates, chiral-methyl phosphonates, 2-O-methyl ribonucleotides, and peptide-nucleic acids. Examples of nucleic acid base modifications include, but are not limited to, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), or propyne modifications. Examples of nucleic acid sugar modifications include, but are not limited to, 2'-sugar modification, e.g., 2'-O-methyl nucleotides, 2'-deoxy-2'-fluoro nucleotides, 2'-deoxy-2'-fluoroarabino, 2'-O-methoxyethyl nucleotides, 2'-O-trifluoromethyl nucleotides, 2'-O-ethyl-trifluoromethoxy nucleotides, 2'-O-difluoromethoxy-ethoxy nucleotides, or 2'-deoxy nucleotides. Polynucleotides can be obtained commercially synthesized to include such modifications (for instance, Dharmacon Inc., Lafayette, Colo.).

Polynucleotides described herein are biologically active. A biologically active polynucleotide causes the post-transcriptional inhibition of expression, also referred to as silencing, of a target-coding region. Without intending to be limited by theory, after introduction of a polynucleotide described herein into a fungal cell, the polynucleotide will hybridize with a target mRNA and signal cellular endonucleases to cleave the target mRNA or to inhibit translation of the target mRNA. The result is the inhibition of expression of the polypeptide encoded by the mRNA. Whether the expression of a target mRNA is inhibited can be determined by, for instance, measuring a decrease in the amount of the target mRNA in the cell, measuring a decrease in the amount of polypeptide encoded by the mRNA, or by measuring a change in a phenotype associated with expression of the polypeptide encoded by the mRNA.

Examples of polynucleotides that may be used to silence the expression of mRNAs disclosed herein include those shown below.

TABLE 1

DsRNA molecules synthesized to target specific genes in *S. sclerotiorum*

| Gene | Exemplary dsRNA molecule for use in gene silencing (one strand shown) |
|---|---|
| SS1G_06487 (SEQ ID NO: 1) | CGUAGCAUAUCCGACCGAGUCGCCGGAUUCUUCGCCGAA AACGAAACCGCCCAAGUAAUCAAGAAAUUUCGUGAAAUG GAUCCCUCCUUCCAAAUGGAACCUUUCCUUCGCGAAAUG CGCGAAUACAUCCUCCCUGAAGUCCUAGACGCCUACGUG AAAGGCGAUACUGAAACCCUCAAACUCUGGCUCUCAGCA GCUCAAUUCUCCGUCU (nucleotides 508-718 of SEQ ID NO: 1) |
| SS1G_01703 (SEQ ID NO: 2) | UUCUGCCGGAAACCCUCUUCCUCUAGGUGUAUAUUACCA CGGCGGAGGCUGUUGCCUCGGGGAUCUCGAUUCCGAGGA UCCGUGGUGUCGUUAUAUCGCUAAGACGGUUCCGUGUGU UCUCGUCUCAGUCGAGUAUAGAUUAGGUCCUGAGUAUAA GAUGCCGGUCAUGUUGGAUGAUAGUCUUAAGGCUUUUGA AUGGGCACGAAACCACGCCUCAGAACUUAACGCCAACCC GGCGCAAGUCUUCACAAUCGGCGGU (nucleotides 225-483 of SEQ ID NO: 2) |
| SS1G_05899 (SEQ ID NO: 3) | GCUCACACUGCUGCCGUAUAUCUUGCGCGUGCGGAAUUA AAACCAAAUGGAAUUGCUGCCGGUGGACAAUUGACUACU ACCACCGAUGUAGAGAAUUUCCCUGGUUUCCCUAAAGGA AUCGGUGGACAAGAACUUAUGGAUAAUAUGCGCGCACAA UCCGAACGAUUCGGUACUCAAAUCAUCACCGAAACAGUU GCAAAAGUUGAUCUCUCCAAACGUCCUUUCAAAUACUGG ACCGAAUGGGAUGACAAGACAGAACACACAGCAGAUUCC AUCAUCAUCGCUACGGGUGCAUCAGCUCGCAGACUCGGU CUUCCAGGUGAGGAGAAAUACUGGCAAAAUGGUAUCUCU GCUUGCGCAGUCUGCGAUGGAGCCGUGCCAAUUUUCAGA AAUAAGCCCUUGGUAGUUAUUGGUGGUGGAGAUAGUGCU GCGGAG (nucleotides 40-474 of SEQ ID NO: 3) |
| SS1G_02495 (SEQ ID NO: 4) | UCGUGAAUGAAGCAGGCCAAUGGAAUCUCACCAUCACCG CCGCAGUCCGCGCCGAUCGUGUCGGGGAACCUGUAGCUU UCGACUGGGUUUACAAACGCUUCAUCCAAGGCGUAAUGA UAAACCAAUUGGAGGUACAACGUACGGUUAUGGAGAAAG CGAGUGAGGAGAUUGGUGGAUAUUAUCUUUACACGGCGA CAAAGCCAAUUGAUACGGUACAGUGGUCGACAACA (nucleotides 1292-1521 of SEQ ID NO: 4) |

TABLE 1-continued

DsRNA molecules synthesized to target specific genes in *S. sclerotiorum*

| Gene | Exemplary dsRNA molecule for use in gene silencing (one strand shown) |
|---|---|
| SS1G_11912 (SEQ ID NO: 5) | UCGUAAAUGGCUGCGUACCAUUCCCAGCCGUUGAUGCCG CUGGAAACACCAAUGCCGGGUUAAAACCAAGUGGCAGUA GCAAUGGUGAUUGCAGUAGUAGUACCGGACAAGUAUAUG UUCGAGGUGCUCAAAAUGGUUCAUACUACGGACUGAUGU AUUCCUGGUACAUGCCCAAAGACGAGCCCUCACCAGGCA UCGGCCACCGCCACGACUGGGAAGGCGUAAUCCUCUGGC UCAGCAGCUCCACCUCCACCACCGCCAGCAACAUCGUUGC CGUCUGUCCCUCCGCACACGGAGGCUGGGAUUGCACCCG AGACCAAUACACACUCUCUGGCACAUUCCC (nucleotides 191-533 of SEQ ID NO: 5) |
| SS1G_07873 (SEQ ID NO: 6) | UUCGAAACACCCUGCUACCUUUCCUCAAACUAAGAGCG CCUCGUUCAGCUAGCAUUAAAGUUAUAACCGAUUUCGCA CGGAAAACGGGUGAUUUGGAAGUACUUAGCAGACAGGAU AUCCAUUUAAUGGCACUAGCAUAUGAGCUUGAAUGUGAA CGGAAUCAUGGAGAUUGGAGAUUACGAAGUGUGCCAGGA CAGAAGAGAUUAAAUGGAGCUCCCCCUGCAUCAUUAACA GAAGAGAAACCGGCCGAUACCACAGAGGCGCAAGAAGCA UCCAUGGAUGCUGCAGCGCAACCAAAAAUUGAAACUAGA GGCGCAUGGG (nucleotides 163-484 of SEQ ID NO: 6) |
| SS1G_09665 (SEQ ID NO: 7) | UUCGCGAUCUCCAAACCGAAUAUGAUCUCAAAGGAUCUC UAAAGACGGAAAAAGCAUCUCAUGAACUAUGUGUAGCGA UGACCUUGAGAGAUUGUUCCUUAUACAUACGAAUGGAUA AAAAUCAUCAAGUCAUAGAAGCUCGUCUAGGAGAUUUAG AUUAUAAAUCACCUAAUAAGUAUUCAUCAUGGAGAAGAA AAGAACAGGAAUUAAUCGACGAGGGAUGGUAUUGUGGUG (nucleotides 789-1021 of SEQ ID NO: 7) |
| SS1G_08218 (SEQ ID NO: 8) | ACAGAUGCGCUCCAACAACUUGGUUAUGAUGAGUGCGUC AAACGUUUGAAGGUUGCUCGUGAGCUUGGUGCAGAUGUU GGCUUGCUCGAGGGUUACACUUCAAAGGAGAUGGCUGCA AAGACUGUUAAGGAGUUCGCCCCAUGGCCAAUACUUUUG AACAUGGUCGAGAACGGCGCUACUCCUAUCAUCACCACC AAGGAGGCACAAGAGAUGGGAUUCCGUAUCAUGAUCUUC UCCUUCGCUGCUCUCGCCCCAGCCAUGUUGGCUAUCCAAG AGACUUUCGUGCGUUUGAAGAACGAGGGUGUCGUAGGAA CUCCAAAGAACGUUACACCAAGGGCC (nucleotides 598-936 of SEQ ID NO: 8) |

TABLE 2

DsRNA molecules synthesized to target specific genes in *B. cinerea*

| Gene | Exemplary dsRNA molecule for use in gene silencing (one strand shown) |
|---|---|
| BC1G_10306 (SEQ ID NO: 9) | CCCUUUCGGUCUUGGCAUCUACAGUCAUUGCCAUCCCUACA CCAUCACAACUUGAGUCUCGGGCCGUUAUCGAUUCCGAUGC CGUUGUAGGAUUUGCCGAAACUGUUCCCAGUGGGACCGUA GGAACAGUUUAUGAGGCAUAUAAACCAUUCCUUAAAGUCG UAAAUGGAUGCGUACCAUUCCCUGCCGUCGAUGCAUCGGGU AACACAGGUGGUGGUUUGUCACCAACUGGCAGUAGCAAUG GUGGUUGCAGCAGCAGUACCGGUCAAGUAUAUGUUCGAGG AGGACAAAGCGGAUCAAACUACGCCA (nucleotides 32-340 of SEQ ID NO: 9) |
| BC1G_04775 (SEQ ID NO: 10) | GGACGCCCACAAGUAAACAGAUUUCUCUGUCUUCAAUCGCG AGACCUUCAUCCAAUGGCUCCACCCUUCGUCGCCAGACAGU UCAACAAAAUCGGAAUUUACAAUUUUCUACAGCGGGACAU UCGAGGCCUGCGACUCUUUCAUAUCCUGCGCCUUUGCGAUC ACGAUUCCUUCCAGAAGAAAUUAGAUCUGUAGCAUGCCCA GC (nucleotides 29-233 of SEQ ID NO: 10) |
| BC1G_07805 (SEQ ID NO: 11) | CGCAUGAACCUCAACCUCCUCUCCCCCUCUCUUCAACGCAU CCGCCAGCUCAAAACUUGGGUCCUAAGGUGCCACGCUUGUU UCUCUAUCACUCGAGAAAUGACCCGACAAUUCUGUUCCCGC |

TABLE 2-continued

DsRNA molecules synthesized to target specific genes in *B. cinerea*

| Gene | Exemplary dsRNA molecule for use in gene silencing (one strand shown) |
|---|---|
| | UGCGGUAAACCUACACUCCUCCGCACCUCUUGCUCAACCGA UAAAGACGGAGUGGUAAAAAUCCACCUUAAGAAAAAUAUG CAGUGGAAUAACAGAGGAAAUGUAUACAGUGUCCCCAAAC CAGUUGCCGGGACAGCGAACGGAAAGAAUAUCAAAGGGGG UGGUAAAGGUGGAUGGGGUAAUGAUUUGAUAUUGGCGGAG GAUCAAAAAGAAUACGUGAGAGAAAUGGCCACGGA (nucleotides 886-1244 of SEQ ID NO: 11) |
| BC1G_04955 (SEQ ID NO: 12) | GCUCUGACAUCUUCGCUCGAAUGAUCGAUACUGUCCCUGCA GACGUCACACUUUCUGAAGUCAUCACACCUAUCGAAGUAAA GCCAUCGCAAAUUGCUCUUACCCUAGCUGGAAAUAACACUC UAUCCUUCGGAGGAUACAUCCGCCUUCGCACCACCAACCGC AACGCCGAUGAUGUGACCGUAUCCCUUCAAUACCGUGAUCG UAAUAACAAUACUUCGAACACCACAAUUCCCGUCAGCAGAG AGAAUUACUUGUUGGGUCAAAGCUAUGGCUUCGGUUCAGA GGUG (nucleotides 827-1116 of SEQ ID NO: 12) |
| BC1G_01592 (SEQ ID NO: 13) | GCGCGGAAUUGAAACCUGUUCUUUAUGAAGGUUUCCUUGC CAAUGGAAUUGCUGCCGGUGGUCAAUUGACUACCACUACU GAUGUAGAGAACUUCCCUGGUUUCCCCAAGGGAAUUGGCG GACAAGAACUGAUGGAUAACAUGCGCGCACAAUCCGAACG AUUUGGCACCCAAAUCAUCACCGAAACCGUCGCCAAAGUAG AUCUCUCUAAACGUCCUUUCAAAUACUGGACCGAAUGGGA UGACAAAACAGAACACACAGCCGAUUCUAUCAUCAUCGCUA CUGGUGCC (nucleotides 68-357 of SEQ ID NO: 13) |

The skilled person will understand that a portion of each of the exemplary dsRNAs may be used to silence expression of a target mRNA, and that longer dsRNAs may also be used. Also understood by the skilled person is the ability to use other dsRNAs to silence expression of the target mRNAs disclosed herein. The skilled person will also recognize that antisense RNA molecules can be produced that target the coding regions listed in Tables 1 and 2, and homologues of the coding regions.

Polynucleotides useful in the methods described herein can be designed using methods that are routine and known in the art. For instance, candidate dsRNA polynucleotides or antisense polynucleotides that inhibit the expression of a coding region encoding an mRNA described herein may be based on a selected series of nucleotides, and may be identified using readily available algorithms. A candidate polynucleotide is the polynucleotide that is being tested to determine if it decreases expression of one of the coding regions encoding an mRNA described herein. The candidate polynucleotide can be identical to nucleotides located in the region encoding the polypeptide, or located in the 5' or 3' untranslated regions of the mRNA. Candidate polynucleotides may be screened using publicly available algorithms (e.g., BLAST) to compare the candidate polynucleotide sequences with coding sequences present in the fungal pathogen and/or plants that may be treated to prevent infection by a fungal pathogen. Those that are likely to form a duplex with an mRNA expressed by a non-target coding region are typically eliminated from further consideration. The remaining candidate polynucleotides may then be tested to determine if they inhibit expression of a coding region.

In general, candidate polynucleotides are individually tested by introducing a candidate polynucleotide into a cell that expresses the appropriate mRNA and polypeptide. In one embodiment, the candidate polynucleotides may be prepared in vitro and then introduced into a fungal cell that expresses the target mRNA. Methods for in vitro synthesis include, for instance, chemical synthesis with a conventional DNA/RNA synthesizer. Commercial suppliers of synthetic polynucleotides and reagents for such syntheses are well known. Methods for in vitro synthesis also include, for instance, in vitro transcription using a circular or linear vector in a cell free system. In one embodiment, the candidate polynucleotide may be introduced into a cell as a dsRNA or as an antisense ssRNA. In one embodiment, a candidate polynucleotide may be introduced into a cell as a construct that encodes the candidate polynucleotide. The cell may be a fungal pathogen. Such constructs are known in the art and include, for example, a vector encoding and expressing a sense strand and an antisense strand of a candidate polynucleotide, and RNA expression vectors that include the sequence encoding the sense strand and antisense strand of a candidate polynucleotide flanked by operably linked regulatory sequences to drive expression of the candidate polynucleotide. In another embodiment, a polynucleotide that is operably linked to a regulatory sequence encodes the antisense strand, the transcription of which produces a polynucleotide which can form secondary structures that affect expression of a target mRNA.

When evaluating whether a candidate polynucleotide functions to inhibit expression of a target mRNA described herein, the amount of target mRNA in a cell containing a candidate polynucleotide can be measured and compared to a control cell (e.g., the same type of cell that does not contain the candidate polynucleotide). Methods for measuring mRNA levels in a cell are known in the art and routine. Such methods include quantitative reverse-transcriptase polymerase chain reaction (qRT-PCR). Primers and specific conditions for amplification of a target mRNA can be readily determined by the skilled person. Other methods include, for instance, Northern blotting, and array analysis.

Other methods for evaluating whether a candidate polynucleotide functions to inhibit expression of a polypeptide encoded by a target mRNA includes monitoring the polypeptide. For instance, assays can be used to measure a decrease in the amount of polypeptide encoded by the mRNA, or to measure a decrease in the activity of the polypeptide encoded by the mRNA. Methods for measuring a decrease in the amount of a polypeptide include assaying for the polypeptide present in cells containing a candidate polynucleotide and comparing to a control cell. Whether a cell expresses one of the polypeptides can be determined using methods that are routine and known in the art including, for instance, Western immunoblot, ELISA, immunoprecipitation, or immunohistochemistry.

In one embodiment, a candidate polynucleotide is able to decrease the expression of a target mRNA, or the polypeptide encoded by the target mRNA, by at least 5%, at least 10%, at least 15%, at least 20%, at least 30%, at least 40%, at least 50%, at least 60%, at least 70%, at least 80%, at least 90% or 100% when compared to a control cell (e.g., a fungal pathogen that does not include the candidate polynucleotide).

A polynucleotide, such as a dsRNA, described herein can be encoded by a polynucleotide present in a vector. A vector is a replicating polynucleotide, such as a plasmid, phage, or cosmid, to which another polynucleotide may be attached so as to bring about the replication of the attached polynucleotide. Construction of vectors containing a polynucleotide described herein employs standard ligation techniques known in the art (see, e.g., Sambrook et al, *Molecular Cloning: A Laboratory Manual*., Cold Spring Harbor Laboratory Press (1989)). A vector can provide for further cloning (amplification of the polynucleotide), i.e., a cloning vector, or for expression of the polynucleotide, i.e., an expression vector. The term vector includes, but is not limited to, plasmid vectors. In one embodiment, such as when the dsRNA is expressed in a plant cell, a vector may result in integration into a cell's genomic DNA. Typically, a vector is capable of replication in a bacterial host, for instance *E. coli*, and optionally, in other cells. A polynucleotide described herein can be present in a vector as two separate complementary polynucleotides, each of which can be expressed to yield a sense and an antisense strand of the dsRNA, or as a single polynucleotide containing a sense strand, a loop region, and an anti-sense strand, which can be expressed to yield an RNA polynucleotide having a sense and an antisense strand of the dsRNA.

Selection of a vector depends upon a variety of desired characteristics in the resulting construct, such as a selection marker, vector replication rate, and the like. Suitable host cells for cloning or expressing the vectors herein are prokaryote or eukaryotic cells. Suitable prokaryotes include members of the domain Bacteria and members of the domain Archaea. In one embodiment, a suitable prokaryote is *E. coli*. An example of a eukaryotic cell is a plant cell.

An expression vector optionally includes regulatory sequences operably linked to the polynucleotide of the present disclosure. Typically, the promoter results in the production of an RNA polynucleotide. Examples of such promoters for use in prokaryotic cells include a T7 promoter, a T3 promoter or an SP6 promoter. Examples of such promoters for use in eukaryotic cells include those that cause binding of an RNA polymerase, such as an RNA polymerase III complex, to initiate transcription of an operably linked polynucleotide of the present disclosure. In one embodiment, examples of such promoters include constitutive promoters such as the CaMV35S promoter from the cauliflower mosaic virus, plant-derived actin promoters and ubiquitin promoters, leaf-localized promoters such as photosynthesis-associated nuclear genes (PhANGS) promoters, the chlorophyll a/b-binding proteins (Cab) promoter, or the small subunit of Rubisco (RbcS) promoter. A promoter may be constitutive or inducible. Another regulatory sequence is a transcription terminator. Suitable transcription terminators are known in the art.

The polynucleotide, such as a dsRNA, is introduced into the fungal pathogen. In one embodiment, the dsRNA is expressed by a transgenic plant. As used herein, the term "transgenic plant" refers to a plant that has been transformed to contain at least one polynucleotide to result in expression of a dsRNA. The term "transgenic plant" includes whole plants, plant parts (stems, roots, leaves, fruit, etc.) or organs, plant cells, seeds, and progeny of same. A transformed plant can be a direct transfectant, meaning that the DNA construct was introduced directly into the plant, such as through *Agrobacterium* or other methods, or the plant can be the progeny of a transfected plant. The second or subsequent generation plant can be produced by sexual reproduction, i.e., fertilization. Furthermore, the plant can be a gametophyte (haploid stage) or a sporophyte (diploid stage).

Examples of plants include, but are not limited to, herbaceous, succulent plants, particularly flowers and vegetables. Specific examples include, but are not limited to, oil seed crops such as canola, mustard, flax, sunflower, corn, oat, cotton, camelina, crambe, safflower, rice, sunflower, soybean, peanut, rapeseed, coconut, and oil palm. Other plants include borage, potato, pea, bean, lentil, chickpea, and forage legumes.

Transgenic plants described herein may be produced using routine methods (see, for instance, Waterhouse et al., US Patent Application 2006/0272049). Methods for transformation and regeneration are known to the skilled person. Transformation of a plant cell with a polynucleotide described herein to yield a recombinant host cell may be achieved by any known method for the insertion of nucleic acid sequences into a prokaryotic or eukaryotic host cell, including *Agrobacterium*-mediated transformation protocols, viral infection, whiskers, electroporation, microinjection, polyethylene glycol-treatment, heat shock, lipofection, particle bombardment, and chloroplast transformation. Also provided are transgenic plants expressing one or more of the polynucleotides described herein.

Techniques for the transformation of monocotyledon species include direct gene transfer into protoplasts using PEG or electroporation techniques, particle bombardment into callus tissue or organized structures, as well as *Agrobacterium*-mediated transformation.

The cells that have been transformed may be grown into plants in accordance with conventional techniques. See, for example, McCormick et al. (1986, Plant Cell Reports, 5:81-84). These plants may then be grown and evaluated for expression of the dsRNA. These plants may be either pollinated with the same transformed strain or different strains, and the resulting hybrid having desired phenotypic characteristics identified. Two or more generations may be grown to ensure that the desired expression of one or more dsRNAs is stably maintained and inherited and then seeds harvested to ensure stability of the desired characteristics have been achieved.

In another embodiment, a polynucleotide, such as a dsRNA, is introduced into the fungal pathogen by topical application of the polynucleotide, such as a dsRNA, to a plant having or at risk of having an infection by a fungal plant pathogen. Application of a polynucleotide to a plant may be by spraying, brushing, or any other method. The application can be to the entire plant or to a portion thereof, such as a leaf, a flower, a fruit, a seed, or a vegetable. Polynucleotides may be applied to a plant in any suitable composition. The composition may be aqueous or nonaqueous. In one embodiment, the composition includes agents to aid in stability of the polynucleotide, ability of the polynucleotide to enter the fungal plant pathogen, and/or ability to remain associated with the surface of the plant. Such an agent may be physically associated with the polynucleotide. The composition may include other agents to aid in the topical application of a dsRNA molecule including, but not limited to, a surfactant (for instance, anionic, cationic, amphoteric, nonionic), a biosurfactant, a wetting agent, a penetrant, a thickener, an emusifier, a spreader, a sticker, an oil, an alkyl polyglucoside, an organosilicate, an inorganic salts, or a combination thereof. Also provided is a composition that includes a polynucleotide described herein.

Also provided by the present disclosure are plants having a polynucleotide described herein on its surface. The polynucleotide can be present on the entire plant or on a part of the plant, such as one or more leaves of the plant. Also provided herein are methods for applying a polynucleotide to a plant, or a part of the plant, with a composition that includes a polynucleotide described herein.

In one embodiment, more than one polynucleotide can be expressed in a transgenic plant or applied to a plant. For instance, multiple polynucleotides targeting different areas of a mRNA can be expressed in a transgenic plant or applied to a plant. In another example, multiple polynucleotides targeting different mRNA molecules can be expressed in a transgenic plant or applied to a plant. The number of different polynucleotides can be at least 2, at least 3, at least 4, at least 5, or at least 6. It is expected there is no upper limit to the number of different polynucleotides that can be expressed in a transgenic plant or applied to a plant, but in one embodiment the number is no greater than 15, or no greater than 10. In one embodiment, one or more polynucleotides can be expressed in a transgenic plant and one or more polynucleotides can be applied to the same plant.

Treatment of a plant can be prophylactic or, alternatively, can be initiated after the development of disease caused by a fungal plant pathogen. Treatment that is prophylactic, for instance, initiated before a plant manifests signs of disease, is referred to herein as treatment of a plant that is "at risk" of having an infection. Treatment can be performed before, during, or after the occurrence of an infection by a fungal plant pathogen. Treatment initiated before the development of disease may result in decreasing the risk of infection by the fungal pathogen. Treatment initiated before development of disease includes applying a polynucleotide described herein to the surface of a plant, use of a transgenic plant that expresses a polynucleotide described herein, or a combination there. Treatment initiated after the development of disease may result in decreasing the severity of the signs of the disease, or completely removing the signs. A sign of disease by a fungal pathogen includes, but is not limited to, one or more lesions on the surface of the plant. The dosage administered to a plant is sufficient to result in decreased risk of infection or decreased severity of the signs of the disease (e.g., reduce number of lesions, reduced size of lesions, or a combination thereof). Decreased risk of infection or decreased severity of the signs of the disease can be the result of reduced growth of the pathogen, increased resistance of the plant to the pathogen, or a combination thereof. Such a dosage can be easily determined by the skilled person.

In one embodiment, decreased risk of infection or decreased severity of signs of disease can be determined by reduction of lesion size. Lesion size on leaves or other parts of a plant can be measured using standard methods. The reduction in lesion size can be at least 3%, at least 10%, at least 20%, at least 30%, at least 40%, at least 50%, at least 60%, at least 70%, at least 08%, or at least 90% compared to a control plant (e.g., the same type of plant that was not treated with the composition, or the same type of plant that does not express the polynucleotide). In one embodiment, lesions on a plant are not detectable.

In one embodiment, a composition applied to a surface of a plant includes a polynucleotide, such as a dsRNA, at a dose of 0.1 nanogram per square millimeter (ng/mm$^2$) to 15 ng/mm$^2$. For example, dsRNA may be applied at a dose of at least 0.1 nanogram per square millimeter (ng/mm$^2$), at least 0.5 ng/mm$^2$, at least 1 ng/mm$^2$, at least 5 ng/mm$^2$, or at least 10 ng/mm$^2$. For example, dsRNA may be applied at a dose of no greater than 15 ng/mm$^2$, no greater than 10 ng/mm$^2$, no greater than 5 ng/mm$^2$, no greater than 1 ng/mm$^2$, or no greater than 0.5 ng/mm$^2$. In one embodiment, more than one polynucleotide may be expressed by a transgenic plant or applied to a plant.

The present disclosure is illustrated by the following examples. It is to be understood that the particular examples, materials, amounts, and procedures are to be interpreted broadly in accordance with the scope and spirit of the disclosure as set forth herein.

Example 1

A technology that could provide a suite of new options to control *Sclerotinia* is RNA interference (RNAi). RNAi is a sequence-specific method of reducing or silencing a gene's expression following the introduction of double-stranded RNAs (dsRNAs) into a cell. Once within the cell, the dsRNA mediates the destruction of any RNA with identical sequence, thereby silencing the gene's expression. Using bioinformatics tools, it is possible to design dsRNAs to selectively target just one gene in an organism, and also design dsRNA to target only one species or alternatively, a group of related species. With its incredible ability to silence a gene's expression, RNAi is being considered for a great many applications, including a variety of crop protection technologies [6]. We have previously developed transgenic plants that expressed species-specific insecticidal dsRNAs that targeted genes essential to the insects' growth, and thereby killed insects that fed on the plants [7]. Because of RNAi's sequence-specificity, it can be readily adapted to selectively target any pest or pathogen, without adversely affecting other organisms. RNAi has previously been proven effective in protecting transgenic tobacco plants from the pathogenic fungus *Fusarium verticillioides* [8]. In this study, we examined the utility of RNAi technologies to suppress *S. sclerotiorum* growth, with the aim of developing topically-applied dsRNAs as an alternative to transgenic-mediated protection of the plants. We first demonstrated that exogenously-supplied dsRNA can be taken up by the fungus and that gene-specific knockdown of mRNA transcripts occurs. Secondly, we have identified the repertoire of genes that are expressed by *S. sclerotiorum* during early stages of infection in canola plants. By using moderate through-put screening methods, we have identified which of these fungal genes are the most sensitive RNAi targets, to minimize infection in the plants. RNAi can target a specific gene or a family of genes, and hence, the technology offers the ability to produce a vast number of anti-*Sclerotinia* dsRNAs, which will provide a rich supply of fungal-control dsRNAs if resistant strains arise. The technology could also be developed to control other fungal pathogens that affect other commercial crops.

Our approach to develop an RNAi-based method of controlling *Sclerotinia* stem rot in canola included three main components: 1) a proof-of-concept demonstration that topically-applied dsRNAs can induce RNAi and inhibit *S. sclerotiorum* growth in fungal growth bioassays; 2) identification of additional fungal target genes using transcriptomic analyses and moderate throughput RNAi functional screening and 3) testing of topical application formulations of dsRNAs to assess whether plants can be protected from *Sclerotinia* infection without using transgenic technologies, which may serve as a safer, ready-to-use, more species-specific alternative to fungicides.

Results

1. Transcriptomic Analyses of Canola Infected with *S. sclerotiorum* have Identified Thousands of Putative RNAi Targets.

To identify differentially expressed genes during the infection process, we sequenced rapidly infecting *S. sclerotiorum* infected canola leaf tissues. We selected two cultivars with varying levels of susceptibility, Westar (susceptible) and ZhongYou821 (tolerant), to compare responses within *Sclerotinia*. RNA samples were extracted and we performed high-throughput RNA sequencing on the Illumina HiSeq platform. One hundred paired end sequence reads generated by the Illumina Hiseq 2500 were quality filtered through the FASTX toolkit, trimmed using a sliding window and headcrop with the jar program Trimmomatic. Samples were aligned to the *S. sclerotiorum* reference genome using TopHat2 in high sensitivity mode. Raw counts were used as input to DESeq2 for lists of differentially expressed genes and TopHat to identify splice junctions.

We compared gene lists to fungus grown on plates with that grown on leaves to identify thousands of differentially expressed genes that represent excellent targets for RNAi to impede and suppress fungal growth. Infection on the two cultivars was also compared to identify genes important to infection on canola. We identified 10,003 genes as being present before during and after the infection process. We then used previously obtained gene ontology (GO) terms, BLAST, and protein FASTA files to assign predicted biological function.

2. Transcriptomic Analyses can Provide Information on Gene Expression Levels to Enable Faster Identification of Genes Expressed During the Earliest Phases of Infection.

To identify genes important to the infection process, we found 1,858 genes up-regulated in response to infection in both cultivars. These genes probably represent ideal targets for RNA interference. These genes significantly up-regulated and considered a minimum false discovery rate of 0.05. GO terms and BLAST queries guided the choice of targets. We also targeted some essential genes listed in publically available databases to extend choosing targets without requiring transcriptomic data and develop a bioinformatics pipeline. Targets chosen for *S. sclerotiorum* are shown in Table 3.

To synthesize dsRNA for the chosen targets, *Sclerotinia* gene sequences were acquired from Genbank and primers were designed to PCR amplify gene fragments ranging between 180 and 480 bp in length (shown in Table 4). Each product was ligated into a vector, between two T7 RNA polymerase promoter sequences, which then was used to PCR-amplify the gene fragments. The PCR products were then used as templates to prepare dsRNAs by in vitro transcription using T7 RNA polymerase.

TABLE 3

*S. sclerotiorum* targets for RNA interference

| Gene | Accession | Gene Ontology | Experiment |
|---|---|---|---|
| SS1G_06487 | XM_001592197.1 | TIM44 | Foliar application |
| SS1G_01703 | XM_001597459.1 | Aminoacyl-tRNA ligase activity | Foliar application; Transgenic approach |
| SS1G_05899 | XM_001592927.1 | Thioredoxin reductase | Foliar application |
| SS1G_02495 | XM_001596225.1 | Peroxidase activity | Foliar application |
| SS1G_11912 | XM_001586833.1 | Necrosis/ethylene inducing peptide 2 | Foliar application |
| SS1G_07873 | XM_001591197.1 | Pre-40S ribosomal particle | Foliar application |
| SS1G_09665 | XM_001588982.1 | Inositol pentakisphosphate 2-kinase | Transgenic approach |
| SS1G_08218 | XM_001590428.1 | Oxaloacetate acetylhydrolase | Transgenic approach |

TABLE 4

*S. sclerotiorum* primers used to clone and synthesize select dsRNA

| Gene | Forward Primer | Reverse Primer |
|---|---|---|
| SS1G_06487 | CGTAGCATATCCGACCGAGT (SEQ ID NO: 14) | AGACGGAGAATTGAGCTGCT (SEQ ID NO: 15) |
| SS1G_01703 | TTCTGCCGGAAACCCTCTTC (SEQ ID NO: 16) | ACCGCCGATTGTGAAGACTT (SEQ ID NO: 17) |
| SS1G_05899 | GCTCACACTGCTGCCGTATA (SEQ ID NO: 18) | CTCCGCAGCACTATCTCCAC (SEQ ID NO: 19) |
| SS1G_02495 | TCGTGAATGAAGCAGGCCAA (SEQ ID NO: 20) | TGTTGTCGACCACTGTACCG (SEQ ID NO: 21) |
| SS1G_11912 | TCGTAAATGGCTGCGTACCA (SEQ ID NO: 22) | GGGAATGTGCCAGAGAGTGT (SEQ ID NO: 23) |

TABLE 4-continued

*S. sclerotiorum* primers used to clone and synthesize select dsRNA

| Gene | Forward Primer | Reverse Primer |
|---|---|---|
| SS1G_07873 | TTCGAAACCACCCTGCTACC (SEQ ID NO: 24) | CCCATGCGCCTCTAGTTTCA (SEQ ID NO: 25) |
| SS1G_09665 | TTCGCGATCTCCAAACCGAA (SEQ ID NO: 26) | CACCACAATACCATCCCTCGT (SEQ ID NO: 27) |
| SS1G_08218 | ACAGATGCGCTCCAACAACT (SEQ ID NO: 28) | GGCCCTTGGTGTAACGTTCT (SEQ ID NO: 29) |

3. *S. sclerotiorum* Fungal Hyphae can Take in Exogenous dsRNA to Induce RNA Interference Over Time DsRNA targeting *Sclerotinia* gene SS1G_05899 was synthesized as described above. Fungus was grown from a *sclerotium* on potato dextrose agar (PDA). A plug of about 1 mm in diameter was taken from the actively growing edge of the fungal colony and placed in 3 mL of potato dextrose broth (PDB). The fungus grew for 48 hours before 500 ng of dsRNA was added. Fungus was taken at time points 0, 24, 28, 72, and 96 hours post-inoculation; RNA was extracted; cDNA prepared; and qRT-PCR was used to assess the level of mRNA transcripts for the target gene. A maximum knockdown of 47% was observed after 4 days of incubation (Table 5). The knockdown trend in the SS1G 05899 dsRNA treated tubes opposed the trend observed in the GFP dsRNA treated tubes. The GFP did not have any negative impact on the accumulation of the target transcript and this was due to the application of the target dsRNA. The timing of the RNAi effect was consistent with what is observed in human cell lines and insect experiments.

TABLE 5

% *Sclerotinia* gene expression after treatment with 500 ng of gene-specific dsRNA overtime

| | Time (hours) | | | | |
|---|---|---|---|---|---|
| Gene | 0 | 24 | 48 | 72 | 96 |
| SS1G_05899 | 100 ± 16 | 82 ± 15 | 64 ± 11 | 49 ± 9 | 47 ± 9 |
| GFP (control) | 100 ± 14 | 165 ± 24 | 154 ± 19 | 221 ± 30 | 244 ± 35 |

1. Gene expression relative to beta tubulin (SS1G_04652) gene transcript levels
2. Gene expression relative to 0 hours.
3. Error is equivalent to standard deviation 4. *S. sclerotiorum* Fungal Hyphae can Take in Exogenous dsRNA to Elicit RNA Interference at Various Doses Fungus was grown from a *sclerotium* on PDA. A plug of about 1 mm in diameter was taken from the actively growing edge of the fungal colony and placed in 3 mL of PDB. Specific doses (100 ng, 200 ng, 500 ng, and 1000 ng) of SS1G_07873 dsRNA were added to the medium. In parallel, SS1G_06487, SS1G_05899, and SS1G_02495 dsRNA were tested at the 500 ng dose level. The fungi grew for 3 days before the tissue was collected, RNA extracted, and cDNA synthesized. qRT-PCR was used to assess the level of mRNA transcripts for target genes. Water (0 ng) was used to compare accumulation levels. All genes showed a significant knockdown at all doses tested with a maximum knockdown of 53% (Tables 6 and 7). This suggests that molecules function in reducing the accumulation of the transcript in recipient *Sclerotinia*.

TABLE 6

Changes in target gene expression levels following dsRNA treatments in *Sclerotinia*.

| Gene | 0 ng | 100 ng | 200 ng | 500 ng | 1000 ng |
|---|---|---|---|---|---|
| SS1G_07873[1] | 100 ± 5.6 | 69.0 ± 6.2 | 77.5 ± 13 | 58.9 ± 6.9 | 65.1 ± 3.4 |

A. Gene expression relative to: [1]Beta tubulin
B. Error corresponds to standard deviation

TABLE 7

Observed knockdown of gene transcripts in *Sclerotinia* following treatment with dsRNA

| Gene | Dose (ng) | % expression in qPCR |
|---|---|---|
| SS1G_06487[1] | 500 | 54.9 ± 5.1 |
| SS1G_07873[1] | 500 | 58.9 ± 6.9 |
| SS1G_05899[1] | 500 | 47 ± 9 |
| SS1G_02495[1] | 500 | 68.4 ± 9 |

A. Gene expression relative to: [1]Beta tubulin
B. Gene expression relative to 0 ng (water dose) control
C. Error corresponds to standard deviation 5. A Topical Application of dsRNA on Canola Leaves can Reduce *S. sclerotiorum* Growth.

To mimic field conditions, senescing canola (*B. napus*) petals were coated with 200 ng of dsRNA, and then 10 μl of fungal spores (~5000 spores) were applied to each petal. After 3 days, a further application of 200 ng of dsRNA was applied to leaf surfaces and the petals placed onto the leaves. Plants were incubated in high humidity conditions, essential for causing an aggressive infection. Leaves were imaged and the lesion measured using ImageJ software. The majority of the genes tested showed a significant reduction in lesion size up to 85.32% (Table 8). The results suggest that topical application of dsRNAs directly on the leaf surface protects the plant from *S. sclerotiorum* proliferation.

TABLE 8

Reduced *Sclerotinia* infection of canola leaves using a canola petal assay

| Gene | Percent reduction in lesion size (%) |
|---|---|
| SS1G_06487 | 85.32 ± 16.2 |
| SS1G_01703 | 84.93 ± 16.3 |
| SS1G_05899 | 76.93 ± 12.5 |
| SS1G_02495 | 70.74 ± 24.8 |
| SS1G_11912 | 66.24 ± 16.3 |

TABLE 8-continued

Reduced *Sclerotinia* infection of canola leaves using a canola petal assay

| Gene | Percent reduction in lesion size (%) |
|---|---|
| SS1G_07873 | 63.91 ± 28.1 |
| SS1G_09665 | 3.10 ± 31.1 |
| SS1G_08218 | −8.94 ± 29.3 |

A. Lesion size relative to water control (no dsRNA)
B. Error corresponds to standard deviation 6. DsRNA Expressing *A. thaliana* Plants are Protected Against *Sclerotinia* Infection

*Sclerotinia* gene targets used to protect plants using a foliar application were selected to evaluate a transgenic approach for RNAi technology. The primers used to synthesize the dsRNA (Table 4) were reused to develop transgenic plants expressing the same targeting region. Products were amplified using PCR and each product was shuttled into a vector for sequencing before being recombined into a final vector, which produces hairpin RNA (hpRNA). The vectors were transformed into *Agrobacterium tumefaciens*, which allowed *A. thaliana* plants to be transformed using established transformation protocols. Transgenic plants were selected using kanamycin MS plates and the plants were grown for 3 weeks. At this stage, approximately 10 μL of 10000 spores suspended in glucose-phosphate buffer [9] were dispensed onto the surface of the leaves. The plants were placed in a humidity chamber and the infection progressed for 4 days before the lesions were assessed using photography and ImageJ. All of the hpRNA expressing plants showed a reduction in lesion size up to 74.5% compared to the wild-type Columbia *A. thaliana* (Table 9). In general, the transgenic plants showed a higher level of protection compared to the foliar application of dsRNA molecules.

TABLE 9

*Sclerotinia* lesion reduction on hpRNA-expressing *A. thaliana* plants specifically targeting *Sclerotinia* genes.

| Gene | Reduction in lesion size (%) |
|---|---|
| SS1G_01703 | 65.7 ± 19 |
| SS1G_09665 | 57.83 ± 18 |
| SS1G_08218 | 74.5 ± 9 |

A. Lesion sizes relative to wild-type Columbia *Arabidopsis thaliana* plants
B. Error corresponds to standard deviation 6. *Sclerotinia* Homologs in *Botrytis cinerea* are Effective at Reducing Growth With the success of the *Sclerotinia* targets, homologs of some *S. sclerotiorum* genes were targeted in *B. cinerea* to extend our targets beyond *Sclerotinia* (Table 10). Homologs were identified using the BLASTP (available on the world wide web at blast.ncbi.nlm.nih.gov/Blast.cgi?PAGE=Proteins) and then the Genbank accessions could be found. Similar to *S. sclerotiorum*, primers were designed to PCR amplify gene fragments ranging between 180 and 480 bp in length (shown in Table 11). Each product was ligated into a vector, between two T7 RNA polymerase promoter sequences, which then was used to PCR-amplify the gene fragments. The PCR products were then used as templates to prepare dsRNAs by in vitro transcription using T7 RNA polymerase.

Once dsRNA was synthesized, canola leaves of approximately 4 weeks of age were taken and placed in large petri plates containing dampened paper towel. 500 ng of dsRNA was spread over a 4 $cm^2$ area. To facilitate infection, a small puncture was made in the middle of the 4 $cm^2$ area and then approximately 1000 spores of *B. cinerea* were placed on the punctured region. The infection proceeded for 4 days before the lesions were photographed and measured using ImageJ software. Lesion sizes were reduced up to 73% (Table 12) suggesting that homologous dsRNAs could be designed for other pathogenic species and would be effective at controlling other plant diseases.

TABLE 10

*B. cinerea* topical homologs targeted for RNA interference

| Gene | *Sclerotinia* homolog | Accession | ID |
|---|---|---|---|
| BC1G_10306 | SS1G_06487 | XM_001550999.1 | Necrosis peptide, Ure2p Glutathione S-transferase |
| BC1G_04775 | SS1G_02495 | XM_001556707.1 | Mitochondrial protein import |
| BC1G_07805 | SS1G_07873 | XM_001553668.1 | 20S proteosome maturation |
| BC1G_04955 | SS1G_11912 | XM_001556287.1 | Peroxidase acitivity |
| BC1G_01592 | SS1G_05899 | XM_001559983.1 | Thioredoxin reductase |

TABLE 11

*B. cinerea* primers used for cloning

| Gene | Forward Primer | Reverse Primer |
|---|---|---|
| BC1G_10306 | CCCTTTCGGTCTTGGCATCT (SEQ ID NO: 30) | TGGCGTAGTTTGATCCGCTT (SEQ ID NO: 31) |
| BC1G_04775 | GGACGCCCACAAGTAAACAG (SEQ ID NO: 32) | GCTGGGCATGCTACAGATCT (SEQ ID NO: 33) |
| BC1G_07805 | CGCATGAACCTCAACCTCCT (SEQ ID NO: 34) | TCCGTGGCCATTTCTCTCAC (SEQ ID NO: 35) |

TABLE 11-continued

| B. *cinerea* primers used for cloning | | |
|---|---|---|
| Gene | Forward Primer | Reverse Primer |
| BC1G_04955 | GCTCTGACATCTTCGCTCGA (SEQ ID NO: 36) | CACCTCTGAACCGAAGCCAT (SEQ ID NO: 37) |
| BC1G_08022 | CGTAACCGCACACCCATCTT (SEQ ID NO: 38) | TCCTTTCCACACGTAGCGAT (SEQ ID NO: 39) |
| BC1G_01592 | GCGCGGAATTGAAACCTGTT (SEQ ID NO: 40) | GGCACCAGTAGCGATGATGA (SEQ ID NO: 41) |

TABLE 12

Reduction in *B. cinerea* lesions on canola when targeted by homologous dsRNAs from *Scleortinia*

| *Botrytis* Gene | % Lesion reduction |
|---|---|
| BC1G_04775 | 73 ± 30 |
| BC1G_04955 | 53 ± 26 |
| BC1G_07805 | 42 ± 33 |
| BC1G_10306 | 46 ± 29 |
| BC1G_01592 | 54 ± 20 |

A. Lesion size relative to GFP control

B. Error corresponds to standard deviation

CITATIONS 1. canolacouncil.org;
2. Baharlouei et al., 2011, African J Biotech 10: 5785-5794;
3. Litholdo et al., 2010, Genetics Molec Res 10: 868-877;
4. Hu et al., 2011, Can J Microbiology 57: 539-546;
5. gov.mb.ca;
6. Ali et al. 2010. GM Crops 1: 207-213.
7. Waterhouse et al. 2005, WO 2005/049841.
8. Tinoco et al. 2010, BMC Biology 8: 27.
9. Garg et al. 2010, Annals of Botany 106:897-908

Example 2

Other targets for RNA interference were evaluated as described in Example 1. The following coding regions, when targeted for decreased expression, were found to result in reduced growth of *S. sclerotiorum*: XM_001591197.1 (SS1G_07873, SEQ ID NO:42), XM_001590273.1 (SS1G_09088, SEQ ID NO:43), XM_001596198.1 (SS1G j2468, SEQ ID NO:44), XM_001587661.1 (SS1G_11704, SEQ ID NO:45), XM_001596446.1 (SS1G 02716, SEQ ID NO:46), XM_001586961.1 (SS1G_12040, SEQ ID NO:47), XM_001589214.1 (SS1G j9897, SEQ ID NO:48), XM_001592927.1 (SS1G_05899, SEQ ID NO:49), XM_001592197.1 (SS1G j6487, SEQ ID NO:50), XM_001597459.1 (SS1G j1703, SEQ ID NO:51), XM_001596225.1 (SS1G_02495, SEQ ID NO:52), XM_001586833.1 (SS1G_11912, SEQ ID NO:53), XM_001589938.1 (SS1G j8752, SEQ ID NO:54), XM j01588858.1 (SS1G_10456, SEQ ID NO:55), XM_001588798.1 (SS1G_10396, SEQ ID NO:56), XM_001594135.1 (SS1G_03992, SEQ ID NO:57), XM_001586701.1 (SS1G_11780, SEQ ID NO:58), XM_001591282.1 (SS1G_07958, SEQ ID NO:59), XM_001594183.1 (SS1G_04040, SEQ ID NO:60), XM_001598634.1 (SS1G_00773, SEQ ID NO:61), XM_001598299.1 (SSIG_00435, SEQ ID NO:62), XM_001593489.1 (SS1G j4966, SEQ ID NO:63), XM_001588511.1 (SS1G_10108, SEQ ID NO:64), XM_001594947.1 (SS1G_04805, SEQ ID NO:65), XM_001594144.1 (SS1G_04001, SEQ ID NO:66), XM_001592623.1 (SS1G_06914, SEQ ID NO:67), XM_001591055.1 (SS1G_07730, SEQ ID NO:68), XM_001588997.1 (SS1G_09680, SEQ ID NO:69), XM_001594134.1 (SS1G_03991, SEQ ID NO:70, XM_001588201.1 (SS1G_10698, SEQ ID NO:71), XM_001590641.1 (SS1G_08431, SEQ ID NO:72), XM_001585413.1 (SS1G_13702, SEQ ID NO:73), XM_001595070.1 (SS1G_03208, SEQ ID NO:74), XM_001587072.1 (SS1G_12152, SEQ ID NO:75), XM_001595209.1 (SS1G_03348, SEQ ID NO:76), XM_001585128.1 (SS1G_13746, SEQ ID NO:77), XM_001592539.1 (SS1G_06830, SEQ ID NO:78), XM_001586999.1 (SS1G_12078, SEQ ID NO:79), XM_001553779.1 (SS1G_08022, SEQ ID NO:80), XM_001595070.1 (SS1G_03208, SEQ ID NO:81), XM_001594134.1 (SS1G_03991, SEQ ID NO:82), XM_001593489.1 (SS1G_04966, SEQ ID NO:83), XM_001592539.1 (SS1G_06830, SEQ ID NO:84), XM_001588997.1 (551G_09680, SEQ ID NO:85), XM_001586942.1 (SS1G_12021, SEQ ID NO:86), XM_001586603.1 (SS1G_12640, SEQ ID NO:87), XM_001585850.1 (SS1G_12992, SEQ ID NO:88), XM_001585413.1 (SS1G_13702, SEQ ID NO:89), or XM_001585128.1 (SS1G_13746, SEQ ID NO:90).

TABLE 13

Reduced *Sclerotinia* infection of canola leaves using a canola petal assay

| Gene | Percent reduction in lesion size (%) |
|---|---|
| SS1G_06487 | 85.32 ± 16.2 |
| SS1G_01703 | 84.93 ± 16.3 |
| SS1G_05899 | 76.93 ± 12.5 |
| SS1G_02495 | 70.74 ± 24.8 |
| SS1G_11912 | 66.24 ± 16.3 |
| SS1G_07873 | 63.91 ± 28.1 |
| SS1G_08752 | 62.79 ± 59.4 |
| SS1G_10456 | 60.39 ± 25.5 |
| SS1G_10396 | 59.30 ± 17.8 |
| SS1G_03992 | 57.85 ± 10.9 |
| SS1G_09088 | 55.07 ± 37.4 |
| SS1G_11780 | 51.38 ± 16.1 |
| SS1G_02468 | 51.24 ± 15.4 |
| SS1G_07958 | 48.89 ± 19 |
| SS1G_04040 | 47.32 ± 20.8 |
| SS1G_11704 | 47.19 ± 28.2 |
| SS1G_09897 | 45.33 ± 17 |
| SS1G_00773 | 43.17 ± 22.1 |
| SS1G_02716 | 40.79 ± 10.9 |

TABLE 13-continued

Reduced *Sclerotinia* infection of canola leaves using a canola petal assay

| Gene | Percent reduction in lesion size (%) |
|---|---|
| SS1G_00435 | 35.18 ± 22.5 |
| SS1G_04966 | 34.93 ± 20.7 |
| SS1G_10108 | 33.78 ± 24 |
| SS1G_04805 | 33.20 ± 10.2 |
| SS1G_04001 | 33.00 ± 21.8 |
| SS1G_06914 | 32.68 ± 20.3 |
| SS1G_07730 | 31.99 ± 18.8 |
| SS1G_09680 | 30.78 ± 25.7 |
| SS1G_03991 | 30.56 ± 14.3 |
| SS1G_10698 | 28.80 ± 23.5 |
| SS1G_12040 | 26.72 ± 23.5 |
| SS1G_08431 | 24.32 ± 21.5 |
| SS1G_13702 | 23.85 ± 35.5 |
| SS1G_03208 | 23.68 ± 16.8 |
| SS1G_12152 | 23.51 ± 29 |
| SS1G_03348 | 23.28 ± 26.4 |
| SS1G_13746 | 20.63 ± 26.1 |
| SS1G_06830 | 20.34 ± 17.4 |
| SS1G_12078 | 10.92 ± 64.9 |
| SS1G_09665 | 3.10 ± 31.1 |
| SS1G_08218 | −8.94 ± 29.3 |

A. Lesion size relative to water control (no dsRNA)
B. Error corresponds to standard deviation The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A plant comprising a polynucleotide that reduces expression of a coding region having a sequence SS1G_01703 (SEQ ID NO:2), or a homolog of SS1G_01703 (SEQ ID NO:2), wherein the polynucleotide comprises a sense strand of at least 21 nucleotides of SEQ ID NO:2 and the complement thereof.

2. The plant of claim 1 wherein growth of a fungal pathogen comprising the coding region on the plant is reduced compared to a control plant.

3. The plant of claim 2 wherein lesion size after administration of the fungal pathogen to leaves of the plant is reduced by at least 3% compared to a control plant that does not comprise the polynucleotide.

4. The plant of claim 1 wherein the polynucleotide reduces expression of the coding region or a homolog thereof in a plant pathogen *Sclerotinia sclerotiorum* or *Botrytis cinerea.*

5. The plant of claim 1 wherein the polynucleotide comprises a double stranded RNA (dsRNA).

6. The plant of claim 1 wherein the polynucleotide is present on a surface of the plant, and wherein the surface is a leaf, a flower, a fruit, a seed, a vegetable, or a combination thereof.

7. The plant of claim 1 wherein the plant is canola, mustard, flax, sunflower, corn, oat, cotton, camelina, *crambe*, safflower, rice, sunflower, soybean, peanut, rapeseed, coconut, oil palm, borage, potato, pea, bean, lentil, chickpea, or a forage legume.

8. A method for making the plant of claim 1 comprising applying a composition to a surface of the plant, wherein the composition comprises the polynucleotide.

9. The method of claim 8 wherein the applying comprises spraying the plant.

10. The method of claim 8 wherein the applying comprises application of the composition to a leaf, a flower, a fruit, a seed, a vegetable, or a combination thereof, of the plant.

11. The method of claim 8 wherein the composition is applied at a dose of 0.1 nanogram polynucleotide per square millimeter (ng/$mm^2$).

12. A transgenic plant comprising a polynucleotide that reduces expression of a coding region having a sequence SS1G_01703 (SEQ ID NO:2), or a homolog of SS1G_01703 (SEQ ID NO:2), wherein the polynucleotide comprises a sense strand of at least 21 nucleotides of SEQ ID NO:2 and the complement thereof.

13. The plant of claim 12 wherein growth of a fungal pathogen comprising the coding region on the plant is reduced compared to a control plant.

14. The plant of claim 13 wherein lesion size after administration of the fungal pathogen to leaves of the plant is reduced by at least 3% compared to a control plant that does not comprise the polynucleotide.

15. The plant of claim 12 wherein the polynucleotide reduces expression of the coding region or a homolog thereof in a plant pathogen is *Sclerotinia sclerotiorum* or *Botrytis cinerea.*

16. The plant of claim 12 wherein the polynucleotide comprises a double stranded RNA (dsRNA).

17. A method for making the plant of claim 12 comprising:

transforming a cell of a plant with a polynucleotide to obtain a recombinant plant cell;

generating a transgenic plant from the recombinant plant cell, wherein the plant comprises a polynucleotide that reduces expression of a coding region having a sequence SS1G_01703 (SEQ ID NO:2), or a homolog of SS1G_01703 (SEQ ID NO:2), wherein the polynucleotide comprises a sense strand of at least 21 nucleotides of SEQ ID NO:2 and the complement thereof.

18. The plant of claim 1 wherein the sense strand and the complement thereof are covalently attached.

19. The plant of claim 1 wherein the sense strand and the complement thereof are not covalently attached.

20. The plant of claim 1 wherein the polynucleotide comprises at least 25 nucleotides of SEQ ID NO:2 and the complement thereof.

21. The plant of claim 12 wherein the sense strand and the complement thereof are covalently attached.

22. The plant of claim 12 wherein the sense strand and the complement thereof are not covalently attached.

23. The plant of claim 12 wherein the polynucleotide comprises at least 25 nucleotides of SEQ ID NO:2 and the complement thereof.

24. The plant of claim 17 wherein the sense strand and the complement thereof are covalently attached.

25. The plant of claim 17 wherein the sense strand and the complement thereof are not covalently attached.

26. The plant of claim 17 wherein the polynucleotide comprises at least 25 nucleotides of SEQ ID NO:2 and the complement thereof.

* * * * *

SEQUENCE LISTING

```
<160> NUMBER OF SEQ ID NOS: 90

<210> SEQ ID NO 1
<211> LENGTH: 1035
<212> TYPE: RNA
<213> ORGANISM: Sclerotinia sclerotiorum

<400> SEQUENCE: 1

augucaagcg ugcuagacaa gcuuuucgaa acuacgacug gagcuguauc uucgacaacu     60

ggcaaaguuu uaaagaccac ugcaggugcg guagguaagg gagcugccug gacuugggaa    120

acuccuguug uaaagggagu gagaacuacc gucaaugcua cagccaaugu acuugacaag    180

gcgacgcaac caauucgaca gacagaggca uauaagaaug ucaagaacgu gauugaugau    240

ggaaguaguu cgagguacgg agggugggug gagaaggaag agagacggaa agcaagagaa    300

uuacgggaau uagaagaagg aaccacuggc aaaagcaagg agguuccugu agaagacccg    360

aacgccggca caaacguuac cguacacaaa gacuccgcau acaaggaggc cuggagagau    420

uuccgugacu caaauagacu caugcaaucu uuauucucca ugaaaaccgu cuacaaugaa    480

ucugaaaauc ccuuaaucuc caccgcccgu agcauauccg accgagucgc cggauucuuc    540

gccgaaaacg aaaccgccca aguaaucaag aaauuucgug aaauggaucc cuccuuccaa    600

auggaaccuu uccuucgcga aaugcgcgaa uacauccucc cugaaguccu agacgccuac    660

gugaaaggcg auacugaaac ccucaaacuc uggcucucag cagcucaauu cuccgucuac    720
```

gaugcccuuu ccaagcaaua uacaaccgcu ggucucaaau ccgauggucg cauucucgau 780
aucagacaug uugaaguccu aucugcaagg auguuagaua augauauccc agucuucauc 840
auuacaugca gaacacagga aguccacgua uauagaaacg cgaagacgaa ucaacuagcc 900
gccggcaugg aagauaaggu ucaauugguc accuaugcaa uuggugguuac gagaguagca 960 gaagauguua auaaucccga gacgagaggu uggagacuca uugaguugca gaagagcgga 1020
agagauuaua uauga 1035

<210> SEQ ID NO 2
<211> LENGTH: 969
<212> TYPE: RNA
<213> ORGANISM: Sclerotinia sclerotiorum

<400> SEQUENCE: 2
auggcaacuc caucaaccga ggguuaugcg cccgaauggc ucgaggucga gaaaacccug 60
ggaggucguc cucuccucga aggcaagcca cuagaaauua gaaagcaaua cagcgaacua 120
guccgcacca ucgcagcgca auccgcaggc cccgauuccu ccguccaaac ucgugauauc 180
uccgccgacg gaaucccagu ucguaucuac accccuccaa auacuucugc cggaaacccu 240
cuuccucuag guguauauua ccacggcgga ggcuguugcc ucggggaucu cgauuccgag 300
gauccguggu gucguuauau cgcuaagacg guuccgugug uucucgucuc agucgaguau 360
agauuagguc cugaguauaa gaugccgguc auguuggaug auagucuuaa ggcuuuugaa 420
ugggcacgaa accacgccuc agaacuuaac gccaacccgg cgcaagucuu cacaaucggc 480
gguucagcag gcggcugucu aucucucacc guagcaaacg aucucaucgu cgcugguaaa 540
aaagaccaca uccaaggcau cgucucccug gucccc guaa ccgcccaucc aucuuccauc 600
ccugccgcuu acaaggaaca cuauaaaucg uacgaggaaa acgcagcugg uguuccgauu 660
cuagaucgag ccgcuaugga uguauuucuu ggggcuauug aggcggaucc ucaugaugag 720
agaauuuuua caacgcuuuc caagcaucuc gaucaauuuc cuccuacgua uauugcuacg 780
ugugggaaag auccuuuaag agaugauggu acgguauugg aaauaauguu gaaggagaag 840
gggaucaaga cgaagaguga uuuuuaugau ggugugccgc auuacuuuug gauguucccc 900
gguaugaagg guagagauga auuuuuggac aauguuugug cgggcgugaa guucguuuug 960
gguauuuag 969

<210> SEQ ID NO 3
<211> LENGTH: 1017
<212> TYPE: RNA
<213> ORGANISM: Sclerotinia sclerotiorum

<400> SEQUENCE: 3
augcauagua agguuguuau uauuggcuca ggcccggcgg cucacacugc ugccguauau 60
cuugcgcgug cggaauuaaa accaaaugga auugcugccg guggacaauu gacuacuacc 120
accgauguag agaauuuccc ugguuucccu aaaggaaucg guggacaaga acuuauggau 180
aauaugcgcg cacaauccga acgauucggu acucaaauca ucaccgaaac aguugcaaaa 240
guugaucucu ccaaacgucc uuucaaauac uggaccgaau gggaugacaa gacagaacac 300
acagcagauu ccaucaucau cgcuacgggu gcaucagcuc gcagacucgg ucuuccaggu 360
gaggagaaau acuggcaaaa ugguaucucu gcuugcgcag ucugcgaugg agccgugcca 420
auuuucagaa auaagcccuu gguaguuauu gguggugggag auagugcugc ggaggaagcu 480
auguuccuua cgaaauacgg aucucauguu acgguuuugg uccgaaaaga ucauuuacgu 540
gcaucgaaaa cgauggcuaa gagauuacuu gccaacaaga aaguuacugu uaaauucaac 600
acgguuggag gcgaaauuac ugguaaugau aagggauuga ugacgcauau gguuuuuaag 660
aacgucguua cuggagagga agagaaagca gaagccaaug gauuauucua ugccguagga 720
caugauccag cuacugcauu guucaaagag caaaucgaca cugauuccga gggauauauu 780
guaaccaagc ccggaacgag uuacacaaau guggagggag uuuuugccgc aggugauguu 840
caggauaaga gauacagaca ggcuauuacu agugccgggu cuggauguau agcagcuuug 900
gaggcagaaa aauuccucgc ugagcaagag gauggggaaa augauuugga gaagacggau 960
gcugaaaagg guagcaaugu uguuguuccu gaguauagau cuaacccuuu gcuuuaa 1017

<210> SEQ ID NO 4
<211> LENGTH: 1731
<212> TYPE: RNA
<213> ORGANISM: Sclerotinia sclerotiorum

<400> SEQUENCE: 4
augaagacac aaucucuaau caguaugggc uuauugccua uacuaucagu aaacgcagca 60
uauaccuggc cuucaaaaua cgacgaauua gaggauauuc uuuaccuaca agcaggauac 120
agacgcuacg gauuuagaga cgguguuaca ccauguggcu ucucagcuga ugguaguaau 180
cgagagacag cugcagaaug gaucaaaacg gcuuaccaug auauggcaac gcaugaugua 240
gaaacugguc uuggaggacu ugaugcuucg auagcuuaug agcuuggucg ugcagagaau 300
cccgguucgg cuuucaaugg uacuuuugga uucacaaaca acuaugccuc gaucaaaucg 360
ucuaacucug aucuucucgc caugucuguc guuguugccu ccauggcaug cggaggucca 420
auuauuccau uucgagcugg acgaauugau gccgugcagg cuggugacc agguguccu 480 caaccugauc aagauuuggc cacgcacacu gccauuuucg caaagcaggg uuucaacacu 540
accgagauga uuaccauggu agcaugugga cauguucucg gaggaguuca uggcgucgau 600
uucccucaga uuacugguga uaauaacgaa acuaguuucc cacauuuuaa cagccaauac 660
gacaacuuua ccaacuccau cguaaccgaa uaccuagagg auaaaucaau cgacgugcuu 720
gugguuggca aaaacgacac cuuuaacucc gacaagcgua ucuucggugc ugauaacaac 780
aaaaccauga cuucucuagc agauccuucu aauuuccaag cgcagugccg cgacauuuuu 840
gcccgcauga ucgacaccgu uccugcaagc gucacacuuu cagaagucau cacccccauc 900
gaagugaagc caaccgagcu uucccucgcc uuaggcgcaa acaacacauu auccuucaca 960
gguucuaucc gcgugcguac cacccaccgc aacgccgaca acguuaccgu aucccuccgc 1020
uaccgugauc gcaacaacaa ccucucaaac accaccaucu caaccgaacg cggacgcugg 1080
caacuaggcc aaagcuaugg auucgccagg gaagucuuca ccuucuauga auucgacacu 1140
gcuuucgaug uuacauccag caucucaucu uucgacguca ucauccauac agcuggcgaa 1200
gcugaugaga ucaacaccaa caauggccuc ggauuucccg ucucagacgc aauucuuuug 1260
caagcaccac aauccuguca accacaaaua aucgugaaug aagcaggcca auggaaucuc 1320
accaucaccg ccgcaguccg cgccgaucgu gucggggaac cuguagcuuu cgacuggguu 1380
uacaaacgcu ucauccaagg cguaaugaua aaccaauugg agguacaacg uacgguuaug 1440
gagaaagcga gugaggagau ugguggauau uaucuuuaca cggcgacaaa gccaauugau 1500
acgguacagu ggucgacaac auuugacuug guauugggcg agggagacaa ugucuccaag 1560
cuugaguucc ugucgacugg aaacuuggcc ucuaccuccu gguuggacga aaagguacag 1620
gagagggaag augcacacaa aacuaggagg agugcuguug gugcaaggga uauccuguac 1680
ucgauauuau ucgauauagu ugcagcaaca caacaugucc ucagaauuua a 1731

<210> SEQ ID NO 5
<211> LENGTH: 738
<212> TYPE: RNA
<213> ORGANISM: Sclerotinia sclerotiorum

<400> SEQUENCE: 5
augguugccu uugccaaauc ucuccaacuu ucccucucac ucuuggcaag uaccgccaua 60
gccauucccu ucccaucaga gcucgaaucc cgagcugaaa ucaacuccga ugccguugug 120
ggauuucccg aaaccguucc uaguggcaca guaggcacac ucuaugaagc cuacaaacca 180
uaccucgaug ucguaaaugg cugcguacca uucccagccg uugaugccgc uggaaacacc 240
aaugccgggu uaaaaccaag uggcaguagc aauggugauu gcaguaguag uaccggacaa 300
guauauguuc gaggugcuca aaaugguuca uacuacggac ugauguauuc cugguacaug 360
cccaaagacg agcccucacc aggcaucggc caccgccacg acugggaagg cguaaauccuc 420 uggcucagca gcuccaccuc caccaccgcc agcaacaucg uugccgucug ucccuccgca 480
cacggaggcu gggauugcac ccgagaccaa uacacacucu cuggcacauu cccucucauc 540
aaauaugaag gcauuuggcc ucucgaucau uccuguggcuc uuaccaguac ucagggugga 600
cgacaaccga ugguugcgug ggaaucucuu acaccagcug cgcaaagugc gcuugagaau 660
acggauuuug gaaaggcgaa uguuccguuc aagaaugcua auuuugagaa uaacuuugug 720
aaggcuagua guuucuag 738

<210> SEQ ID NO 6
<211> LENGTH: 1368
<212> TYPE: RNA
<213> ORGANISM: Sclerotinia sclerotiorum

<400> SEQUENCE: 6
auggccacaa auacuaccaa gcccauacau agucuuguca uugaugcagg accaauaauu 60
aagaaugauc ccucagccuc uacgcuucuu ggacaagcag aaaaccucua cacaauuccc 120
cucguuauug acgaaaucaa agaugccguu acaagagcca gauucgaaac cacccugcua 180
ccuuuccuca aacuaagagc gccucguuca gcuagcauua aaguuauaac cgauuucgca 240
cggaaaacgg gugauuugga aguacuuagc agacaggaua uccauuuaau ggcacuagca 300
uaugagcuug aaugugaacg gaaucaugga gauuggagau uacgaagugu gccaggacag 360
aagagauuaa auggagcucc cccugcauca uuaacagaag agaaaccggc cgauaccaca 420
gaggcgcaag aagcauccau ggaugcugca gcgcaaccaa aaauugaaac uagaggcgca 480
uggggaacau caauaccuca agcagcagaa gaauccagca ucgagacuca aucuauugag 540
gaagcauuag aagccgccca cauauccacc aucgaggagc cggaaagcau agacaaacca 600
gcagaagcau cagucacagg agaacaggcc gaagaaccaa cuuccacaac agagcccgaa 660
acaacucgcg aaacugcgca ugaaucaacg aauauagaag aaguucccgc guccgaaucc 720
gacgcugaag acgacggcga aggauggauc acgccuucca accucaaaaa gcaccaacaa 780
aaagacaaca acggcaccuu cgagccccag gaagaacaaa aaacaaucca aguagccacc 840
aucaccagcg auuacgccau gcaaaacguc augcuacgua ugaaccucaa cuuacucuca 900
cccucucucc aacgcauucg ucaacucaaa accugggucu ugcgaugcca cgccuguuuu 960
ggcaucacca gagauaugac gaagcaauuc ugcggacgcu gcggaaaacc cacuuuacuc 1020
cgaacauccu gcuccaccga caaagaugga aaugucaagg ugcaucucaa gaagaauaug 1080
caauggaaca acagaggaaa uguauacagu gugcccaaac cgguugccgg gacagcgaau 1140
ggaaagaaua uuaagggugg uggaaaggga gggugggua augauuugau auuggcugaa 1200
gaucaaaagg aguaugugag agaaauggcu acuucuagga gaaagaagga caaggaucuc 1260
auggaugaag auuaucuacc caguauucug acuggagacc gugggcgggc aggcgguaga 1320
ccaaaaguug gagcgggcaa aaauguuaau uccaaaaagc gacauuag 1368

<210> SEQ ID NO 7
<211> LENGTH: 1080
<212> TYPE: RNA
<213> ORGANISM: Sclerotinia sclerotiorum

<400> SEQUENCE: 7
augaagaacu uaucuauuca accucaucac cuacccaaca auaacaucug cauuaaaguu 60
cuugcugaag gugcugcaaa ugucauauau cagauuacca uugauccaaa aucacagggg 120
guuaucgagg uagacaagga ucaucaagau uuggauuauc uuucuggaaa auuauuacgu 180
cuucgaaaag auguuccuac uaccgcucca acuucagaau cauaccaaca guggcuuaca 240
uauauuguac cccuauucaa acccgaacaa auagucauuc aagaauugau uuacauuggu 300
caccuuaaug uaaucccugg uuuaaauacu gaucucagac guuuugauaa uccugguaca 360
uguaccacga aucaucuugu cccaccacca aaagggaaau uuuaucgcuc cagagcucaa 420
agugguacuu ucuuggcaaa agaugauuau ggucuuuuga uuacagauau gacaccuaga 480
aaauccgcac aagagacggu uguagaauuc aaaccaaaau ggcucucacc aucccaugaa 540
uuaccaucua aagcuauccg uugcagaacu ugugcacuuc acgcacgucg aguagccuuu 600
ggagaagaaa gaaaaaacac ugaucuucaa uccuaucuuu guccacucaa acucgucgau 660
gaugacccua aauuaaaauu cgaaaguuac cuagcuuccg ccucucaugu auuacacaaa 720
ccucaugaaa cacccuccgu acaaucacuc gcaagaugga uccacgaaaa uccauugcua 780
aaacgacuuc gcgaucucca aaccgaauau gaucucaaag gaucucuaaa gacggaaaaa 840
gcaucucaug aacuaugugu agcgaugacc uugagagauu guuccuuaua cauacgaaug 900
gauaaaaauc aucaagucau agaagcucgu cuaggagauu uagauuauaa aucaccuaau 960
aaguauucau cauggagaag aaaagaacag gaauuaaucg acgagggaug guauuguggu 1020
gaagaaagua aggaauuaaa acaaccaauc gaugaauguu uauuaucacg aaggauuuga 1080

<210> SEQ ID NO 8
<211> LENGTH: 1017
<212> TYPE: RNA
<213> ORGANISM: Sclerotinia sclerotiorum

<400> SEQUENCE: 8
auggcuccca ucauggaugc acucccaauc gucgaggaca agccaacggc ugcugucacu 60
gacuucucgg ucuccagucc ucaagaugga gcuguuguug cgccaccuac cacagucuac 120
cagaccggug ccaccaaguu gaagaacaug cucagagacu cgaaugaguu gauuguuugu 180
cccggugucu augauggaau cucaacccga guugcccuuc aaguuggcuu cccagcucuu 240
uacaugaccg gagcaggcac uacugcuucc cgccuuggaa uggcagaucu cggcauugcu 300
caucuuuccg acaugaagga ccacgcugag augauugcaa accucgaccc uuuuggacca 360
cccuugauug cugauaugga caccggauac gguggaccuc ucauuguuga caaagccguc 420

-continued

```
aaggccuaca ucagagccgg uguugcugga uuccauaucg aagaucaaau ucaaaacaag    480

cguuguggcc aucuugcagg caagaagguu gucccugaag aagaguacua caugagaauu    540

cgugccgcca agggugccaa agaugccaug aaauccgaua uuguguugau ugcacgcaca    600

gaugcgcucc aacaacuugg uuaugaugag ugcgucaaac guuugaaggu ugcucgugag    660

cuuggugcag auguuggcuu gcucgagggu uacacuucaa aggagauggc ugcaaagacu    720

guuaaggagu ucgccccaug gccaauacuu uugaacaugg ucgagaacgg cgcuacuccu    780

aucaucacca ccaaggaggc acaagagaug ggauuccgua ucaugaucuu cuccuucgcu    840

gcucucgccc cagccauguu ggcuauccaa gagacuuucg ugcguuugaa gaacgagggu    900

gucguaggaa cuccaaagaa cguuacacca agggccuugu uugagguaug cggucugcaa    960

gagaguauug uuauugauac ugcggcuggu ggugggcuu ucgccgaugg uguuuaa      1017
```

<210> SEQ ID NO 9
<211> LENGTH: 735
<212> TYPE: RNA
<213> ORGANISM: Botrytis cinerea

<400> SEQUENCE: 9

```
augguugccu ucucaaaauc auuacagcuu ucccuuucgg ucuuggcauc uacagucauu     60

gccaucccua caccaucaca acuugagucu cgggccguua ucgauuccga ugccguugua    120

ggauuugccg aaacuguucc caguggggacc guaggaacag uuuaugaggc auauaaacca    180

uuccuuaaag ucguaaaugg augcguacca uucccugccg ucgaugcauc ggguaacaca    240

gguggugguu ugucaccaac uggcaguagc aaugguggguu gcagcagcag uaccggucaa    300

guauauguuc gaggaggaca aagcggauca aacuacgcca ucauguacuc cugguacaug    360

ccaaaggacg agcccucaac cgguauuggu caccgucacg auugggaagg uguaauuguc    420

uggcucucca gcgccaccgc cacaacugcc gacaacaucu uagccguuug uccuuccgcc    480

cacggaggcu gggauuguuc cacggauggc uauucccuuu cugguaccag cccucuuauc    540

aaguacgaaa guaucuggcc cgucgaucac ucaaugggguc uuacuaguac uguuggugga    600

aaacaaccua ugauugcuug ggagucuuua ccaacugcug cucaaacugc ucuugagaac    660

accgauuucg gugcugcgaa uguuccauuc auuccggcug uuuucacaga caaucuugcg    720

aaggcuacuu ucuag                                                     735
```

<210> SEQ ID NO 10
<211> LENGTH: 1626
<212> TYPE: RNA
<213> ORGANISM: Botrytis cinerea

<400> SEQUENCE: 10

```
augaacgggc uacgaacagc ggcgacaagg acgcccacaa guaaacagau uucucugucu     60

ucaaucgcga gaccuucauc caauggcucc acccuucguc gccagacagu ucaacaaaau    120

cggaauuuac aauuuucuac agcgggacau ucgaggccug cgacucuuuc auauccugcg    180

ccuuugcgau cacgauuccu uccagaagaa auuagaucug uagcaugccc agcauccucg    240

cggcauuuuc augaaagcug gagauugggc aaagaaaaga aggcaaaacc aguagaucca    300

gcggacgcag cugcaaagga agaagcuaca gaagaagagc cuagcaaaaa ggauucugcu    360

aaagacucag aaucuacuuc uggagagggu aagacuaagg aagaaggaga gggcagugaa    420

ggcaaaaaag aagaauccaa agaggcaccu ccaccccac cacccacgg agacaaaacu    480

ccauggcaag ucuucaccga aacccugcaa accgaauuca aggcaucaaa agaauggaau    540
```

-continued gaauccacaa agcaauuagc agaaggugcc caucaauuua cagagaacga aaacgucaag 600
cgugcuagac aagcuuucga aacuacuacu ggagcaguau cuucgacgac aggcaaaguu 660
uuaaagacua cugcaggcgc aguugguaag ggagcugcuu ggacuuggga aacuccagua 720
gugaagggag uaagaacuac ugucaaugcc acagcaaaug ugcuugacaa ggcgacacaa 780
ccaauccgac aaacggaggc auacaagaau guuaagaaug ugauugauga uggaaguagu 840
ucgagguaug gaggaugggu ugagaaggag gagagacgua aagcaagaga auugcgagaa 900
uugcaagagg guaccaccgg caaaaccaag gagguoccaa uagaagaucc aaacgccgga 960
acaaauguua cccugcacaa agacucagca uacaaagagg cuuggagaga uuuccgggac 1020
ucgaaucgug ucaugcaauc uuuauucucc augaaaaccg ucuacaacga auccgagaau 1080
cccuugaucu caacugcccg cagcauaucu gaucgaguug cuggguucuu cgccgaaaau 1140
gaaaccgccc aaguaauuaa gaaauuccgc gaaauggacc ccucauucca aauggaaccu 1200
uuccuccgcg aaaugcgcga guacauucuc ccagaagucc ucgaugccua cguaaaaggc 1260
gauaccgaaa cccucaagcu cuggcuuucc gcagcccaau uuuccgucua ugaugcucuc 1320
ucaaaacaau acacaacugc uggucucaaa ucugauggcc gcauucucga uauccgacau 1380
guugaagucc ucucagcgag aauguuagau aaugauaucc caguuuucau cauuacaugc 1440
agaacccaag aaguucacgu auauagaaac gcaaagacga accaauuagc ugcugguaug 1500
gaagauaagg uacaacuggu caccuaugcc auuggaguua caagaguggc ggaagauguu 1560
aauaauccag agacgagagg uuggagacuc auugaguugc agaagagugg aagggauuac 1620
auauga 1626

<210> SEQ ID NO 11
<211> LENGTH: 1377
<212> TYPE: RNA
<213> ORGANISM: Botrytis cinerea

<400> SEQUENCE: 11
auggcuacaa auacuaccaa accuauacau agucuuauca uugacgcagg accaauuauu 60
aagaaugacc cuucagucuc uacgcuucuu ggccaagcag aaaaccuuua uacaaucccc 120
cucguuaucg acgaaaucaa agaugccguc acaagagcca gauucgaaac cacauuacua 180
cccuuucuca aauuaagagc gccuagauca gcuagcauua aaguuauaac ugaauucgcg 240
cgcaaaacgg gugaucugga aguacucagc agacaggaua uccauuugau ggcuuuagca 300
uaugagcuug aaugugaacg aaaucaugga gauuggagau uacgaagugu acccggacaa 360
aagagauuaa auggagcacc ucccgcauca uuaaguggcg aaagaccugc cgaugcuaca 420
gaggcaucac aaacaucuac agaugcagcg gcgcaaccag caaucgaaac cagaggcgca 480
uggggaacau caauaccuca agcaacagaa gaaucuacag uggagacaca gcccauugag 540
gaagcauuag aggcuaccca uauaucaaca gccgaugagg caaagagcgc agagaaacca 600
gcagaggaug cagucacaga agaaucgacc aaagauggag ucacagagga acaaacccaa 660
gaaccaaccg ccgcaacaga acccgaaacc auuccagaaa caaucgaaga aguucccgcc 720
uccgaauccg acgccgaauc cgacggcgaa ggcuggauca cccccuccaa ccucaaaaag 780
caccaacaaa aagacacuaa cucuucguuc uccccccaag aagaauccaa aacuauccaa 840
guagcuacca ucaccaccga uuacgccaug caaaacguca uguuacgcau gaaccucaac 900
cuccucuccc ccucucuuca acgcauccgc cagcucaaaa cuugggaccu aaggugccac 960

-continued

```
gcuuguuucu cuaucacucg agaaaugacc cgacaauucu guucccgcug cgguaaaccu   1020

acacuccucc gcaccucuug cucaaccgau aaagacggag ugguaaaaau ccaccuuaag   1080

aaaaauaugc aguggaauaa cagaggaaau guauacagug uccccaaacc aguugccggg   1140

acagcgaacg gaaagaauau caaagggggu gguaaaggug gaugggguaa ugauuugaua   1200

uuggcggagg aucaaaaaga auacgugaga gaaauggcca cggaaaagag gagaaaggaa   1260

aaggaucuua uggacgaaga uuauuuaccu aguaucuuga cgggagaucg uggaagagcu   1320

gguggaagac caaaaguugg agcaggcaag aaugucaauu caaggaaacg acauuag      1377
```

<210> SEQ ID NO 12
<211> LENGTH: 1614
<212> TYPE: RNA
<213> ORGANISM: Botrytis cinerea

<400> SEQUENCE: 12

```
augaaggggu caucuuuaau caguuugggc uugcuacccg ugcugucagu uaaugcggcu     60

uauacuuggc ccucagagua ugaucaacua gaagacauuc uauaucuuca gcaagguuuc    120

auacguuuug gccucagaga ugguguuacg ccgugcucuu ucucaucgga uggagguggu    180

cgucaggcgg cugcggaaug gauaagaacu gcuuaucaug auauggcuac ccaugauguc    240

gauacugguc uuggaggacu ugaugguucu auagccuuug agcuugggcg agcggagaac    300

ccuggugaug cuuucaauuc uaccuuugca uuuacagaaa accuccgcuc aaucagagcu    360

ucgucuuccg aucuucuugc aauguccguu gucguugcca caauggcuug cggcggucca    420

auaauuccau uuagaggugg acgaaucgau gccaugaaag cugguguuuc uggcgugccc    480

gagccugauc aagauuuggc gacacacacu gcaaucuucg caaagcaagg auucaacacu    540

gcugagauga uaaccauggu agcaugcggc cacacucucg gagguguuca uggugucgau    600

uuuccccaga uuaccggcaa cggugacgca gaaaacuucc caaaauucga cagcaccuac    660

accgcauucg auaacacugu uguaacagag uauuugggga acaauucaac cgacccgcuu    720

gugaucagua aaaaugauac cuucaauucc gauaaacgca uuuuuggcgc cgacaacaac    780

aaaacgauga cuucuuuagc agacccaacc aauuuccaga aacaaugcuc ugacaucuuc    840

gcucgaauga ucgauacugu cccugcagac gucacacuuu cugaagucau cacaccuauc    900

gaaguaaagc caucgcaaau ugcucuuacc cuagcuggaa auaacacucu auccuucgga    960

ggauacaucc gccuucgcac caccaaccgc aacgccgaug augugaccgu aucccuucaa   1020

uaccgugauc guaauaacaa uacuucgaac accacaauuc ccgucagcag agagaauuac   1080

uuguugggguc aaagcuaugg cuucgguuca gagguguuca cuugguaugg auucaauacu   1140

guucuugaug cuaaaaccgg cauuucgucu uucgauguca ucuuacauac ugucggugca   1200

gcugaugaaa ucaucaccaa uaacggu ggg gguuucccac ucacagacgc aauucucuac   1260

caaccagcac aauccuguca gccacagaua ucugucaaug acgcaggcca guggaauaua   1320

acagucacug cagcuguucg ugcugaucgu aucaacgagc cuguugccuu ugacugggug   1380

ucucagcgua ccauaccagg cgcgaugguu aaagcacuag aagugcaacg uacagcuaug   1440

gagaaaguga gugaggagau cgauggauau uaucuuuuca gcggaaccag gucgcucgau   1500

aacguacaau ggucuacuac uuuugaugug guauugggag agggagauga cguaucgaaa   1560

guagaguucc agucgacguc ggcaauggcc acgagcugcg aggcauuuuc uuga         1614
```

<210> SEQ ID NO 13
<211> LENGTH: 1041

-continued

<212> TYPE: RNA
<213> ORGANISM: Botrytis cinerea

<400> SEQUENCE: 13

```
augcauagca agguuguuau uauuggcucu ggcccggcgg cucacacugc ugcuguuuau     60

cuuucgcgcg cggaauugaa accuguucuu uaugaagguu uccuugccaa uggaauugcu    120

gccggugguc aauugacuac cacuacugau guagagaacu ucccugguuu ccccaaggga    180

auuggcggac aagaacugau ggauaacaug cgcgcacaau ccgaacgauu uggcacccaa    240

aucaucaccg aaaccgucgc caaaguagau cucucuaaac guccuuucaa auacuggacc    300

gaaugggaug acaaaacaga acacacagcc gauucuauca ucaucgcuac uggugccucu    360

gcucgcagac ucggucuucc aggagaggag aaauauuggc aaaaugguau cuccgcaugc    420

gcagucugcg auggagccgu uccaauuuuc agaaacaagc cuuugguagu uauuggugu    480

ggagacagug cugccgaaga ggcuauguuc cucacgaaau acggauccca cguuacuguu    540

uugguccgaa aagaucaucu acgugcaucg aaaacgaugg cgaagagauu gcuugccaau    600

aagaaaguua cgguuagauu caacacugua ggaggcgaaa ucaccgguga ugauaaggga    660

uugaugaccc acaugguuuu caagaacgcc acuacuggcg aggaggaaaa gguagaggcc    720

aauggcuugu uuuacgcagu aggacaugau ccagcuaccg cauuguucaa ggaacaaauu    780

gagacagauu cugagggaua uauugucacc aagcccggaa ccaguuacac caacauugag    840

gguguuuuug cugcugguga uguucaggau aagagauaca gacaggcuau uacuagugca    900

ggaucuggau guauagcagc ucuugaggcc gagaaauucc uugcugagca agaagaugcg    960

gaaaaugauu uggaaaagac agaugccgag aagggcagca auguuguugu uccugaguau   1020

agaucaaacc cuuugcuuua g                                             1041
```

<210> SEQ ID NO 14
<211> LENGTH: 20
<212> TYPE: DNA
<213> ORGANISM: artificial
<220> FEATURE:
<223> OTHER INFORMATION: Primer

<400> SEQUENCE: 14

```
cgtagcatat ccgaccgagt                                                  20
```

<210> SEQ ID NO 15
<211> LENGTH: 20
<212> TYPE: DNA
<213> ORGANISM: artificial
<220> FEATURE:
<223> OTHER INFORMATION: Primer

<400> SEQUENCE: 15

```
agacggagaa ttgagctgct                                                  20
```

<210> SEQ ID NO 16
<211> LENGTH: 20
<212> TYPE: DNA
<213> ORGANISM: artificial
<220> FEATURE:
<223> OTHER INFORMATION: Primer

<400> SEQUENCE: 16

```
ttctgccgga aaccctcttc                                                  20
```

<210> SEQ ID NO 17

<211> LENGTH: 20
<212> TYPE: DNA
<213> ORGANISM: artificial
<220> FEATURE:
<223> OTHER INFORMATION: Primer

<400> SEQUENCE: 17
accgccgatt gtgaagactt 20

<210> SEQ ID NO 18
<211> LENGTH: 20
<212> TYPE: DNA
<213> ORGANISM: artificial
<220> FEATURE:
<223> OTHER INFORMATION: Primer

<400> SEQUENCE: 18
gctcacactg ctgccgtata 20

<210> SEQ ID NO 19
<211> LENGTH: 20
<212> TYPE: DNA
<213> ORGANISM: artificial
<220> FEATURE:
<223> OTHER INFORMATION: Primer

<400> SEQUENCE: 19
ctccgcagca ctatctccac 20

<210> SEQ ID NO 20
<211> LENGTH: 20
<212> TYPE: DNA
<213> ORGANISM: artificial
<220> FEATURE:
<223> OTHER INFORMATION: Primer

<400> SEQUENCE: 20
tcgtgaatga agcaggccaa 20

<210> SEQ ID NO 21
<211> LENGTH: 20
<212> TYPE: DNA
<213> ORGANISM: artificial
<220> FEATURE:
<223> OTHER INFORMATION: Primer

<400> SEQUENCE: 21
tgttgtcgac cactgtaccg 20

<210> SEQ ID NO 22
<211> LENGTH: 20
<212> TYPE: DNA
<213> ORGANISM: artificial
<220> FEATURE:
<223> OTHER INFORMATION: Primer

<400> SEQUENCE: 22
tcgtaaatgg ctgcgtacca 20

<210> SEQ ID NO 23
<211> LENGTH: 20
<212> TYPE: DNA
<213> ORGANISM: artificial
<220> FEATURE:
<223> OTHER INFORMATION: Primer

<400> SEQUENCE: 23

-continued

```
gggaatgtgc cagagagtgt                                                20


<210> SEQ ID NO 24
<211> LENGTH: 20
<212> TYPE: DNA
<213> ORGANISM: artificial
<220> FEATURE:
<223> OTHER INFORMATION: Primer

<400> SEQUENCE: 24

ttcgaaacca ccctgctacc                                                20


<210> SEQ ID NO 25
<211> LENGTH: 20
<212> TYPE: DNA
<213> ORGANISM: artificial
<220> FEATURE:
<223> OTHER INFORMATION: Primer

<400> SEQUENCE: 25

cccatgcgcc tctagtttca                                                20


<210> SEQ ID NO 26
<211> LENGTH: 20
<212> TYPE: DNA
<213> ORGANISM: artificial
<220> FEATURE:
<223> OTHER INFORMATION: Primer

<400> SEQUENCE: 26

ttcgcgatct ccaaaccgaa                                                20


<210> SEQ ID NO 27
<211> LENGTH: 21
<212> TYPE: DNA
<213> ORGANISM: artificial
<220> FEATURE:
<223> OTHER INFORMATION: Primer

<400> SEQUENCE: 27

caccacaata ccatccctcg t                                              21


<210> SEQ ID NO 28
<211> LENGTH: 20
<212> TYPE: DNA
<213> ORGANISM: artificial
<220> FEATURE:
<223> OTHER INFORMATION: Primer

<400> SEQUENCE: 28

acagatgcgc tccaacaact                                                20


<210> SEQ ID NO 29
<211> LENGTH: 20
<212> TYPE: DNA
<213> ORGANISM: artificial
<220> FEATURE:
<223> OTHER INFORMATION: Primer

<400> SEQUENCE: 29

ggcccttggt gtaacgttct                                                20


<210> SEQ ID NO 30
<211> LENGTH: 20
<212> TYPE: DNA
```

-continued

<213> ORGANISM: artificial
<220> FEATURE:
<223> OTHER INFORMATION: Primer

<400> SEQUENCE: 30
ccctttcggt cttggcatct 20

<210> SEQ ID NO 31
<211> LENGTH: 20
<212> TYPE: DNA
<213> ORGANISM: artificial
<220> FEATURE:
<223> OTHER INFORMATION: Primer

<400> SEQUENCE: 31
tggcgtagtt tgatccgctt 20

<210> SEQ ID NO 32
<211> LENGTH: 20
<212> TYPE: DNA
<213> ORGANISM: artificial
<220> FEATURE:
<223> OTHER INFORMATION: Primer

<400> SEQUENCE: 32
ggacgcccac aagtaaacag 20

<210> SEQ ID NO 33
<211> LENGTH: 20
<212> TYPE: DNA
<213> ORGANISM: artificial
<220> FEATURE:
<223> OTHER INFORMATION: Primer

<400> SEQUENCE: 33
gctgggcatg ctacagatct 20

<210> SEQ ID NO 34
<211> LENGTH: 20
<212> TYPE: DNA
<213> ORGANISM: artificial
<220> FEATURE:
<223> OTHER INFORMATION: Primer

<400> SEQUENCE: 34
cgcatgaacc tcaacctcct 20

<210> SEQ ID NO 35
<211> LENGTH: 20
<212> TYPE: DNA
<213> ORGANISM: artificial
<220> FEATURE:
<223> OTHER INFORMATION: Primer

<400> SEQUENCE: 35
tccgtggcca tttctctcac 20

<210> SEQ ID NO 36
<211> LENGTH: 20
<212> TYPE: DNA
<213> ORGANISM: artificial
<220> FEATURE:
<223> OTHER INFORMATION: Primer

<400> SEQUENCE: 36
gctctgacat cttcgctcga 20

<210> SEQ ID NO 37
<211> LENGTH: 20
<212> TYPE: DNA
<213> ORGANISM: artificial
<220> FEATURE:
<223> OTHER INFORMATION: Primer

<400> SEQUENCE: 37
cacctctgaa ccgaagccat 20

<210> SEQ ID NO 38
<211> LENGTH: 20
<212> TYPE: DNA
<213> ORGANISM: artificial
<220> FEATURE:
<223> OTHER INFORMATION: Primer

<400> SEQUENCE: 38
cgtaaccgca cacccatctt 20

<210> SEQ ID NO 39
<211> LENGTH: 20
<212> TYPE: DNA
<213> ORGANISM: artificial
<220> FEATURE:
<223> OTHER INFORMATION: Primer

<400> SEQUENCE: 39
tcctttccac acgtagcgat 20

<210> SEQ ID NO 40
<211> LENGTH: 20
<212> TYPE: DNA
<213> ORGANISM: artificial
<220> FEATURE:
<223> OTHER INFORMATION: Primer

<400> SEQUENCE: 40
gcgcggaatt gaaacctgtt 20

<210> SEQ ID NO 41
<211> LENGTH: 20
<212> TYPE: DNA
<213> ORGANISM: artificial
<220> FEATURE:
<223> OTHER INFORMATION: Primer

<400> SEQUENCE: 41
ggcaccagta gcgatgatga 20

<210> SEQ ID NO 42
<211> LENGTH: 1368
<212> TYPE: RNA
<213> ORGANISM: Sclerotinia sclerotiorum

<400> SEQUENCE: 42
auggccacaa auacuaccaa gcccauacau agucuuguca uugaugcagg accaauaauu 60
aagaaugauc ccucagccuc uacgcuucuu ggacaagcag aaaaccucua cacaauuccc 120
cucguuauug acgaaaucaa agaugccguu acaagagcca gauucgaaac cacccugcua 180
ccuuuccuca aacuaagagc gccucguuca gcuagcauua aaguuauaac cgauuucgca 240
cggaaaacgg gugauuugga aguacuuagc agacaggaua uccauuuaau ggcacuagca 300

-continued uaugagcuug aaugugaacg gaaucaugga gauuggagau uacgaagugu gccaggacag 360
aagagauuaa auggagcucc cccugcauca uuaacagaag agaaaccggc cgauaccaca 420
gaggcgcaag aagcauccau ggaugcugca gcgcaaccaa aaauugaaac uagaggcgca 480
uggggaacau caauaccuca agcagcagaa gaauccagca ucgagacuca aucuauugag 540
gaagcauuag aagccgccca cauauccacc aucgaggagc cggaaagcau agacaaacca 600
gcagaagcau cagucacagg agaacaggcc gaagaaccaa cuuccacaac agagcccgaa 660
acaacucgcg aaacugcgca ugaaucaacg aauauagaag aaguucccgc guccgaaucc 720
gacgcugaag acgacggcga aggauggauc acgccuucca accucaaaaa gcaccaacaa 780
aaagacaaca acggcaccuu cgagccccag gaagaacaaa aaacaaucca aguagccacc 840
aucaccagcg auuacgccau gcaaaacguc augcuacgua ugaaccucaa cuuacucuca 900
cccucucucc aacgcauucg ucaacucaaa accugggucu ugcgaugcca cgccuguuuu 960
ggcaucacca gagauaugac gaagcaauuc ugcggacgcu gcggaaaacc cacuuuacuc 1020
cgaacauccu gcuccaccga caaagaugga aaugucaagg ugcaucucaa gaagaauaug 1080
caauggaaca acagaggaaa uguauacagu gugcccaaac cgguugccgg gacagcgaau 1140
ggaaagaaua uuaagggugg uggaaaggga ggguggggua augauuugau auuggcugaa 1200
gaucaaaagg aguaugugag agaaauggcu acuucuagga gaaagaagga caaggaucuc 1260
auggaugaag auuaucuacc caguauucug acuggagacc gugggcgggc aggcgguaga 1320
ccaaaaguug gagcgggcaa aaauguuaau uccaaaaagc gacauuag 1368

<210> SEQ ID NO 43
<211> LENGTH: 1071
<212> TYPE: RNA
<213> ORGANISM: Sclerotinia sclerotiorum

<400> SEQUENCE: 43
augucgucuu uugcgcuaga gaaggaaucg ccuuugggcu uccuuuacaa uaaugcuguc 60
gcuggggcuu ugucaaauuc auacaauacu uuccaagaga agagggaagc gcugggucuu 120
ucaaaccccg gaacaguuga gaauauugcu agagagguuc aacgcgaugu uuuucucaac 180
aauuacacau ucucuggucu gagggcggau cugaccaagc cuuucagcau ggcuccauua 240
uuccaagucu cucaugcauu cucuauggga ucucaagguu uaccaccaua uacauuuggu 300
gcuuuauucg gcacaaacaa gaucuuuaug caaggaaaca uggacaauga aggucaacuc 360
accacucgau ucaauuacag auggacucca gcuuucguua ccaagaccca acuacaaguc 420
gccccugguc aagcuaugau gcaauuagac aacgaguaua cuggaaaaga uuuuacagcu 480
ucgaucaaau cucuuaaccc uucaauacuu gauggaggau ucacagguau cuuuauuggu 540
caauacuuac aagcuguuac uccaaaucuc gcuuuggguu uggaggcugu cuggcaacga 600
gcggcaauga accaaggucc cgaaacugca gucucauacu gugccaaaua caaggguagu 660
gauuggaucg ccagugcuca auuacaagcc caaggagccg uaaacacauc uuucuggaga 720
agauugacag auaaggucga agcuggugug gaucuuaacu uacaauucgc cggguugucu 780
ggagcuggua ugaugggagg accuauuaga aaagagggug ucacaacugu uggugccaag 840
uaugacuucc gaaugucuac uuucagagcu caaguugauu caacuggaaa gcugagcugc 900
uuguuagaga agagaguugc accaccuguu caacuuaccu uugccgccga gauggaucau 960
uucaagcaag cagcaaagau cggaguagca guuuccaucg aaucuggcga cgaagcgguc 1020
gaagaacaag caauggcagc uggaggcgcu ccuccucaaa ucccauuuua a 1071

<210> SEQ ID NO 44
<211> LENGTH: 2343
<212> TYPE: RNA
<213> ORGANISM: Sclerotinia sclerotiorum

<400> SEQUENCE: 44
auggauacaa agcagaagaa gcguucucau ucagagacca auggcucuca gaaagcucca 60
aaacgucaaa agauucaaaa gacauccaag aagcaaaaga aagccgcgcc uaagaagcca 120
guugccgugg auuccuuacc auggaacgaa guaaccaugc cagauauguu cgaagaugcu 180
gaggguuucu auggauugga ggaaguagac gauguugagg uuguaaggga uggcgauguu 240
guuacauuug uaucuuccaa aauccagacg aaaaacaacg aggaugaaga guucgaaggc 300
uuuggggaug aaguugaaga uggugggaau gccgcgacgg auaauacugg cgaagugaag 360
ccaauuuuga aaccuacgga agaaagcacg aaaaacgacg uaccgcaggg aaacaaacaa 420
aaaauagaga agaaagcaaa gcccgagaag aaagacaaga aagaaggguc aaauaccgaa 480
gaaggagaag aaaagguacc aagcaaaaag gagaagaagc aaaaacaaga gaagccgcaa 540
aaacagccag uugauaaaga ugcuacccuc aaacaagauc cucuuaagaa ugucuucgag 600
gcacuugacg aagaugccgc aggagaaguc gagguuucag guugggugga gcuagaucuu 660
ucaucaaaua cuuuaauggc auuaucaaaa augggcuucu caaagccaac uccaauucaa 720
ucagaggcua uaccagaagu acucgcggga caugauguug uuggaaaggc aucuacaggu 780
ucuggaaaaa cauuggcauu uggaauaccg auaguugaaa aguggcuuga gguauaugga 840
gaacuugaug aagaugaacu caagaagagc acaagaccuc caaccgcuuu aauucuuucg 900
ccuacgagag aauuggcgca ucaauugacu gaacauauca caacuuuaug uaagggcaug 960
ccuacaaguc cauauguagc ugcuguuacu ggaggacuuu cuguacaaaa acaacaacgu 1020
caauuaucca aggcagauau aauaaucggu acacccgguc gacucuggga aguuaucagc 1080
uccagcaaug aauuaucagc ugguuugaaa cagguuagau uuuuggucau cgaugaagcg 1140
gauagacuuu ugaccgacgg gcauuucaaa gaagcagagg agauucuaaa ugcguuggau 1200
cgcacgcacg ggaaugaaga ugaugacgag gaagacacau uaccucccag gcagacuuug 1260
guuuucucgg ccacuuucca caaaggauug caacagaaac uugcaggcaa gggcaaacaa 1320
ucuuucaagg augauaguca aucuauggag uaccucuuga agaagcucaa uuucagggaa 1380
gaaaaaccua aauuuguuga ugucaacccu aucucgcaaa uggcagcaaa ucugaaagag 1440
ggcaugguag aauguggugg agaagaaaag gaucucuacc uauauucucu ccuucuacau 1500
cauccaaauc aacguacacu caucuucaca aacucaaucc auuccguccg ucgucuaacc 1560
ccuaugcuuc aaacccucaa caucccagcc cacucccucc acucccaaau gauccaaaaa 1620
gcacgcaugc gguccauuga aaaauucucc cgaacaaaca acaccggcuc aguccucgua 1680
gcaaccgacg ucgcagcccg cggucucgac aucggaggcg uccaauuagu aauccauuac 1740
caccuucccc gcaccgcaga cauguaugug caccgcuccg gucgaaccgc gcgugccgcc 1800
gcauccggau ccaguauccu ccucuguggc cccgaagaag uagucggaac ccgccgcuug 1860
guagcuaagg uccacgcgca aaaugcucuu cacggagaag gcaaaaaauc caaauucuac 1920
auccgcuccc ucgauaucga ccgcagggua gucucucguu uaaaaccgcg cguuacccuc 1980
gcgaaaaaaa uagcugauag cgcucucgca aaagagaaaa aaggccacga ugacgauugg 2040
guuaaaaacg cagcggaaga acuaggcguu gaauacgaca gugaggaauu cgaagcauua 2100
ggcggaggaa gaaaggggag aggaacggga agaagaauga aggagaaaga agcgaggggu 2160
augaguaaag gggagguugg ggcccucaga gcagaauuga gagcccuguu ggcucagagg 2220
guuaaugugg guguuaguga gagguauuug acgaguggaa cgguuaaugu uaaugauuug 2280
uugaaggggg cuaagggug a gugguugggu gagguggagg guauugggau ggaggaugau 2340
uga 2343

<210> SEQ ID NO 45
<211> LENGTH: 861
<212> TYPE: RNA
<213> ORGANISM: Sclerotinia sclerotiorum

<400> SEQUENCE: 45
auggccgccg agcaaagaaa gcuguuagag cagcugaugg gcgcgggggc aucaucucgc 60
gcagcucaac ugucaaucac agauccaaag aucugccguu ccuuccucgu cggcaccugu 120
ccucacgauc ucuuuacgaa uacaaagcaa gacuuggggc cauguccaaa aauucauuca 180
gaaccuuuga agacggagua ugaggcugca gccccucccc aaaaacaaaa augggggauuc 240 gaauacgauu acaugcguga cuuacagaag uauaucgaug aaugcaauag gaggauagau 300
guugcgcagc gacgccugga gaaaacgccc gaugaaauuc gacagacgaa cgcccugcug 360
aaacaaauau cugaccuauc gaaaucuauu gagacagggu uguuggagau ucagauucua 420
ggagaacaau cggagguauc gcgcgccuau gaggaauucu uccgcaucag acaagcuaug 480
cagacgaaag uggagaagga aaaggaguug aaggcacuau cagacaccag uggaccuucg 540
ggacaccaga aguuacaagu cugugauguc uguggggcuu auuugagccg guuggauaau 600
gauaggagau uggcggacca uuuuuacggg aaaaugcauu uggguuacgc gcaaaugagg 660
aagacauacg acgcauuucc gaaagagaug aagaggucaa gaccuauggu agaugauaug 720
gaucacaccu cggcgguaag aggcuacgau ggaggauaug gcgacggcgg auacggcggc 780 aggggggcg gguauggagg ucguggugga gggagaggug gcuucagagg caggggaagg 840
ggauucagag guggauggua g 861

<210> SEQ ID NO 46
<211> LENGTH: 1293
<212> TYPE: RNA
<213> ORGANISM: Sclerotinia sclerotiorum

<400> SEQUENCE: 46
augucuuuca gaaauccuaa agcuguagga cagcuuacaa aaagaacuuc acaagcuacu 60
aucucacgcc ucacaagcaa ugucucuccc accacaaccu cauuauugca aaggaacaac 120
gcagaccagu ccagaccuuu ugcgacucca gugccgccgg ugacacaaga ugcgacggga 180
aggaggggac ccacggcaau ggugcucaug aauaugggug guccacaaac cacagaugaa 240
guuggggauu ucuuaaaugc cgauuuaauu ccucuuggac guuuucaaaa cuaccuugga 300
ccucucauuu cgaaacgucg uacgccgaag auucaaaagc aauaugcugc aauuggugc 360 ggcuccccaa uucgaaaaug gucagaacau caggccgaag agaugugcaa guuauuagac 420
aaaaugucac ccgaaaccgc accacacaaa ccauacguug cauucagaua ugcgaauccu 480
uugacugaag agauguauaa uaaguuguug gcggaugguu uuggaggcgg gaaaggugga 540
agagcaguag cauucacaca auauccucaa uacaguuguu ccacaacagg aagcaguuug 600
aaugaauuau ggaaguggag acagagacuc gaaggaaaag cugcuggaag uccaaauggu 660
agugauggaa caaucaauug gaguauuauu gauaggugge cagcacaccc aggucuuguu 720
gaagcuaucg cacaaaacau cgaggcuacu uuagcgacau auccugaaaa ggauagaaag 780
gauguuguau uacuuuucuc cgcccauagu uuaccaaugu cuguggucaa uagaggugau 840
cccuaucccg ccgaaguugc cgcuacaguc uaugcuguga ugcaaagauu aggucacucc 900
caugcauaua gacucuguug gcaaucgcaa guugggccua gugcauggcu aggagcucaa 960
acgagcgaua cugucgagga auaugucaag aagggccaaa cgaagcucau acuuauuccc 1020
gucgcauuca caucagauca uaucgaaaca cuuuaugaau uagacgauga agucauugga 1080
gaaucaggcc acaaagauac uaucaagaga ucugaaaguu ugaauggcuc accaguauuc 1140
auucaagcau uggccgacau ugcuaaagca cauuuagaca gcggaauugc cuguaguguu 1200
caaaugggau uaagaugucc uggaugcacg agugagaaau gcgcagagac uaagaaauuc 1260
uucgcuggaa gugagagaac auuugccgcg uaa 1293

<210> SEQ ID NO 47
<211> LENGTH: 879
<212> TYPE: RNA
<213> ORGANISM: Sclerotinia sclerotiorum

<400> SEQUENCE: 47
augucgacuu ucaaaaguac caucaacauc acccacauug gcacugcuac ugcugugcuc 60
gaaaucgaug gcgucaacuu ccuuaccgac ccuuucuucu cuccagcggg uucuaguuuc 120
cccaucaggg aggacuucgc acuggagguc ucagaggacc cugcccuugg ucugaacgaa 180
cuaccgccaa uugaugcugu uuugcucagu caugaagauc augcugauaa cuuggaugau 240
uauggucgcc agcugcuaaa uggccgucac guuuucacua cuguagaugg ugcuaaaaac 300 cuggcucccgc guccagcagu ccggggaaug aagccuuggg aaagcacaag cguaaacuug 360
gguggcguca aauacacuau caccgccacg ccaacccaac auuuucccgg caaugagugu 420
accggguuua ucuugacgac ugaucgguuc ggccaccaug cugauggacg uccaaacgcg 480
guuugguuua cuggugacac gguuuacauu gaggaguuug cccggauucc agaacaauuc 540
cacguugugg uggcgcugau gaaucugggu ucggccuucg uugagacucc uauuagcgau 600
ggaaagcuug uccagaucac uauggauggc aagcaagcgg gaucccuauu ccgaaugcuu 660
aaagcggacc aucuggugcc gaugcacuau gagucuuggg gacacuuuac acaauuuggc 720
aaggaguuga uggccgacuu caaggaagaa gggguagaag agaagguccg gugguuagua 780
ccuggcaaag cugacccugu acauaucagg acccuguaca cuuuuaccuc aauugcccac 840
auuuguaacg auacuguacc ggaggcagcg gcugccuga 879

<210> SEQ ID NO 48
<211> LENGTH: 1512
<212> TYPE: RNA
<213> ORGANISM: Sclerotinia sclerotiorum

<400> SEQUENCE: 48
augucgagcg ucacugcaaa uucuuucggu cccggugcuu ucgacuuucg ggaucugagc 60
augaagcauu cuaaaucaga cuacuucaug guaaaacccg uucgugguuc uucaccuaca 120
gcaaguuugg cggcagaucu aucacagaau uuucacauug auaugagccc ucaauuaccc 180
acuccucguc gaucucuauu cacgucgaau cuuuuuggaa cauuggaugg cagggauugu 240
guuacuacuc cuccauuacc uuccucuuca ccaggcccau ugaaugaaag aauggauauu 300
uccccucuuc cccauaagca accauauuuc ucugcgcaaa uugagauacc aucaccuaca 360
ccagcaggua caacuacgga agauacaacu auggggucau cuccaauucg uccuaguuua 420
uuggacgccu cgaaaccuuu uggugccgaa agacggaaaa auuuauuauu acgaccaacc 480
uuuucacgca ccaaagguca uucauccagc ucucugccuc gacaaaacuc ugauagucaa 540
ucgccugccu uccgcuucgg ugccggaagc agcaaauugu cuaccuccac aucaaugucu 600
uugggcgaau guuuuaugga aucaccacca cgagaacguc guucacaauc ugcgaauagu 660
ccuaccaugg caccaccacc ucgacuaagc aaaccguucu caagugugc aagcagaguc 720 gugaauggau caccgauugg uagucacuca cgcagaacuu cuaauccguu aguucggccu 780
aggaaacaau uucgacgauc acuuagcaug uuugaaagcc cacaagauau cgucaaggag 840
aaggaaagua ugucaagcaa cuugcauacc guuauggaua uugaugagau acaccaacca 900
auuuuaccac auuucuucca ggaaggucaa ccugacagca uucccaggau ugccaaggag 960
accuuauugg aaauucuuga ugggaaauac gaugaugaau augaucaacg aaugauuguu 1020
gauugcagau ucgaguauga guuugagggu ggacauauug auggugcugu caacuauaau 1080
gacaaagaau uauugaccag ucaauuguuu gaaacaaaua ucccuggcaa aacccuucua 1140
aucuuucauu gcgaauauuc cgcacaucga gcacccauua uggcucguca cguacgacaa 1200
caggaucgua caacuaacgu cgaacaauac ccuaagcuuu ccuacccuga aguguauauc 1260
cucgauggug guuauagugc uuucuucaca gaacaucaag gccguugcuu uccucagaau 1320
uacguugaga uggaugcuaa ggaacaugcu uacaccugug agagggaaau gggaagacuu 1380
cgacaaaaca gaacuaagcu cagcagagca cacacuuaug cuauuggcca acacggacaa 1440
auugaugaca gccccacugc cccuagucga ucaaaaucaa gcggcauccg ucuucaucug 1500
cgaaagguuu aa 1512

<210> SEQ ID NO 49
<211> LENGTH: 1017
<212> TYPE: RNA
<213> ORGANISM: Sclerotinia sclerotiorum

<400> SEQUENCE: 49
augcauagua agguuguuau uauuggcuca ggcccggcgg cucacacugc ugccguauau 60
cuugcgcgug cggaauuaaa accaaaugga auugcugccg guggacaauu gacuacuacc 120
accgauguag agaauuuccc ugguuucccu aaaggaaucg guggacaaga acuuauggau 180
aauaugcgcg cacaauccga acgauucggu acucaaauca ucaccgaaac aguugcaaaa 240
guugaucucu ccaaacgucc uuucaaauac uggaccgaau gggaugacaa gacagaacac 300
acagcagauu ccaucaucau cgcuacgggu gcaucagcuc gcagacucgg ucuuccaggu 360
gaggagaaau acuggcaaaa ugguaucucu gcuugcgcag ucugcgaugg agccgugcca 420
auuuucagaa auaagcccuu gguaguuauu gguggu ggag auagugcugc ggaggaagcu 480
auguuccuua cgaaauacgg aucucauguu acgguuuugg uccgaaaaga ucauuuacgu 540
gcaucgaaaa cgauggcuaa gagauuacuu gccaacaaga aaguuacugu uaaauucaac 600
acgguuggag gcgaaauuac ugguaaugau aagggauuga ugacgcauau gguuuuuaag 660
aacgucguua cuggagagga agagaaagca gaagccaaug gauuauucua ugccguagga 720
caugauccag cuacugcauu guucaaagag caaaucgaca cugauuccga gggauauauu 780
guaaccaagc ccggaacgag uuacacaaau guggagggag uuuuugccgc aggugauguu 840
caggauaaga gauacagaca ggcuauuacu agugccgggu cuggauguau agcagcuuug 900
gaggcagaaa aauuccucgc ugagcaagag gauggggaaa augauuugga gaagacggau 960

-continued gcugaaaagg guagcaaugu uguuguuccu gaguauagau cuaacccuuu gcuuuaa 1017

<210> SEQ ID NO 50
<211> LENGTH: 1035
<212> TYPE: RNA
<213> ORGANISM: Sclerotinia sclerotiorum

<400> SEQUENCE: 50
augucaagcg ugcuagacaa gcuuuucgaa acuacgacug gagcuguauc uucgacaacu 60
ggcaaaguuu uaaagaccac ugcaggugcg guagguaagg gagcugccug gacuugggaa 120
acuccuguug uaaagggagu gagaacuacc gucaaugcua cagccaaugu acuugacaag 180
gcgacgcaac caauucgaca gacagaggca uauaagaaug ucaagaacgu gauugaugau 240
ggaaguaguu cgagguacgg aggguggug gagaaggaag agagacggaa agcaagagaa 300
uuacgggaau uagaagaagg aaccacuggc aaaagcaagg agguuccugu agaagacccg 360
aacgccggca caaacguuac cguacacaaa gacuccgcau acaaggaggc cuggagagau 420
uuccgugacu caaauagacu caugcaaucu uuauucucca ugaaaaccgu cuacaaugaa 480
ucugaaaauc ccuuaaucuc caccgcccgu agcauauccg accgagucgc cggauucuuc 540
gccgaaaacg aaaccgccca aguaaucaag aaauuucgug aaauggaucc cuccuuccaa 600
auggaaccuu uccuucgcga aaugcgcgaa uacauccucc cugaaguccu agacgccuac 660
gugaaaggcg auacugaaac ccucaaacuc uggcucucag cagcucaauu cuccgucuac 720
gaugcccuuu ccaagcaaua uacaaccgcu ggucucaaau ccgauggucg cauucucgau 780
aucagacaug uugaaguccu aucugcaagg auguuagaua augauauccc agucuucauc 840
auuacaugca gaacacagga aguccacgua uauagaaacg cgaagacgaa ucaacuagcc 900
gccggcaugg aagauaaggu ucaauugguc accuaugcaa uuggguguuac gagaguagca 960 gaagauguua auaaucccga gacgagaggu uggagacuca uugaguugca gaagagcgga 1020
agagauuaua uauga 1035

<210> SEQ ID NO 51
<211> LENGTH: 969
<212> TYPE: RNA
<213> ORGANISM: Sclerotinia sclerotiorum

<400> SEQUENCE: 51
auggcaacuc caucaaccga ggguuaugcg cccgaauggc ucgaggucga gaaaacccug 60
ggaggucguc cucuccucga aggcaagcca cuagaaauua gaaagcaaua cagcgaacua 120
guccgcacca ucgcagcgca auccgcaggc cccgauuccu ccguccaaac ucgugauauc 180
uccgccgacg gaaucccagu ucguaucuac accccuccaa auacuucugc cggaaacccu 240
cuuccucuag guguauauua ccacggcgga ggcuguugcc ucggggaucu cgauuccgag 300
gauccguggu gucguuauau cgcuaagacg guuccgugug uucucgucuc agucgaguau 360
agauuagguc cugaguauaa gaugccgguc auguuggaug auagucuuaa ggcuuuugaa 420
ugggcacgaa accacgccuc agaacuuaac gccaacccgg cgcaagucuu cacaaucggc 480
gguucagcag gcggcugucu aucucucacc guagcaaacg aucucaucgu cgcugguaaa 540
aaagaccaca uccaaggcau cgucucccug guccccguaa ccgcccaucc aucuuccauc 600
ccugccgcuu acaaggaaca cuauaaaucg uacgaggaaa acgcagcugg uguuccgauu 660
cuagaucgag ccgcuaugga uguauuucuu ggggcuauug aggcggaucc ucaugaugag 720

-continued agaauuuuua caacgcuuuc caagcaucuc gaucaauuuc cuccuacgua uauugcuacg 780
ugugggaaag auccuuuaag agaugauggu acgguauugg aaauaauguu gaaggagaag 840
gggaucaaga cgaagaguga uuuuuaugau ggugugccgc auuacuuuug gauguucccc 900
gguaugaagg guagagauga auuuuuggac aauguuugug cgggcgugaa guucguuuug 960
gguauuuag 969

<210> SEQ ID NO 52
<211> LENGTH: 1731
<212> TYPE: RNA
<213> ORGANISM: Sclerotinia sclerotiorum

<400> SEQUENCE: 52
augaagacac aaucucuaau caguaugggc uuauugccua uacuaucagu aaacgcagca 60
uauaccuggc cuucaaaaua cgacgaauua gaggauauuc uuuaccuaca agcaggauac 120
agacgcuacg gauuuagaga cgguguuaca ccauguggcu ucucagcuga ugguaguaau 180
cgagagacag cugcagaaug gaucaaaacg gcuuaccaug auauggcaac gcaugaugua 240
gaaacugguc uuggaggacu ugaugcuucg auagcuuaug agcuuggucg ugcagagaau 300
cccgguucgg cuuucaaugg uacuuuugga uucacaaaca acuaugccuc gaucaaaucg 360
ucuaacucug aucuucucgc caugucuguc guuguugccu ccauggcaug cggaggucca 420
auuauuccau uucgagcugg acgaauugau gccgugcagg cuggugugacc aggugucccu 480 caaccugauc aagauuuggc cacgcacacu gccauuuucg caaagcaggg uuucaacacu 540
accgagauga uuaccauggu agcaugugga cauguucucg gaggaguuca uggcgucgau 600
uucccucaga uuacugguga uaauaacgaa acuaguuucc cacauuuuaa cagccaauac 660
gacaacuuua ccaacuccau cguaaccgaa uaccuagagg auaaaucaau cgacgugcuu 720
gugguuggca aaaacgacac cuuuaacucc gacaagcgua ucuucggugc ugauaacaac 780
aaaaccauga cuucucuagc agauccuucu aauuuccaag cgcagugccg cgacauuuuu 840
gcccgcauga ucgacaccgu uccugcaagc gucacacuuu cagaagucau cacccccauc 900
gaagugaagc caaccgagcu uucccucgcc uuaggcgcaa acaacacauu auccuucaca 960
gguucuaucc gcgugcguac cacccaccgc aacgccgaca acguuaccgu aucccuccgc 1020
uaccgugauc gcaacaacaa ccucucaaac accaccaucu caaccgaacg cggacgcugg 1080
caacuaggcc aaagcuaugg auucgccagg gaagucuuca ccuucuauga auucgacacu 1140
gcuuucgaug uuacauccag caucucaucu uucgacguca ucauccauac agcuggcgaa 1200
gcugaugaga ucaacaccaa caauggccuc ggauuucccg ucucagacgc aauucuuuug 1260
caagcaccac aauccuguca accacaaaua aucgugaaug aagcaggcca auggaaucuc 1320
accaucaccg ccgcaguccg cgccgaucgu gucggggaac cuguagcuuu cgacuggguu 1380
uacaaacgcu ucauccaagg cguaaugaua aaccaauugg agguacaacg uacgguuaug 1440
gagaaagcga gugaggagau ugguggauau uaucuuuaca cggcgacaaa gccaauugau 1500
acgguacagu ggucgacaac auuugacuug guauugggcg agggagacaa ugucuccaag 1560
cuugaguucc ugucgacugg aaacuuggcc ucuaccuccu gguuggacga aaagguacag 1620
gagagggaag augcacacaa aacuaggagg agugcuguug gugcaaggga uauccuguac 1680
ucgauauuau ucgauauagu ugcagcaaca caacaugucc ucagaauuua a 1731

<210> SEQ ID NO 53
<211> LENGTH: 738

<212> TYPE: RNA
<213> ORGANISM: Sclerotinia sclerotiorum

<400> SEQUENCE: 53

```
augguugccu uugccaaauc ucuccaacuu ucccucucac ucuuggcaag uaccgccaua     60

gccauucccu ucccaucaga gcucgaaucc cgagcugaaa ucaacuccga ugccguugug    120

ggauuucccg aaaccguucc uaguggcaca guaggcacac ucuaugaagc cuacaaacca    180

uaccucgaug ucguaaaugg cugcguacca uucccagccg uugaugccgc uggaaacacc    240

aaugccgggu uaaaaccaag uggcaguagc aauggugauu gcaguaguag uaccggacaa    300

guauauguuc gaggugcuca aaaugguuca uacuacggac ugauguauuc cugguacaug    360

cccaaagacg agcccucacc aggcaucggc caccgccacg acugggaagg cguaauccuc    420

uggcucagca gcuccaccuc caccaccgcc agcaacaucg uugccgucug ucccuccgca    480

cacggaggcu gggauugcac ccgagaccaa uacacacucu cuggcacauu cccucucauc    540

aaauaugaag gcauuuggcc ucucgaucau uccuguggue uuaccaguac ucagggugga    600

cgacaaccga ugguugcgug ggaaucucuu acaccagcug cgcaaagugc gcuugagaau    660

acggauuuug gaaaggcgaa uguuccguuc aagaaugcua auuuugagaa uaacuuugug    720

aaggcuagua guuucuag                                                  738
```

<210> SEQ ID NO 54
<211> LENGTH: 2544
<212> TYPE: RNA
<213> ORGANISM: Sclerotinia sclerotiorum

<400> SEQUENCE: 54

```
augaauaaaa uuacuucaga guaucuugcg gcagguggca auagacaucc uucugcugcu     60

gauugggaug aaucaggacu ucuagccuau ggaacugaua gaaauaucgc auuaugguau    120

ccuggaaaug aaucuuccag aggaguuuuu gaacuucuca gugcucauac cgauacgguu    180

aaugucguga aauuuauccc uaaaucacau ggucucauac uuaguggauc ggucgauaag    240

acggugagga uuuggaaaca ggaugaugua ucaaagaguu auacuuguau ucaaacuauu    300

accgaucauc agagcacgau caauuguaua gcugucacag aaggcucgaa aaucuuugcu    360

acagguucgg cggaugccgu ugucaagauu uggaaacucg gugaugauaa uguugcaagu    420

uugcagcaau cuaucacgau uacuccgcga uuauuuccau uggcauuggc uuugagcccu    480

uugacugggg caucggauuc uuuacuucuu gcaguagcag gcacaaaaga uaucauucag    540

cuucacgugc ucgaugcuca agcgggauca gaauuuaaau auaaggcuac auuaucugga    600

cacgaaggau ggaucagauc auuagaauuc acaccagaga gcgauagucc aacgagugau    660

uuacuccucu caucagccag ucaggauaaa uauauccgau uguggagaau ucaucaaggc    720

aaagaauuac ccgccgcagc aaccgcagcc gauccaacau ucggagcauu caugccagga    780

aaaucucuau ccaacaaagc gcaucgauuu caagcccaag aauuagauuu cuccgccaca    840

uucgaagcgc uucuccucgg acaugaagau uggaucuaca gcacacgaug gcugaagccc    900

acucuaucuu ccaaccaaaa accacaacuu cucuccuccu cagccgauaa uucucucgcc    960

aucugggagc ccgauacuca cacaggugue uggguaaccg ucgcacgccu cggagaaauc   1020

agugcggaaa aaggaucuac caccgccacc gguagcacgg gagguuucug gaccggucuc   1080

uggucaccca auggcucaac cgucguguge cucggacgaa cugguaguug gcgucucugg   1140

aaccaugaug caucuucuga ucguugggcc cagaguccgg cuauuaccgg ucaugugaaa   1200
```

-continued

```
gcggugaugg gaaucgcgug gucgaaggau ggaaguuauu ugcuaucgac caguacggau   1260

caaacgacua gguugcacgc gcaguggaag agagauggaa aaguuaguug gcaugagaug   1320

gcuagaccac aaauucaugg uuaugauuug aauuguauug auucgcuugg agagacacaa   1380

uucguauccg gcgccgacga gaaauuacuu cgaguauuca augagcccag agcagucgcc   1440

acacuacuca acaaacucug uggaaucggc agcgagaaua ucaacaacau gcccgacgca   1500

gcaaauaugc ccguacuagg acuauccaac aaagccaucg aagccaucag cgacgagcaa   1560

accaucgaaa aucccaacga ccacaaucgc gaagccauag accccgccuc caucguccac   1620

aaauccacac uagaccucuc acacccaccg cucgaagauc aucucucccg ccacacacug   1680

uggcccgaaa ccgaaaaacu cuacggacac ggcuaugaga uuuccgcacu agccaccucc   1740

cacgauggca gcaucaucgc cacagccugc aaagccagcu ccaucgagca cgccguaaauc  1800

cgacucuucg aaacccaaga auggcacgag auaaaaccac cucuuacagc ucacucccuc   1860

acagccgcuc gauuacguuu cucacacgau gacaaguauu uacuuucugu gggacgcgau   1920

cgucaauggg uuguauuuca acgagaugag cgagauccgc uuguguauaa auugguugag   1980

aggaaucuga agggucauuc gaggaugauu cuugaugcug cuugggcucc uacuuucucu   2040

ucaucuucau cuguaucguc aucuacaucu acaucaacau cuacaaauuc ccccaucuuc   2100

gcaacagcag gaagagacaa acaaguuaaa aucuggaguc gcgacagcaa aacccaagcc   2160

caaacugaca ccaauaucga aacagaaaca gagaauaaug ccggaggauu cacaugcaaa   2220

gccacaauac caagcgacgc ccccauaacc gcgcuugauu ucccucgacaa gaucauagga  2280

aacgcuauau auuuagcuau agguacugaa cugggaagau uuaauaucua ucguguuacu   2340

guagauggug augcuauuac uguuacugag guuuuauugg auaugggauc uagcaaaaac   2400

uauuaccccu ccaaagccau cacgcaauua gcauggaaac cccagagauc uagcaauaau   2460

acuccagagc acgacgagaa cauagauaug gaauuggcaa uugcgaguga agauaguucu   2520

uugaggauuu auucuuuaug uuga                                          2544
```

<210> SEQ ID NO 55
<211> LENGTH: 711
<212> TYPE: RNA
<213> ORGANISM: Sclerotinia sclerotiorum

<400> SEQUENCE: 55

```
augggggcga cagguuuccu ucaucauauu ggcacauuuc ugcucuucgc aucugcuauc     60

cuucuccuca uuacaacuau cuccgcaccu guuaucaaug auaucggaau caugaaaguu    120

aaauugacaa auggaacggc aucacaccau uccguugucu cauuugguac auucggauau    180

ugugucuugg augucgauuc agacgguaau gacuacugca ccaaaaaaca uaucggcuac    240

aaccccgcuu ccacaauguc ccaaaucgaa uccacccacu ucagccacgc cuccgaagau    300

acauccaaag cccuaacccg ggucaugauc cuccacccca ucgccugcgg cauaauguuc    360

auugcauuuc uccucgcucu cggcgccgga uucaucggau cauuccucgc ugcgcucguc    420

ucuagcaucg cauuuaucau cucagucgua gccauggcau gcgauuucgu gcucuuugga    480

aucgucaaaa aucauguaaa uggugauaag agcgguaguc augcguauuu uagcgugggc    540

auuuggugua uuuuggcggc gaugauugcg ggguuuuugg gugcgauagu aguguuuauu    600

acguguuuga guaagaggau gcacaagaag aggaguagag ggguggagga gaaggguuau    660

gugggggggug ugaaaccugc uaggagacau uuuuggcaga ggaggggguug a           711
```

-continued

<210> SEQ ID NO 56
<211> LENGTH: 456
<212> TYPE: RNA
<213> ORGANISM: Sclerotinia sclerotiorum

<400> SEQUENCE: 56
augcagagcg acgucacuau gcuuuuuucc cgaagaagag gaucaaacag ccaaccauug 60
gaagagucau ggugugaaug caaggccaag agccucaaaa auucaucgga uaucacggau 120
gacaccucgg gaacagggca uaugcaacuu gcaagugaau ugaguucaac ccaauuccuc 180
ggaaugagug uuuccgugga agaaagucau cuucgaucuc aauucaugcc aaaagccacc 240
acuggcaaga gaagugaguu gugugucgga aagcagagag cgggagcaga agaaaagugc 300
auauggcaug agaugaggaa aggaaauacc aaugaccaag gacuaaugac caaugaacgu 360
ccuccuuguu uuacgagcag gcgggguagu acucguaaau auacuucucu uccaagauca 420
uugguuccaa aggcugugga aggucaaaug gacuga 456

<210> SEQ ID NO 57
<211> LENGTH: 1338
<212> TYPE: RNA
<213> ORGANISM: Sclerotinia sclerotiorum

<400> SEQUENCE: 57
augaccacaa aaccccucgu ugggucacaa gcccaacgac agucgcaaag aucauugaau 60
ccaaacguua ccucgagacc cuccccacaa agaagccuau cgucuaccuc cccgacucga 120
agauacaacg aagccuucau agacuuaacg cuugaugugc cggauucuac aucugugcgu 180
uauggacaaa ccucgagaac aggagggucg cgcuugaagc aagaaauuuc caaugagucg 240
agaaguucaa gucagacgga gacaucaagc ucggguccuu caaauauaau auccaguagg 300
cagacucugc cuccacgcgg ucgaccgcag cuucauuucg augugccuca uacgagagcc 360
accagaucca guuugacguc cgaccaaaac uacagucaag uguuugcgag accauuuccu 420
cuuccuguua ggcccggaag acaugcaccc ccauuugugg aaaagccgag cucaucaauu 480
gggacaucug gaaagaaaga ugcucgcccc aaaccuuuug uuuuagagau accgcccgcu 540
gcgccgucuu auucaccaaa cggucaugcu gauuucuucc cauggaacgg uaaccaugcu 600
gaagaccaau ucacugaaau ugucauccgg ggaggcuucu ucgacaaguc gcaaauguca 660
cagaacgaaa cuggcucggc aaaagccucu auauauccau cuuuaaaaca caaaagcggg 720
cuccaaacac ugucaucauu guuuuccagc guuuuagcuc agcggagggc ucauggaaau 780
aucacggcga acucaacuuu caagccgcca ccccguguaa cgguuacgga cacgaagaga 840
gaaauauggc ucaaggaucu agcuaauccg acuauaucac uccgccgccu cagucgauca 900
auuccccacg ggauuagagg uaaggugcuc cuagaacauu ccccucaacaa aaacaucccu 960 aucgagcggg ccgucugguu agccaagugc guaggggcaa augaacugag gucuuucaag 1020
aggaagggug cgggguggugc uuuugcuaug ggaggugaga cgaaaugggu uagagacuuu 1080
acaguuugug uugaacaggu guuggagagc auaauuggau cauguggaga gaaggacuuu 1140
cgucgcagga ucuauuacgc accgcgagca uuaucuagau uggauacuau caucccucga 1200
ggcuacuucu caagccaaau uaccaauaug guuguugauu gcccaggugu auugggaaga 1260
uauuuugaag uaucggaggu ucgggcgccg guucacaacu acucugcuga aucguuuuuc 1320
agagcauccg gauucuga 1338

<210> SEQ ID NO 58

<211> LENGTH: 1635
<212> TYPE: RNA
<213> ORGANISM: Sclerotinia sclerotiorum

<400> SEQUENCE: 58
auggcggacu acaauacuuc cucuggguggg auggucgacc auaaaugccaa ucaaggacaa 60 uuacaucgaa gaaacguugu cgguauggaa gaaggaccug augcugaugc acaacucgcc 120
gcucaguuug gauaucagcc uguuuucaaa agagaauuug gauaccucuc gacuuucucc 180
uucgccgucu cuaucagugg auuguuugcu acuaucauga ccacuuucuc cuacccaaua 240
augucuggug gaucugcugc ggccgugugg uguugggcaa uaucuggugc ugguugcaug 300
uguaucgcuc uuucuguugc ugagcugguc ucugcguauc cuacauccgg cgguuuauac 360
uuuacaauuu cacgacuugu accgcaaggu ugggugccau cuaucaguug gguuacuggu 420
ugguugaauc uucuuggaca ggucgcuggu guugccucau cucaauaugg ugcaucucaa 480
augcugcuag cagcuguuuc gaucggaaaa gauuucaacu acacaauuga ugcaaauaca 540
acaguuggug ucauggcagg ucuuaugguu cuuacuggcu uggucaauuc uuuaucuacc 600
uacuggaugg aaaagaugac aaagagcuac guuauuuucc auguucuugu uuugguaucg 660
ugcugcauug cucuucuggu caaaaccccg aacaaacaua augccaccua uguauuuacc 720
gauguugauu caaccuccgg cuggaccccu guaggaugga guuucuuguu cgguuuccuu 780
uccguuuccu ggaccaugac cgauuaugau gcuacggcgc acauuaccga agaaauuucc 840
gagccagaga aaaaggcacc cugggcuauc uccauggcua ugcuuuucac cuacaucgcu 900
ggauuccucu ucaacaucgu acuuuguuuc ugcaugggug acccagccga gaucuuggc 960 acaaguauug gucaaccagu cgcucaacuu uucuauaaca gucuuggaaa agcaggaggu 1020
auuuucuaca ccguuugcgg guucauuauu cuugaauucg uaugcuuuac ugcuaugcaa 1080
ucauuggcgc gaacagucuu cgcuuucucu cgugauaagc uugugccauu uuccaaaguc 1140
uggacaaaaa ucuuacccau uacuggaacg ccaaucgcag cugucuggau cucuguugcc 1200
cugugcauug cuaucaaccu uaucggccuu gguuccuaca cugccauuuc uggagucuuc 1260
aacguuugcg ccaucgcuuu agacuggagu uauugcauuc caauugccug uaaacucaug 1320
uuuggcaagu ucgagccagg cccauggcau augggcaaau uuaguacugc cguaaaugca 1380
ugggcuugua ucuggacugu guuugucagu aucaucuuca uucuccccgac ggagcgacca 1440 gugacugccc ucaacaugaa cuacgccauc gccuuccuag gacuaauccu aggauucucu 1500
accauuuacu gguauguuuc cggcaagaag uucuacaccg guccugucau cgaggccgcc 1560
gacggagacu cccucaggaa uucgucagac cguggcucga ggcaggagaa gguggagaac 1620
ggaaauaaau cauaa 1635

<210> SEQ ID NO 59
<211> LENGTH: 1551
<212> TYPE: RNA
<213> ORGANISM: Sclerotinia sclerotiorum

<400> SEQUENCE: 59
auguuugaac aacagagauc agagagcccu guuggcaacc uggagaugaa gaagucugcc 60
aaagaaaaag ucacgccggu aucgagcgag gaagaucuca gcgaucagcc accggcacaa 120
cuauugucca cggcgagaga aauugcuuug gugcuaacau uggccggagc ugguuuccuu 180
aauauuaucu uugugcaauc ugcugugauu auguugccau ccauuagcga agcucucgga 240
auacccccga accgacaaca auggaucacg ucaucauaca auauagcauu ugccuguguu 300

```
cuacuucucu ggggucgucu ugcagauauc uacggccggc gaaucuuuuu cguuuauggu    360
ucgaucuuug ucaccaucau uaccgucgug auucccuucu cccccggcga aauugucuuu    420
gacaucuuac gagcgcugca ggggcucggu agcgccgcaa cgguuccguc cgcggucgga    480
auccuaagcu ccaccuuucc accugguaaa aagagaacuu acgcguucgu uacuuauacc    540
gccacuucgg ccuugggauc gguaauggga aauauuaugg gugggaucau cggcgcuuac    600
cucagcugga aaugggucuu cuggaucauu gcuauucuug ccgcuuucac cacgguggcu    660
gguauuauug uuauuccucg accucaggcg aaaacuauug auucugauag uaaauuauau    720
gucgauugga uuggaggagc guugauaucg acaagcuuga uuacucuuuu guucgcucuc    780
acagagggug guggaauugg guggaguacc ccuuggauuc cugugcucau uguguagcg     840
cuccuccuaa ugguggucuu uuacuuuugg cagcgacauu uggagcguac cgaucgcagu    900
ccacuaguga aaguuuccau guucaaaaau augcaguuua caucugcuuu ugcuauuauc    960
gggguguuuu ucgcaucuua caauagcuau uugaucuuug cgacuuauuu uuaucaggau   1020
uaucucgggc uaggaguuau cgaaacaaca guacgcuucc uuccagcugg aguugcuggc   1080
cuacucguau ccuucguaac agccaaagcc cuaaccaucu ucccugguuu cuacguccuc   1140
gucuucucaa ccaucugcgg cacucuaucu ccucuccucu ucgccguacc cauuucucca   1200
aauacaacau auugggccua cgguuuuccc gccaugugu cucugcaucag cgcagacaug   1260
uuaucaccga caauuaaucu uuucguggua cgucgucucg acgaacgcga ucaaucgcuu   1320
ggaggcgcgc uuuuaaauac cucgaaucaa guugguagau cucuagguuu ggcaauugca   1380
acggcugugc agggagcggu gggaaguaca gggaaagagg gaauuuaucg ugauccaucg   1440
augcuuaagg gacugagagc ggcggagugg guuaauguug gguuggcugc ugcgacgcuu   1500
cuuuugguuu ugguauuuuu uagaggaacg aggcauucgg gugcuucuua g            1551
```

<210> SEQ ID NO 60
<211> LENGTH: 1695
<212> TYPE: RNA
<213> ORGANISM: Sclerotinia sclerotiorum

<400> SEQUENCE: 60

```
auggcagacg acucagcacc ucucgagccc aaggguaaac aaauugccuc ugaagauacc     60
cucggagaua cuaccucuau ccaagcacaa gucgaauccg aaaaugaaga ggauaaugau    120
gaaacaacca cuggcgcaac ugacacgcca gcuaccggaa agaagaagaa aucaaagaga    180
aagaagauaa aggccgcacu aggaguagga gcaucuucaa cuggaucaag cggagauacu    240
acaagagacg accuuucaaa agcuguugcg ggucucagua aaucucaaau uggagaacua    300
cucgcauuaa auccggcucu ggcacaacaa auuggugcug uugauggcga ucugucaggg    360
aagcaagcug cagaagcugu acgaaagcuc aguuuagagg auaucaugac cgguuuagcc    420
ucaagcggga agaacguuaa ggaaaugggc gcauacaagu uuuggcaaac acaaccgguu    480
ccuaaguuug ggaaagcuc agaaguuauu gaagaagguc cauucaaaau uguugauccg     540
gaacaaguac ccaaagaacc ugguccacug auaucuggau uuaauugggu uacaauggau    600
augacaagug augaggcuuu gcaagaaguc uucgauuuau uauauggcca cuacguugaa    660
gaugaugaag cuauguuccg auuuaauuac ucaaagucau ucccucagaug ggcacuuaug   720
ucgccagguu ggaguaagga guggcacguu gguguucgag cuacugcauc agggaaguug    780
gucgcuuuca uaucagccau accaguugca cuucgaguac gaaacaaaac ccucaaagcc    840
```

-continued uccgaaguca acuuccuuug cauccacaag aagcuccgau cgaaacgauu agccccguu 900 cucauuaaag agauuacacg uagauguuac cuacaaggga cauggcaggc aaucuauacu 960
gcugguguug ucuuaccuaa gccagucagu acauguagau auuaucaucg uucuuuggau 1020
uggaaaaagc uacacgaggu caaauucagu ccccuaccac cgggaaguac accagagcga 1080
caaguucgua aauuugcucu accaucgaau acauccacua gaggauugag accuauggaa 1140
uccaaagaua uugaugcggu cuuggaucuu cuaaagaagu accucgcaaa auuugacaug 1200
gcaccaguuu ucacuagaga ggaaguagag cauuggcuuu ucaauagaau ugagaauccu 1260
gcugagcaag ucaucuggug uuauguugug gaggacccua caaccaagaa acucacugau 1320
uucuuuucau uuuacugucu cgaauccucc gucauuggcc accccaagca cacuaauguu 1380
cgcgcugccu aucuuuucua uuacgccuca acgauugccc uugauccagc uagcucuaga 1440
accgaucuug guaaacgccu caaugaacuc acacaugaug cucuuaucau ugcaaagaaa 1500
uuuaaauucg augucuuuaa ugcguugacg cuuauggaua auacuuuguu uuuggaagag 1560
cagaaguucg gugccgguga uggccaguua cauuauuauu uguacaacua uaaggcgaac 1620
aacaucgcgg guggugugga uaaaaugaau aggauccauu cugccggaag uggggugggu 1680
gucguuaugu uguaa 1695

<210> SEQ ID NO 61
<211> LENGTH: 5127
<212> TYPE: RNA
<213> ORGANISM: Sclerotinia sclerotiorum

<400> SEQUENCE: 61
augaaggcua uaacuguccu cgucggcuug agcuggcuuc guugggcuuu agcagacgac 60
auuuauugcg augcuaaugu gccaugugcc auuggaugcu gcgguguuaa aagcaauguu 120
ugcggucucg guccuaauua uugcagugcg gagaacugua ucaauaguug ugacgccaaa 180
gcugagugua acccgggugg cugggcgucc gaguacguca auagcaccac uugcccgcuc 240
aaugucugcu guagcgagua uggauucugu ggcacaggcg agucguucug ugggaccaag 300
acucccacca uacccuccug ugaugucgau ucacaaucaa uaacccgugu caucgguuac 360
uaugccucag gugguguac ucgcgcaugc gaugcaaugc uuccagaguc cuuuccccag 420
ggaauuuauu cgcacaucua uuuugcuuuu ggcaguauca acccagauac uuuugaagua 480
auccccggag cagaugguga ugaagcgcuu uauacaaagc uuucggcccu ccaaacacgc 540
gaugcaacgc agaaauucug guuauccauc ggagggugga cuuucacgga cagugaccag 600
gcuacagcga cgaccuuuuc ggaucucgcc gccgccgaua ucacccacca gaauguguuu 660
uucucuuccu ugacccuuuu caugacgacg uggggauucu caggcguuga uaucgauugg 720
gaguaucccg cggccuccga ucguagugga cgaacugaag auuaugccaa uuacccgaag 780
uucuuagcca auuugaaauc agcacuggau gaguacagcu auggucuuuc cauuacgcug 840
ccuaccagcu acugguaucu acagcauuuu gaucugaucu ccauugaacc cuccguggau 900
ugguucaacu acauggcuua ugauuuacau ggcaccuggg acauugggaa ugaguggacu 960
ggugcuauuc uagaugcaca cacaaaccug acagaaauag aauccucaau gaacuugcua 1020
uggugGaaca auauuacuuc gucuaagguc aacuuagguu uggccuucua cggccguagu 1080
uucaccauug cuagcuccaa cugcgacacc cccggcugcg cguaucuuuc ggcuggagac 1140
gaaggcguuu gcagcgcuuc agcugguauc cuucugagua gugagaucga acagaucaug 1200
agugauaacg accuuacccc aguuuucuac aaggacgcag cugucaaagc cauaacuugg 1260

```
gauaaugacc aauggguuuc auuugaugau caggaaaccu ucaagaucaa gagcgauuuu   1320
gcgaagucgc aaugucuugg gggcguuuug guuuggucug ucgacuauga ugacagcaau   1380
aacacacucu cacgagggcu agcagccgcg cucggcaaug aaaucaacau agauacuucc   1440
acaggucuag cacuuacuga aagugagaca ucggauacga cgacaaccag uaaaggcggg   1500
caggaugcgu acugccgauu cacuaauugu ggagaaacau gucccgcugg uuucaccacu   1560
guuguucgag gcgauaaaaa aucgcaacuu augcucgacg ggucgcagug uuggccaggu   1620
ucuggacuua cgcagaccuu gugcuguccu acuucaaccg acguaccgac uugucaaugg   1680
cgaggcuuuc acaacaaugg uaaaugcaag ggcggcugca acagcggcga agcugaagug   1740
ggaaccaauu ccgccggaug caagucaggc uaucaaucgg cuuguuguac cacuacaucc   1800
ucgacaaagc ccuauuccga gugcgcgugg acuucuagcu gugaaagcga ugacacgugc   1860
ccaucaggcu auucgaauuu uaucguaggg ucccgcgcgg guuggggcgg acgaaaaaaa   1920
ucaugcagug gaaaaaagaa auacaacuau ugcugcgcag acuccguucc agaugccuuc   1980
accaacugcg cuugggcugg auuugagguu gcauucaaga augagaaaua cuguagcgau   2040
accugcccuu cagguacgau ucggauugcc gaacaggaug auuuuggaca aacgccaaac   2100
guugaaaacu gcauuugggg uaaggaggca uauuguugug gugggaccgu uacgacaagc   2160
accguaaguc cgcgagcacc caccuaccag gacaccacag caaaggaguu ugaugcuuau   2220
cucaagaaau acuuggcggc accuauaugc ccuggugggu uugaagcuga guacagcgcc   2280
ucuuucuccu ccgauccuuu ggggguggaag cgaagcauau cgcuagagaa gcgagccacc   2340
gaccaaggca uuacucucga aguucugauu cccauucuuu cgacguggau uacgucccaa   2400
uauccccgaa cugacuugau ggagaucugg aacgaugaua ccagugaagc uggauucggu   2460
agcaugaauu acaccguucu cagggauaca cucuacccga acgcuuggac gggagauccc   2520
gaguaugcca ccgauaccuu gcuaaccgau augcuuugua acauggcuga ggcagcuaac   2580
ggacuugaaa accugcagac agauucauca auuuugugcg ugaguccuga ugaugaugcu   2640
gguaccuggg augaucucgu aaccaccaaa cgagagaucu ccgcccgaag acucgaugaa   2700
augguuucaa cugcccgcac cgccgacgga cuccagccgu cuguuucuca agccaucaga   2760
ggcguauuga acggugauuu gucucugcau uaccuucgcu ggcucaaucc aucaggugcu   2820
caaguuauau uagagcuggc cuuuuggauc gguccuacug caggcguggc ccccacggca   2880
gcucagcgug ccgccuaugc cgacaccaca cauacagcug cagccgaucg cuggaucgua   2940
uuucauuuac auaucccccu ggaucgauac acauuuagac aagagaucac gaaugacgac   3000
acguuuuggc aucugggugu cgguaccaua acuguauauc auggccaaac cgucaauaga   3060
agcccccuc gaucugguga cgacacacuc gagccccgag uagaguuucg cuauucuucc   3120
acuuauguug gggcguaaa uaacggcaac auggcuaauu acaaugcacg cacucaagcu   3180
cugucuuguc cuauaggcga cgauauucag accagaaugu aucuaggucu agacuugaac   3240
gcugcuguuc aagcaucgau acgaccuucu guggggggcua cccuuguaaa uucauuuaau   3300
cuuuggaugu augagcaagg aauuacgagu cuuaccaacu ugcaauaucu auggccauca   3360
uugccagggg aucaaggcgg uuucgaacuu guagguggau ucaauggaaa uuccaaucuc   3420
aauccugaau augcaaaugu uagcgagugg auuauucguc accaaccggu aacaguaucg   3480
cccuaucgcg aauuccagca gccagauaau auuacauccg ucgcucuguu ugaccaugac   3540
ggcaccacgg cccucuacga aaaaggugaa uacgcaaacg cccuuuuaug ucgaauuguc   3600
```

cagcucaaug acgugucugc auuaaaucaa uacuugauaa gagaccccau gcgcggcuug 3660
guggcaaauc uagccauuua cacggacccu uucuacaccg cgaccuauua ugcaucuacc 3720
gauugucuuc gcauacuucu ggagcaucac gcuauccaug gaacuccagc ucaauucgau 3780
gcucccaacu cgacagacua ccugcuauua aauguggcua guagcagagc ucaucuugau 3840
acggcacguu uucuguugga uugucaaccu gcauauguug auauucacgc ccggaaaugg 3900
gacaugacgg ccuugcucug cgcagcugcu ucauuuaccg cgcaccuucc agacauagcg 3960
ccaacaccga gugaaccaaa gggagaccua cgccaucacg uggcucguag ugaggagcuu 4020
augcagcuuc uacuugaccg aggugcuugc gcucgugaug cuacaaauua cgcgaacauu 4080 cauaaaaacgg uucucagucu agcuaucucu agggcuaguc cugaauuugu gaaacgucuc 4140
aucgaugaag gugccgacgu gcaugcaaag acagcaagag agcuagaguc uuggucugga 4200
uacgaugaaa agcuucucca agauuucacu ccucuucaua uggguagcuu guaccuuaau 4260
uccgaaggca uccaaauccu gcuggacugu cgaggcagcg guauggaaau uucagauaug 4320
uuguuaugcc gggauaguuc uggaucucuu ccucuucacu gggccgcugg gagcuucaau 4380
cagccugaga acgaaauuug ggccagagac gauauuguug cccaagcuac caaaaccauu 4440
aaguuacucu ugaaagauag caaucccagc ucuaucaaaa uuccagauaa gcaaggaaac 4500
acgcccuugc aucucgcauc aucuggagaa acaaaaaacg auagcgaaca uuccuuuguc 4560
gcucaggcua uugugaagcu guugcucgaa cacggcgcag acgugggucu acguaaucaa 4620
aaaggacaaa cgccgcuaca uuugauaacu aaggauacgg cacugaugga acuccuucug 4680
gcgaauggcg cggaugucaa ugacgcugau acagauggcg auacugcccu ucacuuugcg 4740
gcgaguaauu ugcguuauau cgaagcagug cgauuucuca ucaguagagg ugcugaucuc 4800
caugcuaaaa acuccaaagg gaauacacca cuacaugaag cagcgggcgg guauuauaua 4860
aaugauaaac ggcguuugac uaguggaucc uaucgcgaug ggaauacgcg uuggacaaac 4920
gcugauuuga ugagauugca ggacgaaguu auaggugucu uuuuggaugc uggaugugau 4980
cuugauggcc aguguaauuu agcugcuaaa acagcucgaa ugauacugga ggaaacgagg 5040
caaaaauggg aagaaaggga agaaacuugg aggaaaaggg accaacuaag ggccggaagg 5100
ggaagaggaa gagguagggg aagguag 5127

<210> SEQ ID NO 62
<211> LENGTH: 675
<212> TYPE: RNA
<213> ORGANISM: Sclerotinia sclerotiorum

<400> SEQUENCE: 62
auggcuccac uucgaucaac ggcgcucucg cgcgauacaa augagacuag uauucaacug 60
gcuaucaauc ucgauggagg ggaauuccca gcagauacug auaagaaguu auucaguggu 120
gaagaggggc augcuuccca agucucaaaa ucgcaacaua uugcuauaca uaccggaauu 180
ggguuuuugg aucauauguu gcaugcuuug gcaaagcaug cugguuggag uuuggcgauc 240
aauuguaaag gagauuuaca cauugaugau caccauaccg cugaagaugu augcauugca 300
cuugguacau cauuugccaa agcucuuggc ucuccuguag gaaucgcacg uuucggaucc 360
gcauacuguc cucucgauga agcacuuucg cgagcuguug ucgauauuuc aaaucguccg 420
uuuaguguga uagauuuggg acucaagaga gagaagauug gagacuugag cugugaaaug 480
auaccacauu gucugcaaag uuucgcgcag ggugcaagaa ucacuuugca uguggauugu 540
uugaggggug auaaaugauca ucauagggcg gagagugccu uuaaagcguu ggcuguggcg 600
guuagacagg cuacuucgau agugaaaggu agagagggug agguuccaag uacgaagggu 660
acuuugagua cuuga 675

<210> SEQ ID NO 63
<211> LENGTH: 1884
<212> TYPE: RNA
<213> ORGANISM: Sclerotinia sclerotiorum

<400> SEQUENCE: 63
auggcggcug aauuaaucga cuuuuaucag aacuuucuac gaacgggauu auacaauggc 60
ggauaugaug augaacuucu cgcucuugca ggagaugauu cuucuggaga agaacagguc 120
gcaacaaaug augggggaag acacaguucu ucaucgccug aucguaaugg ugcgguaaag 180
agugcagcua agaaaggugg aaagaagggg gguagacgaa augaugauuc ugaggaagaa 240
ggugaagcuu cuuccgguga ugaaucuguu cguucggaac gaucagcucc aauggaugaa 300
ucugauuccg auuccgaugg cccaaguuuu cgcgaugaug cugaucgaua uccucucgaa 360
ggucguuuua ugaaugcagc cgauaaagca aguauuaugu cuaugccuga aauucaacgu 420
gagcaggucu uggcugaucg ugcccaagag auugaaaggg accgucaaaa uagagcacuu 480
cgucaacugu uaaaugcccg ugaugcagag aauaaaaaag cggacaaaaa gcgcaaggca 540
gguaccgcgg auuuggagga aaaccagcgc aaaacgucuc gucaacguac caagcuuggu 600
ggugggaagg uuggggaagc uagcacugga auugacaguc uuaagcgugc aagagcugag 660
aaaaacgauc gacaacgucg ucgcgaucaa gauaaggagc gccgugggga ugauggucga 720
agagauaccc gggacgauua uucagaugac gauggugaug gggauaguga gguugaaugg 780
acagcaucaa agucaaagaa aaggucugca ucuccagauu accgagaugc agaaccggcg 840
guucucuaug aucuugaacg aguucgaguu gguagaagua gauuugccau ggucugcuuu 900
uauccugggu uugaugaagc uauuacugga ugcuuuguuc gaguaaauau ugguguugau 960
aaggagacaa aucaaaaccu uuaucgcaug ggacuuguua aaggcuucaa agaagauaaa 1020
ccauacgcua ugaugucuag uaacggaaag caauuuucga caacacaaua ugugauugcu 1080
gcacauggua aaucugagag aucauggcca uuuaucgcau guucagauuc ucgauuuaca 1140
gaggcugaau ggcaaagaua uaagcaaaau uguaucgcug auggcauacc uguuccgaca 1200
aaaccaaagu ugaugcaaaa gugugcagag auuaaugcuc uuguuaacag accuuggacu 1260
gaagccgagc uacaagagaa guugaagaaa uccggugual ugacggaaaa guggaaugca 1320
accgaacgug ugcgucuuaa caacgcuauc aaggaacaga aagcccuugg caauaccgaa 1380
auggaagaaa aguaucguuc agaacuugaa gcgcucgaga auuccaaacu ggcuuaugga 1440
accacccuca aaucaacgcc gaagaagaug guucacucuc aacaagaccg acuugccgaa 1500
uuaaaucgau uaaaucgucg caaaaauauc gaggaaguac gucaagcgca aaucaaugaa 1560
cgucgugcag cucgacaggc ugaagcagcg auugcucgug gagaaguagu ugaugaagau 1620
cacucaaggc gugucaaaac ucgugcuacu uucaaacaug aucauacugg agguaaggau 1680
agcgcaacug cuacuccagu uagugguacu ucgaccaaua auaccccuaa acuuguggcu 1740
aagaaagaug cuuuaccggu accgaauuuu aguaagcuac aaacguccau gaagggugga 1800
guuccuggau ucagaaaacc uuugauggac gaugauauua uugcuaguau cgauauuggu 1860
auuagugaug auuuagaguu guaa 1884

<210> SEQ ID NO 64

<211> LENGTH: 645
<212> TYPE: RNA
<213> ORGANISM: Sclerotinia sclerotiorum

<400> SEQUENCE: 64
augacucaac cuaucgaagu auggacgucg auuccagguc cuaauccuug gaagaaacua 60
gcuaucaucg accccaauac cgacuugaca cuuugggaau caggcgccau cuuacaauau 120
cuugucaaac aguaugauac ggagaagaag uugaccugcg agaaguugca agacgaacau 180
cuccucaauc aauggcucau guuccaaaug agcggucagg gcccauauuu cggacaaugc 240
ggcugguuca auauccugca uuccgagaag aucccauccg ccaucgagcg uuacaauaac 300
gaggucgccc gcauccucgg gguauuggaa cguucgcucg aaggaaaaca auggcuuguu 360
ggugacaagu uuaccuucgc ugaucuuucu uuugcuccuu ggaacgacag aauugacacg 420
uuguuuucau auccaccuug uucuuacgaa gauaaucuuc uuagaaaguu ccccaacgug 480
gaugcuuggc acaagagaau aacagagagg ccagcuugga agagguccau gauugacagg 540
gagaagagaa uggccacuuu gggcuugaug ccaaauggua ugcccaaggg agucucaaac 600
auggaagaau acguagccaa aauggaggcc gaaggagaug ccuag 645

<210> SEQ ID NO 65
<211> LENGTH: 1569
<212> TYPE: RNA
<213> ORGANISM: Sclerotinia sclerotiorum

<400> SEQUENCE: 65
auggguauuc ucgaaacaau ugccgggcca uuggcucaag agauuucgca aaggucaacc 60
uuugcuguug uugcugcugg cguggcagca uucgucguuc uaucugucau ucucaauguc 120
cugaaucaag uguuauuugc gaaccccaau gaaccaccag uggucuucca cugguuucca 180
aucauuggua gcaccgucac uuaugguaug gacccuuaua aauucuucuu cgagugucgc 240
gcaaaguacg gugauauuuu cacauuuguc uugcucggaa agaagaauac aguauaucuu 300
ggacgaaaug gcaaugacuu uauucucaau ggcaagcuua aggaucucaa ugcggaggaa 360
auauauacug uuuugacaac ucccguguuu ggaaaggaug uagucuacga uugccccaau 420
gcgaaauuga uggagcaaaa aaaguucaug aaaauuggcu ugucuacuga agcuuuccga 480
uccuacgucc caauuauaca aauggaagug gaaaacuuca ugaaacguuc uucgguauuc 540
aagggacaaa agggaacugc cgauauuggu cccgcuaugg cugaaaucac caucuauacc 600
gcuucgcaua cucuacaagg aaaggaaguc cgugaucgau uugauacuac uuucgccucu 660
cucuaccacg accuugauau gggcuuuagu cccaucaacu uuaugcuuca cugggcuccu 720
cuuccucaca accgugcccg cgaccaugcg cagagaacug ucgcagcaac auauauggau 780
auuauuaaaa aacgacgugc ucaggcuacg gaagccgacu ucaaauccga cauuaugugg 840
caauugaugc gcucguccua caaagaugga accccccguuc cagaccgaga gauugcucac 900
augaugaucg cucuucucau ggccggacag cacucuuccu caucuucuau cucuuggauu 960
cugcuucguc uugccucacg cccagauauc auggaagaac ucuaucaaga acaaauccaa 1020
guucugggcg ccgaucuccc ugcucucaag uacgaggacc uggccaaacu uccucuucau 1080
caaaacaucu ugaaggaaac ucuccgcauc cacacuccca uccauucuau uaugcgcaaa 1140
gucacaacac caaugccaau uagcggaaca aaauauguca uuccaaccuc gcauacucuu 1200
auggcaucuc cugguuguac aagucgagac gcggauuacu ucccagagcc acuugagugg 1260
gacccucaua gaugggacau uggcucgggc cguguaauug gcaaugauca ggacgaagaa 1320
uuccaagauu auggcuaugg aaugaucagc aaaggugcuu cuaguccuua ccuuccauuc 1380
ggugcuggca gacacaggug uaucggugaa caauucgcca auguacagcu caucacuauc 1440
auggccacug ugguuagaau guucaaauuc aagaacguug auggcagcaa ggaugucauu 1500
gguacugauu acaccaguuu auucaccagg ccauuggcgc cagcaguuau agcaugggag 1560
cgacgauaa 1569

<210> SEQ ID NO 66
<211> LENGTH: 252
<212> TYPE: RNA
<213> ORGANISM: Sclerotinia sclerotiorum

<400> SEQUENCE: 66
auguucucug cacgugcaac ccgagcagcc gcacagcgcg ucgcucgcuc ucaaucuauc 60
cgaacuccau uccaacgacg cuucgccagc agcgagagca ccuucgcugg cgccgaggau 120
aacgcuuuca accgggagcg ucaggccguu aaggaucaug cugcugcuac uagugaucuc 180
uggagaaaau ugucaaucua ugcuacgauu ccuugcuuga ucaucgcaag ugucaaugcu 240
aagaucuugu ga 252

<210> SEQ ID NO 67
<211> LENGTH: 2370
<212> TYPE: RNA
<213> ORGANISM: Sclerotinia sclerotiorum

<400> SEQUENCE: 67
augucaccaa aaccaauacu gccuccacca aaggcaacuc ugccaucauc caacaccauu 60
cuaccugcag augcaaagac acgauuaaaa agagcugaga augcuaggaa acguuuagca 120
ggcggccgca cgguuaucga agaaucagac gaagaagaag aaucggauga cgaggcagaa 180
ugggaaugga uauacgaaag cgggagucau gaagaaacug cuucaucgcc gcagaccaau 240
gccagagggg acgagagcac agcugccaaa agaacccguc gacuuuccag aagcacagga 300
gcuaggagaa uuauuggugc uaaggcugga aaaauugucu gcaagauugc agauuguguu 360
uugauaaaua acgauacuuc gaauacaaau uggguugggg uuauaucagg auucgaggaa 420
gaugaggacu augaugagaa ugcugaauca uaucuugaua uaaugaaagc caguaucugg 480
ugguucagua gcccaaagga uauacacagu aagacaagga agcguucaga uuucuuggaa 540
aacgaguugu acauauccuc ugaucccgau acaaucucuc uggcgaccau uaauggcauu 600
gcuacgaucu uauccgaaga agcuuucaaa gccaaauauc cgacaggaaa aauaccuaga 660
aaucgaaaag aaaaugggaa aacauucaua ugucgucgag gauuacacag uaaaucuguu 720
acauauacag augaauuuau cugggaggaa guauaucaua auacggagga uaguguugaa 780
aaguugaucg agaagauaga gaauagcaua ccaaauaaga agagaaagaa gccuauauuu 840
uccaggaaga agcacgaaga ugaugacgac gcaagugucg caucugagca agaggauuca 900
gaaguggaug aagaaaucuu uacaacaccg cggaaaaggc aaaagacuac gaaagcuaua 960
acaccucgaa aaccacguac gccuuccaaa cuacuaacuc caagccauaa gagaauuguc 1020
gucaaaaagc cacuagaauu cacaccuuua ggaaugcgua ugcucucacc auccguuaau 1080
gcuuccccuu uucaaacagc ucgauuacgu cuucacguau cguccguucc ugauaaaucuc 1140 ccgugucgug aggaagaguu cucauccguc uacacccauc ucgcagcugc uauuacagau 1200
ggcacaggcu cuuguauuua caucuccgga acuccaggaa cuggaaaaac ugcgacgguu 1260
cgggaaguug uugcacagcu uaaugcaucc guucuggccg acgaauuaga uccuuucaua 1320
uucgucgaaa uuaacggaau gaaaguaacu gauccgcauc aaucauaugc auuauugugg 1380
gaagcucuga gaggggacag aguaagucca agucaugcau uagaucuacu agaaagggaa 1440
uucagcaagc caucaccuag gagagaacca ugugugguguu ugauggacga auuggaucag 1500
cuagugacca aaaaccaaag ugucauguau aauuucuuca acuggccugg ucugaggcau 1560
ucaaaacuaa ucgugcucgc cguggccaau accauggauu uaccugaacg uacucuuucc 1620
aauaagauuu cuucacgucu uggucuaacu cguauaaccu uccccggcua cacccaugag 1680
caacuccaaa ccaucauaac uucccgucua gcugacgucc ccucucaccu aauccauccg 1740
gacgcgauuc aauuugccuc ccgcaaaguc gccucuguuu ccggggacgc ccgccgcgcu 1800
uuagauaucu gucgacgagc cgucgaaauc gcagaaucag aauccguuuc uauuccaaac 1860
acgccuucga aaacuccagg ucgugaagag aagaagggga aaggugugggu uagcauagcc 1920 acgguuaaaa aagcaauuaa ugaagcuacg acuaguccgc uucaacaaua uuugagagca 1980
uguccacugg cuacaaaaau guuucuugca gcucuggugc ucagauugag gagggcggga 2040
acgggugagu guuuggguggg ugaaguggug gaugagugua ggagaauggc aaaguuggau 2100
acggggggaa guguggguugg guaucuacuu gcaggugcgg agaacaaggg agguggcggg 2160
ggaaaaacga aaggggcaca aguaggaaaa ggagcaagag uucaaggaau gggugaagcg 2220
gcaauggagc uuauggaggc gggcguuaua ggaauagagg uucgaaaagc ggagaggaug 2280
ggaaagguua gguugaguau uggggaggag gauguuaagg uugcuuuuag ggaugauccg 2340
gagauuaggg gguuggggguu uauggggguag 2370

<210> SEQ ID NO 68
<211> LENGTH: 1419
<212> TYPE: RNA
<213> ORGANISM: Sclerotinia sclerotiorum

<400> SEQUENCE: 68
augaaaacca acucacccgu ccguccccccc cgcagcaccc ucacccguau cgaaacauuc 60
acccaccucu cccucaccau ccucugcauc ucccuccucc ucaaaacccu cuccagagaa 120
aauggcgaac cgcucaucgc cucgcucgcu uucagcggua ucgccuucuc auccaccuau 180
agcaugauuc gcuggcucgg accuacauuc cugcgcgccg gacucaaggg ucgcgaucuc 240
ucgaagcggg aucguagaga gguuccugag acgauggggg cgauuugcgc gguggguuuau 300 uuguuggugg ucauuguuuu uauuccguuu ccguuuuaua aggauauugu ggcggcgacg 360
aguggagggg ggaauaggga ugugggucagg gagauggaga uggaggugcg ugauguggug 420
cagaauggga gguuuuugca ucgguuuccg cauaguaagc uagcauccua ucucuccgcg 480
guucuguccc uccaauccgu aguaauucuu ggaauuggcg acgaccucuu cgauauccgc 540
uggcgccaua aauuuuucau ucccgccauu gccaguaucc cuauucugau cgucuauuuu 600
gucgauuucg gcgucaccca aaucgucgua ccaauucccu uacaacccua ucugggcgag 660
cuuuuccaac ucgguccccu cuacuacauc uacauggcug ggaucgccau cuucugcccc 720
aacaguauca acauccucgc cggcauaaac ggcaucgaag uaucccaauc ccucgucauu 780
gcacuccucc ucguccuaaa cgauacccuc uaccuccuaa caccguaccc acacccagca 840
accgacucgc aucucuucuc ccucuauaug cuccucccccu ucaucggagu cucccucgcc 900
cuccucuccc acaacuggua cccauccucc gucuucguag gcgacaccua cugcuauuuc 960
gccggcaugg ucuucgccau cugcggcauc cuaggucauu ucuccaaaac ccuccuccuc 1020
cuccucaucc cccaaaccuu caacuucccuc uacagcacuc cccaacucuu ccaccuaauc 1080
cccugucccc gccaccgucu ucccegcuac aacucgcaaa ccaaucuccu cgaacccucc 1140 aucaccccccu ggccucaacc cccuaaaccg caccaagcag cgcuccucca ccuccuccau 1200
aaacugcauc uccucucccu cacauugaac aacgaaggca aaauaaucga aagcaguaau 1260
uucacccucu ugaaucuaug gcuuguaugg uuuggucca ggagagaaga ucgcuuagcc 1320
uuagaaaucu uggccaugca gacuauuugu ggauuauucg gcuuguuuca uagucauugg 1380
aucucaauau caaucaccaa cugcacuccc ucuucauag 1419

<210> SEQ ID NO 69
<211> LENGTH: 2028
<212> TYPE: RNA
<213> ORGANISM: Sclerotinia sclerotiorum

<400> SEQUENCE: 69
auggcaaaag uaccagcagu aaagaggcgc aagcuuacac cuccuccaac agaaggggaa 60
gauucaucgc caucgacuuu agagaaugcg ccaaguucga augcguuuuu caagacggcu 120
ucaaaaugga auuuagagca agauuacgaa acgagaccuc ggaaaggcaa gaaggaaaag 180
aaagaaagua caagguuacc aaucaagacu aaggaaggau ugauucagca gguugaagcg 240
ccaguggagg ucaaugaaga agaaagugau uuggaaugga uuggcgcaga cgaugucgag 300
gaggaugagg aacccgaaga gaagguugag gaaaagccuu cugugccgau ccgacagcag 360
auuauggagg ccaaagaaga auuagcacgu auagcauuga uguugaauga ggauccggaa 420
gaaaaugugg gagcauuuag agcuauagca gaauucggga aaucgcaaaa ccuuacgauc 480
aagaaauuag cauuggccac acaauuagcu guuuacaaag auguuauucc aggauacagg 540
auaagaccuu uaucggaaga gaauauggaa gaaaaaguuu cgaaagaagu acgaaaauug 600
agagcauacg aacaggcucu ugugggugga uaucaaggau augugaagga guuggcuagg 660
cuuguaacuu cugggagacc ccagaauaag agugauggug gcgcgagccu gucaacgguu 720
gccauauccu gugcuugcgc auuauuagaa gcuguacccc auuucaauuu ucgaucggau 780
cuauugaaga uauugguagg aaagcuuagu acaagacagg uggacaauga auucgugaag 840
ugucgagaga ccaucgaaac auuguucaag aaugacgaug augggaccuc auccuuggac 900
gcgguaaaua uuuugacgag aaugaugaaa gggagaggau acagagugga cgaaagcgua 960
uugaauaccu ucuuacauuu gagguuacug ucggaauuuu cuggaaaagc cucuacgaau 1020
caugucgagc augaggaaga cagcuuugga ggcaagaaac uuaaggagaa gagaguauuu 1080
cguaccaaga aggagagaaa auugaugaag gagcgcaaag caguugaaaa agagaugauu 1140
caagccgaug caacagucag ccacgaagau cgagagagaa ugcaaucgga aacccugaaa 1200
uugguguuug ugacauauuu ccgcauucug aaaguucgcu ccccaucucu uaugggcgcu 1260
guacuugaag guuuagcaag auacgcucau cucaucaauc aagauuucuu cggugaucuu 1320
cuggaagcgc uuaaggaccu uauuggucau gcugagacag gagaugaugu cgaggaaacc 1380
gaagcagaag augaggauuc agaauccucc cgcaaucuca cccgugaauc ucuccuuugc 1440
aucaucaccg ccuucgcucu ucucgagggu caagaugccc acaaagcuca agcaucgcua 1500
agcuuagauu uaagcuucuu caucacucau cucuaccgca cuuuacacgc ccucucccuc 1560
aacccugaua ucgaacuuug cuccaaaucc cuucaucuac cagaccccaa ugcacccuca 1620
accuccaaca acaaaguuaa cauccaaacc accaccgucc uccuccucaa aucccucuca 1680
ucuguccucu uaccuccucu ggccgcacgc gcagucccac cucucagaau ugcagcuuuc 1740
acuaaacaac uuaugacaug uucucuucaa uuaccugaga aauccgcuac ggccaugaug 1800
gcuuuauuag ggaaaguugc gaaaauucau gagaccaaag ucaaaagccu guggaauaca 1860
gaggagagga aaggugaugg aauguuugau ggauguagug cggaaguuga aggaaguaac 1920
ccgauggcga guacgauuug ggagggagaa cugcugaggu ugcauuauug cccugcgguu 1980
agagaaggcg ugaaaguggu ggagaagaau gugauugguu ugagguga 2028

<210> SEQ ID NO 70
<211> LENGTH: 1662
<212> TYPE: RNA
<213> ORGANISM: Sclerotinia sclerotiorum

<400> SEQUENCE: 70
auggacauug aggaccacaa gauagccguc agcauaucuu ccauaagcaa uguacuacaa 60
cggauaccgg uagcuucaga acgacgaucg cuccaaguug aaaacgaugu caaaagcuua 120
gacgaccuca gaucauuaaa ccgggcaagc aaaucccaca uuggaucuug gcuucgucau 180
gaaguggaag cacagaugcu accguuaagu acagcaucga augaguggaa uagcacauca 240
ccugcggcuc cugauacuuc ugugcuuaug gcggcuacau uuggcaucgu gcgagacuau 300
cuugaaauua uagaugauuu cucuaugcuc gccgauguga uaaagauugc cacggcauca 360
acggauacuc aaacuauugc aucgugcgcc gauacacuua auaugcacgc cgagauauuu 420
gcggccaucg gagcaauuaa gggcuuguuu gauguucuuc uuaaucgcuc gcguucauuu 480
gcagacgauc gugacaucau gccacgaguc auucuggcau ccuuguugga ccucucaucg 540
agaauucccg acagucagaa ucuuaccgcu cggcucgcuc gccaacuugc uuugagugau 600
agaaagugug ccgccgacgu uuguucuccu guaucggauc auauggcggg uagaucacaa 660
aauaacgagg cugaggccga gaguagcgca acgcaaaaag ugggcacuau uguagccacg 720
gaauugcuug cuuuaauugc ggcaccaauc accauaccgg agauucugac aucggacgaa 780
gcauaucgcg uccgacuugu acaaagucgu augcaaauug acaacccuga acuuacauug 840
acgguuauuc ggucagcaau cgaggugugc ucuacaguug uccgcgauau aucauccaac 900
gcccuccacc ccuuaaacgu cuuaggugguu ccagccaugc augaaauacu ucagacgcua 960
gucuugauug guggugauau ggccacaaaa auccuggugc agccuuuauc accugggucu 1020
aucgaugagg augcuuccaa acuaauggua accgcgauaa acaagcuuuu ggcgccuaua 1080
caucagcgug aaaccuccaa uuuuucagug ugugaugcgc uaaaaaucugc gaauuaucug 1140 aaucuaccau uuugccaauu gaagguggcg ucuaccuucc gcucugggaa aaguucccaa 1200
cccacuucca ggaauauggu cccuccucag cucgaugacc uuaaucgugc cguugagucu 1260
gcuauaaugg cagggguac gacaugggcu ugcauuauac caucauuaga uuuugcuacc 1320
auacaauacu uacgacgcgg ugcugagacc caauugcuug cgcuuuucca cgcugccaag 1380
gccucaggcu acaacgacau guugggggaa gagcaccaau ugacgaaagc agaaaauuug 1440
uuggucaucc ucgacuugac cauagacgag auguauacgg aaaaagcaaa cgcgccauau 1500
aauucgcaua gcugcuuugc ggauaucaua aacuuacuca gcggcgccuc gcaauacguc 1560
gcuagcacac aacaaaacgg uuguaaaauu gcauucuuca caaaauggcu accgcugcug 1620
uuaucauuca cagccucaca aacaguagua gcagugcuuu ga 1662

<210> SEQ ID NO 71
<211> LENGTH: 1449

<212> TYPE: RNA
<213> ORGANISM: Sclerotinia sclerotiorum

<400> SEQUENCE: 71
augcgcauuc caauuauucu uggaggcuua gccucaaucg cucuugcuug cgacaaccca 60
gaucacgaug cuugcgcuaa cgcuuucacc guuucugccg cagcugcugg uccuuucugc 120
gccacauaca cucaaucggc aaacgcggca acgaccgauc uucccgcuuu ugcuucagca 180
ugugcauaca agccaaagaa auugucuagu gcaugcagcu gucuuagcgu acccaccacu 240
uuggcuacug uuuccaagag cucaagcgcc gcugucagcg cuucggccac caccucgguc 300
acagcuuuaa cucacguagc aguaaccacc uccgcuucaa gcacugcagu cgcauccagc 360
gcaucugcag cuagcgcagu caucacaccg gcaccaucag ccccagccgg augcacagca 420
acagcuuaug cugauauugc cuccguuguu gccucgugca caaacaucgu cuuggauaac 480
auuucagcac cagcaagcuc caccauugau cuucaaaagc ucaaagacgg aacuaccguc 540
acuuucuccg gaaagacuac uuuuggaacc acuuccgaug auagcuucaa cccaauuguc 600
gucaagggua agaacauuac ccuuacugga gcuccuggac acgucauuga uggaaaugga 660
ccugcauacu gggauggaga ggguucuaac ggaggaacca agaagccuga ucacuucuuc 720
guuguaaagg auaucgucaa ugguguuauc agcaaccuca acauccaaaa cuggccuacu 780
cacugcuucg auaucaccgg ugccaagggu cuuaccgucu caggacuuac ccuugauaac 840
ucugcuggag augccccuaa cucagcaucu ggcagcaaag cagccgcaca caacagugau 900
ggauuugaca uuuccaacuc cgacucugua acccucaaga acauuguugu caagaaccaa 960
gaugauugcg ucgccgucac aucugguucu aacauccucg uaaccggaau ggccuguuca 1020
gguggccacg gucucucuau cggauccguc gguggaaaau ccaacaacac cgucucuggc 1080
guuaccuucu ccgacuccac caucaccaac agucaaaacg gaugccgcau caagucuaac 1140
ucuggcaaga ccgguaccau cgagaacguc acuuacagca acauccagau guccaacauc 1200
uccaacuacg guaucgacgu ucaacaagau uacuugaacg guggaccaac uggcgagcca 1260
acaaacggcg uuaccaucuc caacauugcc uucuccggcg ucaccgguac aaccacuagc 1320
aacgcauaca acuacuacau ccuuugcgga aguggcuccu gcuccaacuu caaauucaca 1380
gauguuagca ucucuggagg uggaaagacc ucauccugca acuucccauc uucuggaugc 1440
ccugcauaa 1449

<210> SEQ ID NO 72
<211> LENGTH: 1260
<212> TYPE: RNA
<213> ORGANISM: Sclerotinia sclerotiorum

<400> SEQUENCE: 72
auggcaaaac caagggggau uaaauucaau caucgaaaug gccgcgccgg uagugauggu 60
cgcagaagca guuucuccga uaucagugaa gcugccucgg agccaagcuc uccaaagaua 120
gcaaaggcag auggugcaag cgaugagaag aaagagacug auauaguugu gccaucggaa 180
uacgagaaga agaagcagac cuuuauuaca cgaucgauau ggacauuugu aaugauuggg 240
ggguuuuuug cguccauguu caugggggcau auauauauca ucgggauugu caccgcagug 300
cagauaauau ccuucaagga agucauugcg auugcaaaug uacccagucg agcucgucga 360
uuacgcuuca caaaagcuuu gaauugguau ugguuggcca cuaccaugua cuucuuauau 420
ggcgagagau ucguauucuu uguugcuucu cuucaagcag gucacuacaa guuucaguuc 480

-continued acgcaauucg ccuggacuca uauggcccug uaccuuaucg ugguccaagc ccauuucauc 540
augaacaacg ucuuugaggg aaugauuugg uucuucuuac cggugucucu ggucauuugc 600
aaugauauau uugcuuauau cugugguauc acguuuggcc gaacccagcu cauuaaacuc 660
ucaccaaaga agaccgucga agguuuuguu ggugcuuggg uuuugacaau cauuuuuggu 720
guaggcauga cuaacguacu caugcgguac aaauacuuca uuugcccugu aaaugaucuu 780
ggugccaacc uauggaccgg ucuugagugu acaccaaacc cuguuuucuu gccucauacc 840
uaucaacucc cuauuugguu uccagucugg aaauccuucu ccauggcacc uaugcaaggu 900
cacauucuug uuuuuggaac uuuugcauca cucauugcac cuuucggugg auucuuugcu 960
ucuggacuga aacgcacuuu caaaaucaag gauuucggcg acucgauucc aggacacggc 1020
ggaaucacgg aucgaaugga uugucaauuu aucauggguu ucuuugccua cgucuauuuc 1080
cacagcuuca uugcuaucua caaaguauca cuuggguggug ucauugaaac ugugaucaac 1140
gguuuaacgc cagaggagca aauggaacuu guuaagggaa ucagcaaaca ucucuauaac 1200 caaggggguca ucggcgacaa gguauuggac ugucuaaacg uggcagcgag uaagagauaa 1260

<210> SEQ ID NO 73
<211> LENGTH: 666
<212> TYPE: RNA
<213> ORGANISM: Sclerotinia sclerotiorum

<400> SEQUENCE: 73
augucguucu gggauaaguu gacagggcga aagccaucau caaaagacac uucuaguggc 60
ggaucaaccu ugaauacccc aacugacaca uucacaccua cacccuucaa cccucaagaa 120
ggucaagaug ucaacucuuu ucuuacaggg ccagagcuca uagauccauc acaacuucau 180
ccuuuggcug gucugaacca acagacucua gacuaucuau cccucgaaga aucuacucuc 240
ucggaucuuc caggaucgca aucugccuua cccucgagag guuggucgga cgauuuaugu 300
uaugguaccg guguuacaua uuugacggca cuaacugugg guggugcuug gggauuacag 360
gaggguuuga ggaggucugc gacgcaacca ccaaaguuac gauugaacuc ggugcugaac 420
gcuguuacga ggcgagggcc auucuugggc aacucggcag gaguaauugc uaugguuuac 480
aacggauuca acucauuuau cggacauaug aggggcaggc augauucggc gaacaguguu 540
cuugcaggug cgcugagugg gaugauuuuu aaaaguacaa gaggaguucg accuaugaug 600
auuuccggug ggaucguggc uucuguagcc ggcgcauggg cacaagaaaa gcaauauuuu 660
aaauga 666

<210> SEQ ID NO 74
<211> LENGTH: 4641
<212> TYPE: RNA
<213> ORGANISM: Sclerotinia sclerotiorum

<400> SEQUENCE: 74
augucaucaa uaccaccacc uccaccgccu ggauggagcu cuucggcgcc uccaucaaug 60
ccucugggcg cgccacccgg ugcuccuccu ccuccagguu aucgaccacc agcggaucca 120
cauguugcga aguuugcgca gaagaagaag gacugguuac gaucucagcg aaaucgauuc 180
ggcgaaaaac gaaaaggugg cuucguagaa acucagaagg cugacaugcc cccagagcau 240
cugcgaaaga ucguuaagga cauuggagau guaucacaaa agaaauucag cagcgacaaa 300
cgaaguuauc ucggugcacu caaguuuaug ccacaugccg ucaugaaauu guuggagaac 360
augccaaugc cuugggaguc ugcgagggag guaaaggugc uguaccaugu caaugguugc 420

```
cugacuuugg uuaaugagau uccacgaguu auagaaccag uguuccacgc acaaugggcu    480
acgaugugga uuuguaugag aagagagaag agugacagaa gacauuucaa gaggaugaga    540
uucccgccau ucgacgacga agagccgccc cuaucauggu cggagaacau ugaagacguc    600
gagccauugg agccaauuca acuggaacuu gaugaggggg aagacggcgc uguuuuugaa    660
ugguuuuacg agaaucgacc acuucuugau acuccacaua ucaacggccc gaguuacaag    720
gaauggaacc uuacguuacc ucaaauggca acuuuauauc gauugagucg gccauuauua    780
agugauuugg uugacaagaa cuacuuucac auguucgagc ugaaaagcuu ccagaccgcc    840
aaagcuuuga auguugcgau uccuggugu ccucgauucg aaccuuuaua uaaagaugug    900
gauccuaaug augaagauuu uggagaguuc aaugcuauug aucgcaucau cuuccgagcu    960
ccaauuagga cagaauaucg uguagcauau cccuaccuuu auaauucacu gccucgcagc   1020
guuaagcuuu ccugguucuc gcauccgcaa gugguauacg uucgugccga ggauccaagu   1080
uuaccagcau uuuauuucga ucccgucauc aacccaaucu cuucaagauc cgucgccccu   1140
aaaaauauca cuaucaguca cgaagacgag auauucggac ccggaaauaa ugaagagcca   1200
gaagaagacg cuuucagauu accagguggu gccgagccau uucuagcaga ugaggaguug   1260
uacacaagcg agaccgcuuc agcaaucucu uuguggugg caccauuucc guuuaaucga   1320
agaucugguc gcaugguucg ggcacaagac guaccucuag uaaaacaaug guaccuugag   1380
cauugcccuc agggucaacc aguaaagguc cgaguuucau aucagaagcu ucugaagacu   1440
uaugucuuga acgagcugca uaagcgcaag ccgaaagcac agaguaaaca gagcuugaug   1500
aagucguuga agcaaacgaa auucuuccag caaacaacaa uugauugggu ugaagcugga   1560
cuucaagucu gcaggcaggg uuucaauaug cuaaaucuuc ugauucaccg caagaaccuc   1620
acauaccuac aucuugauua uaauuucaau uuaaagccug uuaagacauu gacaacaaag   1680
gagagaaaga agucucgauu cggcaaugca uuccaucuca ugcgagagau cuugaagaug   1740
accaagcuca ucguugacgc acaaguucag uaucgccucg gcaauaucga ugcuuuucaa   1800
cucgcggaug guauucuaua ugcuuucaau cauguuggug agcugacugg aauguaucgu   1860
uacaaguaca agcugaugca ucagauucgc ucauguaaag aucugaagca uuuaauauau   1920
uaucgauuca auucuggacc cguagguaaa ggaccugguu gugguuucug ggcaccugcu   1980
uggagaguuu ggcucuuuuu caugcguggu auaauuccau uacuugaaag auggcuugga   2040
aaccuccucu cuaggcaguu ugaaggacgu cauagcaaag guguugcaaa gacagucacg   2100
aaacaacgug uugagucgca cuuugaucuu gaguugcgag caucggucau ggccgaucuu   2160
cuugauauga ugccggaggg uaucaagcaa aacaagguuc aaacgguacu ucaacaucuu   2220
ucagaggcau ggagaugcug gaagaguaau aucccuugga agguuccagg uuuaccggca   2280
cccaucgaga auaucauucu ucguuaugug aagagcaagg cagauuggug gauuucuguc   2340
gcucacuaca aucgugagcg uauccguaga ggagcgacug uggacaaaac cguugcaaag   2400
aagaaucuug gucgucuuac aagacuuugg cucaaggcug aacaagagag gcagcauaac   2460
uauaugaaag acgguccaua cgugucaucc gaagaagcug ucgccaucua uacaaccacu   2520
guccauuggc uggagucacg aaaauucuca ccaauuccau uccccagugu uuccuacaag   2580
cacgauacca aaauccucau ucuugcuuug gaacgucuuc gugaagcaua uucugugaag   2640
ggacgauuga accaaaguca gcgugaggaa cuggccuuga uugagcaggc uuaugacagu   2700
ccuggaacca cuuuggagag aaucaagcgc uuccuacuga cacagagagc uuuuaaagaa   2760
```

guaggaaucg auaugaacga caauuauagc acaaucaacc cuguauauga uaucgagccu 2820
guggaaaaga uuagugaugc cuaucuugac caauaccucu gguaucaagc ugaccagcgc 2880
caccuuuucc cugccuggau caagccuucc gauuccgagg ucccgcccuu acugaccuau 2940
aaaugggcuc aagguauuaa uaaccucgac aaaguauggg agaccgcaga uggagagugu 3000
aauguuauga uugaaacaca auuauccaag guauacgaga agaucgauuu aacucuucuu 3060
aaucguuugc uucgacuuau cauggaccac aaucuggcug auuacauauc guccaaaaau 3120
aacguucaau ugaccuacaa agauaugaau cacgucaaca guuacggaau gaucagaggu 3180
cuucaauucu cggccuucgu uuuccaguac uauggacuug uucucgaccu cuugcuucug 3240
ggccuccaac gcgcuaguga aauugcugga ccaccagcag guccuaacga uuuccuccaa 3300
uuccgcgauc gggagacgga aacaagacau ccaauccguc uauacacaag auauauugau 3360
cguaucuggg uauuuuuccg cuuuacggcc gaugaaucgc gcgaucuuau ccagcgcuuc 3420
cuuacagaac aaccugaucc uaauuuugaa aaugucaucg gcuacaaaaa caagaaaugc 3480
uggccaagag auucuagaau gcgucucaug agacacgacg ucaaucuugg ccgugcuguu 3540
uucugggacu ugaagaaccg cuuaccaaga ucuguuacca cgaucgaaug ggaugauacc 3600
uuuucaagcg uauacagccg agacaacccg aauuuacuuu ucuccaugug cgguuucgaa 3660
guacgaauuc ucccuaaaau ucguaaccag aaugacgaau uuccuguuaa ggacagcgua 3720
ugguccuugg ucgauaacac cagcaaggag agaacggcac augcauucuu gcaggucaca 3780
gaggaagaua ucgcgaaauu caauaaucgc auucgucaaa uuuugauguc aucugggguca 3840 accacauuca caaagauugc uaauaaaugg aauacaaccu ugaucgcccu cuucacauau 3900
uaucgugaag cagcuguauc aacggucaac uugcuggaua ccauugugaa augugagacg 3960
aagauucaga ccagaguuaa gauuggucuu aauucuaaga ugccuucucg uuucccuccu 4020
gcuguuuucu auacaccaaa ggaacuuggu ggucuuggua ugauuuccgg aucacauauc 4080
cucauuccua cgagugacaa aagauggucc aagcagacag acguuggugu uacccauuau 4140
cgugcaggaa ugagccauga ugaggacacu cuuaucccua acauuuucag auacaucaua 4200
ccaugggaag cugaauuuau cgacucccag cgugugugga cugaauauuc ucagaaacgu 4260
caggaggcga aucagcaaaa ucgaagguug acacuugagg aucuugaaga uaguugggau 4320
cguggauuac cucguaucaa uacacuuuuc cagaaagaua gaagcaccuu gaguuuugau 4380
aaaggauucc gcgcacguac ugaguucaag acauaccaac uuaugaagag uaauccauuu 4440
ugguggacua gucaacguca cgaugguaaa uuguggaacc uuaaugccua ucguaccgau 4500
guuauccaag cacuuggugg uguugaaacc auucuugaac auacacucuu caaggcgaca 4560
gcauuuccau ccugggaagg ucucuuuugg gaaaaagcaa guggauuuga agagcgagua 4620
gacccuugcc cccaaguuug a 4641

<210> SEQ ID NO 75
<211> LENGTH: 1203
<212> TYPE: RNA
<213> ORGANISM: Sclerotinia sclerotiorum

<400> SEQUENCE: 75
augucuucag uuccuccagu uuauauuguc uccgcuguga gaacacccau cgguucauuc 60
uuggguuccc uuucuagcaa gacugcaacu gaacucggug gcauugccau caaggcugcc 120
guugaacgug uaccagaaau caaacccgga gauguugaag aaaucuucuu ugguaauguu 180
uuguccgcaa acuugggaca gaacccugcu cgucaaugug cuauugcugg uggccucacu 240
gaagguguag ucugcaccac cgucaacaaa guuugugcuu ccggcacuaa ggcaaucauc 300
cuugccgcuc agacaaucau cacuggcaac gccgauauag uuguagccgg uggugcggag 360
uccaugucua auguuccuca uuaccuucca acucuccgaa auggugccaa guauggugac 420
caaacuuugg uagacggugu ucucaaggac ggucucaccg augccuacaa caagaaagag 480
cauaugggaa uggcugcuga agagugccau guugaucacg acauuagcag agagcaacaa 540
gaugaguaug ccaucaaguc auaccaaaaa gcacaaaagg cgacugaagc cgguaucuuc 600
aagaccgaga uuguuccagu ugaaguuagc gguggccgcg gcaagccaaa uguuaagguu 660
gagaaagacg acgagguuaa gaacuugaac auugagaagc ucaaggccau gagaccugcu 720
uucaugccua acggaggaac ugucaccgca ccaaaugcug caccaauuaa cgacggagcu 780
ucagcucuug uccuugucuc ggaggcuaag uuaaaggaac ucggucuuaa accuuuagca 840
aagauucuug guuggggguga ugcugaaaag gcaccaagca aguucaccac ugcaccaucu 900
uuggcuauuc cuaaggcucu gaagcaugcc aagauugaug cuucagccgu ugauuacuau 960
gagaucaacg aggcuuucuc gguugucgca uuggcaaaca ugaagauucu cggauuggau 1020
gaauccaagg ucaacaucca uggaggugcc guugcuauag gacacccucu ugguugcucc 1080
ggagcuagaa ucgucaccac auugaucaau guguugagag aacaaaaggc aaagaucggu 1140
guugcuggua ucugcaacgg ugggggugga gccuccgcuc uugucaucga aucuuuacag 1200
uaa 1203

<210> SEQ ID NO 76
<211> LENGTH: 1044
<212> TYPE: RNA
<213> ORGANISM: Sclerotinia sclerotiorum

<400> SEQUENCE: 76
auggauacug cuuucaagac uugggagcuu gacaacaacg uccagcucgu ggaucccaac 60
cgcgacgccc ucuacaccua cgaccccaaa gaacaaagag ccauccaaga ugccaaacca 120
uggaagaccg acccucacca cuucaaaaau guccggauau ccgcugucgc ucuucugaaa 180
augguuaugc acgcccgcuc uggagguucu aucgaaguua ugggcuuaau gcagggaaag 240
auugcgggcg auacuaucau cgucacagau gcauuccgcc ugccugucga agggacggaa 300
acuaggguga augcucaaga cgaagcgaau acauauaugg uggaguaccu acaacacugu 360
agagaucagg gcaaguugga gaaugcugua ggcugguauc auagucaccc aggcuauggu 420
uguugguuga guggcauuga ugucgggacg caagcgacgc aacagauguu uucggacccu 480
uuccuugcug ugguuauuga uccugaucgc acuaucucug cugggaaagu cgagaucggg 540
gcauucagaa ccuauccuga uaauuacaag ccuguggaug cagggucugg agauggauau 600
caaacgauuc cacuugcaaa gauugaagau uuuggugcac acagcagccg auauuacucu 660
uuggaggucu cacauuucaa gaguucauua gacacgcauc uuuuggaguu auuauggaac 720
aaauauuggg uucagacauu gagucaaagu ccuuuauuca ccaaccgcga auacagcagc 780
aaacagaugc ucgacuugag cuccaagauu cgacaagcua guucugguau uauccguggu 840
gggagaacac cugcuggauc aucguuaagc aaagggaugg aucaacaacu aaugaaggua 900
gucaaggaua guagcaagau ugccggugaa gagaugacgg guuugaaggc uggcgaaguc 960
aaggcacagc uguucaaugg guuaggcgag gcaccgaagg ccacagcugc uccacuugcu 1020 ccggcggug a cggccgcaga auga 1044

<210> SEQ ID NO 77
<211> LENGTH: 1344
<212> TYPE: RNA
<213> ORGANISM: Sclerotinia sclerotiorum

<400> SEQUENCE: 77
augucuuccg aaccaccuuu ggaccccuac aaacccucuc ucuucgaacu uuuguccucc 60
acccaacuuu cgucacuccu uccucccucu cuccacuacc uccuaaccau cgccacacac 120
cgacauccgc gacaccuccu cccaauccuc aacuccuuuc acgaaaucca cgcucuccuc 180
uuccuagcaa ucgaacacca cuaucuaacc accuacucuu cuucauuugu cgaaaacuuu 240
uauucucuaa aacgggaacg cgccuuaccu gcggcaguag gcgaucugcg acuuacggcc 300
gaagcagcca augccagucu acgcgaaacg acaaaacuua caagagggga uguauggaag 360
aaucuugcug ugcucguugg aauuccauau cuuaaacguc gacucgauga gucucaggag 420
aucaaugcac cgagagcacu ucucggcgca aauuauacac gcaugccacc gaauccaacg 480
cucaaacaac gauuucuaca uuauuaucgu ugguuucuua cgaauguaua ucccagcgug 540
aaugccgcau auuauuucag uaucuuagca uuuaaucuac gauaccuauu uucggguucg 600
aaaucuggcu cugguguaua uuccgaucca uuuuuauggu uaauaggaac gcggauacga 660
agauuaaguc aagcagauuu ccaagcuuuu gaagcgauua agaaugcugc aucuucaaua 720
ccagggucga aucuaggaau aagaagucua uuggauccaa gacuggcaau gggaagaaua 780
gguucuggau uaaaacuauu acuaccaacc aguaucuuug cgcugaaauu ccuggaaugg 840
uggcaugcga gugauuuugc aagacaauua ucucgaaaag caauagaagg auuagaauua 900
ccaccgccua uuauaucaua caccccuucu ccuguaacaa aaccggagac cacgucaaaa 960
uccucaucag aagaaaaaca accgucagaa guagaagaac caacaaaucc cccgaucuca 1020
accauaaccc aacuccccau cuaugucguc ccagcuccuu ccaccucgac cuccuuagaa 1080
aauugcccaa ucugucucga agaaaucacg acgccaaccg cgugucaaac aggauaugug 1140
uauuguuaua cuuguauuca uagguggauu gaggggguugc augauuugca ggagaaguuu 1200
augaagggug augugaaggu ggaugggggaa gggaaaggag agaagggaag agaagggaag 1260
ugggaaagug gagcaggcag augugcgguu aguggacgga ggguauuagg gggugucggu 1320
ggguugagga ggguuuuggu uuaa 1344

<210> SEQ ID NO 78
<211> LENGTH: 1587
<212> TYPE: RNA
<213> ORGANISM: Sclerotinia sclerotiorum

<400> SEQUENCE: 78
auggacgaca agaauguaga acugggcgug aucgcuaggu cgucgucuuc ugaugagaua 60
ccucaugccg ggucgaaagg caauacgagc agagaugauc gagaaauggc auauuuugga 120
aaacgccagc aauugaagcg uaauuuuggc uucuugucga uugcggguuu cgucugcagu 180
uugcuuucga caugggaagg aauguucgcg gucuuccuuu acggauucca aaacggugga 240
ccggcaggau uaguuuacgg cuacaucuuc uguuucuuug guacauuaug uacggucgcc 300
aguuuggcag agauguccuc caugaugccc uugagcggcg gccaauauca cugggugucg 360
auucucgccc cuaaguccca cgcaaaguuc cucucauaca ugacaggcug gcuuacgguc 420
auuggcuggc aagcaggcca agcaaguguu gcuuuccucu gcgcaacuuu aguccaggcu 480
uuggugauau uaaaucaucc aacauacguc ccugagcgau ggcaggcaac uuuaauauuc 540

```
uacgcgguuc uagcuguugu uuuguuuguc aauacguauu uggcucgcug guugccaaag    600

auugaaggau ugguucuuug cauccauaua cuuggguucu uuggguguucu uauuccucua    660

gucuaccuug caucucaugg aaaggcaagu gaugucuuug cuacguuugu caacggguggc    720

gguuggucca cagauggaau aucauucuuu auuggccuaa uuacaagugu uuucuccuuu    780

cuuggagccg auucugcuug ccauaugagu gaagaaauuc acaaugccuc uaccgucgug    840

ccuugggcaa ugaucaccac gauucuuuug aauggugcuu uagguuucgc acugcuuaua    900

gcccuucucu ucugucucgg agauaucaau gacgcucuua cuucuccuac cggcuucccg    960

uucauugaga uauuuaggca agccacuaau aguaacucug cugcaacugg aaugacaugu   1020

aucauuguga uaaucauguu ugccgcggcu auugguauua uggcaacugc cucacguuua   1080

uugugggcuu ucgcgagaga ccauggagua ccagguagcg cauaucuguc ucgugugcac   1140

gaaccaacag cacuaccauu auacucuauu cuagucagug ccauuauuuc acucuuauug   1200

gcacucauaa auauuggaag cacugccgca uucaacucga ucgucuccgu uaauguugcg   1260

gcauucuuua ccuccuacau gauaccuauc guccugaucc ucaaaaaacg ucuucgcaga   1320

gauccaauaa aagauaagau acauugggga ccguggagaa uggguccaau ucuuggucca   1380

auugucaaug uugccggauu gauuuauucg augaucacca uguuuuucag cuucuggcca   1440

aauacacaag ucguuacucc aguuaccaug aauuggucu guguuauuuu ugcugcugcu   1500

aucauuuaca gcgugguguu cuacaugauu uggggguaaac acucuuacaa guggccaaua   1560

gucgauccua uaagaaggca gcaguag                                       1587
```

<210> SEQ ID NO 79
<211> LENGTH: 2769
<212> TYPE: RNA
<213> ORGANISM: Sclerotinia sclerotiorum

<400> SEQUENCE: 79

```
auggcuacca cagaugucuu uauuauaucc ucuucaccac cacgacgauu gguuucucau     60

auugcaucuu caccgccuuu accuucuuua gacaagaugg ucaauggaaa gaaagccucc    120

aauuugcgac aagguaguag uguugcaccu auuccuacag gcgcgacaau cuuugcgagc    180

gcauccacuu uguugaggga auccucuucu ggaucucuuc aaggauuuga caacgcucgg    240

ucguuuguaa caucugcagu gcaagaugaa aaugauuuga agaaaucugc gaaaccgaaa    300

gccccacgaa aaacggcucc aaaaaaggaa gaugggacag uugagaaggu ggcaaaagcg    360

ucucggaaga cuguaaaaaa gaaggauaaa gauguuucug gggauuucgu ggaugaguua    420

gugggagagg cugcagaaau uauagccgaa aagaaaccgc gaaagccuag agcuaagaag    480

ggagauaaug cagaaggaaa gagugggagu guugcagagg cgacugugga aaagaaaccg    540

cgcaaaucua gggcuaagaa agcgguugac gcuacagggg aggaucuuaa ggagaaggua    600

ccgcgcaaau cuagggcgaa gaagaccgau guugaagcug gaauugaaac ggugccaaag    660

gaaaaggcag ugaggaagcc gcgagcuaag aacucagauu uggacucaaa uuuacaaucu    720

aagaugguaa aaggcagagu gaccaagucc gccgucaaug cuucaaauac ccacaaaguc    780

gaaaccucga aagccgauac agguaacaaa cauuuugcgc ccaauccaau cgucgaagau    840

auaguugcag augaaggauu ugguuuagug gaagcaauca ggagaagaac gaauuggacu    900

ccaccaaaau cgacaaaggu uccaauugac cuagaggaua guccagaagc ucaagaauca    960

gacaccagca aaggauucgc agaguuauua gggagcuuug gguacagcag uuaccaggcg   1020
```

gauucuauag agaagagaau aucuucuggg guauccaaug gagccgcugc aacaaggaag 1080
aggaaguuaa uugagauggu cacuacaaau auucccagag aacccggcuc aaaaacaaca 1140
aaagagaaag cugucaagaa gaaggcuagg acgcucaccg accuugccac aucugcuuau 1200
gcaacagcgg aagaugauga uaaucuccuu gaugcgccca cgccuuuacu ccaauacuuc 1260
ccucaugcag cucccgaagg auccacaaau aauggcuuca aaauaccgcc aaagccgagg 1320
ucaaagagcc caaugaagag agugcaaaag ucaaaaacgg gcucugcaga agagccaauu 1380
cuucuaucuc cagaaucugc gaugaagcaa guuaguaauc aagacuuugu guucggaacu 1440
ucaagucaau uggcaagaga agacucuccu ucauugcuac gcgauuuaca ugaugcuaug 1500
caagcaucua augaauugga ugauuaugau gauccuuucg uuucaccucc uaccaagaua 1560
gccgagagag gaaaagcugu uguugcugcg aaacggaauc uuugguccau ugcugcucgu 1620
gauaaccaug ggaucugau ggauguugag acaauagacu uagcacauac accaguugcg 1680
aagccagaua gaaucaugcu aucacaaaag ccuucaucau uaguuacgcc cgguaaggau 1740
gauugguuug auauugacga aauugaagau aaccgacccc cuucuacuca aguuccauua 1800
agggagacgg gacccauuga gagaucuaua aauuuucaac uuuuggauag uccuacucaa 1860
ccuaagaaua ccucgaagga uagcuccaaa guuuucccac agaagaaagg caccaaaucu 1920
uugguugaua aaagcaccac uccuaagaag gucgaugccu ccaagaugcc ugacuacgaa 1980
ucauucacua caccacaauu gacgagggaa auucaaaagu acaaguucaa gcaaaucaaa 2040
agucgaaaga ggaugauuga uuuauuaauu caguguuaug aaagucagaa ucguccagcc 2100
uuggguguuu uacaaggaaa cauuccaauu aucacgcaaa auucguugga aaagucuaaa 2160
gauguagccg acucauccac ucagguuaag cccaccauuc cuucuccucg acgaggccga 2220
gcgaagaaag uuacuaccuc cacugccuca uuacccaaau caaaggcaaa gucaaagaug 2280
acagauacag uggcauucuu agaaauggau agugauacac cacucucuaa gauccgcaca 2340
ccccaaaaau cccguaaggg aaaacaaccc cucgaagaua uuuucgacuc ugaucacccu 2400
aucacgccau caccaccacg gcgaucggau ucccaaauuc gaaaaauauc caaggcucug 2460
gaauuaucuc cugauaauaa ucaagacgac gaagcucagc aagcacagcu uuucacucau 2520
aucuacacug caauuaccaa agcuccaccu ucacaagacc cauucaaucc aagcuggcau 2580
gaaaaaauac ugcucuauga uccaauuauu cuagaagauc uagcaucgug guugaauacu 2640
ggagcacuga guaaaguggg cugggaugaa gaaguagcuc cauuagaagu uaagaaaugg 2700
ugugaaagua agaguauuug uuguuugugg aaggaaaauc aaggugugg ggcuaggagu 2760 agauauuga 2769

<210> SEQ ID NO 80
<211> LENGTH: 744
<212> TYPE: RNA
<213> ORGANISM: Sclerotinia sclerotiorum

<400> SEQUENCE: 80
augggagauu caucaggugc agauuauaaa ccggaauggc ucgagcuuga aaagucccuc 60
gguacacguc cucuucucgu aggugaucca gccaacaucg aagagcaauu caaccgccua 120
cucgcagcgc ucgacgcuga gagacccccu cccgauuccu caguccagac ucgugauacu 180
uccgcagacg gcguuccguc cuacaaacac gccucggaac uccacgccuc ccaaucccaa 240
cucuucacca uuggcagcuc cgccggugge ggucuagcuc uuaccguagc acacgaccuc 300
aucggcgcag guaaaaaauc acaaaucaaa ggcaucgugg ccauggucce cguaaccgca 360 cacccaucuu cuauucccgc agccuacaaa aaucacuaca aauccuacga ugagaaugcg 420
cacgacgugc ccauuauaga uuuagauacg augaauacgu uuuucggagc cguggaugcg 480
gauccgcugg acccgagagu uuuugugacg cucucgaguc auuuggauga guuuccuccg 540
acuuauaucg cuacgugugg aaaggauccg uugcgggaug auggucaggu guuggaaaug 600
auguugaagg auaagggugu cacgacaaag agugauuauu augaaggggu accgcauuac 660
uuuuggcuuu uucccgguau uaagggugga gaugaauuuu uggauaaugu uaguaaaggg 720
gugaaguuug uucuggguau cuag 744

<210> SEQ ID NO 81
<211> LENGTH: 4641
<212> TYPE: RNA
<213> ORGANISM: Sclerotinia sclerotiorum
<400> SEQUENCE: 81
augucaucaa uaccaccacc uccaccgccu ggauggagcu cuucggcgcc uccaucaaug 60
ccucugggcg cgccacccgg ugcuccuccu ccuccagguu aucgaccacc agcggaucca 120
cauguugcga aguuugcgca gaagaagaag gacugguuac gaucucagcg aaaucgauuc 180
ggcgaaaaac gaaaaggugg cuucguagaa acucagaagg cugacaugcc cccagagcau 240
cugcgaaaga ucguuaagga cauuggagau guaucacaaa agaaauucag cagcgacaaa 300
cgaaguuauc ucggugcacu caaguuuaug ccacaugccg ucaugaaauu guuggagaac 360
augccaaugc cuugggaguc ugcgagggag guaaaggugc uguaccaugu caaugguugc 420
cugacuuugg uuaaugagau uccacgaguu auagaaccag uguuccacgc acaaugggcu 480
acgaugugga uuuguaugag aagagagaag agugacagaa gacauuucaa gaggaugaga 540
uucccgccau ucgacgacga agagccgccc cuaucauggu cggagaacau ugaagacguc 600
gagccauugg agccaauuca acuggaacuu gaugaggggg aagacggcgc uguuuuugaa 660
ugguuuuacg agaaucgacc acuucuugau acuccacaua ucaacggccc gaguuacaag 720
gaauggaacc uuacguuacc ucaaauggca acuuuauauc gauugagucg gccauuauua 780
agugauuugg uugacaagaa cuacuuucac auguucgagc ugaaaagcuu ccagaccgcc 840
aaagcuuuga auguugcgau uccugguggu ccucgauucg aaccuuuaua uaaagaugug 900
gauccuaaug augaagauuu uggagaguuc aaugcuauug aucgcaucau cuuccgagcu 960
ccaauuagga cagaauaucg uguagcauau cccuaccuuu auaauucacu gccucgcagc 1020
guuaagcuuu ccugguucuc gcauccgcaa gugguauacg uucgugccga ggauccaagu 1080
uuaccagcau uuuauuucga ucccgucauc aacccaaucu cuucaagauc cgucgccccu 1140
aaaaauauca cuaucaguca cgaagacgag auauucggac ccggaaauaa ugaagagcca 1200
gaagaagacg cuuucagauu accaggugguu gccgagccau uucuagcaga ugaggaguug 1260
uacacaagcg agaccgcuuc agcaaucucu uugugguggg caccauuucc guuuaaucga 1320
agaucugguc gcaugguucg ggcacaagac guaccucuag uaaaacaaug guaccuugag 1380
cauugcccuc agggucaacc aguaaagguc cgaguuucau aucagaagcu ucugaagacu 1440
uaugucuuga acgagcugca uaagcgcaag ccgaaagcac agaguaaaca gagcuugaug 1500
aagucguuga agcaaacgaa auucuuccag caaacaacaa uugauugggu ugaagcugga 1560
cuucaagucu gcaggcaggg uuucaauaug cuaaaucuuc ugauucaccg caagaaccuc 1620
acauaccuac aucuugauua uaauuucaau uuaaagccug uuaagacauu gacaacaaag 1680

-continued

```
gagagaaaga agucucgauu cggcaaugca uuccaucuca ugcgagagau cuugaagaug   1740
accaagcuca ucguugacgc acaaguucag uaucgccucg gcaauaucga ugcuuuucaa   1800
cucgcggaug guauucuaua ugcuuucaau cauguugguc agcugacugg aauguaucgu   1860
uacaaguaca agcugaugca ucagauucgc ucauguaaag aucugaagca uuuaauauau   1920
uaucgauuca auucuggacc cguagguaaa ggaccugguu gugguuucug ggcaccugcu   1980
uggagaguuu ggcucuuuuu caugcguggu auaauuccau uacuugaaag auggcuugga   2040
aaccuccucu cuaggcaguu ugaaggacgu cauagcaaag guguugcaaa gacagucacg   2100
aaacaacgug uugagucgca cuuugaucuu gaguugcgag caucggucau ggccgaucuu   2160
cuugauauga ugccggaggg uaucaagcaa aacaagguuc aaacgguacu ucaacaucuu   2220
ucagaggcau ggagaugcug gaagaguaau aucccuugga agguuccagg uuuaccggca   2280
cccaucgaga auaucauucu ucguuaugug aagagcaagg cagauuggug gauuucuguc   2340
gcucacuaca aucgugagcg uauccguaga ggagcgacug uggacaaaac cguugcaaag   2400
aagaaucuug gucgucuuac aagacuuugg cucaaggcug aacaagagag gcagcauaac   2460
uauaugaaag acgguccaua cgugucaucc gaagaagcug ucgccaucua uacaaccacu   2520
guccauuggc uggagucacg aaaauucuca ccaauuccau uccccagugu uuccuacaag   2580
cacgauacca aaauccucau ucuugcuuug gaacgucuuc gugaagcaua uucugugaag   2640
ggacgauuga accaaaguca gcgugaggaa cuggccuuga uugagcaggc uuaugacagu   2700
ccuggaacca cuuuggagag aaucaagcgc uuccuacuga cacagagagc uuuuaaagaa   2760
guaggaaucg auaugaacga caauuauagc acaaucaacc cuguauauga uaucgagccu   2820
guggaaaaga uuagugaugc cuaucuugac caauaccucu gguaucaagc ugaccagcgc   2880
caccuuuucc cugccuggau caagccuucc gauuccgagg ucccgcccuu acugaccuau   2940
aaaugggcuc aagguauuaa uaaccucgac aaaguauggg agaccgcaga uggagagugu   3000
aauguuauga uugaaacaca auuauccaag guauacgaga agaucgauuu aacucuucuu   3060
aaucguuugc uucgacuuau cauggaccac aaucuggcug auuacauauc guccaaaaau   3120
aacguucaau ugaccuacaa agauaugaau cacgucaaca guuacggaau gaucagaggu   3180
cuucaauucu cggccuucgu uuuccaguac uauggacuug uucucgaccu cuugcuucug   3240
ggccuccaac gcgcuaguga aauugcugga ccaccagcag guccuaacga uuuccuccaa   3300
uuccgcgauc gggagacgga aacaagacau ccaauccguc uauacacaag auauauugau   3360
cguaucuggg uauuuuuccg cuuuacggcc gaugaaucgc gcgaucuuau ccagcgcuuc   3420
cuuacagaac aaccugaucc uaauuuugaa aaugucaucg gcuacaaaaa caagaaaugc   3480
uggccaagag auucuagaau gcgucucaug agacacgacg ucaaucuugg ccgugcuguu   3540
uucugggacu ugaagaaccg cuuaccaaga ucuguuacca cgaucgaaug ggaugauacc   3600
uuuucaagcg uauacagccg agacaacccg aauuuacuuu ucuccaugug cgguuucgaa   3660
guacgaauuc ucccuaaaau ucguaaccag aaugacgaau uuccuguuaa ggacagcgua   3720
ugguccuugg ucgauaacac cagcaaggag agaacggcac augcauucuu gcaggucaca   3780
gaggaagaua ucgcgaaauu caauaaaucgc auucgucaaa uuuugauguc aucuggguca   3840
accacauuca caaagauugc uaauaaaugg aauacaaccu ugaucgcccu cuucacauau   3900
uaucgugaag cagcuguauc aacggucaac uugcuggaua ccauugugaa augugagacg   3960
aagauucaga ccagaguuaa gauuggucuu aauucuaaga ugccuucucg uuucccuccu   4020
gcuguuuucu auacaccaaa ggaacuuggu ggucuuggua ugauuuccgg aucacauauc   4080
```

cucauuccua cgagugacaa aagauggucc aagcagacag acguuggugu uacccauuau 4140
cgugcaggaa ugagccauga ugaggacacu cuuaucccua acauuuucag auacaucaua 4200
ccaugggaag cugaauuuau cgacucccag cgugugugga cugaauauuc ucagaaacgu 4260
caggaggcga aucagcaaaa ucgaagguug acacuugagg aucuugaaga uaguugggau 4320
cguggauuac cucguaucaa uacacuuuuc cagaaagaua gaagcaccuu gaguuuugau 4380
aaaggauucc gcgcacguac ugaguucaag acauaccaac uuaugaagag uaauccauuu 4440
ugguggacua gucaacguca cgaugguaaa uuguggaacc uuaaaugccua ucguaccgau 4500 guuauccaag cacuuggugg uguugaaacc auucuugaac auacacucuu caaggcgaca 4560
gcauuuccau ccugggaagg ucucuuuugg gaaaaagcaa guggauuuga agagcgagua 4620
gacccuugcc cccaaguuug a 4641

<210> SEQ ID NO 82
<211> LENGTH: 1662
<212> TYPE: RNA
<213> ORGANISM: Sclerotinia sclerotiorum

<400> SEQUENCE: 82
auggacauug aggaccacaa gauagccguc agcauaucuu ccauaagcaa uguacuacaa 60
cggauaccgg uagcuucaga acgacgaucg cuccaaguug aaaacgaugu caaaagcuua 120
gacgaccuca gaucauuaaa ccgggcaagc aaaucccaca uuggaucuug gcuucgucau 180
gaaguggaag cacagaugcu accguuaagu acagcaucga augaguggaa uagcacauca 240
ccugcggcuc cugauacuuc ugugcuuaug gcggcuacau uuggcaucgu gcgagacuau 300
cuugaaauua uagaugauuu cucuaugcuc gccgauguga uaaagauugc cacggcauca 360
acggauacuc aaacuauugc aucgugcgcc gauacacuua auaugcacgc cgagauauuu 420
gcggccaucg gagcaauuaa gggcuuguuu gauguucuuc uuaaucgcuc gcguucauuu 480
gcagacgauc gugacaucau gccacgaguc auucuggcau ccuuguugga ccucucaucg 540
agaauucccg acagucagaa ucuuaccgcu cggcucgcuc gccaacuugc uuugagugau 600
agaaagugug ccgccgacgu uuguucuccu guaucggauc auauggcggg uagaucacaa 660
aauaacgagg cugaggccga gaguagcgca acgcaaaaag ugggcacuau uguagccacg 720
gaauugcuug cuuuaauugc ggcaccaauc accauaccgg agauucugac aucggacgaa 780
gcauaucgcg uccgacuugu acaaagucgu augcaaauug acaacccuga acuuacauug 840
acgguuauuc ggucagcaau cgaggugugc ucuacaguug uccgcgauau aucauccaac 900
gcccuccacc ccuuaaacgu cuuaggugu ccagccaugc augaaauacu ucagacgcua 960
gucuugauug guggugauau ggccacaaaa auccuggugc agccuuuauc accugggucu 1020
aucgaugagg augcuuccaa acuaauggua accgcgauaa acaagcuuuu ggcgccuaua 1080
caucagcgug aaaccuccaa uuuuucagug ugugaugcgc uaaaaucugc gaauuaucug 1140
aaucuaccau uuugccaauu gaagguggcg ucuaccuucc gcucugggaa aaguucccaa 1200
cccacuucca ggaauauggu cccuccucag cucgaugacc uuaaucgugc cguugagucu 1260
gcuauaaugg caggggguac gacaugggcu ugcauuauac caucauuaga uuuugcuacc 1320
auacaauacu uacgacgcgg ugcugagacc caauugcuug cgcuuuucca cgcugccaag 1380
gccucaggcu acaacgacau guugggggaa gagcaccaau ugacgaaagc agaaaauuug 1440
uuggucaucc ucgacuugac cauagacgag auguauacgg aaaaagcaaa cgcgccauau 1500

-continued

```
aauucgcaua gcugcuuugc ggauaucaua aacuuacuca gcggcgccuc gcaauacguc   1560

gcuagcacac aacaaaacgg uuguaaaauu gcauucuuca caaaauggcu accgcugcug   1620

uuaucauuca cagccucaca aacaguagua gcagugcuuu ga                      1662


<210> SEQ ID NO 83
<211> LENGTH: 1884
<212> TYPE: RNA
<213> ORGANISM: Sclerotinia sclerotiorum

<400> SEQUENCE: 83

auggcggcug aauuaaucga cuuuuaucag aacuuucuac gaacgggauu auacaauggc     60

ggauaugaug augaacuucu cgcucuugca ggagaugauu cuucuggaga agaacagguc    120

gcaacaaaug auggggaag acacaguucu ucaucgccug aucguaaugg ugcgguaaag    180

agugcagcua agaaaggugg aaagaagggg gguagacgaa augaugauuc ugaggaagaa    240

ggugaagcuu cuuccgguga ugaaucuguu cguucggaac gaucagcucc aauggaugaa    300

ucugauuccg auuccgaugg cccaaguuuu cgcgaugaug cugaucgaua uccucucgaa    360

ggucguuuua ugaaugcagc cgauaaagca aguauuaugu cuaugccuga aauucaacgu    420

gagcaggucu uggcugaucg ugcccaagag auugaaaggg accgucaaaa uagagcacuu    480

cgucaacugu uaaaugcccg ugaugcagag aauaaaaaag cggacaaaaa gcgcaaggca    540

gguaccgcgg auuuggagga aaaccagcgc aaaacgucuc gucaacguac caagcuuggu    600

ggugggaagg uuggggaagc uagcacugga auugacaguc uuaagcgugc aagagcugag    660

aaaaacgauc gacaacgucg ucgcgaucaa gauaaggagc gccgugggga ugauggucga    720

agagauaccc gggacgauua uucagaugac gauggugaug gggauaguga gguugaaugg    780

acagcaucaa agucaaagaa aaggucugca ucuccagauu accgagaugc agaaccggcg    840

guucucuaug aucuugaacg aguucgaguu gguagaagua gauuugccau ggucugcuuu    900

uauccugggu uugaugaagc uauuacugga ugcuuuguuc gaguaaaauau uggugugugau    960

aaggagacaa aucaaaaccu uuaucgcaug ggacuuguua aaggcuucaa agaagauaaa   1020

ccauacgcua ugaugucuag uaacggaaag caauuuucga caacacaaua ugugauugcu   1080

gcacauggua aaucugagag aucauggcca uuuaucgcau guucagauuc ucgauuuaca   1140

gaggcugaau ggcaaagaua uaagcaaaau uguaucgcug auggcauacc uguuccgaca   1200

aaaccaaagu ugaugcaaaa gugugcagag auuaaugcuc uuguuaacag accuuggacu   1260

gaagccgagc uacaagagaa guugaagaaa uccggugu au ugacggaaaa guggaaugca   1320

accgaacgug ugcgucuuaa caacgcuauc aaggaacaga aagcccuugg caauaccgaa   1380

auggaagaaa aguaucguuc agaacuugaa gcgcucgaga auuccaaacu ggcuuaugga   1440

accacccuca aaucaacgcc gaagaagaug guucacucuc aacaagaccg acuugccgaa   1500

uuaaaucgau uaaaucgucg caaaaauauc gaggaaguac gucaagcgca aaucaaugaa   1560

cgucgugcag cucgacaggc ugaagcagcg auugcucgug gagaaguagu ugaugaagau   1620

cacucaaggc gugucaaaac ucgugcuacu uucaaacaug aucauacugg agguaaggau   1680

agcgcaacug cuacuccagu uagugguacu ucgaccaaua auaccccuaa acuuguggcu   1740

aagaaagaug cuuuaccggu accgaauuuu aguaagcuac aaacguccau gaagggugga   1800

guuccuggau ucagaaaacc uuugauggac gaugauauua uugcuaguau cgauauuggu   1860

auuagugaug auuuagaguu guaa                                          1884
```

<210> SEQ ID NO 84
<211> LENGTH: 1587
<212> TYPE: RNA
<213> ORGANISM: Sclerotinia sclerotiorum

<400> SEQUENCE: 84
auggacgaca agaauguaga acugggcgug aucgcuaggu cgucgucuuc ugaugagaua 60
ccucaugccg ggucgaaagg caauacgagc agagaugauc gagaaauggc auauuuugga 120
aaacgccagc aauugaagcg uaauuuuggc uucuugucga uugcggguuu cgucugcagu 180
uugcuuucga caugggaagg aauguucgcg gucuuccuuu acggauucca aaacggugga 240
ccggcaggau uaguuuacgg cuacaucuuc uguuucuuug guacauuaug uacggucgcc 300
aguuuggcag agauguccuc caugaugccc uugagcggcg gccaauauca cugggugucg 360
auucucgccc cuaaguccca cgcaaaguuc cucucauaca ugacaggcug gcuuacgguc 420
auuggcuggc aagcaggcca agcaagugu gcuuuccucu gcgcaacuuu aguccaggcu 480
uuggugauau uaaaucaucc aacauacguc ccugagcgau ggcaggcaac uuuaauauuc 540
uacgcgguuc uagcuguugu uuuguuuguc aauacguauu uggcucgcug guugccaaag 600
auugaaggau ugguucuuug cauccauaua cuuggguucu uuggguguucu uauuccucua 660 gucuaccuug caucucaugg aaaggcaagu gaugucuuug cuacguuugu caacggugge 720 gguuggucca cagauggaau aucauucuuu auuggccuaa uuacaagugu uuucuccuuu 780
cuuggagccg auucugcuug ccauaugagu gaagaaauuc acaaugccuc uaccgucgug 840
ccuugggcaa ugaucaccac gauucuuuug aauggugcuu uagguuucgc acugcuuaua 900
gcccuucucu ucugucucgg agauaucaau gacgcucuua cuucuccuac cggcuucccg 960
uucauugaga uauuuaggca agccacuaau aguaacucug cugcaacugg aaugacaugu 1020
aucauuguga uaaucauguu ugccgcggcu auugguauua uggcaacugc cucacguuua 1080
uugugggcuu ucgcgagaga ccauggagua ccagguagcg cauaucuguc ucgugugcac 1140
gaaccaacag cacuaccauu auacucuauu cuagucagug ccauuauuuc acucuuauug 1200
gcacucauaa auauuggaag cacugccgca uucaacucga ucgucuccgu uaauguugcg 1260
gcauucuuua ccuccuacau gauaccuauc guccugaucc ucaaaaaacg ucuucgcaga 1320
gauccaauaa aagauaagau acauugggga ccguggagaa uggguccaau ucuuggucca 1380
auugucaaug uugccggauu gauuuauucg augaucacca uguuuuucag cuucuggcca 1440
aauacacaag ucguuacucc aguuaccaug aauugguccu guguuauuuu ugcugcugcu 1500
aucauuuaca gcgugguguu cuacaugauu uggggguaaac acucuuacaa guggccaaua 1560
gucgauccua uaagaaggca gcaguag 1587

<210> SEQ ID NO 85
<211> LENGTH: 2028
<212> TYPE: RNA
<213> ORGANISM: Sclerotinia sclerotiorum

<400> SEQUENCE: 85
auggcaaaag uaccagcagu aaagaggcgc aagcuuacac cuccuccaac agaaggggaa 60
gauucaucgc caucgacuuu agagaaugcg ccaaguucga augcguuuuu caagacggcu 120
ucaaaaugga auuuagagca agauuacgaa acgagaccuc ggaaaggcaa gaaggaaaag 180
aaagaaagua caagguuacc aaucaagacu aaggaaggau ugauucagca gguugaagcg 240
ccaguggagg ucaaugaaga agaaagugau uuggaaugga uuggcgcaga cgaugucgag 300

-continued gaggaugagg aacccgaaga gaagguugag gaaaagccuu cugugccgau ccgacagcag 360
auuauggagg ccaaagaaga auuagcacgu auagcauuga uguugaauga ggauccggaa 420
gaaaaugugg gagcauuuag agcuauagca gaauucggga aaucgcaaaa ccuuacgauc 480
aagaaauuag cauuggccac acaauuagcu guuuacaaag auguuauucc aggauacagg 540
auaagaccuu uaucggaaga gaauauggaa gaaaaaguuu cgaaagaagu acgaaaauug 600
agagcauacg aacaggcucu ugugggugga uaucaaggau augugaagga guuggcuagg 660
cuuguaacuu cugggagacc ccagaauaag agugauggug gcgcgagccu gucaacgguu 720
gccauauccu gugcuugcgc auuauuagaa gcuguacccc auuucaauuu ucgaucggau 780
cuauugaaga uauugguagg aaagcuuagu acaagacagg uggacaauga auucgugaag 840
ugucgagaga ccaucgaaac auuguucaag aaugacgaug augggaccuc auccuuggac 900
gcgguaaaua uuuugacgag aaugaugaaa gggagaggau acagagugga cgaaagcgua 960
uugaauaccu ucuuacauuu gagguuacug ucggaauuuu cuggaaaagc cucuacgaau 1020
caugucgagc augaggaaga cagcuuugga ggcaagaaac uuaaggagaa gagaguauuu 1080
cguaccaaga aggagagaaa auugaugaag gagcgcaaag caguugaaaa agagaugauu 1140
caagccgaug caacagucag ccacgaagau cgagagagaa ugcaaucgga aacccugaaa 1200
uugguguuug ugacauauuu ccgcauucug aaaguucgcu ccccaucucu uaugggcgcu 1260
guacuugaag guuuagcaag auacgcucau cucaucaauc aagauuucuu cggugaucuu 1320
cuggaagcgc uuaaggaccu uauuggucau gcugagacag gagaugaugu cgaggaaacc 1380
gaagcagaag augaggauuc agaauccucc cgcaaucuca cccgugaauc ucuccuuugc 1440
aucaucaccg ccuucgcucu ucucgagggu caagaugccc acaaagcuca agcaucgcua 1500
agcuuagauu uaagcuucuu caucacucau cucuaccgca cuuuacacgc ccucucccuc 1560
aacccugaua ucgaacuuug cuccaaaucc cuucaucuac cagaccccaa ugcacccuca 1620
accuccaaca acaaaguuaa cauccaaacc accaccgucc uccuccucaa aucccucuca 1680
ucuguccucu uaccuccucu ggccgcacgc gcagucccac cucucagaau ugcagcuuuc 1740
acuaaacaac uuaugacaug uucucuucaa uuaccugaga aauccgcuac ggccaugaug 1800
gcuuuauuag ggaaaguugc gaaaauucau gagaccaaag ucaaaagccu guggaauaca 1860
gaggagagga aaggugaugg aauguuugau ggauguagug cggaaguuga aggaaguaac 1920
ccgauggcga guacgauuug ggagggagaa cugcugaggu ugcauuauug cccugcgguu 1980
agagaaggcg ugaaaguggu ggagaagaau gugauugguu ugagguga 2028

<210> SEQ ID NO 86
<211> LENGTH: 5802
<212> TYPE: RNA
<213> ORGANISM: Sclerotinia sclerotiorum
<400> SEQUENCE: 86
augucgggac acccaccaca acaaggugg u caauacgacg aaggcuacgg ccaucaagcg 60
ggcaauaccg auucuuauua ccaagaugag cacggagggc aacaauauua ugacaauaau 120
gguggcuacg aacagggcca cgggggucau cagcaagaag gugcugaagg auauuaugau 180
gaaucaggcu auuacaaugc ugaugccaac aauccauauc aacaagaagg aggguacuac 240 gaaggugug aucagcauca aggccaauau caagaugaau acuacaacga ccaguacuau 300
gaucaggggg gugcagccgg cggugaggca ccccaagcua aacgucgagg cgauucggaa 360
gaggauuccg aaaccuucag cgacuuuacc augagaucag acauggcucg agccaccgau 420

-continued

```
auggauuacu auggacgcgg ugacgagaga uauaacagcu acaaugagag ucaaaugggu    480
ggucgugguu acagaccacc aucuucgcag guuucauaug gugguaauag auccuccgga    540
gcaucgacgc caaauuacgg cauggacuac aacaacgucc uuccaccugg acagcgaucu    600
aaggagccgu auccugccug gaccucugac gcucaaauuc cucuguccaa agaagaaguu    660
gaggacauuu uccuggauuu gacagccaag uuugguuucc agcgugacag caugagaaac    720
guuuacgauc auuugaugac ucugcucgau ucgagagcuu cgcgcaugac cccgaaucaa    780
gcgcuccugu cacuacacgc agacuauauc gguggugaca augccaacua ccgaaagugg    840
uauuuugcug cucaucucga uuuagaugau gcggugggau ucgccagcau gaaacuuggc    900
aaaggagauc gucguacucg caaagcccgc aaagcagcca aggcagcgcc accggacccu    960
caaaacgagg cgcaaacccu ugagcaaaug gagggugaua acagucucga agcugcggag   1020
uacagaugga agacucguau gaaccgaaug ucccaacacg accgaguucg ucaauuggcu   1080
cucuaccuuc ucuguugggg ugaggccaac cagguucgau ucaugcccga aguucuaugc   1140
uucauuuuca aaugugcaga ugacuaccuc aacucuccug ccugccaaaa cuugguugaa   1200
ccaguggaag aauuaacauu ccucaacaac guuauaacgc cucuuuacca auacugucga   1260
gaucaaggau augaaauuca agacggcaag uauguucgac gagaacggga ucauaaugaa   1320
auuaucgggu acgaugauug caaccaguug uuuugguauc ccgaggguau ugagaaaauc   1380
guccuagaag auaagucucg cuuggugguau cucccuguug cggaacguua ucucaaacuc   1440
aaggauguca acuggaacaa guccuuuuuc aaaacguacc ucgaaaaacg uucuugguuc   1500
cacauguugg ucaacuucaa ucgcauuugg guuauccaca ucagugccuu cugguuuuuu   1560
acugcuaaga auucgccaac acuccuggaa aagaauuacc gacaacagga gaacaaucag   1620
ccuccugccu cugcgcagug guccgcgguu gcuuugggug gugcaauugc aagucuuauu   1680
auggucgucg cuacaaucug ugaauggucc uauguuccuc gucgaugggc aggugcucag   1740
cauuugacca agaaacuguu guuccucauc gcuguucuca uucucaaugu cgccccaagu   1800
guguacauuu ucaucauucc caacacacag aagacgaagc uugcuuugau uuugggcauu   1860
guccaguucu ucaucgcccu ggucacauac uucuucuucu cgaucaugcc uaugggagga   1920
uuguucggua guuacuugac caggaacucc agacaguacg uugcuaguca gaccuuuacu   1980
gccagcuauc cucgucugac ugguaaugau auguggaugu cuuacggucu cuggaucacu   2040
gucuucggag cuaaacuugc cgaguccuac gucuucuuga ccuuguccuu ccgugauccu   2100
aucagauacu uggacagcau ggaaaucucu uacugugcug gugaugcucu guuuggcgau   2160
guucucugua aauuacagcc caagauucuc cucggucuca uguucgucac cgaucuuacg   2220
uuguucuucu uggauacuuu cauguggauau auuaucauga acgccauuua cucggucgcu   2280
cgauccuucu accuuggugu uuccaucugg acaccaugga gaaauaucuu cucgcguuug   2340
ccaaagcgua ucuauuccaa gguucucgcc acgacugaua uggaaaucaa guacaagcca   2400
aagguccuca ucucucagau cuggaacgcu auugucauuu ccauguacag ggagcaucuc   2460
cuugcuaucg accacgucca aaagcuucuc uaccaucaag uuccuuccga acaagaaggc   2520
aaaagaacuc uccgagcgcc aacuuucuuc gucucgcagg aagaucacuc uuucaagacc   2580
gaauuuuucc caaaccagag ugaggccgag cgucguaucu cuuucuucgc ucaaucuuug   2640
ucaacuccua uuccggaacc acuuccaguc gauaacaugc caacuuucac ugucaugauu   2700
ccgcauuacg gagagaagau uuuguucucc cugcgugaaa ucauucguga agaugagcca   2760
```

-continued

```
uacucccgcg uuacuaugcu ugaguacuug aagcaauugc acccucacga gugggauugc   2820
uucguaaagg auacuaaaau ucuugcagau gagaccucac aauuuaaugg cgauuacgaa   2880
aaggaugaga agaauacugc caagagcaag auugaugauc uuccuuucua uugcauaggu   2940
uucaagucgg ccgcucccga guacacucuc cgcacacgua uuugggcuuc uuugagagca   3000
caaacccuuu accgcacaau cucugguuuc augaauuaua gucgugcuau caaacuccuc   3060
uaucguguug aaaaucccga agucguucaa auguuuggug gcaacucgga caagcuugaa   3120
cgcgagcuug agcguauggc ccgucgcaag uuuaagcuau guguuucuau gcaacguuau   3180
gccaaauuca agaaagagga gauggaaaac accgaauuuc uucuccgugc cuacccugau   3240
cuccaaauug cuuaccugga ugaagaagcu ccucucgccg aaggggaaga gccacgucuu   3300
uacuccgcuc ucauugaugg ucacuccgaa cuuauggaaa auggaaugcg cagacccaag   3360
uuccgcauuc aacuuuccgg uaacccaauu cuuggugaug gaaaaucuga caaccaaaac   3420
caugccauca ucuuuuaccg cggcgaguac auucaacuua uugaugccaa ucaagacaac   3480
uauuuagaag aaugcuugaa gauucgaagu guuuuggccg aguucgagga aaugacaacu   3540
gaaaacgucu cuccuuacac uccuggugua uccaacccca aggucgcccc gguugccauu   3600
cucggugcuc gugaauauau uuucucugag aauauuggua uuuugggaga ugucgcugcc   3660
ggaaaggaac aaacauucgg uacgcucuuc gcacguacgc uugcugccau uggugguaag   3720
cuucauuaug gacauccuga uuuccugaac gguaucuuca ugacuacgag agguggugau   3780
uccaaggcuc agaagggucu ucaucuuaac gaggauauuu augcugguau gacugcacuu   3840
cuucguggag gucgcaucaa gcauugcgag uacuaccagu gugguaaagg ucgugaucug   3900
gguuuuggcu cgauucuuaa cuucaccaca aagauuggaa cugguauggg ugagcaaaug   3960
cuuucgcgug aguauuauua ucucgguacu caacuuccua uugaucgcuu cuuguccuuc   4020
uacuaugccc auccugguuu ccauuugaac aauauguuca ucauguuguc cgucaacuug   4080
uucaugcucu gcuugaucaa cuuaggagcc cucagaaacc aggucaucga guguaaaauau   4140
aacgucaacg ucccuauuac cgauccacuc uauccaacug guugugcaaa caucauuccc   4200
auuaugaauu ggguuuaucg uugcauuauc uccaucuuca ucguguucuu caucucuuuc   4260
guacccuuga cauuacagga auugacagag cgugguuucu ggcgugcggc uacccgucuc   4320
ggaaagcaau ucaguucuuu gucgccuuuc uucgaaguuu ucgucuguca aauuuaugcg   4380
aacgcuguuc agcaagaucu uucguucggu ggugcccgau acaucggaac gggucguggu   4440
uucgcuacug cccgcauucc cuucgguauu cucuucucuc gauucgccgg ucccucgauc   4500
uaucucggag cuagauuacu uaugauguug uuauucgcaa ccaucacugu cuggcaagcu   4560
gcguugguau acuucugggu uacucuccuu gcuuugugca uuucuccauu cuuguauaau   4620
ccucaucaau uugccuggaa cgauuucuuc auugacuaca gagacuaccu caggugguug   4680
ucucgcggaa auucgcguuc ucacgcaucg aguuggauug cuuacugccg ucucucucgu   4740
acuagaauua cagguuauaa acgcaagauu cuuggagacc caucugccaa gaugucuggc   4800
gacacugccc gugccucauu cuccaaucuc uucuuuggag aaaucguggg accgcucaug   4860
gucguugcuc ucaccuugau uccauaucuc uacauaaaug cccagacugg ugucauucca   4920
agcaucaacg auaacgucga aacuaaagcg acgaacgccu ugauucgugu ugguauugua   4980
gccuuggcuc cuauugcagu caacgcaggu guccuggcug ucauguuuag uauggcuugu   5040
uguaugggac cucuccuugg cauguguugc aagaaauucg gauccguucu cgccgcaauu   5100
gcacaugccc uggccgucgu cuucugccug guuuucuucg aagucauguu cuucuuggaa   5160
```

```
ggauuugacu ucgccaagac ucuguuggga augauugcgu ccgccgccau ucagagauuu   5220

gucuacaagc ucaucaucag ucuagcacug accagagaau ugaagaccga cacauccaau   5280

auagcuuucu ggacugguaa augguauucc augguuggc acacgauuuc ccaaccuggu   5340

cgugaauuuc uuuguaagau caccgagcuu ggaauguuug cuggggacuu uguucuuggu   5400

caucuccuuc ucuucaucau gcuucccguc aucgccauac cucaaauuga caagcuucau   5460

ucugugaugc ucuucuggcu ucguccca gu cgacaaauuc guccuccaau cuacuccuua   5520

aagcaaucca aguuacgaaa gaaacguguc uggcgguacg ccuguguaua uuucgcucug   5580

uuugucgucu ucccucgcacu gcuugugggc ccacuuguug uuggcaagaa gaucuugacc   5640

ccuagcuuga uaaguaagau uccacagaag cucuuccagc cuaucaacca gaacaacaac   5700

gacacaagag guuacaacca gaccgguacu gguugcguga caugcuccac agccucugcc   5760

acuucaacca aaacugcugc ugcuaagauu cgauuguucu aa                      5802
```

<210> SEQ ID NO 87
<211> LENGTH: 702
<212> TYPE: RNA
<213> ORGANISM: Sclerotinia sclerotiorum

<400> SEQUENCE: 87

```
augccgggcc acauagauug uuaucucgau ugcucuucau ucuacagcua cgcugcaaua     60

gcacaucucc gaaagaaccg agaaguucuu cuuacucaug auguuaccgu gaauaucauu    120

ccagucuucc ucggcggcau aaacaacggc ucgggaaaca aaccgccaug gagucuuccu    180

gccaaagcaa aguauagcaa auucgauagu gcucgcacga uaucauauca ugggcuuccg    240

gaucuucaag cuccugauuu cuucccgccu gugacacuuc uuccucaaag agcacucugc    300

uucaucaaau cccguuaucc ugucgaaaca uucgagaaaa cauucuugag cauuuucaau    360

gcccuuuggg uugccccuca caaaaacauc acgauuccug acgaacuccg ggaguuccua    420

aguaagcuag gcucguucga ugagaagcag guagaggaga uuauggcaau ggcggcggag    480

aaagagugga aggauaaguu acuggagaau acaaaagaug cgcuugggaa gggugcauuu    540

ggggcaccgu gguugugggu uaggaauggg gagggauugg aggaaccguu uuuugggagu    600

gauagguuuc auuuuauuug gaaguuuuua ggggguugacu uuagggaugu ggagauugug    660

gaaggugaua agggggaagg gaggaagaag gccaaguugu ga                       702
```

<210> SEQ ID NO 88
<211> LENGTH: 1149
<212> TYPE: RNA
<213> ORGANISM: Sclerotinia sclerotiorum

<400> SEQUENCE: 88

```
auggcugauc gaaaugcguc aaauacuuca aauggugaau augaucaugc gugggcaaaa     60

gauuuaagac aacaauucga agguuuauua aggacgaaaa gauuaaauga auuggauaga    120

ucaagaucac gaaauccuuc accaucaccu agagaacgau caucuucauc aaaucuccga    180

gcuucaucuu cacaaaauca accacaaucu uccaacuuuc gacccacuuc uucaucaaau    240

aaucaaucaa aaccuccaac ucccuccagca uauucuucua caagaaguuu accaaagauu    300

ccuucuccac cagcagaugc ucaaucacaa aaguuucgaa auuuauuaau cuccaucuca    360

caaacaccaa cgaaauauga aaaucccggu uuauuggaug aagcuuuaca acauuuacca    420

cuagauagaa uuuauggaga agcagaagaa gaaagucaaa ucuuacaagc ugaggccgaa    480
```

agcaugggag auggaaggaa accagaaugg gguuaucaag auugugucau ucgagcuuua 540
cugaguaugu ugugucgcgc cguuggaggu cguguaagau ggguuuggaa uguugaagau 600
cauguuugga cggaaguuua uucggauacg aaaaagagau ggauucaugu ugaugcaugu 660
gaagaagcuu gggauaaucc aagguuauau gccgaagguu gggguaagaa gaugucuuau 720
uguauugcuu uuucaaugga aggugcgacc gauguuacuc gaagauaugu acgcaaaccc 780
gaucaugcuc ucccacgaaa ucgauguccg gaagaaguua uguuauauau ucaaaacgaa 840
auucggggac uucggagauc aaauaugaau aaggaugaaa gauuucgauu ggaaaaggaa 900
gaugcgaggg aagauaagga auugaggggu uaugugguag caucaauugc gcaauccguc 960
guaucgaauu ugagaccaga aggaucguca caucaacaaa uaacaccucc accuccacga 1020
caagaagauc agaaauuacc agcugaacaa ccugguagac aaacuggugc acaagaaugg 1080
gcaaaugcua gaggugaagc uggaagacga aaucaacauc caagggaucc uucacaacau 1140
ggaccuuga 1149

<210> SEQ ID NO 89
<211> LENGTH: 666
<212> TYPE: RNA
<213> ORGANISM: Sclerotinia sclerotiorum

<400> SEQUENCE: 89
augucguucu gggauaaguu gacagggcga aagccaucau caaaagacac uucuaguggc 60
ggaucaaccu ugaauacccc aacugacaca uucacaccua cacccuucaa cccucaagaa 120
ggucaagaug ucaacucuuu ucuuacaggg ccagagcuca uagauccauc acaacuucau 180
ccuuuggcug gucugaacca acagacucua gacuaucuau cccucgaaga aucuacucuc 240
ucggaucuuc caggaucgca aucugccuua cccucgagag guuggucgga cgauuuaugu 300
uaugguaccg guguuacaua uuugacggca cuaacugugg gugguguuug gggauuacag 360
gaggguuuga ggaggucugc gacgcaacca ccaaaguuac gauugaacuc ggugcugaac 420
gcuguuacga ggcgagggcc auucuugggc aacucggcag gaguaauugc uaugguuuac 480
aacggauuca acucauuuau cggacauaug aggggcaggc augauucggc gaacaguguu 540
cuugcaggug cgcugagugg gaugauuuuu aaaaguacaa gaggaguucg accuaugaug 600
auuuccggug ggaucguggc uucuguagcc ggcgcauggg cacaagaaaa gcaauauuuu 660
aaauga 666

<210> SEQ ID NO 90
<211> LENGTH: 1344
<212> TYPE: RNA
<213> ORGANISM: Sclerotinia sclerotiorum

<400> SEQUENCE: 90
augucuuccg aaccaccuuu ggaccccuac aaacccucuc ucuucgaacu uuuguccucc 60
acccaacuuu cgucacuccu ucccucccucu cuccacuacc uccuaaccau cgccacacac 120
cgacauccgc gacaccuccu cccaauccuc aacuccuuuc acgaaaucca cgcucuccuc 180
uuccuagcaa ucgaacacca cuaucuaacc accuacucuu cuucauuugu cgaaaacuuu 240
uauucucuaa aacgggaacg cgccuuaccu gcggcaguag gcgaucugcg acuuacggcc 300
gaagcagcca augccagucu acgcgaaacg acaaaacuua caagagggga uguauggaag 360
aaucuugcug ugcucguugg aauuccauau cuuaaacguc gacucgauga gucucaggag 420
aucaaugcac cgagagcacu ucucggcgca aauuauacac gcaugccacc gaauccaacg 480

-continued

```
cucaaacaac gauuucuaca uuauuaucgu ugguuucuua cgaauguaua ucccagcgug     540
aaugccgcau auuauuucag uaucuuagca uuuaaucuac gauaccuauu uucggguucg     600
aaaucuggcu cugguguaua uuccgaucca uuuuuauggu uaauaggaac gcggauacga     660
agauuaaguc aagcagauuu ccaagcuuuu gaagcgauua agaaugcugc aucuucaaua     720
ccagggucga aucuaggaau aagaagucua uuggauccaa gacuggcaau gggaagaaua     780
gguucuggau uaaaacuauu acuaccaacc aguaucuuug cgcugaaauu ccuggaaugg     840
uggcaugcga gugauuuugc aagacaauua ucucgaaaag caauagaagg auuagaauua     900
ccaccgccua uuauaucaua caccccuucu ccuguaacaa aaccggagac cacgucaaaa     960
uccucaucag aagaaaaaca accgucagaa guagaagaac caacaaaucc cccgaucuca    1020
accauaaccc aacuccccau cuaugucguc ccagcuccuu ccaccucgac cuccuuagaa    1080
aauugcccaa ucugucucga agaaaucacg acgccaaccg cgugucaaac aggauaugug    1140
uauuguuaua cuuguauuca uagguggauu gagggguugc augauuugca ggagaaguuu    1200
augaagggug augugaaggu ggaugggcaa gggaaaggag agaagggaag agaagggaag    1260
ugggaaagug gagcaggcag augugcgguu aguggacgga ggguauuagg gggugucggu    1320
ggguugagga ggguuuuggu uuaa                                           1344
```

UNITED STATES PATENT AND TRADEMARK OFFICE
CERTIFICATE OF CORRECTION

| | |
|---|---|
| PATENT NO. | : 11,085,052 B2 |
| APPLICATION NO. | : 16/098387 |
| DATED | : August 10, 2021 |
| INVENTOR(S) | : Steve Whyard and Mark Belmonte |

It is certified that error appears in the above-identified patent and that said Letters Patent is hereby corrected as shown below:

In the Claims

In Column 132, Claim 15, Line 49: please delete "is" between "pathogen" and "Sclerotinia".

Signed and Sealed this
Sixteenth Day of May, 2023

Katherine Kelly Vidal
*Director of the United States Patent and Trademark Office*